US012648787B2

(12) United States Patent (10) Patent No.: US 12,648,787 B2

Arevalos et al. (45) Date of Patent: Jun. 9, 2026

(54) TRANSCATHETER DEVICE FOR INTERATRIAL ANASTOMOSIS

(71) Applicant: Texas Medical Center, Houston, TX (US)

(72) Inventors: Christopher Alexander Arevalos, Houston, TX (US); Albertien Greijdanus, Houston, TX (US); Jacob Kriegel, Houston, TX (US); Avni Patel, Houston, TX (US)

(73) Assignee: Texas Medical Center, Houston, TX (US)

( * ) Notice: Subject to any disclaimer, the term of this patent is extended or adjusted under 35 U.S.C. 154(b) by 0 days.

(21) Appl. No.: 19/054,245

(22) Filed: Feb. 14, 2025

(65) Prior Publication Data

US 2025/0235240 A1 Jul. 24, 2025

Related U.S. Application Data

(63) Continuation of application No. 16/533,655, filed on Aug. 6, 2019, now abandoned, which is a
(Continued)

(51) Int. Cl.
*A61B 17/3205* (2006.01)
*A61B 17/32* (2006.01)
(Continued)

(52) U.S. Cl.
CPC ................. *A61B 17/32053* (2013.01); *A61B 17/320016* (2013.01); *A61B 2017/00247* (2013.01);
(Continued)

(58) Field of Classification Search
CPC .......... A61B 17/32053; A61B 17/0057; A61B 17/12122; A61B 2018/00357;
(Continued)

(56) References Cited

U.S. PATENT DOCUMENTS 5,312,341 A 5/1994 Turi
5,403,338 A 4/1995 Milo
(Continued)

FOREIGN PATENT DOCUMENTS

CN 1684644 A 10/2005
CN 101057986 A 10/2007
(Continued)

OTHER PUBLICATIONS

CN201880024192.6 Notification to Grant issued Feb. 9, 2022.
(Continued)

*Primary Examiner* — Sarah W Aleman
(74) *Attorney, Agent, or Firm* — Goodwin Procter, LLP

(57) ABSTRACT

The present disclosure relates to a device assembly and a method for treating heart failure by normalizing elevated blood pressure in the left atrium of a heart of a mammal. Disclosed herein is a transcatheter interatrial septum excision device assembly configured to create a sized interatrial aperture between the right and left atria of a heart for the relief of elevated left atrial pressure. The device assembly comprises a delivery catheter, a tissue stabilizer attached to a first catheter having a central lumen and a penetrating tip that permits passage of a guidewire, and a cutter attached to a second catheter having a central lumen that permits passage of the first catheter. Alternative configurations comprise a (third) catheter having a central lumen that permits passage of the aforementioned components to and from the right atrium, a tissue retention mechanism and an optional coaxial alignment mechanism.

17 Claims, 53 Drawing Sheets

Related U.S. Application Data continuation of application No. PCT/US2018/017487, filed on Feb. 8, 2018.

(60) Provisional application No. 62/558,178, filed on Sep. 13, 2017, provisional application No. 62/532,223, filed on Jul. 13, 2017, provisional application No. 62/473,027, filed on Mar. 17, 2017, provisional application No. 62/457,605, filed on Feb. 10, 2017.

(51) Int. Cl.

| | |
|---|---|
| A61B 17/00 | (2006.01) |
| A61B 17/22 | (2006.01) |
| A61B 17/34 | (2006.01) |
| A61B 18/00 | (2006.01) |
| A61B 18/02 | (2006.01) |
| A61B 18/14 | (2006.01) |
| A61M 25/01 | (2006.01) |

(52) U.S. Cl.
CPC ............... *A61B 2017/00867* (2013.01); *A61B 2017/22044* (2013.01); *A61B 17/320068* (2013.01); *A61B 2017/3488* (2013.01); *A61B 2018/00357* (2013.01); *A61B 2018/0212* (2013.01); *A61B 18/1492* (2013.01); *A61M 25/0108* (2013.01)

(58) Field of Classification Search
CPC .... A61B 2017/00247; A61B 2017/348; A61B 2017/3482; A61B 2017/3488; A61B 2017/00243; A61B 2017/00575; A61B 2017/320082; A61B 17/32; A61B 17/320016; A61M 25/00; A61M 25/0102; A61M 2025/0004; A61M 2025/0039; A61M 2025/0175; A61M 2025/0293; A61M 2025/1047; A61F 2/24; A61F 2/95
See application file for complete search history.

(56) References Cited

U.S. PATENT DOCUMENTS

| | | | |
|---|---|---|---|
| 5,509,900 A * | 4/1996 | Kirkman | A61M 25/04 |
| | | | 606/198 |
| 5,725,552 A | 3/1998 | Kotula et al. | |
| 5,951,576 A | 9/1999 | Wakabayashi | |
| 6,471,709 B1 | 10/2002 | Fawzi et al. | |
| 6,699,256 B1 | 3/2004 | Logan et al. | |
| 7,048,733 B2 | 5/2006 | Hartley et al. | |
| 7,056,294 B2 | 6/2006 | Khairkhahan et al. | |
| 7,112,197 B2 | 9/2006 | Hartley et al. | |
| 7,340,307 B2 | 3/2008 | Maguire et al. | |
| 7,729,738 B2 | 6/2010 | Flaherty et al. | |
| 7,771,442 B2 | 8/2010 | Shriver | |
| 7,799,041 B2 | 9/2010 | Beane et al. | |
| 7,935,129 B2 | 5/2011 | Gifford et al. | |
| 7,947,040 B2 | 5/2011 | Davies et al. | |
| 8,091,556 B2 | 1/2012 | Keren et al. | |
| 8,096,990 B2 | 1/2012 | Swanson et al. | |
| 8,114,069 B2 | 2/2012 | Sliwa, Jr. et al. | |
| 8,147,424 B2 | 4/2012 | Kassab et al. | |
| 8,157,860 B2 | 4/2012 | McNamara et al. | |
| 8,192,425 B2 | 6/2012 | Mirza et al. | |
| 8,226,670 B2 | 7/2012 | Beane et al. | |
| 8,292,910 B2 | 10/2012 | Chanduszko et al. | |
| 8,308,723 B2 | 11/2012 | Kulesa et al. | |
| 8,417,321 B2 | 4/2013 | Saadat et al. | |
| 8,496,655 B2 | 7/2013 | Epp et al. | |
| 8,500,697 B2 | 8/2013 | Kurth et al. | |
| 8,679,107 B2 | 3/2014 | Mirza et al. | |
| 8,679,138 B2 | 3/2014 | Beane et al. | |
| 8,771,305 B2 | 7/2014 | Shriver | |
| 8,882,697 B2 | 11/2014 | Celermajer et al. | |

| | | | |
|---|---|---|---|
| 8,900,224 B2 | 12/2014 | Ollivier | |
| 8,961,550 B2 | 2/2015 | Lenker et al. | |
| 9,055,959 B2 | 6/2015 | Vaska et al. | |
| RE45,638 E | 8/2015 | Tartaglia et al. | |
| 9,101,375 B2 | 8/2015 | Biadillah et al. | |
| 9,138,231 B2 | 9/2015 | Weisshaupt et al. | |
| 9,168,085 B2 | 10/2015 | Juzkiw et al. | |
| 9,232,997 B2 | 1/2016 | Sugimoto et al. | |
| 9,277,957 B2 | 3/2016 | Long et al. | |
| 9,526,573 B2 | 12/2016 | Lopes et al. | |
| 9,545,265 B2 | 1/2017 | Maisano et al. | |
| 9,597,146 B2 | 3/2017 | Davies et al. | |
| 9,629,715 B2 | 4/2017 | Nitzan et al. | |
| 9,707,007 B2 | 7/2017 | Lenker et al. | |
| 9,713,696 B2 | 7/2017 | Yacoby et al. | |
| 9,724,126 B2 | 8/2017 | Gerber et al. | |
| 9,775,636 B2 | 10/2017 | Fazio et al. | |
| 9,808,283 B2 | 11/2017 | Spence et al. | |
| 9,814,483 B2 | 11/2017 | Vardi | |
| 9,821,145 B2 | 11/2017 | Kurth et al. | |
| 10,179,009 B2 | 1/2019 | Abdul-Karim | |
| 10,271,894 B2 | 4/2019 | Woo et al. | |
| 10,292,690 B2 | 5/2019 | Celermajer et al. | |
| 10,413,286 B2 | 9/2019 | McNamara et al. | |
| 11,304,753 B2 | 4/2022 | Pate et al. | |
| 11,389,185 B2 | 7/2022 | Golden et al. | |
| 11,612,432 B2 | 3/2023 | Pate et al. | |
| 11,871,987 B2 | 1/2024 | Pate et al. | |
| 2002/0082614 A1 | 6/2002 | Logan et al. | |
| 2002/0091398 A1 | 7/2002 | Galdonik et al. | |
| 2002/0128672 A1 | 9/2002 | Dinger et al. | |
| 2002/0143302 A1 | 10/2002 | Hinchliffe et al. | |
| 2003/0236564 A1 * | 12/2003 | Majercak | A61F 2/958 |
| | | | 606/198 |
| 2005/0075665 A1 | 4/2005 | Brenzel et al. | |
| 2005/0159738 A1 | 7/2005 | Visram et al. | |
| 2006/0111704 A1 | 5/2006 | Brenneman et al. | |
| 2006/0210605 A1 | 9/2006 | Chang et al. | |
| 2008/0004485 A1 | 1/2008 | Moreschi | |
| 2008/0015466 A1 | 1/2008 | Lerman | |
| 2009/0143808 A1 | 6/2009 | Houser | |
| 2010/0114140 A1 | 5/2010 | Chanduszko et al. | |
| 2010/0160725 A1 | 6/2010 | Kiser et al. | |
| 2011/0270239 A1 | 11/2011 | Werneth | |
| 2011/0306959 A1 | 12/2011 | Kellerman et al. | |
| 2012/0065597 A1 | 3/2012 | Cohen | |
| 2012/0165812 A1 | 6/2012 | Christian | |
| 2012/0259263 A1 | 10/2012 | Celermajer et al. | |
| 2012/0265296 A1 | 10/2012 | McNamara et al. | |
| 2013/0267885 A1 | 10/2013 | Celermajer et al. | |
| 2013/0310804 A1 | 11/2013 | Jabba et al. | |
| 2014/0012247 A1 | 1/2014 | Bakos et al. | |
| 2014/0046356 A1 | 2/2014 | Abdul-Karim | |
| 2014/0128796 A1 | 5/2014 | Keren et al. | |
| 2014/0206987 A1 | 7/2014 | Urbanski et al. | |
| 2014/0228843 A1 | 8/2014 | O'Donnell et al. | |
| 2014/0236207 A1 | 8/2014 | Makower et al. | |
| 2014/0277045 A1 | 9/2014 | Fazio et al. | |
| 2014/0277114 A1 | 9/2014 | Walters | |
| 2014/0350565 A1 | 11/2014 | Yacoby et al. | |
| 2015/0031959 A1 | 1/2015 | Beane et al. | |
| 2015/0094715 A1 | 4/2015 | Laufer et al. | |
| 2015/0157353 A1 | 6/2015 | Lenker et al. | |
| 2015/0173794 A1 | 6/2015 | Kurth et al. | |
| 2015/0223839 A1 | 8/2015 | Spence et al. | |
| 2015/0359556 A1 | 12/2015 | Vardi | |
| 2015/0359563 A1 | 12/2015 | Kume et al. | |
| 2015/0374431 A1 | 12/2015 | Davies et al. | |
| 2016/0000499 A1 | 1/2016 | Lennox et al. | |
| 2016/0000501 A1 | 1/2016 | Davies et al. | |
| 2016/0100859 A1 | 4/2016 | Sapir et al. | |
| 2016/0158045 A1 * | 6/2016 | Havel | A61F 2/9662 |
| | | | 623/1.12 |
| 2016/0220245 A1 | 8/2016 | Hausen | |
| 2016/0262795 A1 | 9/2016 | Urbanski et al. | |
| 2016/0264637 A1 | 9/2016 | Romeuf et al. | |
| 2016/0270810 A1 | 9/2016 | Vardi et al. | |
| 2016/0374751 A1 | 12/2016 | Davies et al. | |
| 2017/0020540 A1 | 1/2017 | Chou et al. | |

(56) References Cited

U.S. PATENT DOCUMENTS

| | | | |
|---|---|---|---|
| 2017/0042572 A1 | 2/2017 | Jimenez et al. |
| 2017/0113026 A1 | 4/2017 | Finch |
| 2017/0296781 A1 | 10/2017 | Sapir et al. |
| 2018/0064460 A1 | 3/2018 | Vardi et al. |
| 2018/0168687 A1 | 6/2018 | Drake et al. |
| 2018/0177516 A1 | 6/2018 | Vardi et al. |
| 2018/0199915 A1 | 7/2018 | Coker et al. |
| 2019/0008628 A1 | 1/2019 | Eigler et al. |
| 2019/0029705 A1 | 1/2019 | Vardi et al. |
| 2019/0216528 A1 | 7/2019 | Woo et al. |
| 2019/0231424 A1 | 8/2019 | Davies et al. |
| 2019/0239924 A1 | 8/2019 | Urbanski et al. |
| 2019/0269392 A1 | 9/2019 | Celermajer et al. |
| 2019/0374254 A1 | 12/2019 | Arevalos et al. |
| 2019/0374281 A1 | 12/2019 | Davies et al. |
| 2020/0289196 A1 | 9/2020 | Arevalos et al. |
| 2021/0077186 A1 | 3/2021 | Pate et al. |
| 2022/0211380 A1 | 7/2022 | Pate |

FOREIGN PATENT DOCUMENTS

| | | | |
|---|---|---|---|
| CN | 201743767 U | 2/2011 |
| CN | 202365919 U | 8/2012 |
| CN | 104125815 A | 10/2014 |
| CN | 104997574 A | 10/2015 |
| CN | 105920720 A | 9/2016 |
| EP | 3154450 A1 | 4/2017 |
| EP | 2673038 B1 | 7/2017 |
| EP | 3275390 B1 | 1/2018 |
| EP | 3329860 A1 | 6/2018 |
| GB | 2498162 A | 7/2013 |
| JP | 2013514107 A | 4/2013 |
| JP | 2015504330 A | 2/2015 |
| JP | 2017512569 A | 5/2017 |
| TW | 200938241 A | 9/2009 |
| WO | 8907422 A1 | 8/1989 |
| WO | WO-2001015618 A2 | 3/2001 |
| WO | WO-2003077733 A2 | 9/2003 |
| WO | 2010024761 A1 | 3/2010 |
| WO | WO-2013158354 A1 | 10/2013 |
| WO | 2015085094 A1 | 6/2015 |
| WO | WO-2015192109 A1 | 12/2015 |
| WO | WO-2017006323 A1 | 1/2017 |
| WO | WO-2017118920 A1 | 7/2017 |
| WO | WO-2018148456 A1 | 8/2018 |
| WO | WO-2018165277 A1 | 9/2018 |
| WO | WO-2019035993 A1 | 2/2019 |
| WO | 2019109013 A1 | 6/2019 |
| WO | 2019226817 A1 | 9/2019 |
| WO | 2021091566 A1 | 5/2021 |

OTHER PUBLICATIONS

EP18751313.0 Extended European Search Report mailed Nov. 12, 2020.

PCT/US2018/017487 International Search Report and Written Opinion dated May 21, 2018.

PCT/US2018/063439 International Search Report and Written Opinion dated Feb. 5, 2019.

CN201880024192.6 Office Action dated Mar. 31, 2021, 16 pages.

CN201880024192.6 Office Action dated Sep. 18, 2021, 6 pages.

CN201880024192.6 Notification to Grant issued Feb. 9, 2022, 3 pages.

Extended European Search Report pertaining to European Application No. 24183489.4, Date of Mailing Nov. 15, 2024, pp. 9.

International Search Report pertaining to International Application No. PCT/US2020/050533, Date of Mailing Jan. 19, 2021, pp. 6.

Written Opinion of the International Searching Authority pertaining to International Application No. PCT/US2020/050533, Date of Mailing Jan. 19, 2021.

U.S. Final Office Action pertaining to U.S. Appl. No. 16/533,655, Date of Mailing Feb. 26, 2024, pp. 11.

U.S. Final Office Action pertaining to U.S. Appl. No. 16/533,655, Date of Mailing Jun. 6, 2023 pp. 9.

U.S. Final Office Action pertaining to U.S. Appl. No. 16/533,655, Date of Mailing Aug. 19, 2024 pp. 12.

U.S. Final Office Action pertaining to U.S. Appl. No. 16/533,655, Date of Mailing Aug. 25, 2022 pp. 8.

U.S. Final Office Action pertaining to U.S. Appl. No. 18/160,253, Date of Mailing Oct. 2, 2023 pp. 12.

U.S. Final Office Action pertaining to U.S. Appl. No. 17/019,042, Date of Mailing Oct. 20, 2023 pp. 17.

U.S. Final Office Action pertaining to U.S. Appl. No. 17/019,042, Date of Mailing Dec. 5, 2024 pp. 16.

U.S. Final Office Action pertaining to U.S. Appl. No. 16/533,655, Date of Mailing Dec. 17, 2021 pp. 9.

U.S. Notice Of Allowance pertaining to U.S. Appl. No. 17/730,731, Date of Mailing Jan. 10, 2023 pp. 8.

U.S. Notice Of Allowance pertaining to U.S. Appl. No. 18/160,253, Date of Mailing Dec. 1, 2023 pp. 8.

U.S. Notice Of Allowance pertaining to U.S. Appl. No. 17/354,855, Date of Mailing Mar. 7, 2022 pp. 11.

U.S. Office Action pertaining to U.S. Appl. No. 16/533,655, Date of Mailing Mar. 4, 2021 pp. 10.

U.S. Office Action pertaining to U.S. Appl. No. 17/019,042 Date of Mailing Mar. 18, 2024 pp. 16.

U.S. Office Action pertaining to U.S. Appl. No. 16/533,655, Date of Mailing Mar. 29, 2022 pp. 9.

U.S. Office Action pertaining to U.S. Appl. No. 17/569,383 Date of Mailing Apr. 8, 2025 pp. 19.

U.S. Office Action pertaining to U.S. Appl. No. 17/019,042, Date of Mailing Apr. 28, 2023 pp. 15.

U.S. Office Action pertaining to U.S. Appl. No. 16/533,655, Date of Mailing Sep. 18, 2023 pp. 9.

U.S. Office Action pertaining to U.S. Appl. No. 18/160,253, Date of Mailing May 22, 2023 pp. 21.

U.S. Office Action pertaining to U.S. Appl. No. 17/730,731, Date of Mailing Sep. 21, 2022 pp. 19.

U.S. Office Action pertaining to U.S. Appl. No. 17/354,855, Date of Mailing Nov. 3, 2021 pp. 19.

U.S. Office Action pertaining to U.S. Appl. No. 16/533,655, Date of Mailing Dec. 5, 2022 pp. 10.

U.S. Notice Of Allowance pertaining to U.S. Appl. No. 17/730,731, Date of Mailing Feb. 1, 2023 pp. 2.

EP Application No. 25176599.6, Extended European Search Report mailed Oct. 24, 2025, Applicant Alleviant Medical, Inc., 9 pages.

* cited by examiner

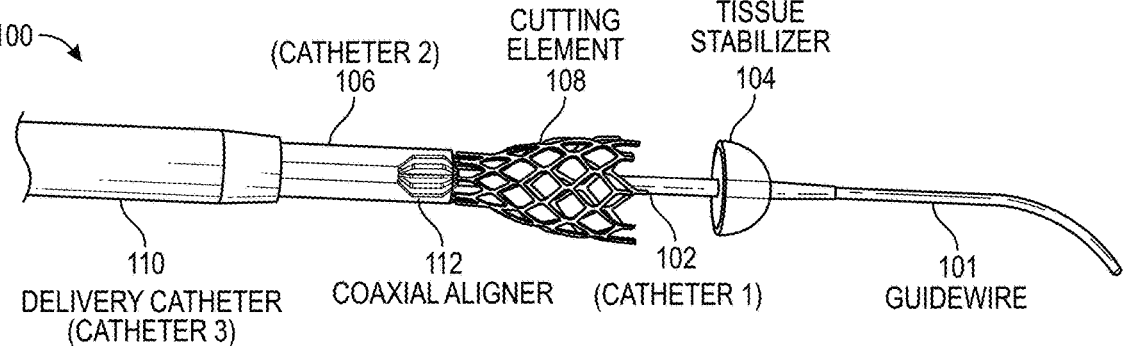
100
(CATHETER 2)
106
CUTTING
ELEMENT
108
TISSUE
STABILIZER
104
110
DELIVERY CATHETER
(CATHETER 3)
112
COAXIAL ALIGNER
102
(CATHETER 1)
101
GUIDEWIRE
FIG. 1
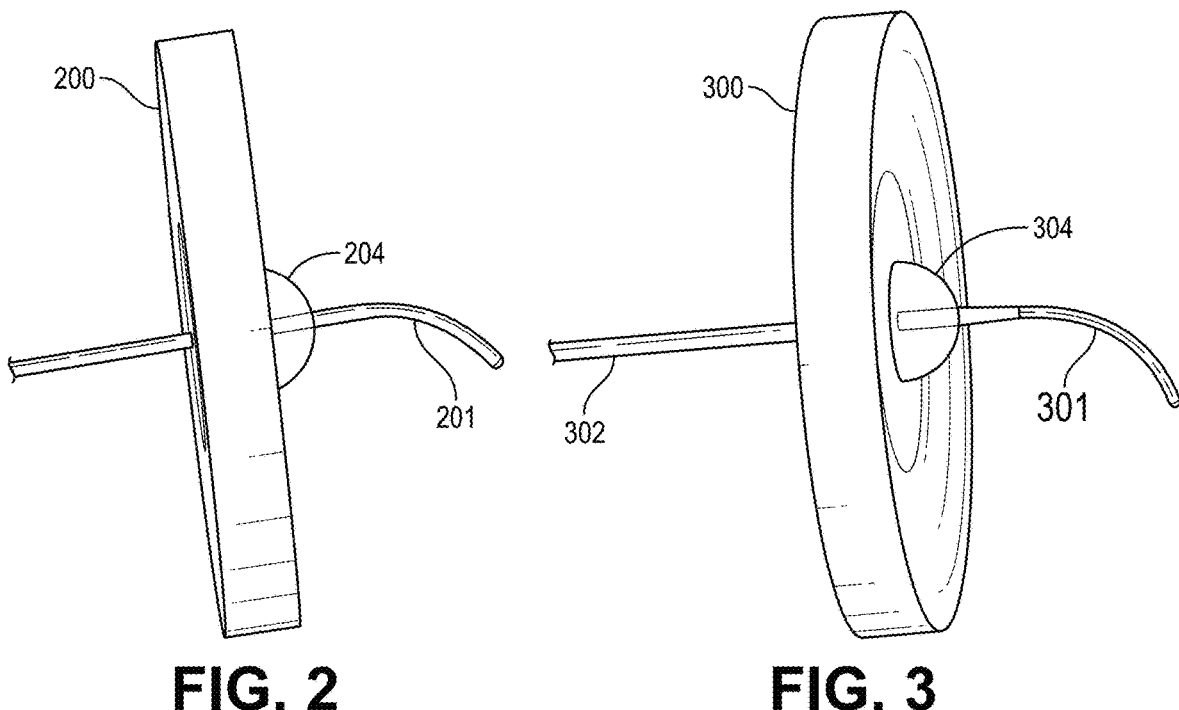
200
204
201
FIG. 2
300
304
302
301
FIG. 3

CROSS-SECTIONAL VIEW WHILE HOUSED

700

702

710
HOUSING SHEATH

701
GUIDE WIRE

706
TENSIONING
BALLOON CATHETER

708
SELF-EXPANDING
NITINOL STENT-BLADE

800

801

800

805

801

800

805

801

904

901

902

900

1900

1907    1908    1920

1904

1901

1910    1906    1914    1902    1909

2000

2001

2002

END VIEW

SIDE VIEW

2008

2004

A

A

DETAIL 'A'

OBLIQUE VIEW

2200

2214

2212

2201

2208

2201

2214

2300

2302

2301

2308

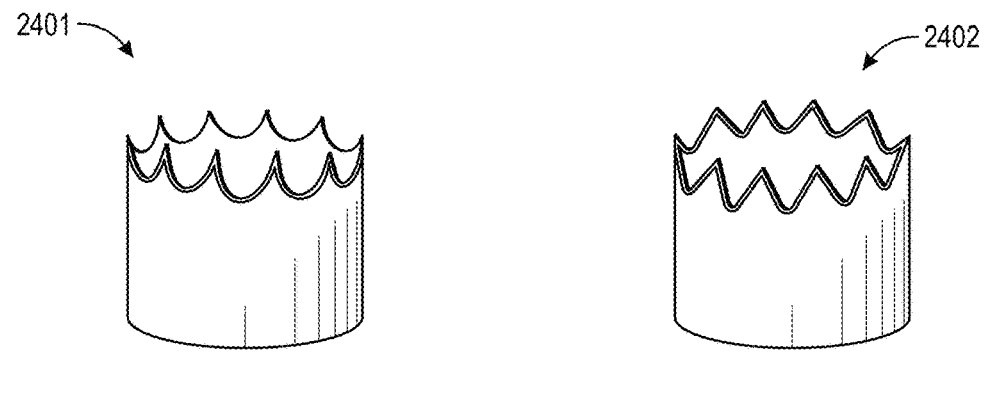
2401
2402
FIG. 24A          FIG. 24B
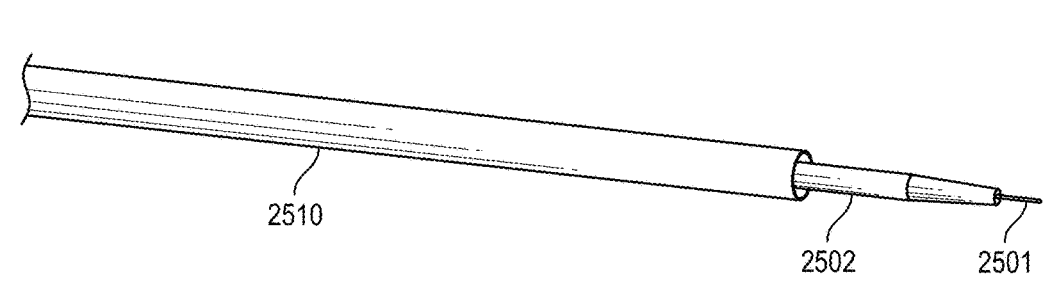
2500
2510
2502          2501
FIG. 25A
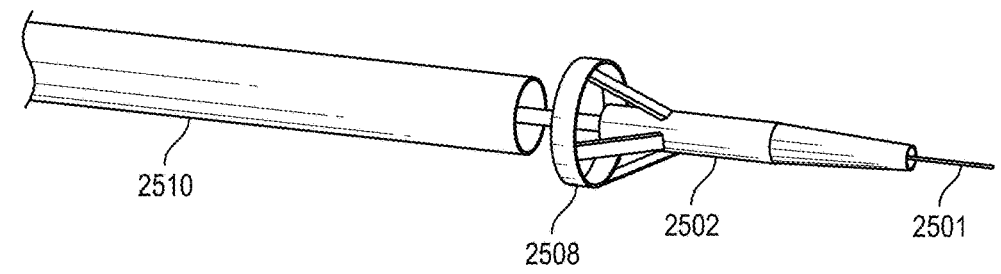
2510
2508          2502          2501
FIG. 25B
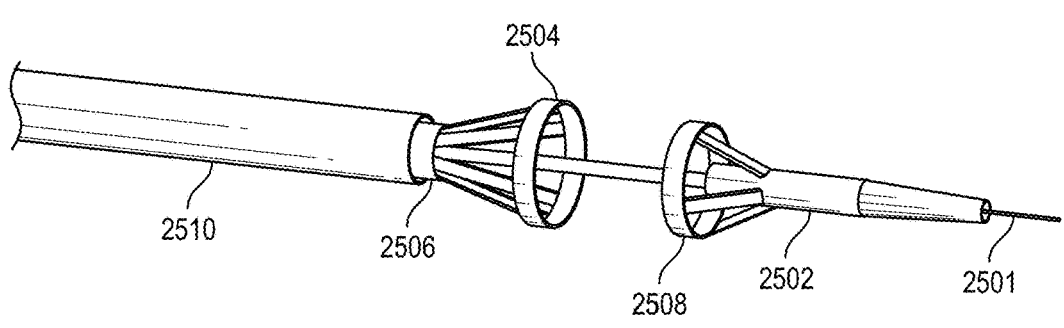
2504
2510          2506          2508          2502          2501
FIG. 25C

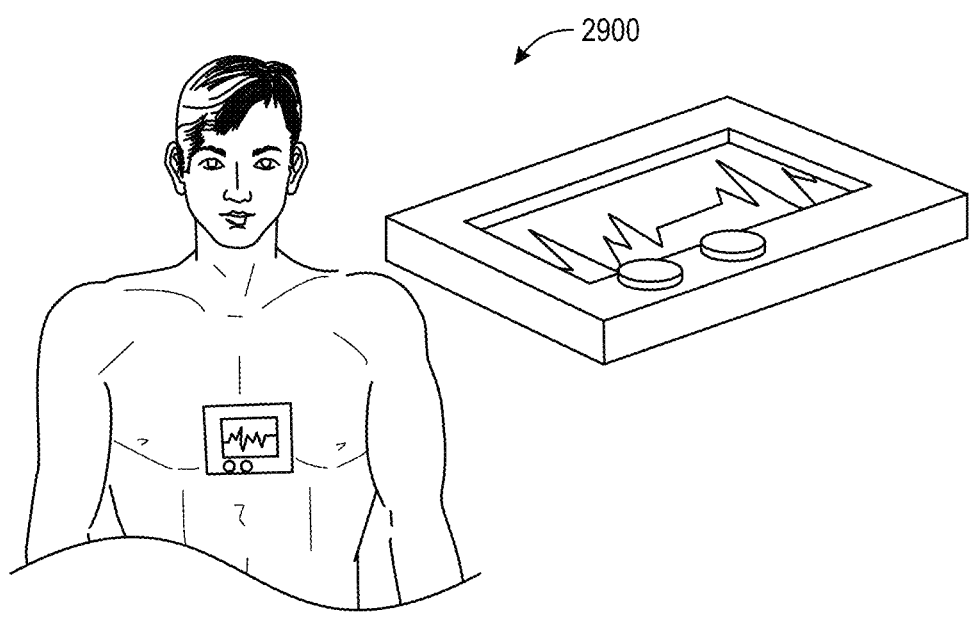
FIG. 29
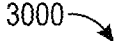
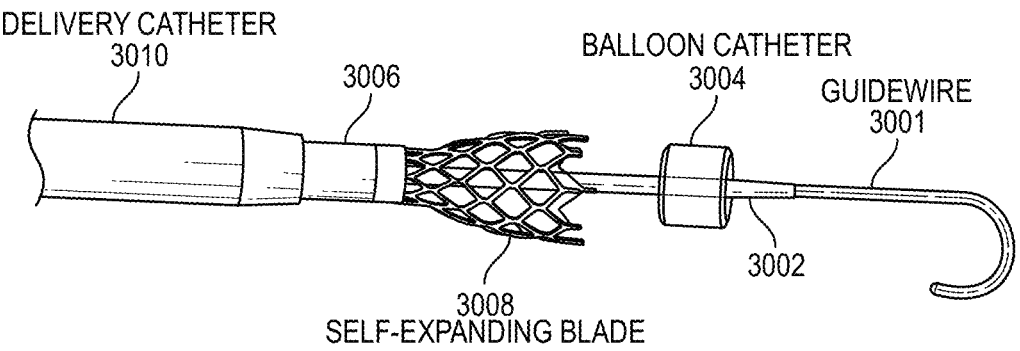
FIG. 30

3100

3018

RIGHT
ATRIUM

LEFT
ATRIUM

3020

3014,3016

3001

3002

3004

3016

3010

SELF-EXPANDING
BLADE
3608

DELIVERY
CATHETER
3610

BLADE
CATHETER
3606

GUIDE CATHETER
(DASHED)

3602
NITINOL MESH
HOUSING
CATHETER

3604
NITINOL MESH
CATHETER
(1-3DISCS)

3801
GUIDE WIRE

3803
GUIDE CATH

GUIDE WIRE REMOVED

3804
NITINOL
MESH CATH

GUIDE WIRE REMOVED

Guide Wire Removed

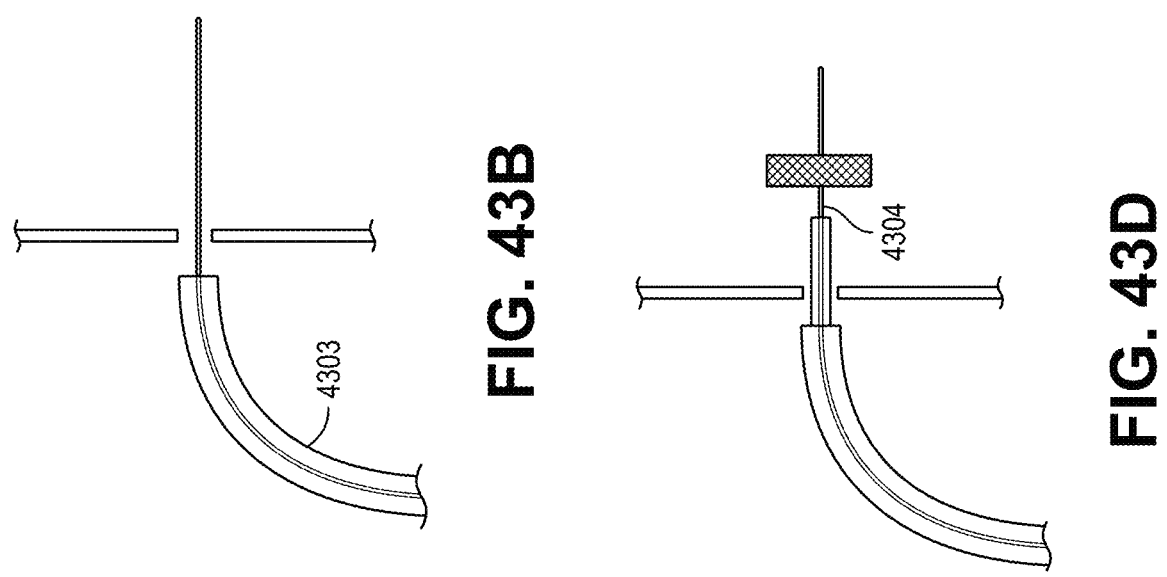
FIG. 43A
FIG. 43B
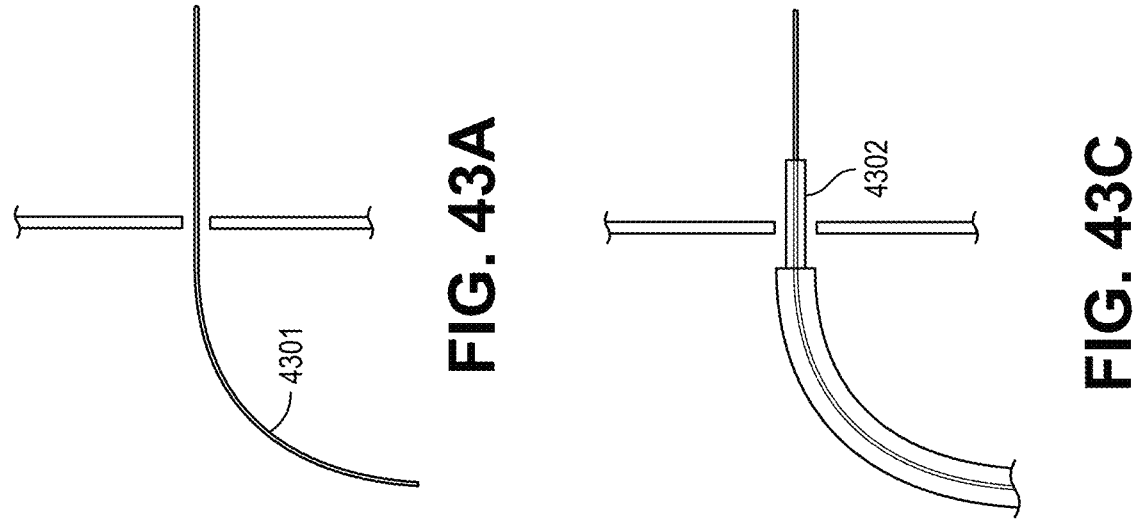
FIG. 43C
FIG. 43D

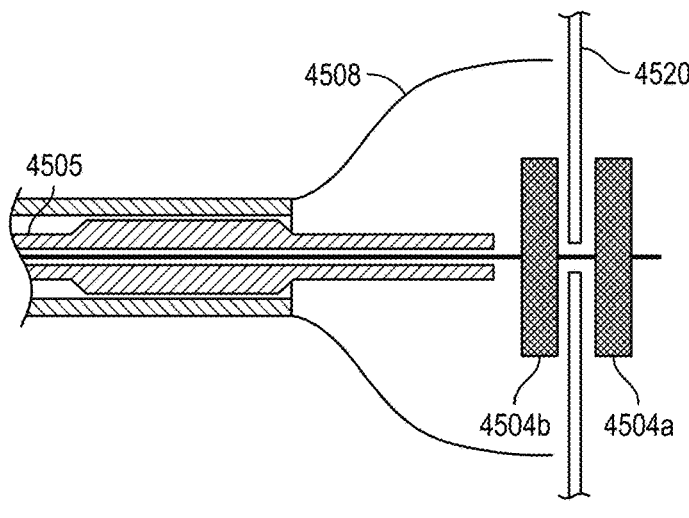
FIG. 45
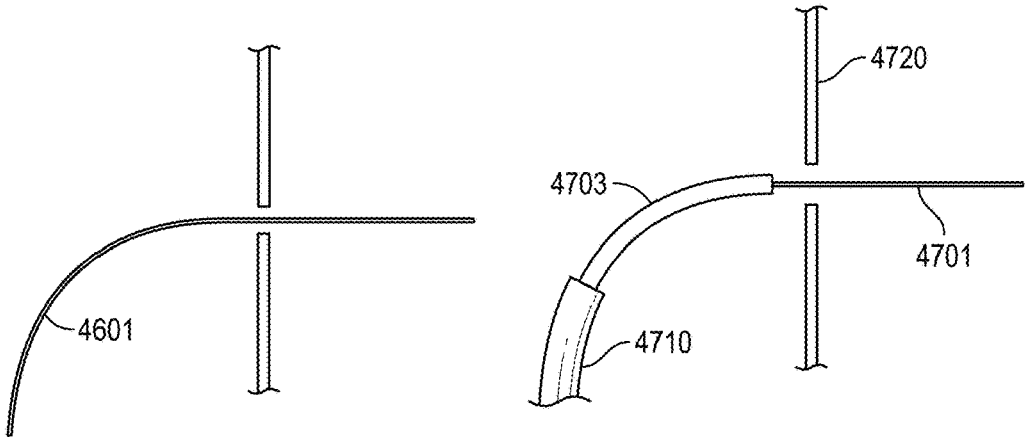
FIG. 46          FIG. 47
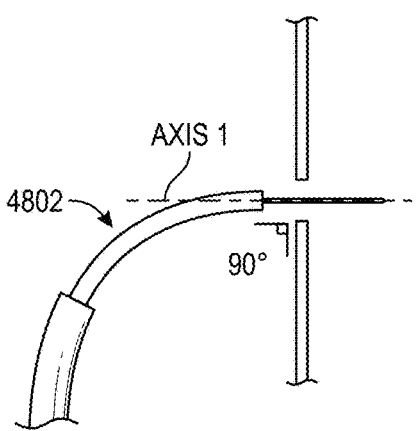          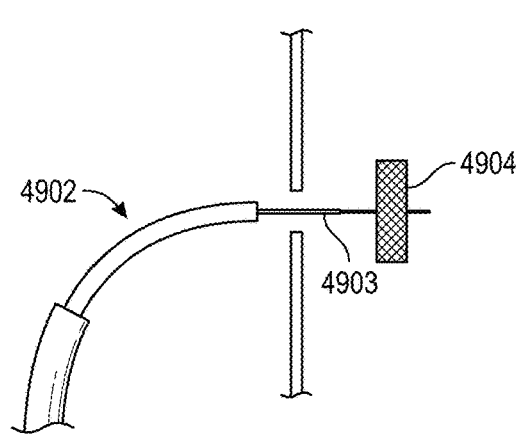
FIG. 48          FIG. 49

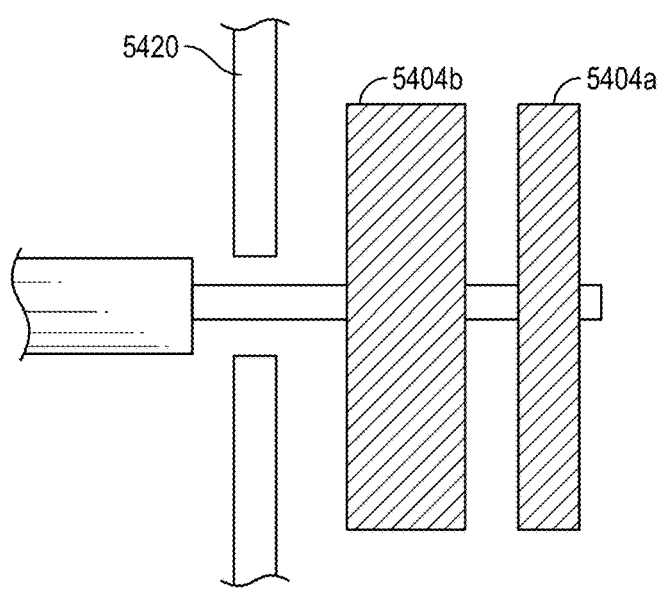
FIG. 54
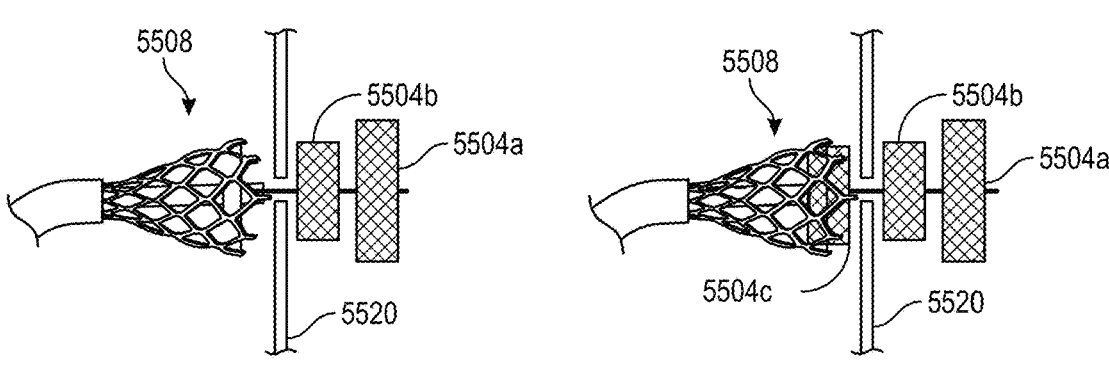
FIG. 55A                        FIG. 55B
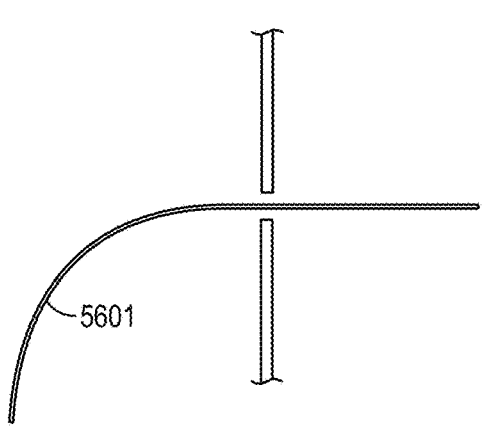 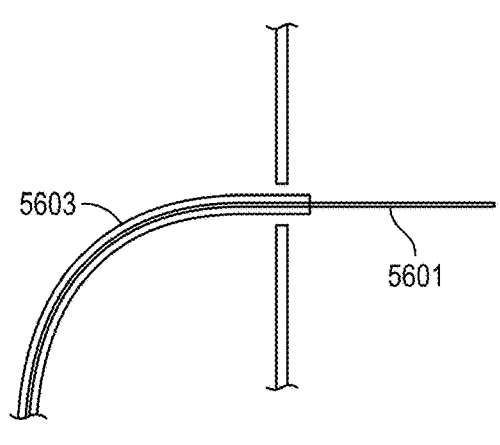
FIG. 56A                        FIG. 56B

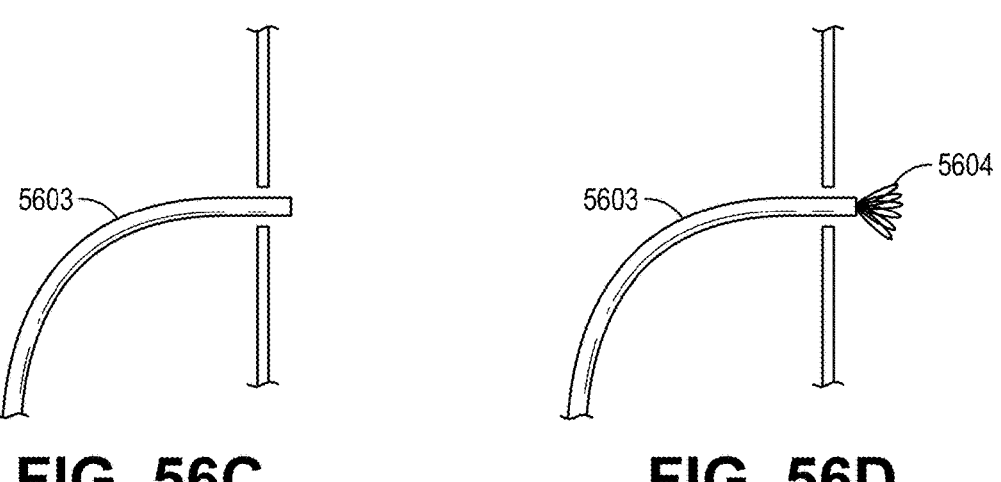
FIG. 56C          FIG. 56D
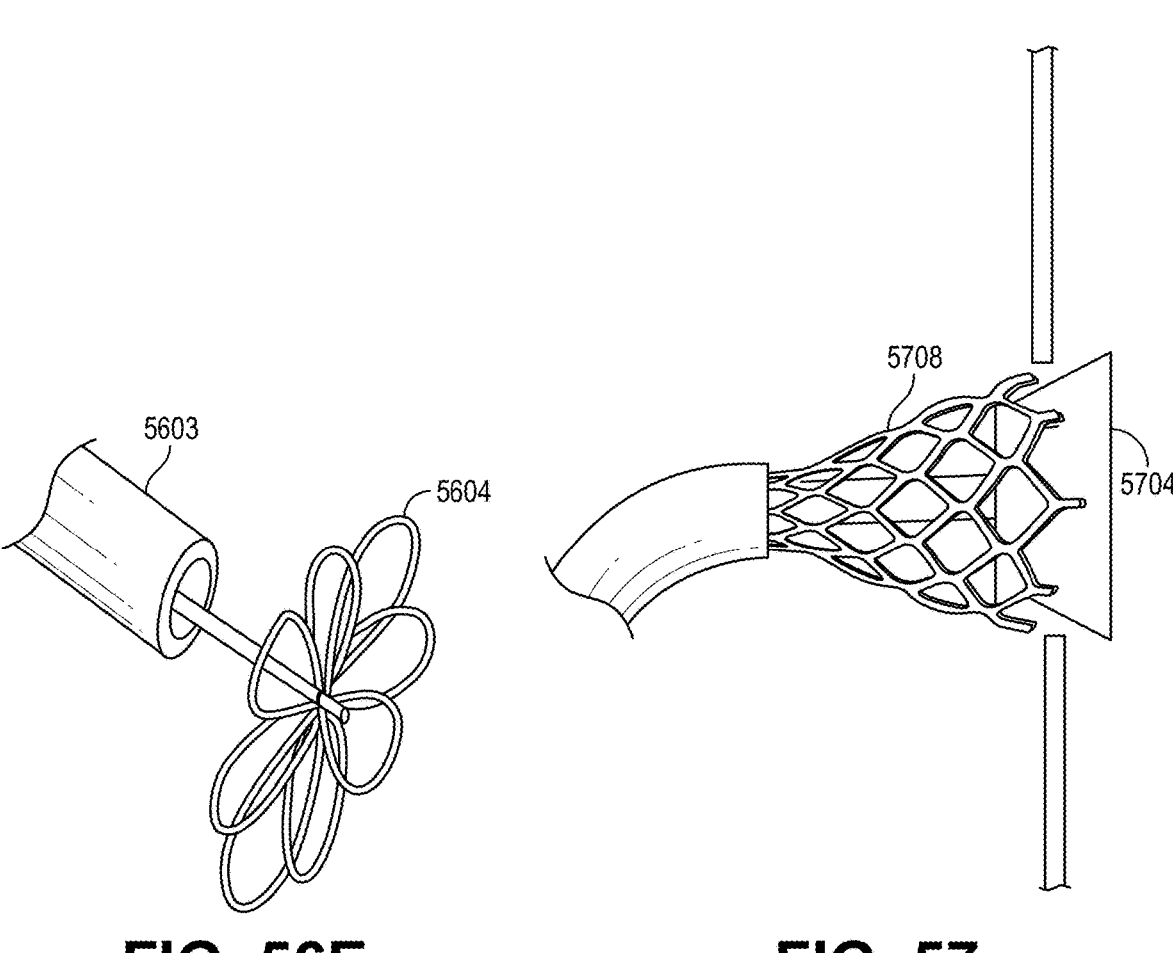
FIG. 56E          FIG. 57

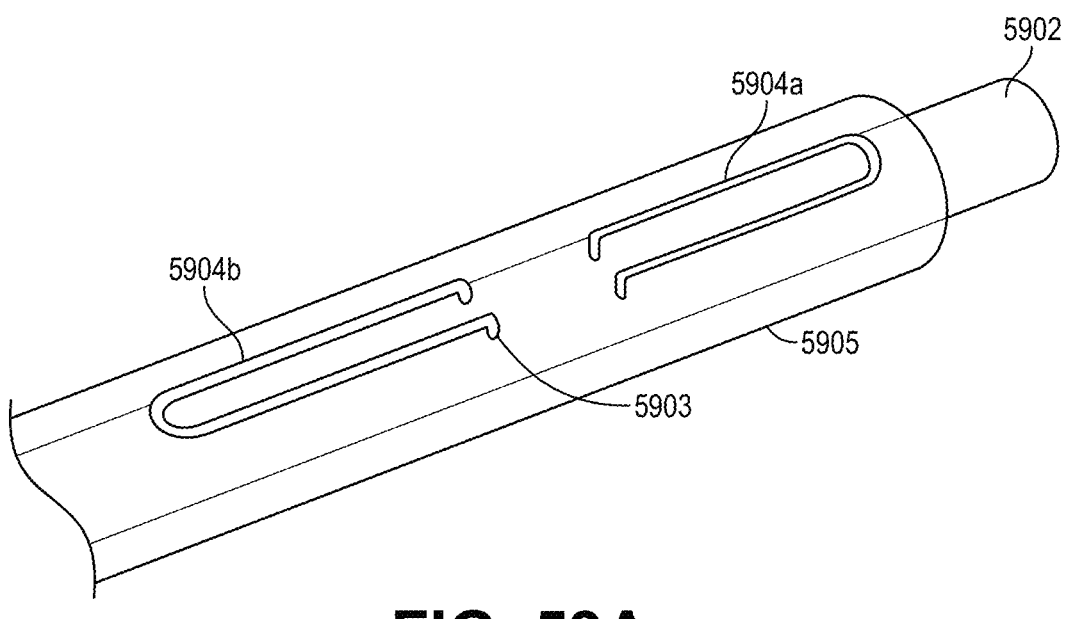
FIG. 59A
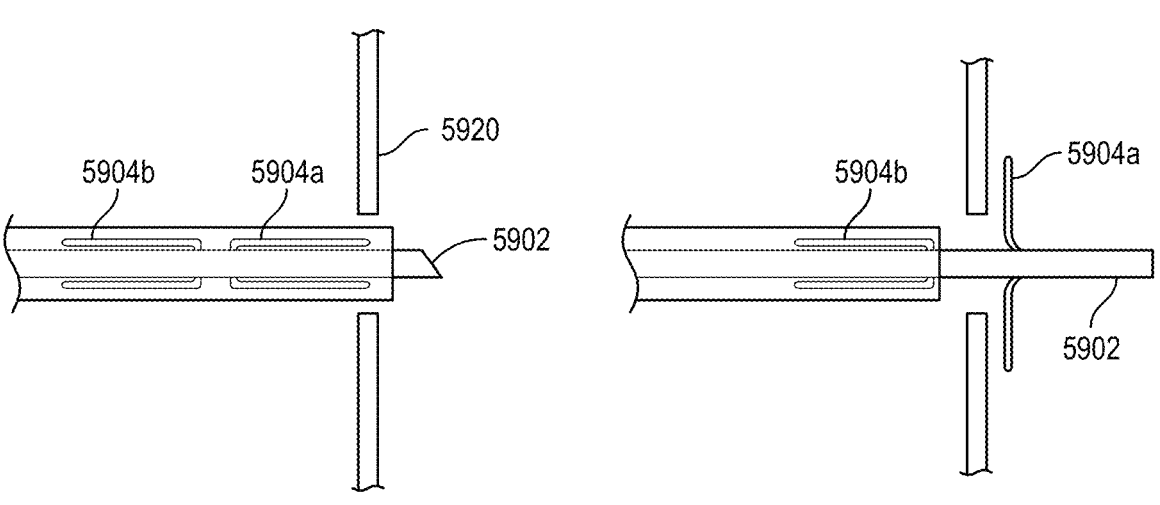
FIG. 59B          FIG. 59C

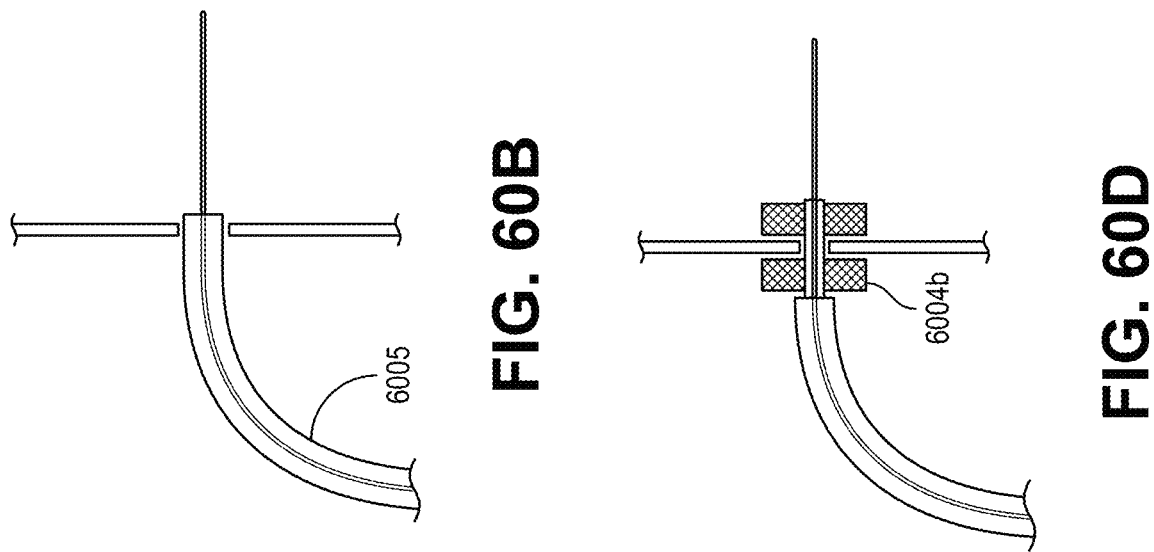
FIG. 60A
FIG. 60B
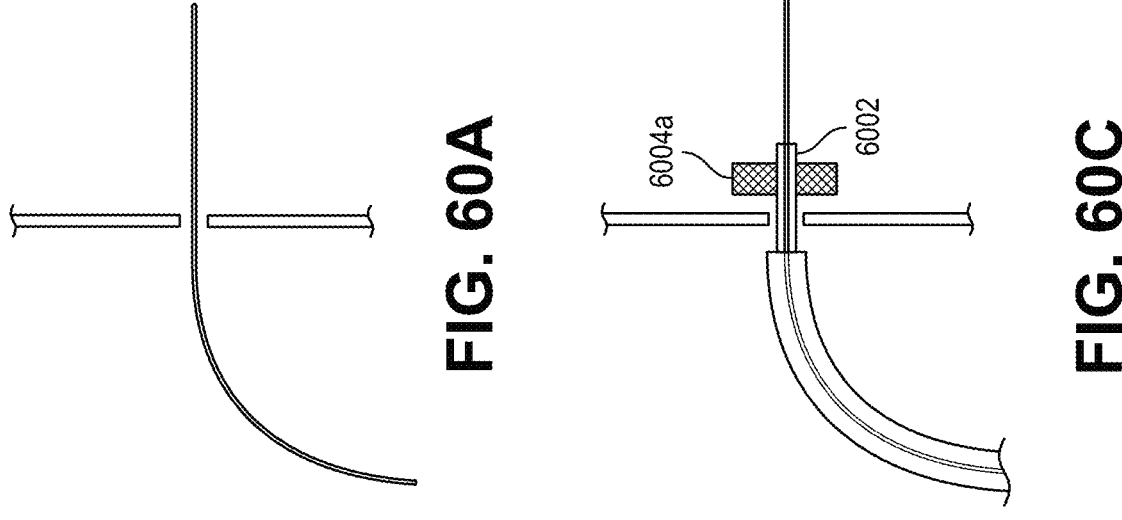
FIG. 60C
FIG. 60D

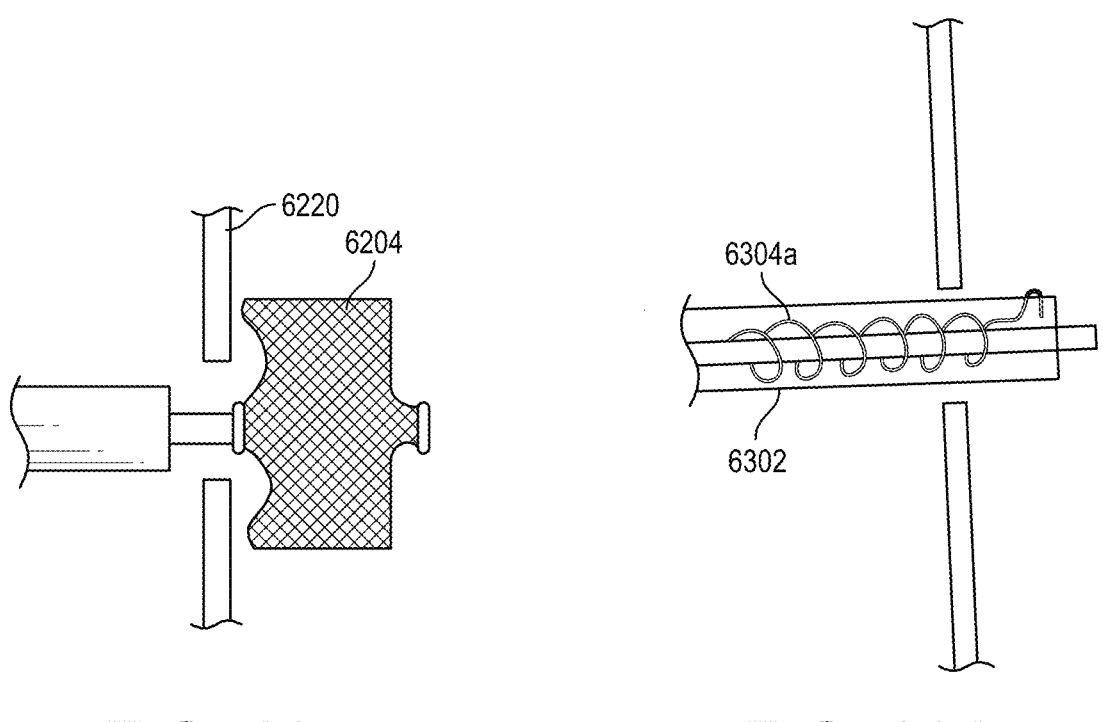
FIG. 62
FIG. 63A
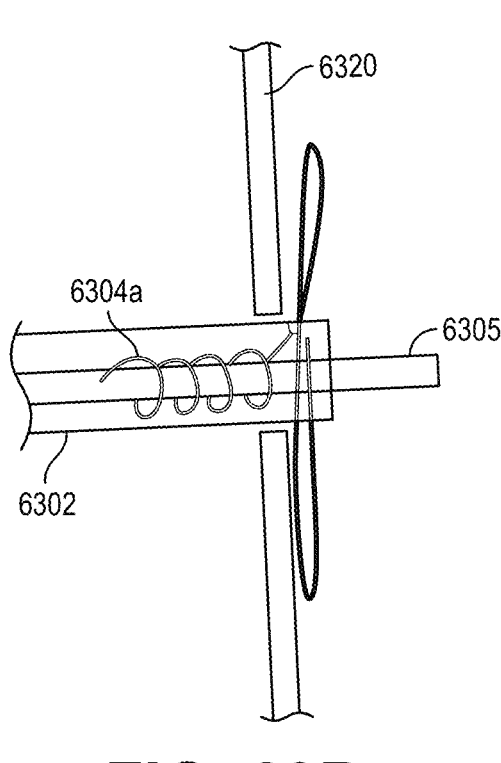
FIG. 63B

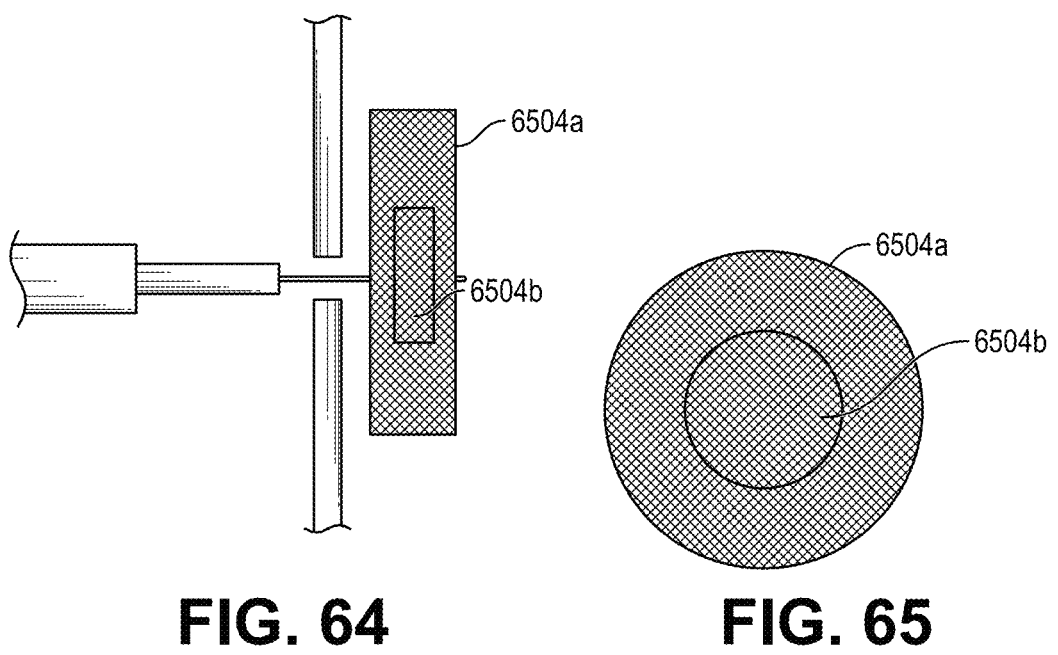
FIG. 64                    FIG. 65
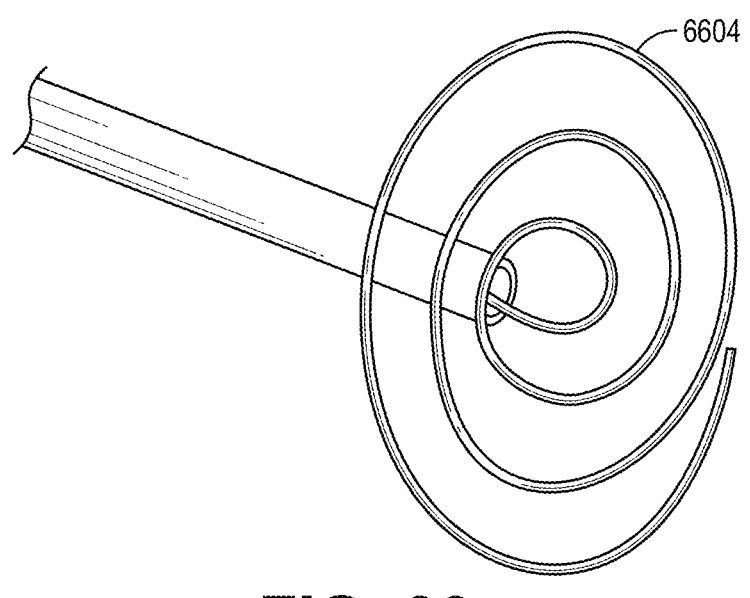
FIG. 66

7101

7220

7202

7201

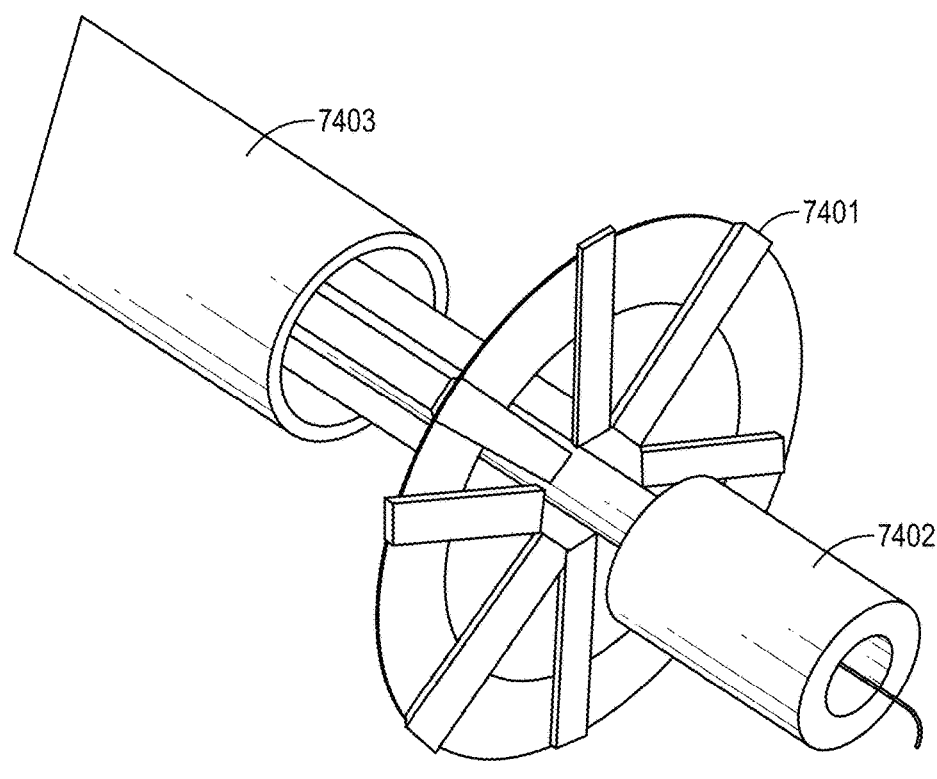
FIG. 74A
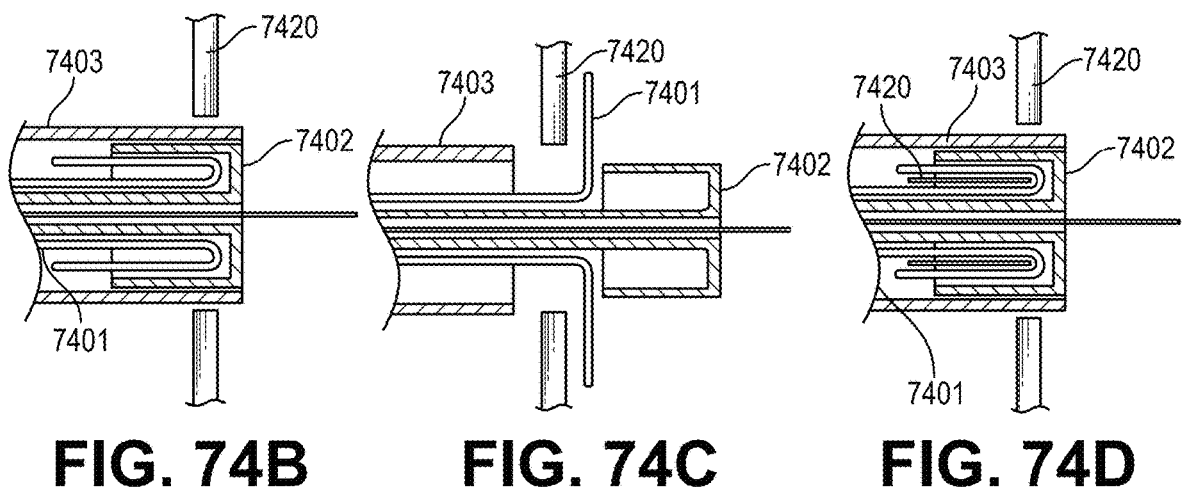
FIG. 74B  FIG. 74C  FIG. 74D

TRANSCATHETER DEVICE FOR INTERATRIAL ANASTOMOSIS

CROSS-REFERENCE

This application is a continuation of U.S. application Ser. No. 16/533,655, filed on Aug. 6, 2019, which is a continuation of International Application No. PCT/US2018/017487, filed Feb. 8, 2018, which claims the benefit of U.S. Provisional Application No. 62/457,605, filed Feb. 10, 2017, U.S. Provisional Application No. 62/473,027, filed Mar. 17, 2017, U.S. Provisional Application No. 62/532,223, filed Jul. 13, 2017, and U.S. Provisional Application No. 62/558, 178, filed Sep. 13, 2017, which applications are incorporated herein in their entirety by reference.

BACKGROUND OF THE INVENTION

Congestive heart failure (CHF) is a chronic condition affecting 6 million people in the US and 23 million people worldwide. Incidence is expected to rise in the next 10 years with 650,000 new cases diagnosed annually in the US. Once a patient is diagnosed with CHF, 5 and 10-year survival rates are estimated at 50% and 10% respectively. Heart failure is the most common cause of U.S. hospital admission in patients over 65 and accounts for almost 1 million hospitalizations annually with this number set to rise substantially. Thus, heart failure remains a major epidemic with significant associated healthcare costs.

SUMMARY OF THE INVENTION

Provided herein are device assemblies (alternatively referred to as transcatheter device for interatrial anastomosis assemblies) configured to create a defined aperture between the right and left atria of the heart of a mammal for the relief of elevated left atrial pressure. In some embodiment, the aperture is sized to prevent closure such that the aperture becomes a permanent aperture without need for a mechanical prop, such as a stent to keep the aperture open after the aperture creation procedure. In some embodiment, the aperture is sized to prevent closure such that the aperture becomes a permanent aperture without need for a medicament to prevent closure of the aperture during the healing process. Disclosed herein are transcatheter interatrial septum excision device assemblies (alternatively called device assemblies, or excision device assemblies herein) configured to create a sized interatrial aperture between the right and left atria of a heart for the relief of elevated left atrial pressure. The excision device assemblies comprise a delivery catheter, a tissue stabilizer attached to a first catheter having a central lumen and a penetrating tip that permits passage of a guidewire, and an expandable cutter attached to a second catheter having a central lumen that permits passage of the first catheter. In some embodiments, configurations comprise a third catheter having a central lumen that permits passage of the aforementioned components to and from the right atrium, a tissue retention mechanism, and an optional coaxial alignment mechanism.

Disclosed herein, are device assemblies for treating heart failure, the device assemblies comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; and an expandable cutter attached to and positioned along the outer length of second internal coaxial catheter and configured to slidably traverse or engage within the central delivery lumen of the delivery catheter. In some embodiments, the first internal coaxial catheter having a first lumen further comprises a needle-like puncture tip configured to penetrate the interatrial septum. In some embodiments, the device assemblies further comprise a coaxial guidewire slidably engageable within the first lumen of the first internal coaxial catheter. In some embodiments, a cutting dimension of the expandable cutter is adjustable in situ. In some embodiments, a dimension of the expandable tissue stabilizer is adjustable in situ. In some embodiments, a coaxial guidewire is configured to extend from a distal end of the first lumen of the first internal coaxial catheter and pass through an initial puncture site in an interatrial septum between a right atrium and a left atrium of a heart of a mammal at approximately a fossa ovalis to provide a working track for the device assemblies into the left atrium. In some embodiments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the dimension thereof is sufficiently large enough to prevent the tissue stabilizer from being pulled back through the initial puncture site and such that the tissue stabilizer provides a supporting, tensioning effect on the wall of the atrial septum surrounding the initial puncture site. In some embodiments, the second internal coaxial catheter is extended relative to the delivery catheter such that the expandable cutter is slidably advanced and coaxially expanded to a cutting dimension greater than the expanded dimension of the tissue stabilizer. In some embodiments, the second internal coaxial catheter is further extended until the fully expanded cutter engages or traverses the right atrial side of the interatrial septum at or about the fossa ovalis, such that the cutter pierces and cuts completely through the septum, thereby creating an interatrial pressure relief opening in the interatrial septum, wherein the interatrial pressure relief opening is sufficiently sized to allow blood flow through the opening from the left atrium to the right atrium such that no more than 50% of left atrial blood is shunted to the right atrium. In some embodiments, the interatrial pressure relief opening includes a diameter of about 8 mms, in the range of about 3 mms to about 14 mms, in the range of about 5 mm to about 12 mms, in the range of about 6 mms to about 10 mms, or in the range of about 7 mms to about 9 mms. In some embodiments, the interatrial pressure relief opening includes an area of about 50 $mm^2$. In some embodiments, the interatrial pressure relief opening includes an area of about 30 $mm^2$ to about 70 $mm^2$. In some embodiments, the interatrial pressure relief opening includes an area of up to 200 $mm^2$, up to about 180 $mm^2$, up to about 160 $mm^2$, up to about 140 $mm^2$, up to about 120 $mm^2$, up to about 100 $mm^2$, up to about 80 $mm^2$, up to about 60 $mm^2$, up to about 40 $mm^2$, up to about 20 $mm^2$, up to about 10 $mm^2$, up to about 5 $mm^2$, from about 5 $mm^2$ to about 10 $mm^2$, from about 5 $mm^2$ to about 20 $mm^2$, from about 10 $mm^2$ to about 20 $mm^2$, from about 15 degree angle to about 30 $mm^2$, from about 20 $mm^2$ to about 40 $mm^2$, from about 30 $mm^2$ to about 45 $mm^2$, from about 35 $mm^2$ to about 50 $mm^2$, from about 40 $mm^2$ to about 60 $mm^2$, from about 45 $mm^2$ to about 70 $mm^2$, from about 60 $mm^2$ to about 80 $mm^2$, from about 70 mm$^2$ to about 90 mm$^2$, from about 80 mm$^2$ to about 110 mm$^2$, from about 90 mm$^2$ to about 130 mm$^2$, from about 100 mm$^2$ to about 150 mm$^2$, from 35 mm$^2$ to 65 mm$^2$, from 40 mm$^2$ to 75 mm$^2$, from 45 mm$^2$ to a 80 mm$^2$, from 50 mm$^2$ to 85 mm$^2$, from 20 mm$^2$ to 60 mm$^2$, from 30 mm$^2$ to 80 mm$^2$, or from 35 mm$^2$ to 65 mm$^2$. In some embodiments, the interatrial pressure relief opening is sufficiently large, in order to slow a natural healing process of the tissue to maintain patency of the interatrial pressure relief opening in the interatrial septum without implanting a stent, mechanical implant, or valve therein. In some embodiments, the interatrial pressure relief opening is sufficiently large and of such shape, in order to slow a natural healing process of the tissue to maintain patency of the interatrial pressure relief opening in the interatrial septum without implanting a stent, mechanical implant, or valve therein. In some embodiments, the interatrial pressure relief opening is sufficiently large or of such shape, in order to slow a natural healing process of the tissue to maintain patency of the interatrial pressure relief opening in the interatrial septum without implanting a stent, mechanical implant, or valve therein. In some embodiments, the interatrial pressure relief opening is sufficiently large, and of such shape, in order to slow a natural healing process of the tissue to maintain patency of the interatrial pressure relief opening in the interatrial septum without mechanical support (e.g. stent, shunt, or valve) and without localized delivery of a non-proliferative or anti-inflammatory agent to the tissue surrounding the opening. In some embodiments, the interatrial pressure relief opening is sufficiently large or of such shape, in order to slow a natural healing process of the tissue to maintain patency of the interatrial pressure relief opening in the interatrial septum without mechanical support (e.g. stent, shunt, or valve) and without localized delivery of a non-proliferative or anti-inflammatory agent to the tissue surrounding the opening. In some embodiments, the interatrial pressure relief opening is: circular in shape; oval in shape; triangular in shape; squared shaped; rectangular in shape; diamond in shape; polygon in shape; or of any irregular shape. In some embodiments, the interatrial pressure relief opening is of a three-dimensional irregular shape. In some embodiments, the cross-section of the interatrial pressure relief opening is circular in shape; oval in shape; triangular in shape; squared shaped; rectangular in shape; diamond in shape; polygon in shape; or of any irregular shape. In some embodiments, the device assemblies further comprise a coaxial alignment component. In some embodiments, said coaxial alignment component is configured to provide centralization between the cutter and the tissue stabilizer. In some embodiments, the tissue stabilizer comprises: an inflatable balloon; expanding tines; an expanding mesh; at least one curved wire; an expanding plate; an expanding disc; an expanding fan; a spring coil; at least one strut; at least one hinged arm; an umbrella stretcher; or a combination thereof. In some embodiments, a tissue stabilizer material for anything other than the inflatable balloon comprises a shape memory alloy comprising: nickel-titanium, copper-aluminum-nickel, zinc-gold-copper, or a combination thereof. In some embodiments, a cutter material comprises a shape memory alloy comprising: nickel-titanium; copper-aluminum-nickel; zinc-gold-copper; or a combination thereof. In some embodiments, the cutter comprises: a wire mesh; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, the cutter is configured such that a cutting tooth of the cutter comprises: a pointed single wire; a single-edge blade shape; a two-edged blade shape or a two-edged scissor blade; an inverted "v"-shape; or a "u"-shape (or scalloped shape); wherein a distal end of every tooth is a cutting point and cutting edges of the cutting teeth, when taken in combination, are configured to cut a complete aperture as the cutter fully crosses the interatrial septum. In some embodiments, the cutter is configured to cut an aperture or hole that is: circular in shape; oval in shape; triangular in shape; squared shaped; rectangular in shape; or polygon in shape; or a combination thereof. In some embodiments, the expanded dimension of the tissue stabilizer is less than the expanded dimension of the cutter. In some embodiments, the expanded dimension of the cutter is between about 1% and about 50% larger than the expanded dimension of the tissue stabilizer. In some embodiments, the expanded dimension of the cutter is between about 0.1% and about 10% larger than the expanded dimension of the tissue stabilizer. In some embodiments, the expanded dimension of the cutter is between about 0.1% and about 20% larger than the expanded dimension of the tissue stabilizer. In some embodiments, the expanded dimension of the cutter is between about 0.1% and about 25% larger than the expanded dimension of the tissue stabilizer. In some embodiments, the expanded dimension of the cutter is between about 1% and about 15% larger than the expanded dimension of the tissue stabilizer. In some embodiments, the expanded dimension of the cutter is between about 1% and about 20% larger than the expanded dimension of the tissue stabilizer. In some embodiments, the expanded dimension of the cutter is between about 1% and about 35% larger than the expanded dimension of the tissue stabilizer. In some embodiments, the device assemblies further comprise a hydrophilic coating on the guidewire. In some embodiments, the device assemblies further comprise a hydrophobic coating on the guidewire. In some embodiments, the device assemblies further comprise a force sensor, pressure sensor, or force and pressure sensor incorporated into the distal tip of the guidewire. In some embodiments, the device assemblies further comprise an oxygen saturation sensor incorporated into the guidewire. In some embodiments, the device assemblies further comprise a cutting point or edge incorporated into the distal tip of the guidewire. In some embodiments, the device assemblies further comprise a curved or shaped end incorporated into the distal tip of the guidewire. In some embodiments, the tissue stabilizer comprising the inflatable balloon further comprises a flat face that assumes a flush configuration with respect to the tissue plane when pulled against the septum wall in the left atrium. In some embodiments, the distal end of the balloon tissue stabilizer comprises a shape that is: rounded; squared; rectangular; tapered; oval shaped; triangular shaped; polygonal shaped; parallel to an interatrial septum; or atraumatic on the portion facing the left atrial free wall. In some embodiments, the tissue stabilizer comprising the inflatable balloon is axially configured to assume a "dogbone" or "dumbbell" shape wherein a portion of the inflated balloon resides on each side of the septum, thereby 'sandwiching' the septum. In some embodiments, the axially configured inflatable balloon comprises two balloons which are filled separately and simultaneously. In some embodiments, the axially configured inflatable balloon comprises two balloons which are filled separately or simultaneously. In some embodiments, the axially configured inflatable balloon is one continuous balloon comprising: the same dimension for each portion of the "dogbone" or "dumbbell", differing dimensions for each portion of the "dogbone" or "dumbbell", or individually translatable portions of the "dogbone" or "dumbbell" (with respect to one another). In some embodiments, the more proximal balloon of the "dogbone" or "dumbbell" configured balloon allows for an early warning if the distal and tissue retaining balloon is at risk of being damaged by the cutter. In some embodiments, the expanded dimension of the tissue stabilizer is significantly less than the expanded dimension of the cutter to permit tissue tenting of the interatrial septum such that the cutter creates creation an aperture that is larger than the expanded dimension of the cutter. In some embodiments, the expanded dimension of the tissue stabilizer is: about 5%; about 10%; about 15%; about 20%; about 25%; about 30%; about 35%; about 40%; about 45%; about 50%; or as much as about 75%; less than the expanded dimension of the cutter. In some embodiments, the tissue stabilizer further comprises radiopaque markers or radiopaque bands at strategic locations to: guide or orient positioning of the stabilizers within the body, orient positioning of the tissue stabilizers with respect to other system components, and to permit visualization and confirmation of its deployed state (i.e.: expanded, or equivalently, collapsed). In some embodiments, the tissue stabilizer further provides embolic protection by ensuring that any excised tissue speared by the first catheter is captured and retained within the device assemblies. In some embodiments, the tissue stabilizer comprising the balloon features a protective skirt to protect the proximal edges of the inflated balloon. In some embodiments, the protective skirt comprises: a single tine element; multiple tine elements; an expanding mesh; at least one curved wire; an expanding disc; an expanding fan; a spring coil; or at least one hinged arm. In some embodiments, the protective skirt expands and collapses relative to the state of the balloon. In some embodiments, the tissue stabilizer comprises tines that expand outward after passing through the septum, having an expanded dimension less than the expanded cutter dimension, and configured to be pulled back to engage with the interatrial septum tissue; the tines further comprise barbs to engage and stabilize the septum tissue prior to and following engagement with the cutter; and wherein, following engagement of the cutter, the tines are collapsed in the same direction from which they expanded, capturing the tissue excised from the septum during resheathing, such that the cutter, excised tissue and tines collapse into the delivery catheter. In some embodiments, a tissue stabilizer comprises tines that expand outward after passing through the septum tissue, having an expanded dimension less than the cutter dimension, and are configured to be pulled back to engage with the septum; the tines further comprise barbs to engage and stabilize the septum tissue prior to and following engagement with the cutter; and wherein, following engagement of the cutter, the tines bend backward from the original deployed state, capturing the tissue excised from the septum during resheathing such that cutter, excised tissue, and tines collapse into the delivery catheter. In some embodiments, the tissue stabilizer comprises: an expanding mesh; an expanding plate; an expanding disc; an expanding fan; or an expanding coil; wherein the tissue stabilizer is fabricated from a shape memory alloy that expands outwards to approximately a 90° angle after passing through the septum, having an expanded dimension, less than the expanded cutter dimension, and configured to be pulled back to engage and stabilize the septum, prior to and following engagement with the cutter, and wherein following engagement of the cutter, the tissue stabilizer is collapsed in the same direction from which it expanded, capturing the tissue excised from the septum during resheathing such that the cutter, excised tissue, and tissue stabilizer collapse into the delivery catheter. In some embodiments, the tissue stabilizer comprising the expanding mesh; or expanding plate; or expanding disc is axially configured to assume a "dogbone" or "dumbbell" shape wherein an element or elements of the expanding structure resides on each side of the septum, thereby 'sandwiching' the septum. In some embodiments with more than one expanding mesh element positioned in a left atrium, the expanded dimension of the tissue stabilizer is: about 5%; about 10%; about 15%; about 20%; about 25%; about 30%; larger than the expanded dimension of the cutter to prevent the cutting teeth from inadvertently damaging structures other than the septum. In some embodiments, the tissue stabilizer comprises: at least one strut; at least one hinged arm; or an umbrella stretcher; wherein the tissue stabilizer expands outward to approximately a 90° angle after passing through the interatrial septum, having an expanded dimension less than the cutter dimension, and is configured to be pulled back to engage and stabilize the septum prior to and following engagement with the cutter; and wherein following engagement of the cutter, the tissue stabilizer is collapsed in the same direction from which it expanded, capturing the tissue excised from the septum during resheathing such that the cutting element, excised tissue, and tissue stabilizer collapse into the delivery catheter. In some embodiments, a tissue stabilizer comprises: at least one curved wire; or a spring coil; wherein the tissue stabilizer is fabricated from a shape memory alloy that is configured to expand after passing through the septum, in an outward direction approximately orthogonal to a longitudinal centerline of the first internal coaxial catheter or the second internal coaxial catheter and having a radial dimension less than a cutter dimension and is configured to be pulled back to engage and stabilize the septum, prior to and following engagement with the cutter; and wherein following engagement of the cutter, the tissue stabilizer is collapsed in the same direction from which it expanded, capturing the tissue excised from the septum during resheathing such that the cutter, the excised tissue, and tissue stabilizer fit into the delivery catheter.

Provided herein are device assemblies for treating heart failure, the device assemblies comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter; and a coaxial alignment mechanism having a third lumen slidably engaged with the outside diameter of the first internal coaxial catheter, slidably engaged with the inside diameter of the second internal coaxial catheter and within the central delivery lumen of the delivery catheter. In some embodiments, the first internal coaxial catheter having a first lumen further comprises a needle-like puncture tip configured to penetrate an interatrial septum. In some embodiments, the device assembly further comprising a coaxial guidewire slidably engaged within the first lumen of the first internal coaxial catheter, configured to provide a working track for the device assembly. In some embodiments, a cutting dimension of the expandable cutter is adjustable and a dimension of the expandable tissue stabilizer is adjustable. In some embodiments, the coaxial alignment mechanism is a third internal coaxial catheter positioned along the entire length of the first and second internal catheters. In some embodiments, a distal end of the coaxial alignment mechanism has a larger dimension to aid in tissue stabilization during a cutting process of an interatrial septum.

Provided herein are device assemblies for treating heart failure, the device assemblies comprising: a delivery catheter having a central delivery lumen; a first internal coaxial catheter having a first lumen, slidably engaged within the central delivery lumen of the delivery catheter; an expandable cutter having a proximal end and a distal end, the proximal end attached to the distal end of a first internal coaxial catheter, coaxial to the central delivery lumen of the delivery catheter and configured to collapsibly reside and slidably traverse or engage within the delivery catheter. In some embodiments, the device assembly further comprises a second internal coaxial catheter having a second lumen slidably engaged within the first lumen of the first internal coaxial catheter. In some embodiments, the second internal coaxial catheter further comprises a needle-like puncture tip configured to penetrate an interatrial septum. In some embodiments, the device assembly further comprising a coaxial guidewire slidably engaged within the second lumen of the second internal coaxial catheter, configured to provide a working track for the device assembly. In some embodiments, a cutting dimension of the expandable cutter is adjustable. In some embodiments, a cutter material comprises a shape memory alloy comprising: nickel-titanium; copper-aluminum-nickel; zinc-gold-copper; or a combination thereof. In some embodiments, the cutter comprises: a wire mesh configuration; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, the expandable cutter is configured to have an expanded cross-sectional shape generally comprising: a circle; a square; a rectangle; a triangle; an oval; or a polygon. In some embodiments, the expandable cutter is exposed and expands from a collapsed dimension to an expanded shape coaxial with an adjustable dimension to the first internal coaxial catheter when the distal end of the delivery catheter is pulled back proximally. In some embodiments, the adjustable dimension of the expandable cutter is controllable by the amount of proximal pull-back of the delivery catheter. In some embodiments, the expandable cutter comprises an expandable lattice and wherein the distal end of the expandable cutter lattice comprises a plurality of sharpened ends configured to perform as tissue cutting blades. In some embodiments, the expandable cutter comprises an expandable lattice comprising a shape memory alloy, and wherein the distal end of the expandable cutter lattice comprises a plurality of sharpened ends configured to perform as tissue cutting blades. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises a continuous blade comprising a shape memory alloy, and wherein the distal end of the continuous blade comprises: a single smooth sharpened knife edge; or plurality of sharpened serrations or teeth along the continuous blade; a single bevel knife edge; a double bevel knife edge; or a combination thereof; configured to perform as a fully-circumferential (continuous) tissue cutting blade. In some embodiments, the single smooth sharpened knife edge or the plurality of sharpened serrations along the continuous blade are configured to perform as tissue cutting blades. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof. In some embodiments, the first internal coaxial catheter further comprises an expandable balloon configured to controllably inflate the expandable cutter, wherein the dimension of the cutter is controlled by the inflation of the expandable balloon positioned within a central portion of the cutter. In some embodiments, the first internal coaxial catheter further comprises expandable struts configured to controllably engage the internal dimension of the expandable cutter, wherein the dimension of the cutter is controlled by the expansion of the expandable struts positioned within a central portion of the cutter.

Provided herein are device assemblies for treating heart failure, the device assemblies comprising: a delivery catheter having a central delivery lumen; a first internal coaxial catheter having a first lumen slidably engaged within the central delivery lumen of the delivery catheter; an expandable cutter attached to, and positioned along the outer length of, the first internal coaxial catheter near a distal end thereof; a second internal coaxial catheter having a second lumen slidably engaged over the first internal coaxial catheter and within the central delivery lumen of the delivery catheter; and an expandable tissue stabilizer attached to, and positioned along the outer length of, the second internal coaxial catheter and over the cutter on the first internal coaxial catheter and configured to slidably traverse or engage within the central delivery lumen of the delivery catheter. In some embodiments, the first internal coaxial catheter having the first lumen further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter is configured to provide a working track for the device assembly. In some embodiments, a coaxial guidewire is configured to extend from a distal end of the first lumen of the first internal coaxial catheter and pass through an initial puncture site in an interatrial septum between a right atrium and a left atrium of a heart of a mammal at approximately a fossa ovalis to provide a working track for the device assembly into the left atrium. In some embodiments, the delivery catheter is extended distally such that the distal end of the first internal coaxial catheter and the distal end of the second coaxial catheter are configured to traverse along the track of the guidewire and pass through the initial puncture site in an atrial septum such that the cutter also extends past the interatrial septum into the left atrium. In some embodiments, the delivery device is configured such that when the delivery catheter is retracted proximally with the distal end of the second coaxial catheter back into the right atrium, bringing with it, the tissue stabilizer, the cutter is configured to coaxially expand radially within the left atrium to an intended dimension, wherein the distal end of the delivery catheter is further retracted back inside the right atrium to allow the tissue stabilizer to expand radially to a sufficiently large dimension, wherein the external expanded dimension of the cutter is less than the internal dimension of the expanded tissue stabilizer, and the radially expanded dimension of the tissue stabilizer provides a supporting, tensioning effect on the right atrial side of the interatrial septum around the initial puncture site. In some embodiments, the internal dimension of the tissue stabilizer is larger than the external dimension of the cutter. In some embodiments, the first internal coaxial catheter is then retracted distally such that the expandable cutter is slidably retracted back to the left atrial side of the interatrial septum and coaxially to the tissue stabilizer. In some embodiments, the first internal coaxial catheter is further retracted until the fully expanded cutter engages or traverses the left atrial side of the interatrial septum such that the cutter pierces and cuts completely through the septum, thereby creating an interatrial pressure relief opening in the interatrial septum. In some embodiments, the interatrial pressure relief opening is sufficiently sized to allow blood flow through the relief opening from the left atrium to the right atrium such that no more than 50% of left atrial blood is shunted to the right atrium. In some embodiments, the interatrial pressure relief opening is sufficiently large and of such shape in order to slow a natural healing process of the tissue to maintain patency of the interatrial pressure relief opening in the interatrial septum without implanting a stent or valve therein. In some embodiments, the interatrial pressure relief opening is sufficiently large or of such shape in order to slow a natural healing process of the tissue to maintain patency of the interatrial pressure relief opening in the interatrial septum without implanting a stent or valve therein. In some embodiments, an excised tissue cut from the interatrial septum is captured and maintained between the cutter and the tissue stabilizer. In some embodiments, the stabilizing element is partially collapsed over the cutter by partially retracting said stabilizing element into the delivery catheter and approximately at the same time, the first internal coaxial catheter is retracted and the cutter is pulled into an opening of the partially collapsed tissue stabilizer positioned on the second internal coaxial catheter, wherein the cutter with the captured tissue stabilizer is collapsed and retracted into the delivery catheter with the captured excised tissue. In some embodiments, the device assembly further comprises a coaxial alignment component. In some embodiments, said coaxial alignment component is configured to provide centralization between the cutter and the tissue stabilizer. In some embodiments, the tissue stabilizer comprises: expanding tines; an expanding mesh; at least one curved wire; an expanding cup; an expanding cone; an expanding cylinder; a spring coil; at least two or more struts; at least two or more hinged arms; or a combination thereof. In some embodiments, a tissue stabilizer material comprises a shape memory alloy comprising: nickel-titanium; copper-aluminum-nickel; zinc-gold-copper; or a combination thereof. In some embodiments, a cutter material comprises a shape memory alloy comprising: nickel-titanium; copper-aluminum-nickel; zinc-gold-copper; or a combination thereof. In some embodiments, the cutter shape comprises: a collapsible hole saw configuration; a collapsible, open-end cylinder-shape configuration; a collapsible, open-end barrel-shape configuration; a collapsible, open-end box-shape configuration; a collapsible, open-end cone-shaped configuration; or a combination thereof. In some embodiments, the tissue stabilizer shape comprises: a collapsible hole saw configuration; a collapsible, open-end cylinder-shape configuration; a collapsible, open-end barrel-shape configuration; a collapsible, open-end box-shape configuration; a collapsible, open-end cone-shaped configuration; or a combination thereof. In some embodiments, the expandable cutter is configured to have an expanded cross-sectional shape generally comprising: a circle; a square; a rectangle; a triangle; an oval; or a polygon. In some embodiments, the expandable cutter comprises an expandable lattice comprising a shape memory alloy, and wherein the distal end of the expandable cutter lattice comprises a plurality of sharpened ends configured to perform as tissue cutting blades. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises a continuous blade comprising a shape memory alloy, and wherein the distal end of the continuous blade comprises: a single smooth sharpened knife edge; or a plurality of sharpened serrations along the continuous blade; configured to perform as a continuous tissue cutting blade. In some embodiments, the single smooth sharpened knife edge or the plurality of sharpened serrations along the continuous blade are configured to perform as fully-circumferential (continuous) tissue cutting blades. In some embodiments, the expandable cutter is configured to penetrate and cut through an interatrial septum. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Provided herein are device assemblies for treating heart failure, the device assembly comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or about the distal end; a third internal coaxial catheter having a third lumen slidably engaged over the outside diameter of the first internal coaxial catheter; a slider element, slidably engaged along the outside diameter of the third catheter and further comprising two or more struts; a second internal coaxial catheter having a second lumen slidably engaged over the third internal coaxial catheter and within the central delivery lumen of the delivery catheter; and an expandable cutter attached to and at a distal end of the second internal coaxial catheter and configured to slidably traverse or engage within the central delivery lumen of the delivery catheter, over the third coaxial catheter, the umbrella sliding element and the two or more struts. In some embodiments, the first internal coaxial catheter having a first lumen further comprises a penetrating tip configured to penetrate the interatrial septum. In some embodiments, the device assembly further comprises a coaxial guidewire slidably engaged within the first lumen of the first internal coaxial catheter. In some embodiments, a cutting dimension of the expandable cutter is adjustable and wherein a dimension of the expandable tissue stabilizer is adjustable. In some embodiments, the coaxial guidewire is configured to provide a working track for the device assembly. In some embodiments, an extended portion of the guidewire is pushed through an initial puncture site in an atrial septum into a left atrium, followed by the penetrating tip of the first internal coaxial catheter into the left atrium of a heart of a mammal at approximately the fossa ovalis. In some embodiments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the expanded size thereof is sufficiently large enough to prevent the tissue stabilizer from inadvertently pulling back through the initial puncture site and such that the tissue stabilizer provides a supporting, tensioning effect on interatrial septum around the initial puncture site. In some embodiments, the delivery catheter is at least partially retracted distally to expose the cutter such that it is expanded, and wherein the third catheter is translated distally such that the slider element is slidably engaged within the cutter causing the two or more struts to engage and radially increase the size of the cutter such that it is greater than the size of the stabilizing element. In some embodiments, the coaxially expandable tissue stabilizer is configured to have an expanded cross-sectional shape generally comprising: a circle; a square; a rectangle; a triangle; an oval; or a polygon. In some embodiments, the expandable cutter comprises an expandable lattice and wherein the distal end of the expandable cutter lattice comprises a plurality of sharpened ends configured to perform as tissue cutting blades. In some embodiments, the expandable cutter comprises a shape memory alloy. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises a continuous blade, and wherein the distal end of the continuous blade comprises: a single smooth sharpened knife edge; or a plurality of sharpened serrations along the continuous blade; configured to perform as a fully-circumferential (continuous) tissue cutting blade. In some embodiments, the expandable cutter comprises a shape memory alloy. In some embodiments, the single smooth sharpened knife edge or the plurality of sharpened serrations along the continuous blade are configured to perform as tissue cutting blades. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Provided herein are device assemblies for treating heart failure, the device assemblies comprising: a delivery catheter having a central delivery lumen; a first internal coaxial catheter having a first lumen slidably engaged within the central delivery lumen of the delivery catheter; an expandable tissue stabilizer attached to, and positioned along the outer length of, the first internal coaxial catheter, at or about the distal end; a second internal coaxial catheter having a second lumen slidably engaged over the outside diameter of the first internal coaxial catheter comprising a compression element for engaging and supporting the septum opposite the tissue stabilizer; a coaxial, spring loaded plunger element, slidably engaged along the outside diameter of the second catheter; a second internal coaxial catheter within the central delivery lumen of the delivery catheter; and an expandable cutter attached to and at a distal end of the second internal coaxial catheter and configured to slidably traverse or engage within the central delivery lumen of the delivery catheter over the first coaxial catheter while compressing the spring loaded plunger. In some embodiments, the first internal coaxial catheter having a first lumen further comprises a penetrating tip configured to penetrate the interatrial septum. In some embodiments, the device assembly further comprises a coaxial guidewire slidably engaged within the first lumen of the first internal coaxial catheter. In some embodiments, a cutting dimension of the expandable cutter is adjustable and wherein a dimension of the expandable tissue stabilizer is adjustable. In some embodiments, the coaxial guidewire is configured to provide a working track for the device assembly. In some embodiments, an extended portion of the guidewire is pushed through an initial puncture site into the left atrium, followed by the penetrating tip of the first internal coaxial catheter to penetrate an interatrial septum from a right atrium into the left atrium of a heart of a mammal at approximately the fossa ovalis. In some embodiments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the expanded size thereof is sufficiently large enough to prevent the tissue stabilizer from inadvertently pulling back through the initial puncture site and such that the tissue stabilizer provides a supporting, tensioning effect on the wall of the atrial septum surrounding the initial puncture site. In some embodiments, the device assembly further comprises a third internal coaxial catheter having a third lumen slidably engaged with the outside diameter of the second internal coaxial catheter, slidably engaged within the central delivery lumen of the delivery catheter; in some embodiments the device assembly further comprises the third internal coaxial catheter having a third lumen slidably engaged with the outside diameter of the first internal coaxial catheter, slidably engaged within the central lumen of the second internal coaxial catheter. In some embodiments, the delivery catheter is at least partially retracted distally to expose the cutter such that it is expanded, and wherein the third catheter is translated distally such that the slider element is slidably engaged within the cutter causing the two or more struts to engage and radially increase the dimension of the cutter such that it is greater than the dimension of the stabilizing element. In some embodiments, the expandable tissue stabilizer is configured to have an expanded cross-sectional shape generally comprising: a circle; a square; a rectangle; a triangle; an oval; or a polygon. In some embodiments, the expandable cutter comprises an expandable lattice and wherein the distal end of the expandable cutter lattice comprises a plurality of sharpened ends configured to perform as tissue cutting blades. In some embodiments, the expandable cutter comprises a shape memory alloy. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof, and wherein the roots of the teeth are either pointed or rounded, or a combination thereof. In some embodiments, the expandable cutter comprises an expandable continuous blade comprising a shape memory alloy, and wherein the distal end of the continuous blade comprises: a single smooth sharpened knife edge; or a plurality of sharpened serrations along the continuous blade; configured to perform as a continuous tissue cutting blade. In some embodiments, the single smooth sharpened knife edge or the plurality of sharpened serrations along the continuous blade are configured to perform as tissue cutting blades. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Provided herein are device assemblies for treating heart failure, the device assemblies comprising: a delivery catheter for vascular access of a mammal having a central delivery lumen; a first internal coaxial catheter having a first lumen, slidably engaged within the central delivery lumen of the delivery catheter; a tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter. In some embodiments, the first internal coaxial catheter having the first lumen further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter, is configured to provide a working track for the device assembly. In some embodiments, the second internal coaxial catheter comprises a predetermined bend, such that upon exiting the central delivery lumen of the delivery catheter, aims the catheters and components therein in a direction orthogonal to an interatrial septum between a right atrium and a left atrium of a heart of a mammal. In some embodiments, the delivery catheter comprises a material sufficiently rigid enough to straighten the shaft of the second catheter while it is within the delivery catheter and wherein other catheters are freely translatable therein.

Provided herein device assemblies for treating heart failure, the device assemblies comprising: a delivery catheter having a delivery lumen that houses all internal components; a first internal coaxial catheter having a first lumen, slidably engaged within the central delivery lumen of the delivery catheter; a tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter. In some embodiments, the device assembly further comprises a third internal coaxial catheter having a third lumen slidably engaged with the outside diameter of the second internal coaxial catheter, slidably engaged within the central delivery lumen of the delivery catheter; in some embodiments the device assembly further comprises the third internal coaxial catheter having a third lumen slidably engaged with the outside diameter of the first internal coaxial catheter, slidably engaged within the central lumen of the second internal coaxial catheter. In some embodiments, the first internal coaxial catheter having the first lumen further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter is configured to provide a working track for the device assembly. In some embodiments, the delivery catheter, or the first or the second or the third internal coaxial catheter comprises a predetermined bend, such that upon exiting the central delivery lumen of the delivery catheter, aims the catheters and components therein in a direction orthogonal to an interatrial septum between a right atrium and a left atrium of a heart of a mammal. In some embodiments, the delivery catheter is substantially rigid so that it straightens out the third catheter while it is inside of the delivery catheter and wherein the other catheters are still freely translatable therein. In some embodiments, the cutter further comprises: an electrocautery element; a cryoablation element; an RF (radio-frequency) element; a thermal ablation element; or a chemical or pharmacologic delivery element; configured to retard tissue regrowth. In some embodiments, the electrocautery element comprises: a monopolar element; or a bipolar element. In some embodiments, the device assembly further comprises radiopaque markers on the delivery catheter to aid in orientation and positioning within the right atrium and to permit visualization in relationship to other assembly components. In some embodiments, the device assembly further comprises a mechanism at or about the proximal end of the device assembly configured to provide a user with alternative actuation and movement of the cutter comprising: a handle; a knob; a hydraulic connection; a pneumatic connection; an electrical motor connection; or a sonic or vibratory connection, wherein the alternative actuation and movement includes rotary and reciprocating movement. In some embodiments, the device assembly further comprises an automated auscultation device for long term non-invasive monitoring of the flow or pressures through or across the created shunt. In some embodiments, the first internal coaxial catheter is a balloon catheter, a shape memory alloy mesh housing catheter, a shape memory alloy mesh catheter, or a guide catheter. In some embodiments, the second internal coaxial catheter is a blade catheter. In some embodiments, the tissue stabilizer is armed or protected against the expandable cutter in its compressed or expanded state. In some embodiments, the cutter comprises one or more collapsible wave forms. In some embodiments, the cutter comprises one or more collapsible sinusoidal wave forms. In some embodiments, the tissue stabilizer comprises more than one expandable mesh discs. In some embodiments, the tissue stabilizer comprises more than one expandable mesh disc, at least one of the more than one expandable mesh discs expands when distal to interatrial septum and in the left atrium. In some embodiments, the tissue stabilizer comprises more than one expandable mesh discs, at least two of the more than one expandable mesh discs are of different thickness. In some embodiments, the guide catheter is configured to be inserted to a right atrium over a coaxial guide wire there within, the coaxial guide wire being previously inserted into the right atrium. In some embodiments, the shape memory alloy mesh housing catheter is configured to be advanced across an interatrial septum to a left atrium. In some embodiments, the coaxial guide wire is configured to be removed after insertion of the shape memory alloy mesh housing catheter to the left atrium. In some embodiments, a shape memory alloy mesh catheter is configured to be inserted through the shape memory alloy housing catheter to the left atrium. In some embodiments, the shape memory alloy mesh housing catheter is configured to enclose a shape memory alloy mesh catheter there within. In some embodiments, the shape memory alloy mesh catheter comprises one or more expandable shape memory alloy meshes configured to be expanded when outside of the shape memory alloy mesh housing catheter. In some embodiments, the one or more expandable shape memory alloy meshes includes at least two expandable shape memory alloy meshes that expands with an interatrial septum therebetween. In some embodiments, the expandable tissue stabilizer is self-expandable when unsheathed. In some embodiments, the expandable cutter is self-expandable when unsheathed. In some embodiments, the delivery catheter is wire-reinforced or braided. In some embodiments, the delivery catheter comprises a reinforced distal tip. In some embodiments, the delivery catheter includes a bend radius of about 0.5 inch to about 4 inches. In some embodiments, the guide catheter is configured to bend in a predetermined manner towards interatrial septum. In some embodiments, the expandable cutter, after expansion, is configured to create a plurality of perforations at an interatrial septum. In some embodiments, the expandable cutter is configured to translate through the interatrial septum thereby creating a complete cut at the interatrial septum after expansion. In some embodiments, the cutter comprises a proximal edge and a distal edge. In some embodiments, the proximal edge does not expand when the cutter is expanded. In some embodiments, the tissue stabilizer comprises more than one expandable mesh discs, at least one of the more than one expandable mesh discs expands when proximal to the interatrial septum and in the right atrium. In some embodiments, two of the more than one expandable mesh discs sandwich the interatrial septum in between when expanded. In some embodiments, two of the more than one expandable mesh discs contacts and sandwich the interatrial septum in between when expanded. In some embodiments, the tissue stabilizer comprises more than one expandable mesh discs, one of the more than one expandable mesh discs is configured to plug a distal opening of the cutter or a distal opening of the delivery catheter when the tissue stabilizer is resheathed. In some embodiments, the shape memory alloy comprises nitinol.

Provided herein are methods for transcatheter interatrial septum excision of a subject using a device assembly, the method comprising: allowing vascular access of the device assembly, the device assembly in a sheathed state; puncturing through a fossa ovalis of an interatrial septum of the subject and advancing a guidewire therethrough to a left atrium; advancing the device assembly over the guidewire into a right atrium in the sheathed state; advancing a guide catheter over the guidewire to be in contact with the interatrial septum; advancing a housing catheter over the guidewire into the left atrium; removing the guidewire from the subject; introducing the tissue stabilizer in a compressed state in a proximal edge of the housing catheter and advancing it towards a distal edge of the housing catheter; expanding the tissue stabilizer in the left atrium; delivering a cutter to the right atrium, wherein the cutter is enclosed in a delivery catheter in a second compressed state; expanding the cutter in the right atrium; translating the cutter forward to cut the interatrial septum while the tissue stabilizer applies counter tension; and resheathing the cutter into the delivery catheter with the cut interatrial septum. In some embodiments, the cut interatrial septum comprises at least a portion of the interatrial septum. In some embodiments, the device assembly comprises a delivery catheter, a guide catheter, a guidewire, a housing catheter of a tissue stabilizer, the tissue stabilizer, and a cutter. In some embodiments, the tissue stabilizer or the cutter is self-expandable. In some embodiments, expanding the tissue stabilizer is via self-expansion. In some embodiments, expanding the tissue stabilizer includes unsheathing one or more discs in the left atrium. In some embodiments, expanding the cutter in the right atrium is via movement of the delivery catheter relative to cutter. In some embodiments, the methods disclosed herein comprise resheathing the cutter, the guiding catheter, the housing catheter, and the tissue stabilizer into the delivery catheter. In some embodiments, the methods disclosed herein comprise removing the resheathed device assembly from the subject. In some embodiments, advancing the guide catheter over the guidewire to the interatrial septum comprises advancing the guide catheter out of the delivery catheter. In some embodiments, the methods disclosed herein comprise puncturing through a fossa ovalis of an interatrial septum of the subject using an off the shelf transseptal puncture kit in order to be able to leave a guidewire behind.

Provided herein are methods for transcatheter interatrial septum excision of a subject using a device assembly, the method comprising: advancing a guide catheter out of a delivery catheter to a right atrium over a guidewire; advancing a housing catheter of a tissue stabilizer out of the guide catheter across an interatrial septum into a left atrium over the guidewire, the tissue stabilizer enclosed in the housing catheter in a compressed state; expanding the tissue stabilizer in the left atrium by moving the tissue stabilizer out of the housing catheter over the guidewire and allowing the tissue-stabilizer to self-expand; expanding the cutter in the right atrium; translating the cutter forward to cut the interatrial septum while the tissue stabilizer applies counter tension to the interatrial septum; and resheathing the tissue stabilizer with the cut interatrial septum into the cutter. In some embodiments, the cut interatrial septum is at least a portion of the interatrial septum. In some embodiments, the methods disclosed herein comprise puncturing through a fossa ovalis of an interatrial septum of the subject and advancing a guidewire therethrough to a left atrium. In some embodiments, the methods disclosed herein comprise advancing the device assembly over a guidewire to a right atrium, the device assembly being sheathed. In some embodiments, the methods disclosed herein comprise moving the tissue stabilizer to be in contact with the interatrial septum at a proximal edge of the tissue stabilizer thereby sandwiching the interatrial septum between a distal edge of the guide catheter and the proximal edge of the tissue stabilizer. In some embodiments, expanding the cutter is via advancing the cutter relative to the right atrium or via pulling back of a delivery catheter relative to the right atrium behind a self-expanding portion of the cutter. In some embodiments, the tissue stabilizer plugs a distal opening of the delivery catheter during resheathing of the cutter and the tissue stabilizer. In some embodiments, the methods herein comprise resheathing the cutter into the delivery catheter, the cutter enclosing the tissue stabilizer and the cut interatrial septum there within. In some embodiments, the tissue stabilizer plugs a distal opening of the delivery catheter during resheathing. In some embodiments, the tissue stabilizer plugs a distal opening of the cutter during resheathing. In some embodiments, the methods herein comprise removing the resheathed device assembly from the subject. In some embodiments, the tissue stabilizer plugs a distal opening of the delivery catheter during removal of the resheathed device assembly. In some embodiments, the methods herein comprise expanding the tissue stabilizer comprising deploying more than one self-expanding discs simultaneously or at different time points. In some embodiments, one of said discs is deployed in the left atrium. In some embodiments, one of said discs is deployed in the right atrium. In some embodiments, the methods herein comprise expanding the tissue stabilizer in the left atrium by moving the tissue stabilizer out of the housing catheter and allowing the tissue-stabilizer to self-expand includes pushing at least a portion of a self-expanding part of the tissue stabilizer past the housing catheter in the left atrium. In some embodiments, the methods herein comprise removing the guidewire from the subject after advancing a housing catheter of a tissue stabilizer out of the guide catheter across an interatrial septum. In some embodiments, the methods herein comprise removing the guidewire from the subject before unsheathing the tissue stabilizer from the housing catheter and allowing the tissue-stabilizer to self-expand in the left atrium.

Provided herein are methods for transcatheter interatrial septum excision of a subject using a device assembly, the method comprising: advancing a guide catheter out of a delivery catheter to a right atrium over a guidewire; advancing a housing catheter of a tissue stabilizer out of the guide catheter across an interatrial septum to a left atrium over the guidewire, the tissue stabilizer enclosed in the housing catheter in a compressed state; allowing a first self-expanding disc of the tissue stabilizer to expand in the left atrium; allowing a second self-expanding disc to expand in the right atrium thereby sandwiching the interatrial septum between the first and second self-expanding discs; expanding the cutter in the right atrium; translating the cutter forward to cut the interatrial septum while the tissue stabilizer applies counter tension; and resheathing the tissue stabilizer into the cutter with the cut interatrial septum. In some embodiments, the cut interatrial septum comprises at least a portion of the interatrial septum. In some embodiments, the methods herein comprise moving the housing catheter into the right atrium thereby allowing the first self-expanding disc to be in contact with the interatrial septum. In some embodiments, the methods herein comprise allowing the first self-expanding disc of the tissue stabilizer to expand is via movement of a self-expanding proximal edge of the cutter passing a distal edge of the housing catheter. In some embodiments, the methods herein comprise allowing a second self-expanding disc to expand in the right atrium via movement of a distal edge of the housing catheter from the left atrium to the right atrium. In some embodiments, the methods disclosed herein comprise bringing a distal portion of the guide catheter to be in contact with a proximal edge of the second self-expanding disc after moving the housing catheter into the right atrium. In some embodiments, the cut interatrial septum is sandwiched in between the first and second self-expanding discs during resheathing. In some embodiments, the methods herein comprise removing the guidewire from the subject after advancing a housing catheter of a tissue stabilizer out of the guide catheter across an interatrial septum to a left atrium over the guidewire. In some embodiments, the methods herein comprise removing the guidewire from the subject before allowing a first self-expanding disc of the tissue stabilizer to expand in the left atrium. In some embodiments, the methods herein comprise puncturing through a fossa ovalis of an interatrial septum of the subject and advancing a guidewire therethrough to a left atrium. In some embodiments, the methods herein comprise advancing the device assembly over a guidewire to a right atrium, the device assembly being sheathed. In some embodiments, the methods herein comprise expanding the cutter via advancing the cutter relative to the right atrium or via pulling back of a delivery catheter relative to the right atrium behind a self-expanding portion of the cutter. In some embodiments, the methods herein comprise resheathing the cutter into the delivery catheter, the cutter enclosing the tissue stabilizer and the cut interatrial septum therewithin. In some embodiments, the tissue stabilizer plugs a distal opening of the delivery catheter during resheathing. In some embodiments, the tissue stabilizer plugs a distal opening of the cutter during resheathing. In some embodiments, the cut interatrial septum is sandwiched in between the first and second self-expanding discs during resheathing. In some embodiments, the methods disclosed herein comprise removing the resheathed device assembly from the subject. In some embodiments, the cut interatrial septum is sandwiched in between the first and second self-expanding discs during removal of the resheathed device assembly from the subject. In some embodiments, the methods herein comprise deploying the tissue stabilizer comprises deploying more than one self-expanding discs simultaneously or at different time points. In some embodiments, at least one of said discs is deployed in the left atrium. In some embodiments, at least one of said discs is deployed in the right atrium.

Provided herein are methods for treating congestive heart failure of a subject using a device assembly, the method comprising: allowing vascular access of the device assembly, the device assembly in a sheathed state; puncturing through a fossa ovalis of an interatrial septum of the subject and advancing a guidewire therethrough to a left atrium; advancing the device assembly over the guidewire into a right atrium in the sheathed state; advancing a guide catheter over the guidewire to be in contact with the interatrial septum; advancing a housing catheter over the guidewire into the left atrium; removing the guidewire from the subject; introducing the tissue stabilizer in a compressed state in a proximal edge of the housing catheter and advancing it towards a distal edge of the housing catheter; expanding the tissue stabilizer in the left atrium; delivering a cutter to the right atrium, wherein the cutter is enclosed in a delivery catheter in a second compressed state; expanding the cutter in the right atrium; translating the cutter forward to cut the interatrial septum while the tissue stabilizer applies counter tension; and resheathing the cutter into the delivery catheter with the cut interatrial septum. In some embodiments, the cut interatrial septum comprises at least a portion of the interatrial septum. In some embodiments, the device assembly comprises a delivery catheter, a guide catheter, a guidewire, a housing catheter of a tissue stabilizer, the tissue stabilizer, and a cutter. In some embodiments, the tissue stabilizer or the cutter is self-expandable. In some embodiments, expanding the tissue stabilizer is via self-expansion. In some embodiments, expanding the tissue stabilizer includes unsheathing one or more discs in the left atrium. In some embodiments, the methods herein comprise expanding the cutter in the right atrium via movement of the delivery catheter relative to the cutter. In some embodiments, the methods disclosed herein comprise resheathing the cutter, the guiding catheter, the housing catheter, and the tissue stabilizer into the delivery catheter. In some embodiments, the methods disclosed herein comprise removing the resheathed device assembly from the subject. In some embodiments, advancing the guide catheter over the guidewire to the interatrial septum comprises advancing the guide catheter out of the delivery catheter. In some embodiments, the methods disclosed herein comprise puncturing through a fossa ovalis of an interatrial septum of the subject using an off the shelf transseptal puncture kit in order to be able to leave a guidewire behind.

Provided herein are methods for treating congestive heart failure of a subject using a device assembly, the method comprising: advancing a guide catheter out of a delivery catheter to a right atrium over a guidewire; advancing a housing catheter of a tissue stabilizer out of the guide catheter across an interatrial septum into a left atrium over the guidewire, the tissue stabilizer enclosed in the housing catheter in a compressed state; expanding the tissue stabilizer in the left atrium by moving the tissue stabilizer out of the housing catheter over the guidewire and allowing the tissue-stabilizer to self-expand; expanding the cutter in the right atrium; translating the cutter forward to cut the interatrial septum while the tissue stabilizer applies counter tension to the interatrial septum; and resheathing the tissue stabilizer with the cut interatrial septum into the cutter. In some embodiments, the cut interatrial septum is at least a portion of the interatrial septum. In some embodiments, the methods disclosed herein comprise puncturing through a fossa ovalis of an interatrial septum of the subject and advancing a guidewire therethrough to a left atrium. In some embodiments, the methods disclosed herein comprise advancing the device assembly over a guidewire to a right atrium, the device assembly being sheathed. In some embodiments, the methods disclosed herein comprise moving the tissue stabilizer to be in contact with the interatrial septum at a proximal edge of the tissue stabilizer thereby sandwiching the interatrial septum between a distal edge of the guide catheter and the proximal edge of the tissue stabilizer. In some embodiments, expanding the cutter is via advancing the cutter relative to the right atrium or via pulling back of a delivery catheter relative to the right atrium behind a self-expanding portion of the cutter. In some embodiments, the tissue stabilizer plugs a distal opening of the delivery catheter during resheathing of the cutter and the tissue stabilizer. In some embodiments, the methods herein comprise resheathing the cutter into the delivery catheter, the cutter enclosing the tissue stabilizer and the cut interatrial septum there within. In some embodiments, the tissue stabilizer plugs a distal opening of the delivery catheter during resheathing. In some embodiments, the tissue stabilizer plugs a distal opening of the cutter during resheathing. In some embodiments, the methods herein comprise removing the resheathed device assembly from the subject. In some embodiments, the tissue stabilizer plugs a distal opening of the delivery catheter during removal of the resheathed device assembly. In some embodiments, the methods herein comprise expanding the tissue stabilizer comprises deploying more than one self-expanding discs simultaneously or at different time points. In some embodiments, one of said discs is deployed in the left atrium. In some embodiments, one of said discs is deployed in the right atrium. In some embodiments, the methods herein comprise expanding the tissue stabilizer in the left atrium by moving the tissue stabilizer out of the housing catheter and allowing the tissue-stabilizer to self-expand includes pushing at least a portion of a self-expanding part of the tissue stabilizer past the housing catheter in the left atrium. In some embodiments, the methods herein comprise removing the guidewire from the subject after advancing a housing catheter of a tissue stabilizer out of the guide catheter across an interatrial septum. In some embodiments, the methods herein comprise removing the guidewire from the subject before unsheathing the tissue stabilizer from the housing catheter and allowing the tissue-stabilizer to self-expand in the left atrium.

Provided herein are methods for treating congestive heart failure of a subject using a device assembly, the method comprising: advancing a guide catheter out of a delivery catheter to a right atrium over a guidewire; advancing a housing catheter of a tissue stabilizer out of the guide catheter across an interatrial septum to a left atrium over the guidewire, the tissue stabilizer enclosed in the housing catheter in a compressed state; allowing a first self-expanding disc of the tissue stabilizer to expand in the left atrium; allowing a second self-expanding disc to expand in the right atrium thereby sandwiching the interatrial septum between the first and second self-expanding discs; expanding the cutter in the right atrium; translating the cutter forward to cut the interatrial septum while the tissue stabilizer applies counter tension; and resheathing the tissue stabilizer into the cutter with the cut interatrial septum. In some embodiments, the cut interatrial septum comprises at least a portion of the interatrial septum. In some embodiments, the methods herein comprise moving the housing catheter into the right atrium thereby allowing the first self-expanding disc to be in contact with the interatrial septum. In some embodiments, allowing the first self-expanding disc of the tissue stabilizer to expand is via movement of a self-expanding proximal edge of the cutter passing a distal edge of the housing catheter. In some embodiments, allowing a second self-expanding disc to expand in the right atrium is via movement of a distal edge of the housing catheter from the left atrium to the right atrium. In some embodiments, the methods disclosed herein comprise bringing a distal portion of the guide catheter to be in contact with a proximal edge of the second self-expanding disc after moving the housing catheter into the right atrium. In some embodiments, the cut interatrial septum is sandwiched in between the first and second self-expanding discs during resheathing. In some embodiments, the methods herein comprise removing the guidewire from the subject after advancing a housing catheter of a tissue stabilizer out of the guide catheter across an interatrial septum to a left atrium over the guidewire. In some embodiments, the methods herein comprise removing the guidewire from the subject before allowing a first self-expanding disc of the tissue stabilizer to expand in the left atrium. In some embodiments, the methods herein comprise puncturing through a fossa ovalis of an interatrial septum of the subject and advancing a guidewire therethrough to a left atrium. In some embodiments, the methods herein comprise advancing the device assembly over a guidewire to a right atrium, the device assembly being sheathed. In some embodiments, expanding the cutter is via advancing the cutter relative to the right atrium or via pulling back of a delivery catheter relative to the right atrium behind a self-expanding portion of the cutter. In some embodiments, the methods herein comprise resheathing the cutter into the delivery catheter, the cutter enclosing the tissue stabilizer and the cut interatrial septum therewithin. In some embodiments, the tissue stabilizer plugs a distal opening of the delivery catheter during resheathing. In some embodiments, the tissue stabilizer plugs a distal opening of the cutter during resheathing. In some embodiments, the cut interatrial septum is sandwiched in between the first and second self-expanding discs during resheathing. In some embodiments, the methods disclosed herein comprise removing the resheathed device assembly from the subject. In some embodiments, the cut interatrial septum is sandwiched in between the first and second self-expanding discs during removal of the resheathed device assembly from the subject. In some embodiments, deploying the tissue stabilizer comprises deploying more than one self-expanding discs simultaneously or at different time points. In some embodiments, at least one of said discs is deployed in the left atrium. In some embodiments, at least one of said discs is deployed in the right atrium.

BRIEF DESCRIPTION OF THE DRAWINGS

The novel features of the device assemblies herein are set forth with particularity in the appended claims. A better understanding of the features and advantages of the present disclosure will be obtained by reference to the following detailed description that sets forth illustrative embodiments, in which the principles of the device assemblies herein are utilized, and the accompanying drawings of which:

FIG. 1 is a side view of an exemplary embodiment of the device assemblies disclosed herein.

FIG. 2 is an illustration of an exemplary embodiment of a transseptal puncture through the fossa ovalis.

FIG. 3 is an illustration of an exemplary embodiment of a balloon catheter with balloon inflated in left atrium.

FIG. 24A is a representative illustration of an embodiment, illustrating the cutter's teeth shaped in a series of scallops that come to a narrow point.

FIG. 24B is a representative illustration of an embodiment, illustrating the cutter's teeth shaped in a series of "U"'s to create a crown like appearance with pointed edges.

FIG. 25A is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3.

FIG. 25B is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3.

FIG. 25C is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3.

FIG. 29 is a general embodiment, illustrating any of the above embodiments, combined as a system with an automated auscultation device for long term non-invasive monitoring of the flow or pressures through or across the interatrial shunt.

FIG. 30 is an exemplary side view of an embodiment of the device assembly.

FIGS. 43A-43D show an exemplary embodiment of sequential steps using the device assembly as disclosed herein eliminating the need to remove the guidewire as the catheter comprising the expandable tissue stabilizer is able to run over the guidewire and is deployed in the left atrium.

FIG. 45 shows an exemplary embodiment of the balloon catheter or nitinol mesh housing catheter disclosed herein, which features a larger outer diameter at its distal end to ensure coaxial alignment with the guide catheter or blade catheter.

FIG. 46 shows an exemplary embodiment of a procedural step using the device assembly as disclosed herein, which is a transseptal puncture through the fossa ovalis of the interatrial septum, leaving a guidewire in place.

FIG. 47 shows an exemplary embodiment of a procedural step using the device assembly as disclosed herein, wherein the guide catheter is introduced out of the delivery catheter over the guidewire and brought into contact with the septum.

FIG. 48 shows an exemplary embodiment of a procedural step using the device assembly as disclosed herein, wherein the shape memory alloy mesh delivery catheter is introduced from the guide catheter over the guidewire through the atrial septum at approximately 90 degrees.

FIG. 49 shows an exemplary embodiment of a procedural step using the device assembly as disclosed herein, wherein through the shape memory alloy mesh delivery catheter the shape memory alloy mesh tissue stabilizing element is introduced into the right atrium where it is deployed through self-expansion.

FIG. 54 shows an exemplary embodiment of the device assembly as disclosed herein in which the shape memory alloy mesh catheter features one or more shape memory alloy mesh discs distal to the one in contact with the septum to serve as a failsafe to 1) ensure that excised (or partially excised) tissue does not come free from the interatrial septum and device, and 2) allow for the blade to continue translating through the septum in the event that one of the shape memory alloy mesh plugs is inadvertently pulled through the septum prior to completion of a full circumferential cut.

FIGS. 55A-55B show exemplary embodiments of the one or more shape memory alloy discs and their sizes relative to the cutter of a device assembly as disclosed herein.

FIGS. 56A-56E show an exemplary sequential embodiment of the deployment of a shape memory alloy mesh a device assembly wherein the delivered shape memory alloy mesh tissue stabilizer takes the form of several overlapping petals.

FIG. 57 shows an exemplary embodiment of the expandable tissue stabilizer of a device assembly as disclosed herein wherein the distal end of the truncated cone (trapezoid shape) tissue stabilizer is oversized to the expanded diameter of the blade to capture the penetrating tips of the cutter after completion of the cut.

FIG. 59A shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.

FIG. 59B shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.

FIG. 59C shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.

FIG. 60A shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back proximally the catheter that houses the tissue stabilizer as well as the guide catheter.

FIG. 60B shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back proximally the catheter that houses the tissue stabilizer as well as the guide catheter.

FIG. 60C shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back proximally the catheter that houses the tissue stabilizer as well as the guide catheter.

FIG. 60D shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back the catheter that houses the tissue stabilizer as well as the guide catheter.

FIG. 62 shows an exemplary embodiment of the tissue stabilizer of a device assembly as disclosed herein wherein the self-expanding mesh disc has a concave side only allowing the outer edges of the mesh to touch the interatrial septum, to help prevent the mesh disc from being pulled through the interatrial septum.

FIG. 63A shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire or expand the tissue stabilizer through a pothole at the distal end of catheter 1.

FIG. 63B shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire or expand the tissue stabilizer through a pothole at the distal end of catheter 1.

FIG. 64 shows an exemplary side view embodiment of the tissue stabilizer of a device assembly as disclosed herein wherein the tissue stabilizer comprises a self-expanding mesh disc that is surrounding an undersized balloon that once inflated will prevent the tissue stabilizer from being pulled through the interatrial septum towards the right atrium.

FIG. 65 shows an exemplary end view embodiment of the tissue stabilizer of a device assembly as shown in FIG. 64 and as disclosed herein wherein the tissue stabilizer comprises a self-expanding mesh disc that is surrounding an undersized balloon that once inflated will prevent the tissue stabilizer from being pulled through the interatrial septum towards the right atrium.

FIG. 66 shows an exemplary embodiment of the tissue stabilizer of a device assembly as disclosed herein wherein the tissue stabilizer is a self-expanding coil.

FIG. 74A shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74B shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74C shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74D shows an exemplary sequential embodiment of the tissue stabilizer of a device assembly as disclosed herein wherein the tissue stabilizer consists of a series of radially self-expanding struts connected circumferentially by a series of shape memory bridges.

FIG. 75C shows an exemplary sequential embodiment of the tissue stabilizer of a device assembly as disclosed herein.

FIG. 75D shows an exemplary sequential embodiment of the tissue stabilizer of a device assembly as disclosed herein.

FIG. 75E shows an exemplary sequential embodiment of the tissue stabilizer of a device assembly as disclosed herein.

DETAILED DESCRIPTION OF THE INVENTION

Figure 4A:
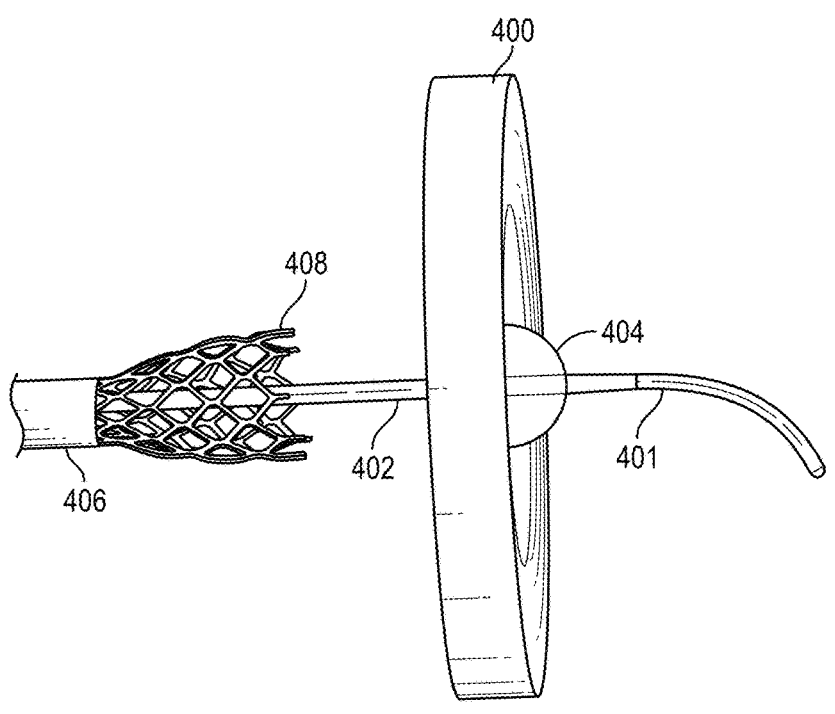
FIG. 4A is an illustration of an exemplary embodiment of the cutter, a self-expanding shape memory stent with sharpened blades on the distal end, delivered (and either partially or wholly un-sheathed) to the right atrium.

CHF is marked by declining function of the heart muscle, either due to a weakening of its pumping ability, known as heart failure with reduced ejection fraction (HFrEF), or a stiffening of the muscle with decreased ability to fill with blood prior to ejection, known as heart failure with preserved ejection fraction (HFpEF). Inability of the heart to eject or fill with blood leads to symptoms of shortness of breath, fatigue, and significant functional limitation. Prevalence of HFrEF and HFpEF are generally equal though rates of HFpEF are rising faster than HFrEF. With poor flow of blood from the heart to vital organs, the renin-angiotensin-aldosterone system (RAAS) is activated which signals the body to retain fluid, thereby increasing pressure in the heart chambers. In particular, as the left atrial pressure (LAP) rises, fluid backs up into the pulmonary circulation leading to pulmonary edema and severe shortness of breath. While LAP in normal adults ranges from 10-15 mmHg, patients with heart failure frequently have LAP in the 30-40 mmHg range, which, in some embodiments, spikes during periods of increased heart demand.

Existing pharmacologic treatments for heart failure attempt to remove excess fluid in the body through renal excretion (diuretics), neurohormonal blockade, or dilation of peripheral blood vessels in order to reduce the stress-load on a failing heart. These pharmacologic therapies offer some symptomatic relief and have shown slight mortality benefit in treating HFrEF, but importantly have not been shown to improve survival for those with HFpEF.

There are limited device-based therapies for heart failure. Mechanical circulatory support, in which a motorized pump is surgically implanted and takes over the function for the failing heart, is highly invasive and is reserved for end-stage progression of disease. Percutaneous mechanical pumps are used in an acute setting but are only approved for short-term use. Similarly, intra-aortic balloon pumps, which decrease cardiac afterload and improve coronary perfusion, are used only in the acute inpatient settings. Finally, cardiac resynchronization therapies, in which an implantable pacemaker improves coordinated contraction of failing ventricles, has shown good results for improving mortality for patients with heart failure and concomitant electrical conduction abnormalities.

Experimental therapies have sought to reduce elevated left atrial pressure by implanting a metal stent within the interatrial septum which creates a shunt between the high-pressure left atrium towards the low-pressure right atrium. Since the right atrium and the venous reservoir are highly compliant, left-to-right blood shunting, in some embodiments, effectively lower left atrial pressure without a significant elevation of right atrial pressure, thereby relieving symptoms and improving cardiac mechanics. Early human data from these interatrial shunts are showing promise with improved functional status and hemodynamic parameters.

The optimal size for these interatrial shunts is unknown, though it has been approximated using simulation data and early animal studies. Importantly, the size of the interatrial aperture must be large enough to allow effective left atrial offloading, without allowing too much blood to flow to the right side such that undue stress is placed on the right atrium and ventricle. It is widely accepted among clinicians that individuals presenting with congenital atrial septal defects warrant closure if the defect size results in a shunt fraction greater than 50%. Accordingly, sizing an interatrial shunt such that no more than 50% of left atrial blood is shunted is important to reduce long-term adverse effects.

Implantable interatrial shunts have a number of disadvantages. Since a foreign body is left within the heart chambers and makes contact with blood, clotting and thrombosis is a risk that will likely require pharmacologic anticoagulation, either long-term or until endothelialization of the device's surface occurs. The implant also carries the risk of device-fracture, dislodgement, or embolization. The implanted stent in some embodiments also makes it difficult for subsequent transseptal procedures as it could limit the degree of freedom for a catheter to move within the left atrium. Finally, should closure ever become desirable, a bulky stent, in some embodiments, adds to the difficulty of sealing off the interatrial shunt.

Balloon atrial septostomy is a procedure with an associated medical device which attempts to create an interatrial aperture to allow mixing of blood between the left and right sides of the heart. This device is used in the pediatric population to treat congenital heart lesions prior to definitive surgical correction. A deflated balloon, with or without blades attached, is introduced via the venous system across the interatrial septum and into the left atrium. The balloon is subsequently inflated and pulled proximally thereby tearing the septum and opening an interatrial aperture. This device generates an interatrial aperture that is not reproducible from patient to patient. Since the septum is torn, the resultant tissue flaps remain in place and eventually fuse back together. The aperture created by these device assemblies uniformly close over a period of months. The temporary nature of these interatrial apertures makes them suitable for the short-term treatment of congenital birth defects but they are not useful in the adult heart failure population where a more durable therapy is desired.

Thus, a device that is capable of creating a sized atrial aperture for the relief of atrial pressure, without requiring an implant and in a manner which ensures "long-term" patency, would be advantageous. Using such a device would achieve the equivalent physiology to an implantable stent without the negative sequelae of a leave-behind device. It is desirable to create a precisely-sized aperture that could remain patent for the duration of a desired therapeutic benefit. Since this therapy would most likely be beneficial for a patient population with high burden of comorbidities, creating such an aperture through a minimally invasive procedure is also advantageous. It is therefore the goal of this device to enable the creation of a precisely-sized aperture through a small (<18 Fr, <6.0 mm, <0.236 in.) percutaneous puncture.

The present disclosure relates to device assemblies and methods for treating heart failure by reducing elevated blood pressure in the left atrium of a heart of a mammal. Disclosed herein, in some embodiments, are transcatheter interatrial septum excision device assemblies configured to create a sized atrial aperture between the right and left atria of a heart for the relief of left elevated atrial pressure to allow shunting of no more than 50% of the left atrium blood to the right atrium of the heart. In some embodiments, the device assemblies comprise a delivery catheter, a tissue stabilizer attached to a first catheter having a central lumen and a penetrating tip that permits passage of a guidewire, and a cutter attached to a second catheter having a central lumen that permits passage of the first catheter. In some embodiments, the device assemblies disclosed herein comprise a (third) catheter having a central lumen that permits passage of the aforementioned components to and from the right atrium or resides coaxially inside the central lumen of the aforementioned components, a tissue retention mechanism, and an optional coaxial alignment mechanism.

In some embodiments, off-the-shelf lumen with penetrating tips and guidewires are configured for use with the transcatheter interatrial septum excision device assemblies herein, thus simplifying the design of the transcatheter interatrial septum excision device assemblies by removing the penetrating tip and guidewire from the main device assembly, thus simplifying the complexity and reducing cost. An example of such an off-the-shelf lumen with penetrating tip and guidewire is the Swartz™ Braided Transseptal Guiding Introducers LAMP™ Series, model number 407366, with a 180 cm length with a 0.035 inch diameter. In some embodiments, an off-the-self vascular access sheath is used to deploy the device assembly into the femoral vein. Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; and an expandable cutter attached to, and positioned along the outer length of, the second internal coaxial catheter and configured to slidably traverse or engage within the central delivery lumen of the delivery catheter. In some embodiments, the first internal coaxial catheter having a first lumen, further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, a coaxial guidewire is configured to extend from a distal end of the first lumen of the first internal coaxial catheter and pass through an initial puncture site in an interatrial septum between a right atrium and a left atrium of a heart of a mammal at approximately a fossa ovalis to provide a working track for the device assembly into the left atrium. In some embodiments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the dimension thereof is sufficiently large enough to prevent the tissue stabilizer from being pulled back through the initial puncture site and such that the tissue stabilizer provides a supporting, tensioning effect on the wall of the atrial septum surrounding the initial puncture site. In some embodiments, the second internal coaxial catheter is extended from the delivery catheter such that the expandable cutter is slidably advanced and coaxially expanded to a cutting dimension greater than the expanded dimension of the tissue stabilizer. In some embodiments, the second internal coaxial catheter is further extended until the fully expanded cutter engages or traverses the right atrial side of the interatrial septum at or about the fossa ovalis, such that the cutter pierces and cuts completely through the septum, thereby creating an interatrial pressure relief opening in the interatrial septum, wherein the interatrial pressure relief opening is sufficiently sized to allow blood flow through the interatrial pressure relief opening from the left atrium to the right atrium such that no more than 50% of left atrial blood is shunted to the right atrium, and wherein the interatrial pressure relief opening is sufficiently sized, and or of such shape, in order to slow a natural healing process of the tissue to maintain patency of the interatrial pressure relief opening in the interatrial septum without implanting a stent or valve therein. In some embodiments, an excised tissue cut from the interatrial septum is captured and maintained between the cutter and the tissue stabilizer. In some embodiments, the stabilizing element is partially collapsed and the first internal coaxial catheter is retracted until the captured excised tissue and at least a portion of the partially collapsed stabilizing element is pulled into an opening of the expanded cutter positioned on the second internal coaxial catheter. In some embodiments, the cutter is withdrawn into the lumen of the delivery catheter and collapsed, wherein the stabilizing element is simultaneously fully collapsed inside the cutter, capturing the excised tissue therein. In some embodiments, the device assembly further comprises a coaxial alignment component. In some embodiments, said coaxial alignment component is configured to provide centralization between the cutter and the tissue stabilizer.

Overview of Device Assembly Elements

As shown in FIG. 1, in some embodiments, the device assembly 100 comprises: a guidewire 101; a tissue stabilizer, or equivalently herein, a tissue stabilizing element, 104 optionally attached to an inner catheter (alternatively called synonymously a first catheter, inner catheter 1, internal catheter 1, first coaxial catheter, first internal coaxial catheter, or catheter 1 herein) 102, wherein catheter 1 has a central lumen that permits passage of the guidewire therethrough; a cutter 108; optionally attached to a second catheter (alternatively called synonymously internal catheter 2, coaxial catheter 2, second coaxial catheter, second internal coaxial catheter, or catheter 2 herein) 106, wherein catheter 2 has a central lumen that permits passage of catheter 1 therewithin; a third delivery catheter (alternatively synonymously referred to as delivery catheter 3, delivery catheter, or housing sheath herein, and in some embodiments is referred to as steerable delivery catheter 3) 110, wherein delivery catheter 3 has a central lumen that permits passage of the aforementioned components therewithin to and from the right atrium; a tissue retention mechanism, which optionally comprises, the tissue stabilizer 104, the cutter 108, the catheter therebetween 102, or any combination thereof; and a coaxial alignment mechanism 112. As noted previously, the guidewire 101 is optionally configured as a separate off-the-shelf component that is packaged and utilized separately or configured to work seamlessly with other elements of the device assembly. Thus, FIG. 1 is a side view of an exemplary embodiment of a device assembly disclosed herein. Shown in FIG. 1 is a device assembly 100 comprising a guidewire 101 that is optionally provided as either an off-the-shelf add-on component or an integral device component, a tissue stabilizer 104 (alternatively called synonymously a tissue stabilizing element herein), a cutter configured to cut the atrial septum tissue and that in some embodiments is collapsible or is made of a memory metal such as NiTi (wherein the cutter is alternatively called synonymously a collapsible cutter or the expandable cutter herein), a first catheter 102 (alternatively called synonymously an inner catheter, inner catheter 1, internal catheter 1, first coaxial catheter, first internal coaxial catheter, or catheter 1 herein) configured to deliver the tissue stabilizer, a second catheter 106 configured to deliver a the cutter (wherein the second catheter is alternatively called synonymously internal catheter 2, coaxial catheter 2, second coaxial catheter, second internal coaxial catheter, or catheter 2 herein), a delivery catheter 110 configured to introduce and carry catheter 1 and catheter 2, or both catheter 1 and catheter 2 (wherein the delivery catheter is alternatively called synonymously delivery catheter 3, delivery catheter, or housing sheath herein, and in some embodiments is referred to as steerable delivery catheter 3), and coaxial aligner 112 located on catheter 2 proximal to the cutter (where proximal refers to closer to the delivery catheter handle in contrast to distal which refers to closer to the guidewire opening of the delivery assembly where the guidewire exits an inner lumen of catheter 1).

In some embodiments, as noted previously, the device assembly is configurable with or without an integral penetrating tip and guidewire. However, whether it is provided as an integral component or an attachment to the Device assembly, once the guidewire is positioned across (through) the interatrial septum, it is utilized by the Device assembly to provide a working track for the components of the device assembly, and removed along with the Device assembly when the procedure is completed.

In some embodiments, the coaxial aligner or the coaxial mechanism through the aligner or other part(s) of the device assembly provides centralization between the cutter, tissue stabilizer, tissue retention elements, or their combinations. The coaxial aligner reduces the risk of incurring inadvertent interaction between the cutter and the tissue stabilizer (for example, as catheter 1 is translated proximally into catheters 2 or 3). The coaxial aligner also serves as a means to ensure the cutter (connected to catheter 2) is advanced centrally over catheter 1 and through the septum.

Figures 7, 8A, 8B, 8C, 9:
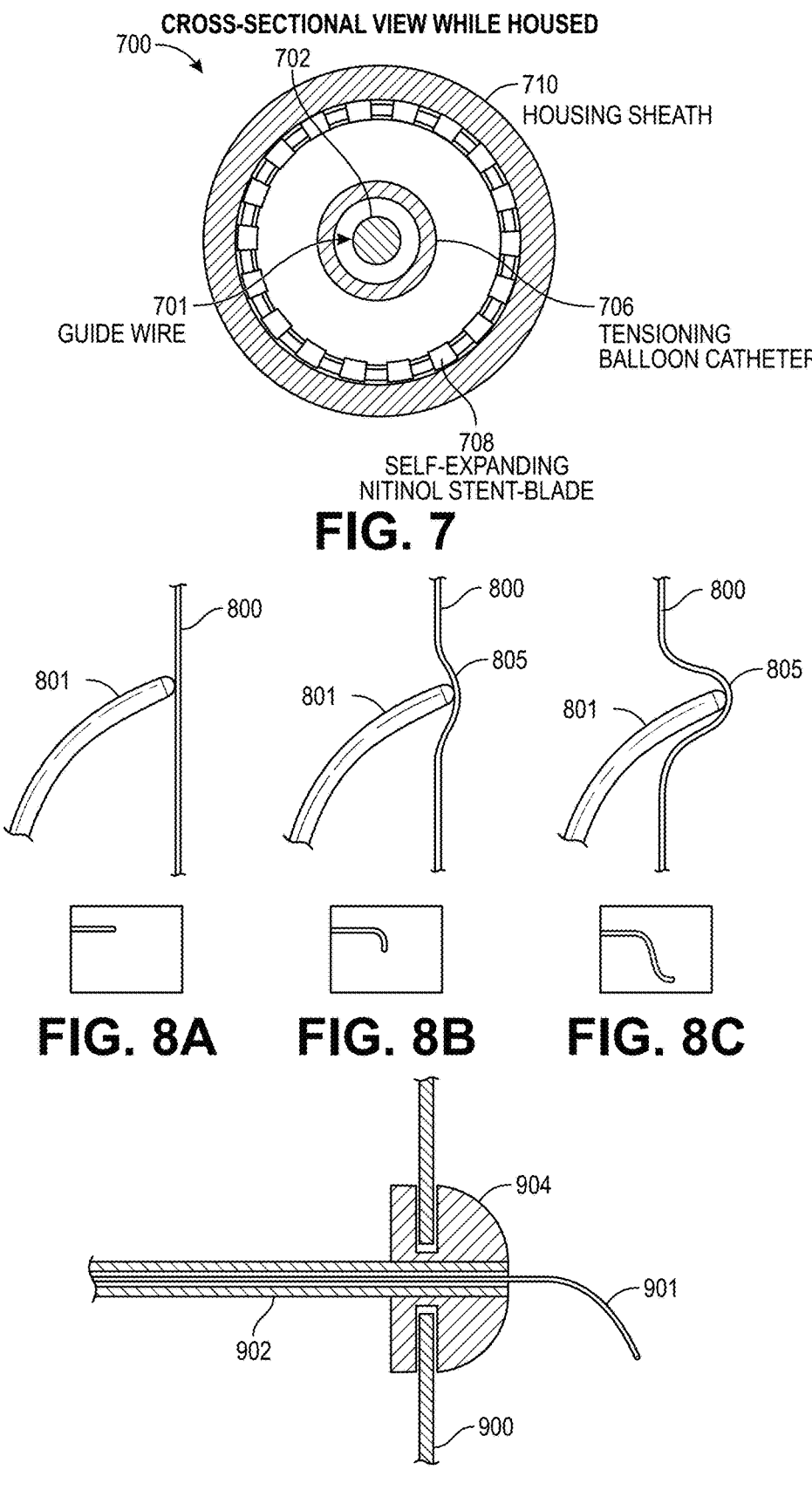
FIG. 7 is a representative cross-sectional view of one embodiment of the device assembly while housed in the delivery catheter.
FIGS. 8A-8C are illustrations of alternative guidewire embodiments having various tip configurations including versions with hydrophilic or hydrophobic coatings, one or more force sensor(s), one or more pressure sensor(s), an oxygen saturation sensor, tissue cutting or puncturing element(s), or tissue stabilizing elements.
FIG. 9 is a representative illustration of one embodiment of a "dumbbell" or "dogbone" shaped tissue stabilizer.

It should also be noted that optionally the entire device assembly is also configurable for delivery through an off-the-shelf steerable catheter configured with an appropriate internal diameter to support the (external) delivery catheter of the device assembly. As further illustrated in the cross-sectional view of FIG. 7, in an exemplary embodiment, the transcatheter interatrial septum excision device assembly 700 comprises catheter 1 702, comprising the tissue stabilizer 706 mounted thereon, catheter 2 comprising a cutter 708, a delivery catheter 3 710 sheathing the catheter 1, the tissue stabilizer in a collapsed state, and the cutter in a collapsed state, and the device assembly 700 is further is configured with or without an integral guidewire 701 having a tissue penetrating tip. In some embodiments an additional catheter will be needed to house the tissue stabilizer that keeps the tissue stabilizer in a collapsed state before it gets deployed, this catheter has a central lumen that permits passage of catheter 1 therewithin and is slidably engaged within the central lumen of catheter 2, 706. In this particular embodiment, elements within the delivery catheter 3 710 are coaxially positioned together, with two or more elements overlapping partially along the longitudinal or elongate direction of the delivery catheter. In some embodiments, elements within the delivery catheter physically contact each other for stability and support of the whole device assembly when the device assembly is deployed. In some embodiments, elements within the delivery catheter remain still with respect to other one or more elements when the device assembly is properly deployed. FIG. 7 thus is a representative cross-sectional view of one or more embodiments of a device assembly.

Figure 28A:
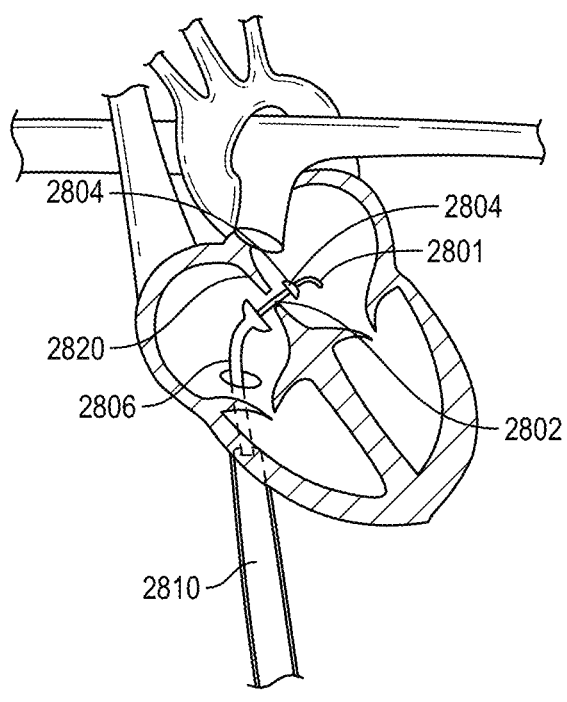
FIG. 28A is a representative illustration of an embodiment of the assembly wherein the internal catheter 2 (catheter that comprises an expanding cutter) has a predetermined, but flexible bend in one of the internal catheters inside of the delivery catheter; but the delivery catheter is strong enough to contain the bend without distortion of the entire delivery catheter.
Figure 28B:
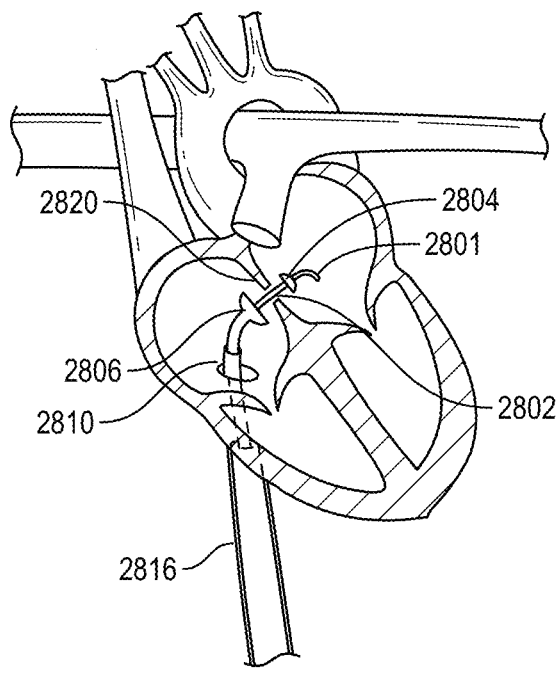
FIG. 28B is an representative illustration of an embodiment of the assembly of FIG. 28A wherein an additional internal catheter has a predetermined, but flexible bend and is outside of the internal catheters, but still inside of the delivery catheter; but the delivery catheter is strong enough to contain the bend without distortion of the entire delivery catheter.

Referring to FIGS. 28A-28B, in a particular embodiment, an interatrial septum orthogonal orientation mechanism of the assembly disclosed herein, is shown, in relation to a heart's anatomy. In the embodiment shown in FIG. 28A, the internal catheter 2, 2806 has a predetermined, but flexible bend; but the delivery catheter 3, 2810 is strong enough to contain the bend therewithin without distortion of the entire delivery catheter prior to deployment. Upon distal deployment of the internal catheter, the device assembly bends generally in an orthogonal direction to point towards the fossa ovalis. In some embodiments, the fossa ovalis is a depression in the right atrium of the heart, at the level of the interatrial septum 2820, the wall between the right and left atrium. The fossa ovalis is the remnant of a thin fibrous sheet that covered the foramen ovale during fetal development. The foramen ovale, in some embodiments, is a small hole located in the septum (wall) between the two upper (atrial) chambers of the heart. The foramen ovale is used during fetal circulation to speed up the travel of blood through the heart. In this particular embodiment, guidewire 2801, catheter 1, 2802, tissue stabilizers 2804 are also shown.

FIG. 28B is an exemplary illustration of an embodiment of the assembly of FIG. 28A wherein an additional internal catheter has a predetermined, but flexible bend and is outside of the internal catheter 2, 2806, but still inside of the delivery catheter 4, 2816 prior to deployment; but the delivery catheter is strong enough to contain the bend without distortion of the entire delivery catheter. Upon distal deployment of the additional internal catheter, the device assembly bends generally in an orthogonal direction to point towards the fossa ovalis, optionally, perpendicular to the fossa ovalis. In some embodiments, the delivery catheter includes optional steering cables. (Not Shown)

Referring to FIG. 29, in an exemplary embodiment, the assembly and its individual parts as disclosed herein, are combined as a system, 2900 with an automated auscultation device assembly for long term non-invasive monitoring of the flow or pressures through or across the created shunt.

Figures 31, 32:
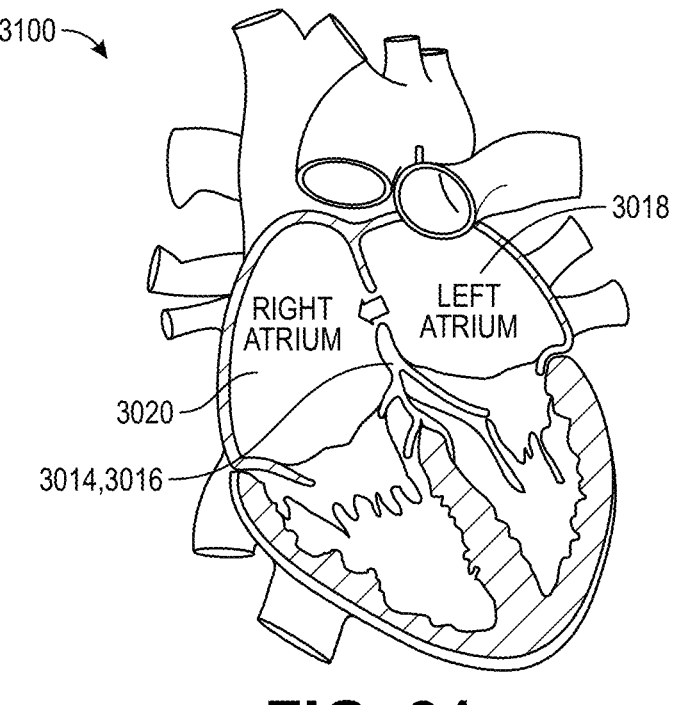
FIG. 31 illustrates a cross-sectional view of a human heart and the left to right direction of blood flow through a pressure relieving shunt between the left and right atrium of the heart.
FIG. 32 is a graphic illustration of an initial puncture of the interatrial septum, with a representative atrial decompression system, by a guidewire and catheter comprising a tissue stabilizing balloon penetrating the left atrium from the right atrium, percutaneously delivered to the heart through an initial groin puncture.
Figure 33:
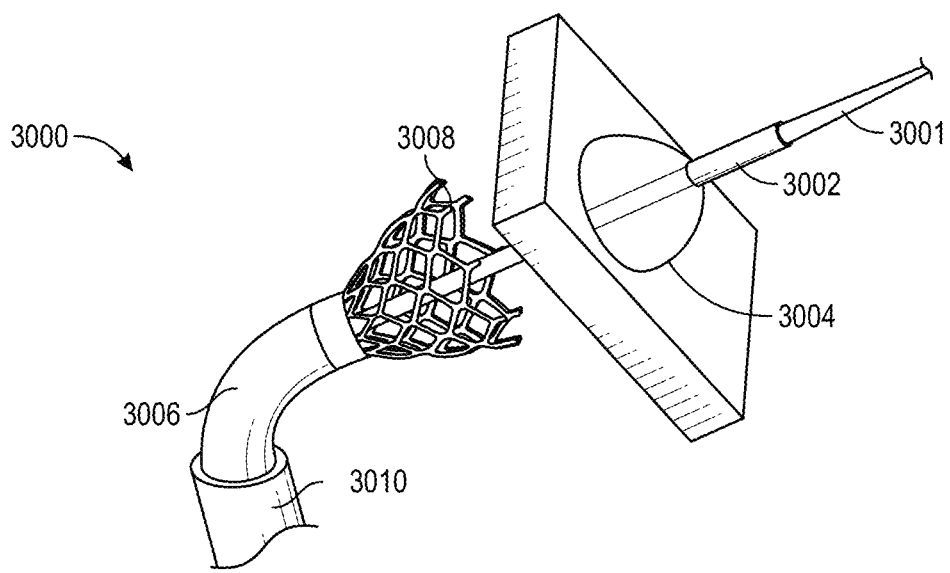
FIG. 33 is a representative illustration of an embodiment of the atrial decompression system of FIGS. 31 and 32, illustrating the sequential deployment of a self-expanding stent blade from a second coaxial catheter in the right atrium, following deployment of the tissue stabilizing balloon in the left atrium.
Figure 34:
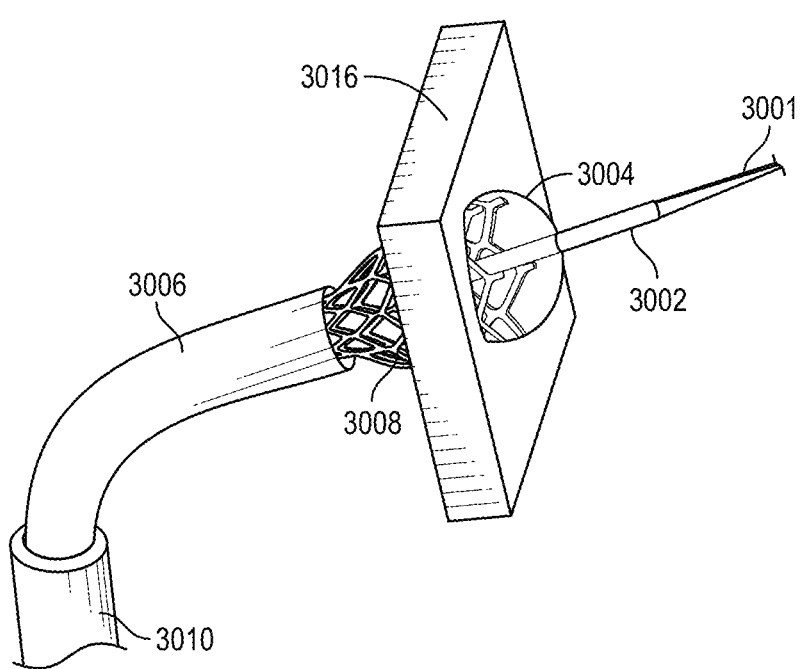
FIG. 34 is a representative illustration of an embodiment of the atrial decompression system of FIGS. 31, 32 and 33, illustrating the sequential creation of the shunt through the interatrial septum, slightly larger than the diameter of the tissue stabilizing balloon, utilizing the self-expanding stent blade.
Figure 35:
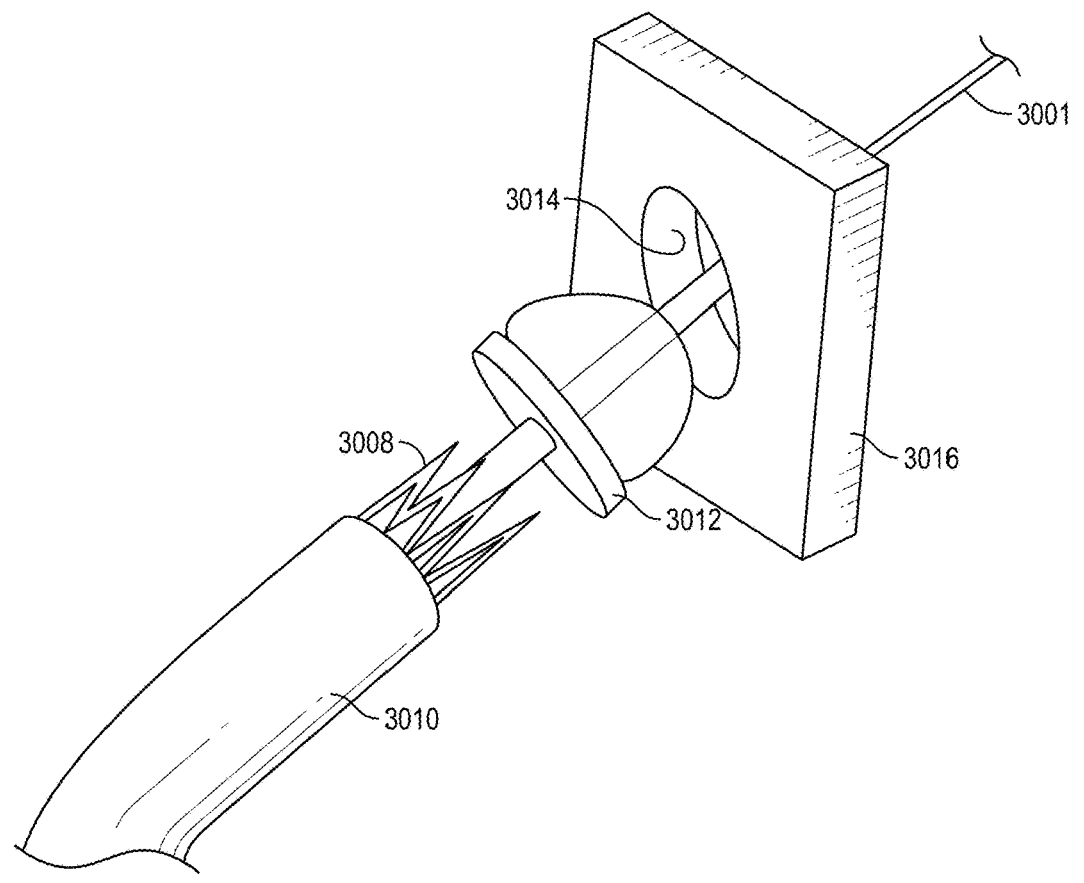
FIG. 35 is a representative illustration of an embodiment of the atrial decompression system of FIGS. 31-34, illustrating the sequential withdrawal of the entire atrial decompression system, with the self-expanding stent blade retracted into the coaxial catheter and delivery catheter, and the excised tissue from the interatrial septum, captured by the tissue stabilizing balloon.

Referring now to FIG. 30, is a graphic illustration of the "working end" (distal end) of the device assembly 3000, in some embodiments, comprising an optionally provided off-the-shelf or integral guidewire 3001 (with puncturing tip), catheter 1, 3002, a tissue stabilizer 3004 (as non-limiting examples, balloon or tines), catheter 2, 3006—(for cutter), the cutter 3008—(self-expanding shape memory stent with blades at the distal end) and the delivery catheter 3, 3010—(optionally steerable, or configurable within a steerable off-the-shelf delivery catheter) and FIG. 31, a cross-sectional view of a human heart 3100 comprising the right atrium 3020, the left atrium 3018 and the anastomosis shunt 3014, illustrating the left to right direction of blood flow through the pressure relieving shunt between the left and right atrium of the heart.

Referring now to FIGS. 31 through 35, one sees a sequential graphic illustration of the creation of the atrial shunt in a human heart utilizing the device assembly in a particular embodiment, comprising one or more of the following steps:

Percutaneously delivering the assembly 3000 (optionally un-deployed or partially deployed) over a guidewire 3001 up through the femoral vein into the inferior vena cava which feeds into the right atrium 3020 of the heart 3100. A delivery catheter 3, 3010, the guidewire 3001 or the steerable catheter 1 3002, in some embodiments, is deployed in this step;

Creating an initial puncture of the interatrial septum 3016, with a guidewire 3001 comprising a puncturing tip and a coaxial catheter 1, 3002 comprising a tissue stabilizer 3004 (e.g.: balloon), penetrating the left atrium 3018 from the right atrium 3020 and expanding the tissue stabilizing balloon against the interatrial septum;

Deployment of a self-expanding cutter 3008 from a coaxial catheter 2, 3006 into the right atrium, following deployment of the tissue stabilizer in the left atrium;

Creation of the anastomosis shunt 3014 through the interatrial septum 3016, slightly larger than the diameter of the tissue stabilizer 3004, utilizing the self-expanding cutter 3008 and capturing the excised tissue 3012; and Withdrawal of the entire atrial decompression system 3000, with the self-expanding cutter retracted into the lumen of the delivery catheter, followed by, or simultaneously with retraction of the excised tissue from the interatrial septum, captured within the collapsed blades of the self-expanding cutter and held in place by the tissue stabilizer into the delivery catheter, then the entire device assembly (including the guidewire) is withdrawn from the heart and body through the initial groin puncture.

FIGS. 8A-C are illustrations of alternative guidewire embodiments having various tip configurations including versions with hydrophilic or hydrophobic coatings, one or more force pressure sensors, an oxygen saturation sensor, penetrating tips or tissue cutting tips or even including tissue stabilizing elements (alternatively called tissue stabilizers herein) thereon. FIG. 9 is a representative illustration of one embodiment of a "dumbbell" or "dogbone" shaped tissue stabilizer, and shows an embodiment guidewire in a lumen running through the tissue stabilizer.

In some embodiments, as shown in FIGS. 8A-C and in FIG. 9, a guidewire 801, 901 is placed across the interatrial septum 800, 900 at or about a weak point 805 of the fossa ovalis of the septum, using standard transseptal puncture techniques. The guidewire 801, 901 provides a working track along which the Device assembly is advanced. Components of the device assembly such as the various catheters 902 and tissue stabilizer 904, in some embodiments, are translated along the guidewire in relation to one another and the septum. The system optionally comprises a transseptal puncture kit with guidewire, often available as a standard off-the-shelf item. By way of example, one such kit is the Swartz™ Braided Transseptal Guiding Introducers LAMP™ Series, model number 407366, with a 180 cm length with an 0.035 inch diameter.

In some embodiments, the guidewire has a hydrophilic coating which allows catheter 1 to translate along its length with low friction. In some embodiments, the tip of the guidewire features a curved or shaped puncturing tip to prevent any inadvertent trauma at its distal end. The curved tip is held straight within the delivery catheter and introduced to the interatrial septum through a dilator and introducer to facilitate penetration of interatrial septum. The curved tip is held straight within the delivery catheter and introduced to the interatrial septum through a dilator or introducer to facilitate penetration of interatrial septum. Once through the interatrial septum, the tip of the puncturing tip is configured to bend over on itself to avoid inadvertent puncture of unintended tissues. A common material for this type of bending tip is nitinol, a nickel-titanium alloy. In some embodiments, other types of materials and shape memory material that functions similarly as nitinol is used in the guidewire. In some embodiments, the guidewire includes a sheath or cover that covers the puncturing tip after puncturing so that the tip does not have to include a self-bending tip. In some embodiments, the tip of the guidewire is mounted to include a detector or sensor that facilitates the delivery of the guidewire, puncturing, and bending after puncturing. In some embodiments, the tip of the guidewire is mounted to include a detector or sensor that facilitates the delivery of the guidewire, puncturing, or bending after puncturing. In some embodiments, therapeutic agents are optionally carried on the tip or along the guidewire to enable drug delivery before or after the Interatrial Anastomosis.

In some embodiments, a force sensor or pressure-sensor 805 is incorporated into the guidewire 801 to help identify the thinnest and most compliant portion of the interatrial septum as the guidewire tip is navigated to probe different regions of the tissue.

In some embodiments, an oxygen saturation method is incorporated into the guidewire to provide confirmation of delivery to the left atrium (oxygenated blood). To provide confirmation, optionally a saturation analysis would first be taken in the right atrium (pre-transseptal puncture), and again after the puncture has taken place into the left atrium with a saturation differential confirming successful puncture. In some embodiments, the analysis occurs only in the left atrium, and comparison to a preselected saturation value confirms proper puncture. In some embodiments, the guidewire features a cutting or puncture element at its distal tip (the tip further away from the operator of the device assembly). In some embodiments, the cutting or puncture element at its distal tip features a curved or shaped tip to prevent any inadvertent trauma at its distal end. In some embodiments, the end of the guidewire introducer sheath comprises a straightener to straighten a cutting or puncture element just prior to delivery or retraction through the interatrial septum.

In some embodiments, the guidewire features a hydrophobic coating.

In some embodiments, the guidewire is coaxially and slidably engaged within the first lumen of the first internal coaxial catheter, configured to provide a working track for the device assembly.

In some embodiments, the guidewire is a solid wire or hollow elongate tube, optionally including a cavity therewithin. In some embodiments, the guidewire includes a weave pattern which encloses a cavity therewithin, such weave pattern better facilitates puncturing or self-bending afterwards than a solid elongate wire. In some embodiments, the guidewire includes a weave pattern which encloses a cavity therewithin, such weave pattern better facilitates puncturing and self-bending afterwards than a solid elongate wire. In some embodiments, materials include metal, alloy, synthetic, or biological is used in the guidewire.

In some embodiments, the guidewire is equivalent to a guide catheter herein. In some embodiments, the guide catheter houses the guidewire therewithin.

In some embodiments, a guidewire is placed across the interatrial septum using standard transseptal puncture techniques. In some embodiments, the guidewire provides a working track along which the device assembly is advanced. Components of the device assembly disclosed herein, in some embodiments, are translated along the guidewire in relation to one another and the septum.

In some embodiments, the guidewire includes a hydrophobic coating thereon. In some embodiments, the guidewire comprise a force sensor or pressure sensor incorporated into the distal tip. In some embodiments, the guidewire comprise an oxygen saturation sensor. In some embodiments, the guidewire includes a cutting point or edge incorporated into the distal tip. In some embodiments, the guidewire include a curved or shaped end at the distal tip.

In some embodiments, the device assembly disclosed herein includes a tissue stabilizer, a tissue stabilizing element, or use of the same. In some embodiments, the tissue stabilizer is equivalent to a tensioning element herein.

In some embodiments, the tissue stabilizer comprises: an inflatable balloon; expanding tines; an expanding mesh; at least one curved wire; an expanding plate; an expanding disc; an expanding fan; a spring coil; at least one strut; at least one hinged arm; an umbrella stretcher; or a combination thereof. In some embodiments, the tissue stabilizer expands in an outward direction to a 75° to 105° angle after completely passing through the septum, having a dimension that is less than the expanded dimension of the cutter, and is configured to be pulled proximally to engage the septum and stabilize it prior to and after engagement with the cutter; and wherein following engagement of the cutter, the tissue stabilizer is collapsed in the same direction from which it opened, capturing an excised tissue cut from the septum as the cutter is resheathed such that the cutter, the excised tissue and tissue stabilizer collapse into the delivery catheter.

Referring now to FIGS. 9-12B, in some embodiments, the device assembly disclosed herein includes a tissue stabilizer 904, 1004, 1104, 1204 (connected to catheter 1) which provides counter tension to the actuation of the cutter 1008, 1108 so as to minimize any unintended tissue deformation, rotation, or displacement due to unbalanced forces. In some embodiments, it also serves to capture the excised tissue from the interatrial septum 900, 1000, 1100 and prevent dislodgement of the tissue following excision.

In some embodiments, the tissue stabilizer element takes the form of an inflatable, deformable, expandable, or biased element, for example, a balloon, an expandable mesh, a coil spring with or without coverage, integrated into a catheter that is advanced over the guidewire and across the septum, where it is subsequently inflated and pulled back to make contact with the left atrial side of the interatrial septum. In some embodiments, the tissue stabilizer includes one or more individual elements at different positions along the elongate direction. In some embodiments, the inflated element features a flat proximal face toward the septum that assumes a flush configuration with respect to the tissue plane when pulled against the septum. In some embodiments, the inflated element features a proximal surface of other appropriate shapes that facilitate stabilization of the device assembly to the septum. In some embodiments, the proximal profile of the balloon lowers the risk of inadvertently pulling the balloon through the septum ensuring tissue retention. The proximal face, optionally flat, of the inflatable element is slightly undersized with respect to the cutter (in its expanded state) to ensure the creation of a specifically defined aperture. The specifically defined aperture in some embodiments is sized to a specific size based on the cutter dimensions. In various embodiments, the distal end of the balloon is rounded, squared, tapered, or atraumatic on the portion facing the left atrial free wall. In some embodiments, the tissue stabilizer when pulled against the septum prevents relative movement of one or more elements of the device assembly toward the right atrium and the left atrium. In some embodiments, the tissue stabilizer when pulled against the septum prevents relative movement of one or more elements of the device assembly toward the right atrium or the left atrium. In some embodiments, the first coaxial catheter features a tissue stabilizing element (or tissue stabilizers, synonymously) at or immediately adjacent to its distal tip. In some embodiments, the first coaxial catheter features a tissue stabilizing element positioned a short distance (i.e.: 3.0-5.0 mm) proximal to its distal tip. In some embodiments, the first coaxial catheter features a plurality of tissue stabilizing elements at multiple locations along its extended length.

In some embodiments, a tissue stabilizer includes a curved wire or a spring coil. In some embodiments, the tissue stabilizer is fabricated from a shape memory alloy that is configured to expand after completely passing through the septum, in an outward direction approximately orthogonal to the longitudinal centerline of the catheter and having a radial dimension that is less than the expanded dimension of the cutter and is configured to be pulled back to engage the septum, to stabilize it prior to and after engagement with the cutter; and wherein following engagement of the cutter, the tissue stabilizer is collapsed in the same direction from which it opened, capturing an excised tissue cut from the septum as the cutter is resheathed such that the excised tissue and tissue stabilizer fit within the delivery catheter.

In some embodiments, as shown in FIG. 9, a balloon 904 (tissue stabilizer) is inflated from catheter 1, 902, on each side of the septum 900 to aid with tissue stabilization. The balloon is axially shaped, similar to a "dogbone", to pinch the tissue in between each end during inflation, forming the "dogbone" shape. Various embodiments could include more than one balloons being inflated together or separately, being one continuous balloon, being of the same diameter, different diameters, or separately inflatable from one another. In addition, the more proximal balloon allows for an early warning if the most distal and tissue retaining balloon is at risk of being damaged by the cutter.

In some embodiments (not shown) the tissue stabilizer comprises expandable and retractable shape memory alloy tines that function in a similar fashion to the inflatable balloon tissue stabilizer described above. In some embodiments, the tissue stabilizer comprises a mechanically expandable and retractable grid or equivalently, mesh that functions similarly to the inflatable element. In some embodiments, the tissue stabilizer comprises a biased element that functions similarly to the inflatable element. In some embodiments, the tissue stabilizer comprises expandable and retractable elements that are expanded by chemical, biological, physical triggers, or a combination thereof.

Figure 10A:
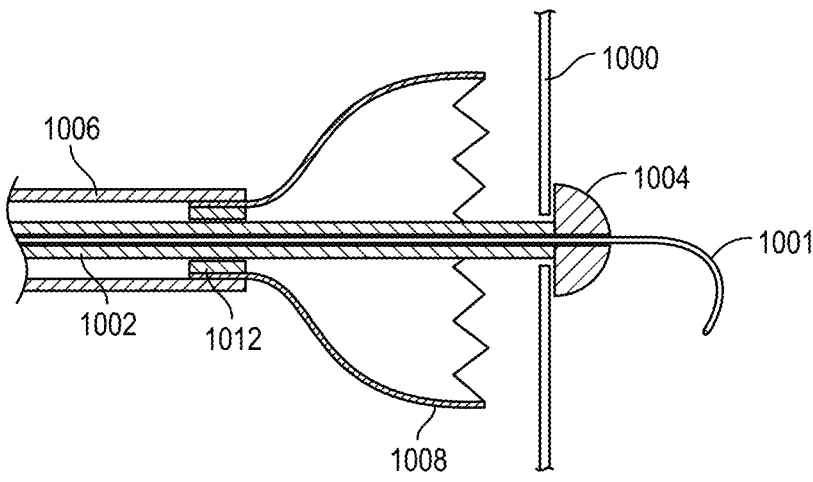
FIG. 10A is a representative illustration of an exemplary embodiment of the diameter of the tissue stabilizer element that is substantially smaller than that of the cutter (in their expanded states) to permit tissue tenting beyond the plane of the cutting face prior to tissue disruption.
Figure 10B:
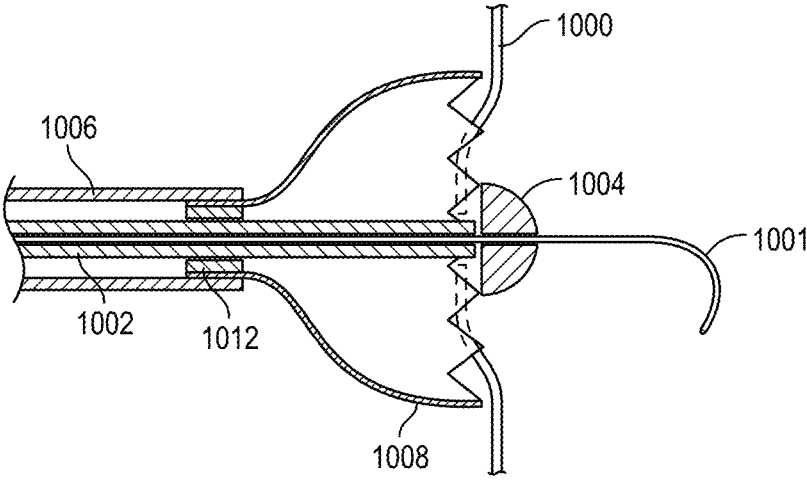
FIG. 10B is a representative illustration of an exemplary embodiment of the diameter of the substantially smaller tissue stabilizer element with the larger diameter the cutter (in their expanded states) creating an anastomosis with tissue tenting beyond the plane of the cutting face at the time of tissue disruption.

In some embodiments, as shown in FIGS. 10A-10B, the diameter of the tissue stabilizer element 1004 is substantially smaller than that of the cutter 1008 (in their expanded states) when deployed from the catheter 1 1002 along guidewire 1001, to permit tissue tenting beyond the plane of the cutting face prior to tissue disruption by pulling the tissue proximally or toward the cutter or a cage formed thereby or the right atrium and artificially creating a larger interatrial septum surface 1000 exposure to the cutter. This conformation permits the creation of an aperture that is larger than the diameter of the cutter. In some embodiments, a coaxial aligner 1012 affixed to catheter 2, 1006, or affixed to the cutter, 1008, ensures coaxial penetration and alignment of components. FIG. 10A is a representative illustration of an exemplary embodiment of the diameter of the tissue stabilizer element that is substantially smaller than that of the cutter (in their expanded states) to permit tissue tenting beyond the plane of the cutting face prior to tissue disruption. FIG. 10B is a representative illustration of an exemplary embodiment of the diameter of the substantially smaller tissue stabilizer element with the larger diameter the cutter (in their expanded states) creating an anastomosis with tissue tenting beyond the plane of the cutting face at the time of tissue disruption.

Figure 11A:
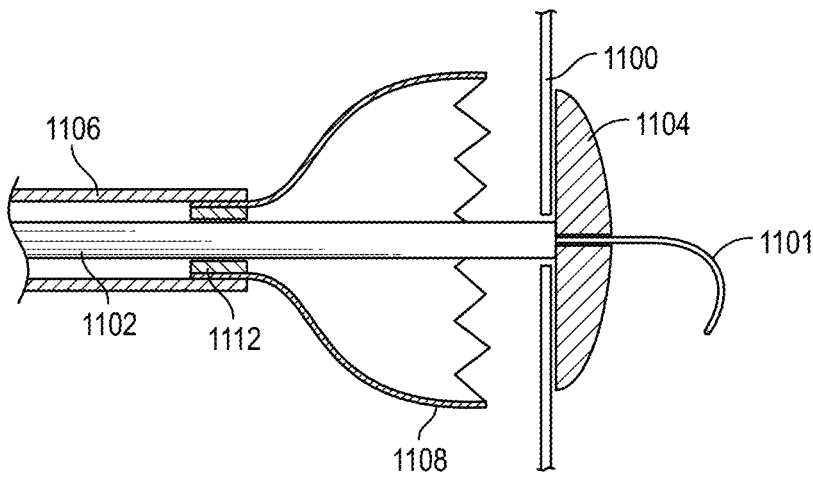
FIG. 11A is a representative illustration of an exemplary embodiment of the tissue stabilizer element sized only slightly smaller than the diameter of the cutter to minimize tissue tenting prior to tissue disruption to yield an aperture that more closely matches the diameter of the cutter.
Figure 11B:
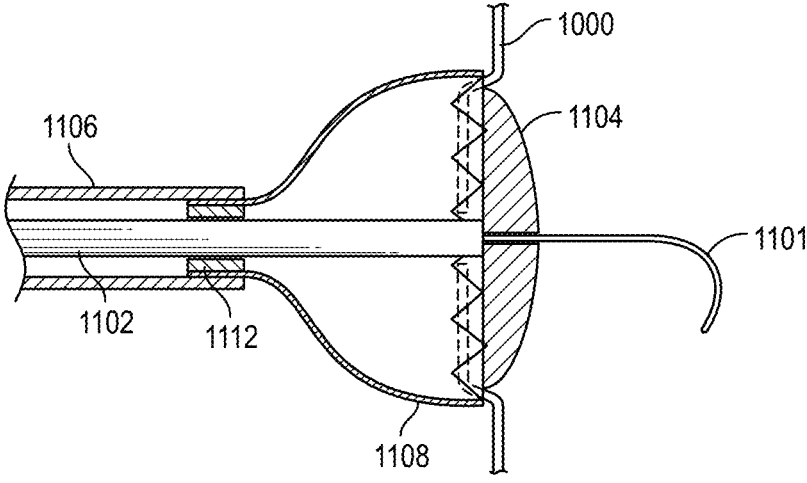
FIG. 11B is a representative illustration of an exemplary embodiment of the tissue stabilizer element sized only slightly smaller than the diameter of the cutter to minimize tissue tenting while creating an anastomosis, to yield an aperture that more closely matches the diameter of the cutter.
Figure 11C:
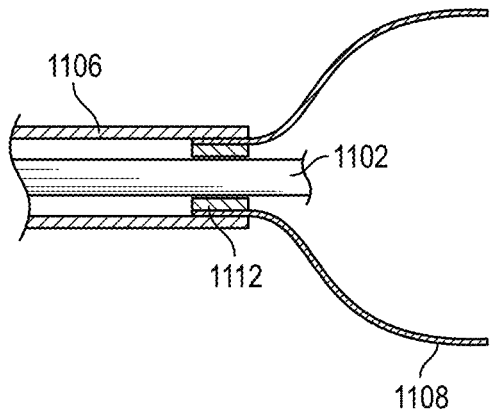
FIG. 11C is a representative illustration of an exemplary embodiment of the alignment between the cutter and catheter land catheter 2.
Figure 11D:
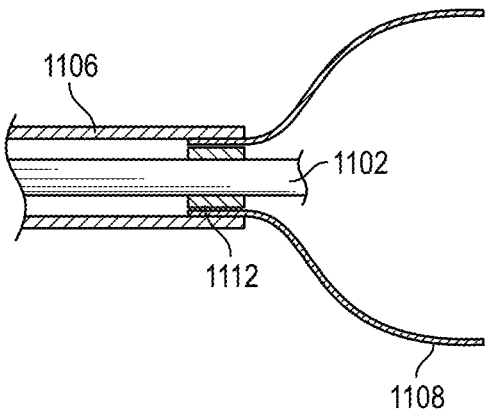
FIG. 11D is another representative illustration of an exemplary embodiment of the alignment between the cutter and catheter 1 and catheter 2.

In some embodiments, as shown in FIGS. 11A & 11B, the tissue stabilizer 1104 element is sized "only slightly" smaller than the diameter of the cutter 1108 to minimize tissue tenting prior to tissue disruption to yield an aperture that more closely matches the diameter of the cutter. In this embodiment, it is important to ensure coaxial alignment with guides 1112, such as shown in FIGS. 11A-11D, between the cutter and the tissue stabilizer to prevent inadvertent contact between the two elements during the cutting process, as well as between the cutter and both catheters 1 and 2. Catheter 1, 1102, catheter 2, 1106, cutter 1108, and coaxial aligner 1112 are also shown in FIGS. 11C & 11D. In some embodiments, (not shown) the tissue stabilizer element features imaging markers, such as radiopaque bands, at strategic locations so as to orient device assembly positioning within the body, its relationship to other system components, and to permit visibility and confirmation of deployed state (expanded or collapsed). FIG. 11A is a representative illustration of an exemplary embodiment of the tissue stabilizer element sized only slightly smaller than the diameter of the cutter to minimize tissue tenting prior to tissue disruption to yield an aperture that more closely matches the diameter of the cutter. FIG. 11B is a representative illustration of an exemplary embodiment of the tissue stabilizer element sized only slightly smaller than the diameter of the cutter to minimize tissue tenting while creating an anastomosis, to yield an aperture that more closely matches the diameter of the cutter. FIG. 11C is a representative illustration of an exemplary embodiment of the alignment between the cutter and catheter 1 and catheter 2. FIG. 11D is another representative illustration of an exemplary embodiment of the alignment between the cutter and catheter land catheter 2.

In some embodiments, the tissue stabilizer element also provides embolic protection by ensuring that the excised tissue post-cutting (speared by catheter 1), is captured and retained within the device assembly, thus permitting safe removal from the body by retracting the catheter 1, the excised tissue and the (minimally deflated) tissue stabilizer, into the coaxial collapsed cutter, when the cutter is retracted into the lumen of the delivery catheter, prior to removal from the right atrium and body.

Figure 12A:
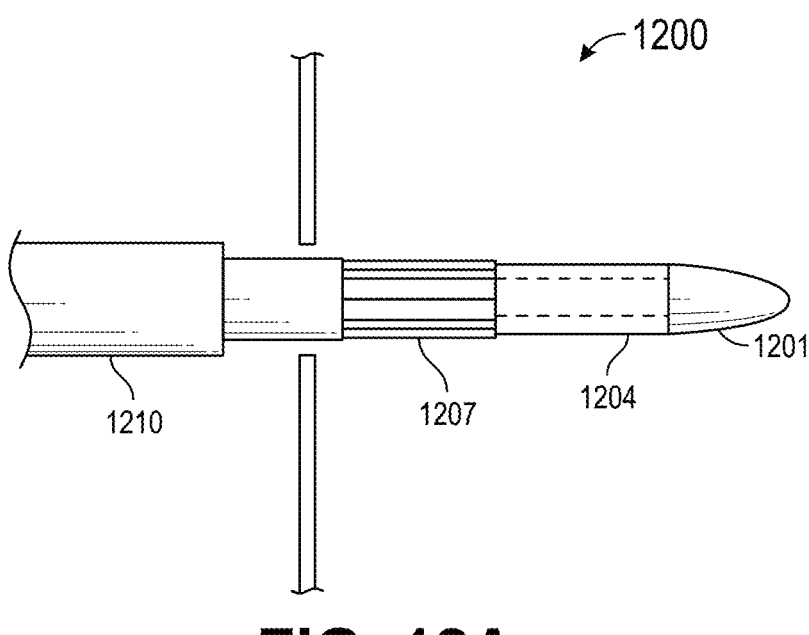
FIG. 12A is a representative illustration of an exemplary embodiment of the tissue stabilizer taking the form of a balloon with a protective skirt to protect the proximal edge of the balloon while it is in its collapsed form.
Figure 12B:
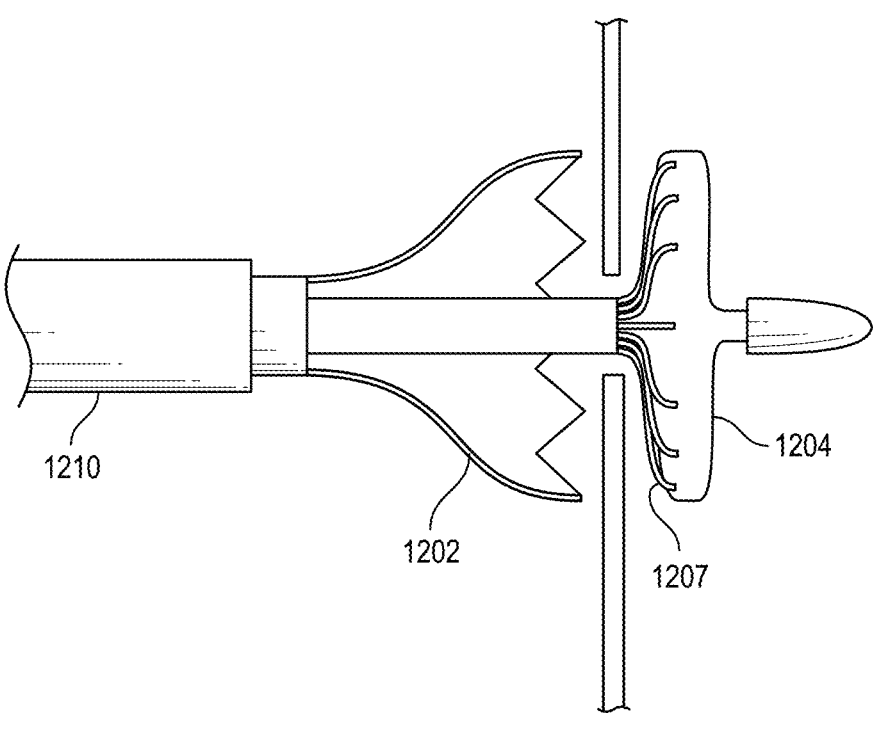
FIG. 12B is a representative illustration of an exemplary embodiment of the tissue stabilizer taking the form of a balloon with a protective skirt to protect the proximal edge of the balloon while it is in its expanded form wherein the protective skirt expands and collapses respective to the state of the balloon.

In some embodiments, as shown in FIGS. 12A & 12B, the tissue stabilizer 1204 is deployed from catheter 1, 1201, tracking along a guidewire (not shown), and takes the form of a balloon 1204 with a protective skirt 1207 that protects the proximal edge of the balloon while it is in its expanded form. This protective skirt expands and collapses respective to the state of the balloon. In some embodiments, the protective skirt, or the like, potentially serves at least two purposes: first, it protects the expanded tissue stabilizer from inadvertent damage due to accidental contact with the cutter 1202 once deployed in the right atrium by unsheathing the delivery catheter 3 1210; and second, it provides a broader or stiffer tissue stabilizing surface. In some embodiments, the protective skirt includes: a single tine element; multiple tine elements; an expanding mesh; at least one curved wire; an expanding disc; an expanding fan; a spring coil; or at least one hinged arm. In some embodiments, the protective skirt expands and collapses relative to the state of the balloon. FIG. 12A is a representative illustration of an exemplary embodiment of the tissue stabilizer taking the form of a balloon with a protective skirt to protect the proximal edge of the balloon while it is in its collapsed form. FIG. 12B is a representative illustration of an exemplary embodiment of the tissue stabilizer taking the form of a balloon with a protective skirt to protect the proximal edge of the balloon while it is in its expanded form wherein the protective skirt expands and collapses respective to the state of the balloon.

Figure 13A:
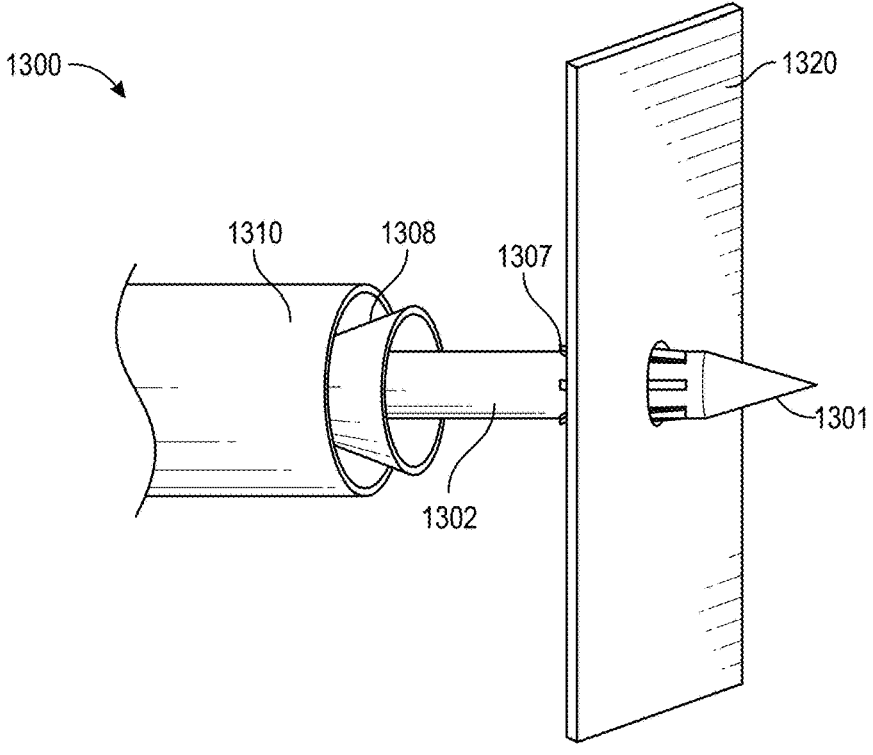
FIGS. 13A-13C are sequential representative illustrations of an exemplary embodiment of the tissue stabilizer taking the form of tines that pass through the septum, but cannot permit reverse passage through the initial puncture upon full deployment wherein the tines are built into the distal end of the catheter 1, and flatten out in response to being pulled flush with the septum.
Figure 13B:
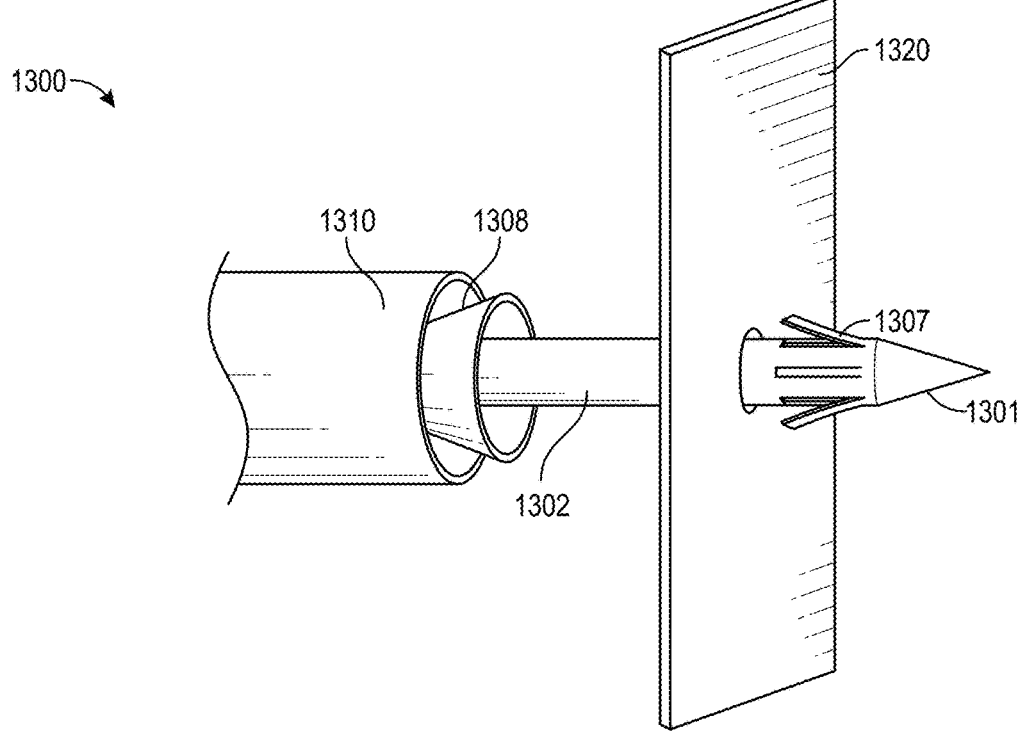
Figure 13C:
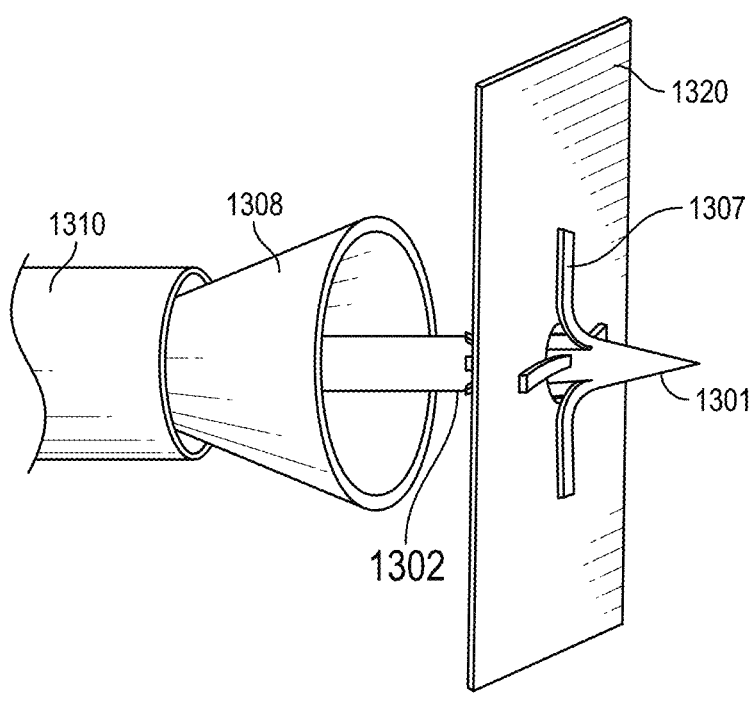

FIGS. 13A-13C are sequential representative illustrations of an exemplary embodiment of the tissue stabilizer taking the form of tines that pass through the septum, but cannot permit reverse passage through the initial puncture upon full deployment wherein the tines are built into the distal end of the catheter 1, and flatten out in response to being pulled flush with the septum. In some embodiments, as shown in FIGS. 13A-13C, the device assembly disclosed herein 1300 includes a delivery catheter 3 1310, and the tissue stabilizer 1307, which is deployed from catheter 1, 1302, after its penetrating tip 1301 has crossed the septum tracking along a guidewire (not shown), and takes the form of a plurality of tines 1307 that pass through the septum 1320 as they were being deployed from the catheter 1, and expand in an umbrella fashion, but cannot permit reverse passage back through the initial puncture upon full deployment. The tines are configured to fit into the distal end of catheter 1 unexpanded and allow to be flatten out against the left atrial side of the interatrial septum in response to being pulled flush with the septum. The tines extend or expand to a diameter less than the expanded diameter of the cutter 1308. In this embodiment, the tissue stabilizer is deformable under physical, chemical, biological triggers, or a combination thereof. Further, the tissue stabilizer, in some embodiments, includes two or more umbrella bones.

Figure 14A:
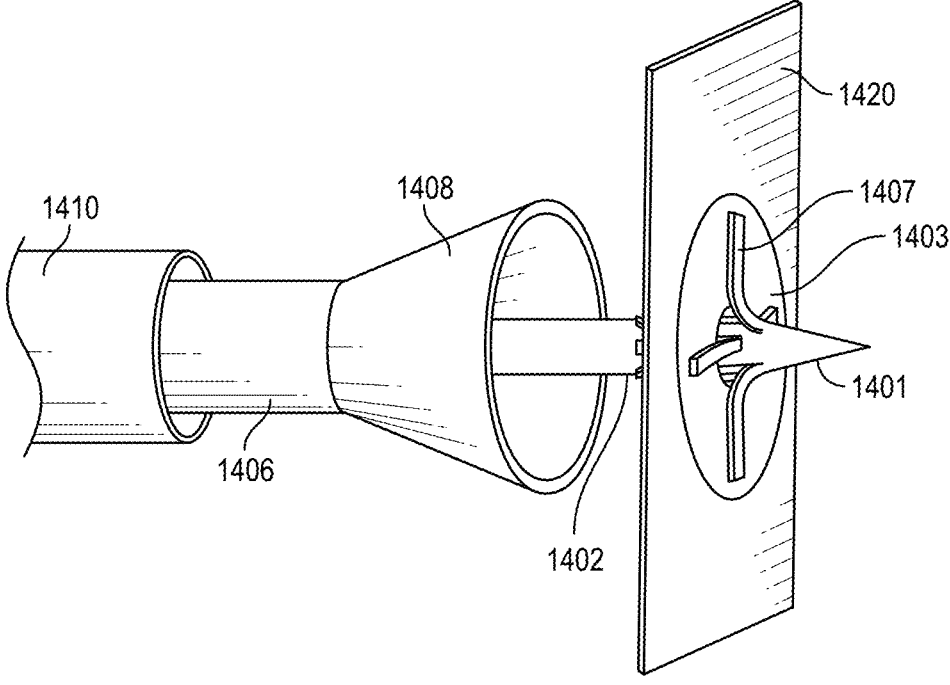
FIG. 14A is a representative illustration of an exemplary embodiment similar to that of FIGS. 13A-13C showing the tines partially pierce through the septum (with or without barbs at the end of each tine) to prevent the septum from moving off of the tines, wherein post-cutting, the expanded struts permit resheathing of a catheter over the tines and excised tissue, followed by removal of the device assembly from the body.
Figure 14B:
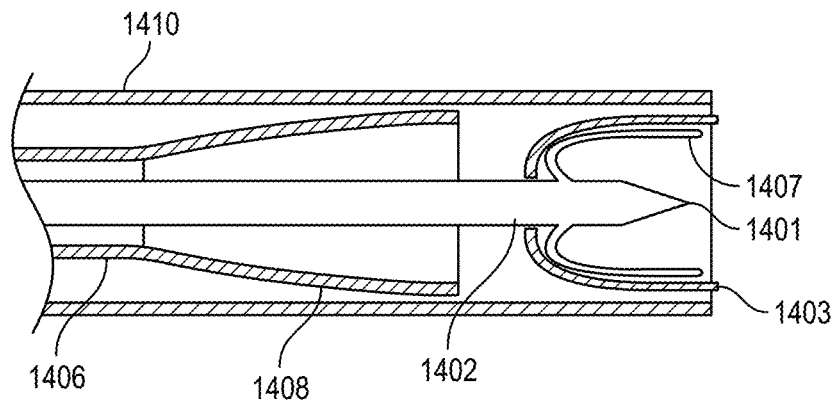
FIG. 14B is a representative illustration of an exemplary embodiment similar to that of FIGS. 13A-13C showing the tines partially pierce through the septum (with or without barbs at the end of each tine) to prevent the septum from moving off of the tines wherein the process of resheathing into the delivery catheter bends the tines backwards such that the tissue and tines fit into the delivery catheter.
Figure 14C:
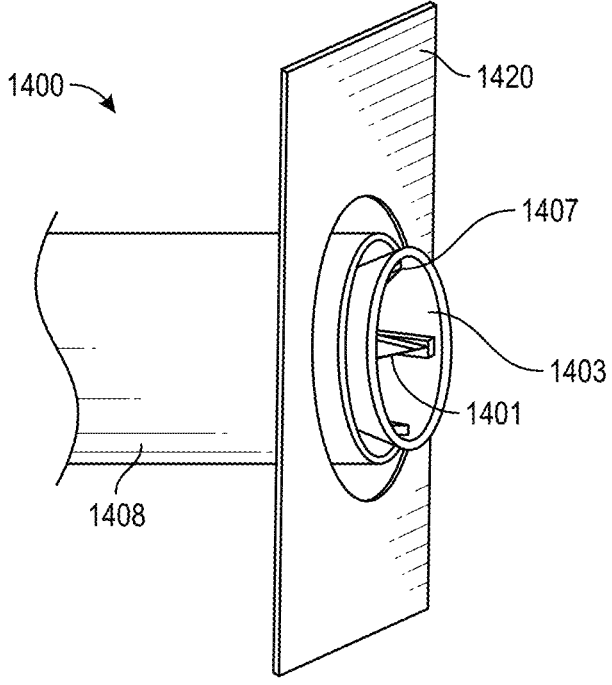
FIG. 14C is another representative illustration of an exemplary embodiment similar to that of FIGS. 13A-13C showing the tines partially pierce through the septum (with or without barbs at the end of each tine) to prevent the septum from moving off of the tines wherein the process of resheathing into the delivery catheter bends the tines backwards such that the tissue and tines fit into the delivery catheter when the delivery catheter is abutting the atrial septum.
Figure 15A:
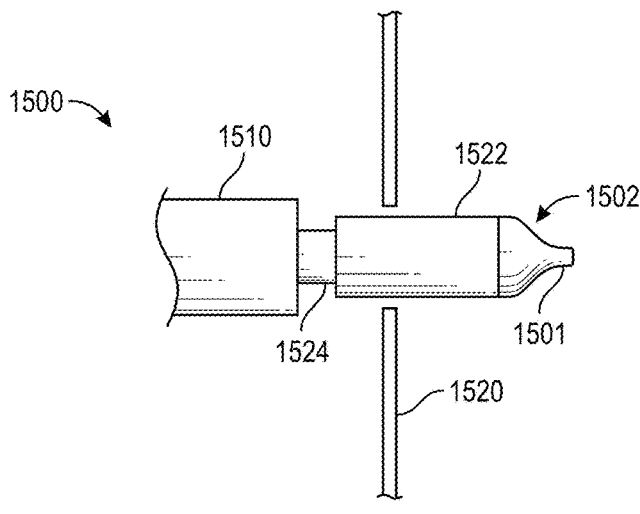
FIGS. 15A-15E are sequential representative illustrations of an exemplary embodiment of the tissue stabilizer taking the form of a loop supported by shape-set tines.
Figure 15B:
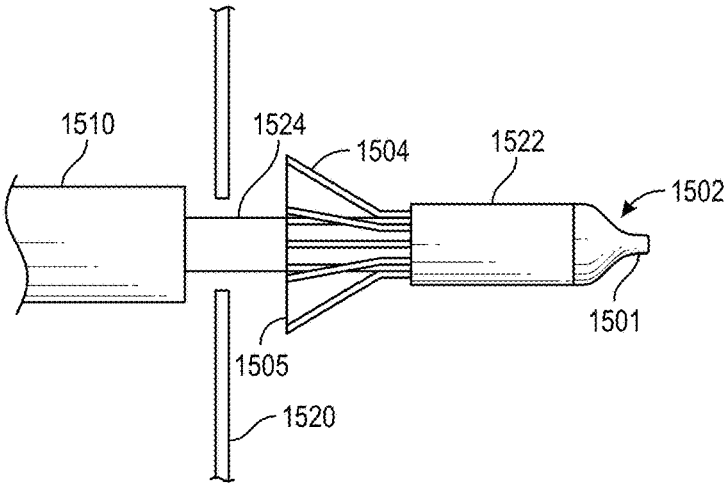
Figure 15C:
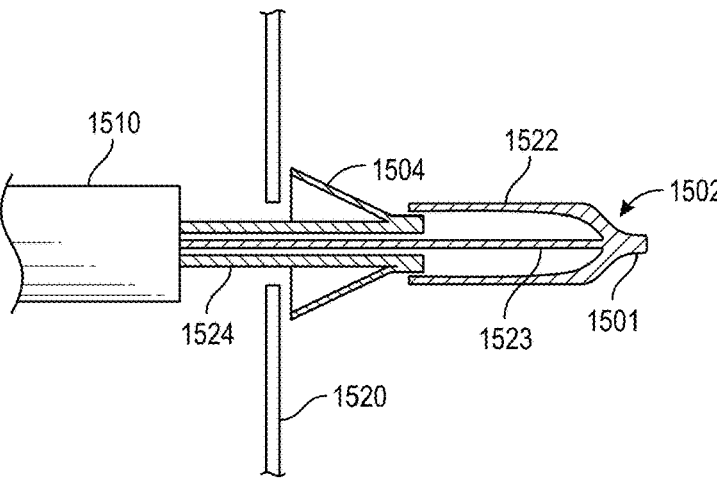
Figure 15D:
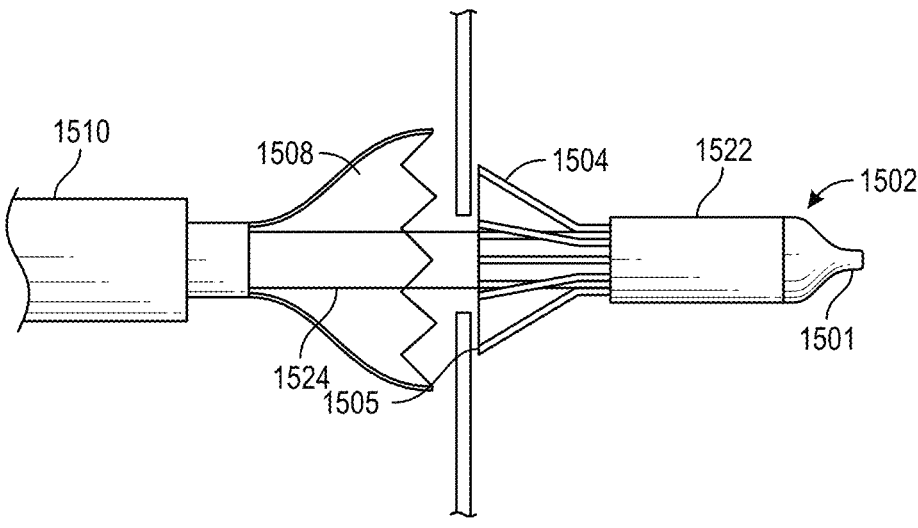
Figure 15E:
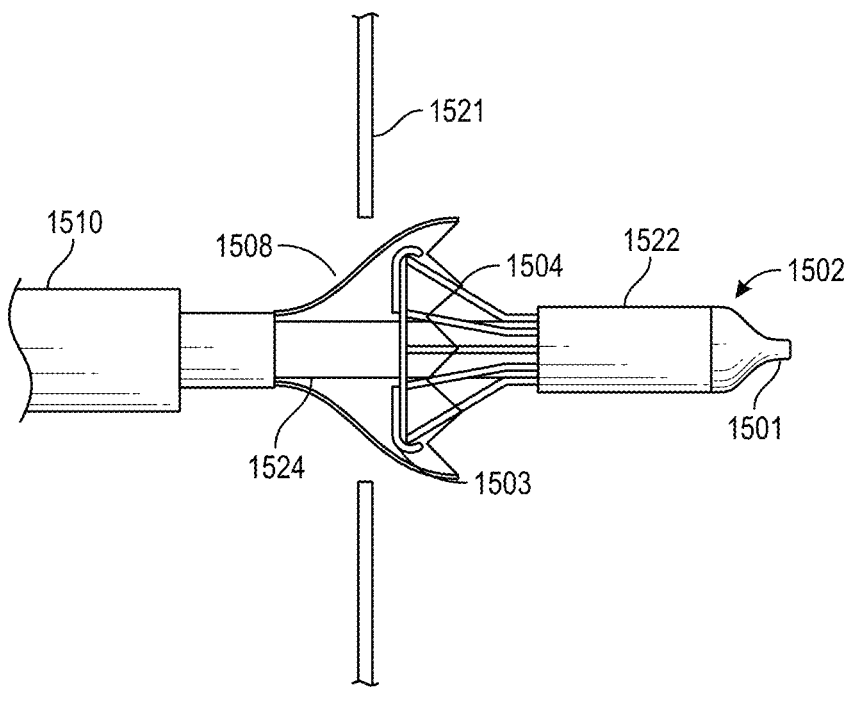

FIG. 14A is a representative illustration of an exemplary embodiment similar to that of FIGS. 13A-13C showing the tines partially pierce through the septum (with or without barbs at the end of each tine) to prevent the septum from moving off of the tines, wherein post-cutting, the expanded struts permit resheathing of a catheter over the tines and excised tissue, followed by removal of the device assembly from the body. FIG. 14B is a representative illustration of an exemplary embodiment similar to that of FIGS. 13A-13C showing the tines partially pierce through the septum (with or without barbs at the end of each tine) to prevent the septum from moving off of the tines wherein the process of resheathing into the delivery catheter bends the tines backwards such that the tissue and tines fit into the delivery catheter. FIG. 14C is another representative illustration of an exemplary embodiment similar to that of FIGS. 13A-13C showing the tines partially pierce through the septum (with or without barbs at the end of each tine) to prevent the septum from moving off of the tines wherein the process of resheathing into the delivery catheter bends the tines backwards such that the tissue and tines fit into the delivery catheter when the delivery catheter is abutting the atrial septum.

In some embodiments, as shown in FIGS. 14A-14C, the tissue stabilizer embodiment 1400 is deployed from catheter 1, 1402, tracking along a guidewire (not shown) and again takes the form of a plurality of tines 1407 that pass through the septum as they were being deployed from the catheter 1, and expand in an umbrella fashion. The tines partially pierce through the septum 1420 (with or without barbs at the end of each tine) to prevent the septum from moving off of the tines. In either embodiment (with or without barbs on the tines), after the cutter 1408 is deployed from the delivery catheter 3 1410, and a portion of the interatrial septum is excised, the expanded tines permit resheathing within the delivery catheter, over the re-collapsed tines and excised tissue 1403, followed by removal of the device assembly from the body, as described previously. In some embodiments, the process of resheathing into the delivery catheter 1410, the tines 1407 bend backwards such that the tissue and tines are easily drawn proximally into the delivery catheter. In this embodiment, the tissue stabilizer is deformable under physical, chemical, biological triggers, or a combination thereof. Further, the tissue stabilizer, in some embodiments, includes two or more umbrella bones. Catheter 2, 1406 and penetrating tip 1401 are also shown in FIGS. 14A-14C.

FIGS. 15A-15E are sequential representative illustrations of an exemplary embodiment of the tissue stabilizer taking the form of a loop supported by shape-set tines. Catheter 1, 1502 comprises a cap, 1523 having a central lumen that houses the collapsed tissue stabilizer. The tissue stabilizer catheter 1524, which is slidably engaged with the outside diameter of the catheter 1, 1502, is translated until its distal tip 1501, crosses the interatrial septum and allows for unsheathing of the catheter that comprises the tissue stabilizer in the left atrium. In some embodiments, as shown in FIGS. 15A-15E, the tissue stabilizer embodiment 1500 is collapsed and housed in catheter 1, 1502, that has a penetrating tip 1501, tracking along a guidewire (not shown) and takes the form of a loop supported by shape-set tines 1504, made with a shape memory metal or alloy. In some embodiments, catheter 1, 1502 comprises a cap 1522 and a shaft 1523. FIGS. 15A-15E are sequential representative illustrations of an exemplary embodiment of the tissue stabilizer taking the form of a loop supported by shape-set tines. Catheter 1, 1502 comprises a cap, 1523, wherein an additional catheter, has a central lumen that houses the collapsed tissue stabilizer. The tissue stabilizer catheter, 1524 is slidably engaged with the outside diameter of the catheter 1, 1502, which comprises the tissue stabilizer, is translated until its distal penetrating tip, 1501, crosses the interatrial septum and allows for unsheathing of the catheter that comprises the tissue stabilizer in the left atrium. After completion of the tissue cutting, the expanded struts then allow for the delivery catheter to be sheathed over the cutter 1508, the extended struts 1504, and the excised tissue 1503, followed by removal of the assembly and the excised tissue from the body. In some embodiments, the tissue stabilizer would take the form of a rigid plate made out of a shape memory metal or struts bridged together by one or more shape memory metal bridges. The loop supported by shape-set tines resembles a variety of shapes such as a teepee shape with a base ring or an umbrella shape with a base ring. In this embodiment, catheter 1, 1502 comprises a puncturing distal tip 1501 that is unsheathed in the left atrium. Upon unsheathing of the cap 1522, an array of tines that support a loop expands, forming an expanded loop 1505 such that the tines resist any deformation beyond a 90 degree angle with the septum. The tines fold up forward into catheter 1, 1502, that houses the tines until deployment into the left atrium where they expand to a range from 30 degrees to a 90 degree angle within the left atrium against the left atrial side of the interatrial septum 1520. In some embodiments, the tines expand up to about a 90 degree angle, up to about a 80 degree angle, up to about a 75 degree angle, up to about a 60 degree angle, up to about a 50 degree angle, up to about a 45 degree angle, up to about a 40 degree angle, up to about a 35 degree angle, up to about a 30 degree angle, from about a 30 degree angle to about a 80 degree angle, from about a 30 degree angle to about a 75 degree angle, from about a 30 degree angle to about a 60 degree angle, from about a 20 degree angle to about a 75 degree angle, from about a 15 degree angle to about a 60 degree angle, from about a 30 degree angle to about a 45 degree angle, from about a 15 degree angle to about a 90 degree angle, up to a 90 degree angle, up to a 80 degree angle, up to a 75 degree angle, up to a 60 degree angle, up to a 50 degree angle, up to a 45 degree angle, up to a 40 degree angle, up to a 35 degree angle, up to a 30 degree angle, from a 30 degree angle to a 80 degree angle, from a 30 degree angle to a 75 degree angle, from a 30 degree angle to a 60 degree angle, from a 20 degree angle to a 75 degree angle, from a 15 degree angle to a 60 degree angle, from a 30 degree angle to a 45 degree angle, or from a 15 degree angle to a 90 degree angle within the left atrium against the left atrial side of the interatrial septum 1520. This action would then be followed by the deployment of the cutter 1508 from the delivery catheter 3 1510 to create the anastomosis shunt 1521. After completion of the tissue cutting, the excised tissue 1503 is trapped in between the cutter and the tissue stabilizer, the expanded struts would then be collapsed by the radial force applied by the cutter as the cutter is collapsed and resheathed in the delivery catheter, followed by removal of the assembly and the excised tissue 1503 from the body, in a manner described herein.

Figure 59D:
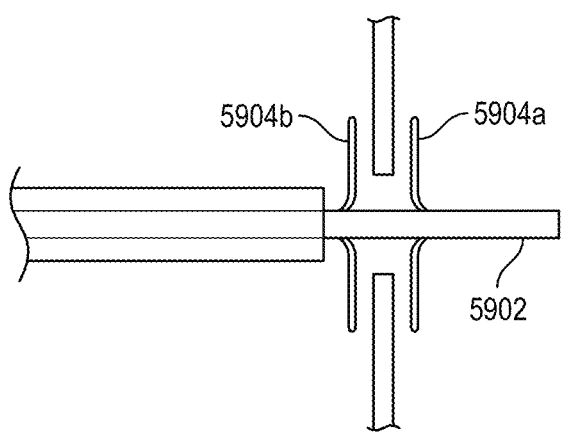
FIG. 59D shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.
Figure 59E:
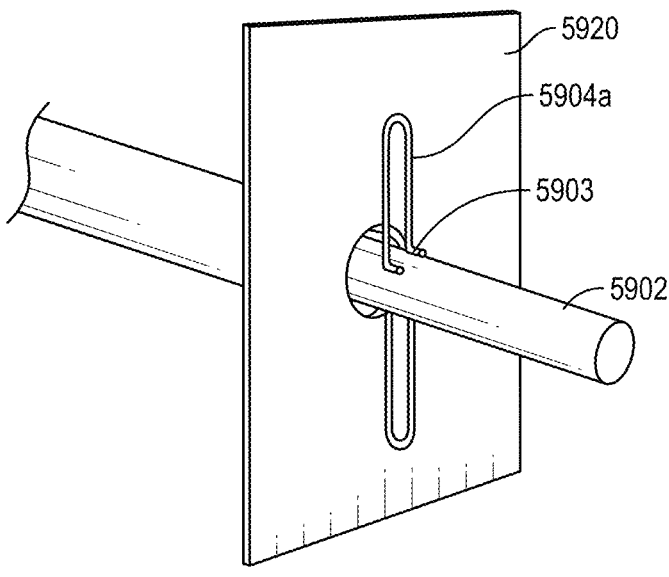
FIG. 59E shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.

Referring to FIGS. 59A-59E, in a particular embodiments, after the device assembly is deployed to the right atrium, the tissue stabilizer housing catheter 5905, optionally with or without other elements enclosing the tissue stabilizer therewithin is advanced to the left atrium, and is pulled proximally to un-sheath half of the self-expanding oval shaped clips 5904*a* in the left atrium and, optionally afterwards, the other half of the self-expanding clips 5904*b* are unsheathed in the right atrium, thus sandwiching the interatrial septum 5920 therebetween. In this particular embodiment, the self-expanding clips are pivotable about a hinge point 5903 on the tissue stabilizer catheter 5902. In its collapsed state the proximal clips are folded towards the proximal end and the distal clips towards the distal end of the device assembly. In some embodiments, both clips could face the same direction when collapsed and enclosed in the housing catheter. In some embodiments, two or more clips are positioned on each side of the septum in order to sandwich the tissue and improve tissue stabilization. FIG. 59A shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum. FIG. 59B shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum. FIG. 59C shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum. FIG. 59D shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum. FIG. 59E shows an exemplary sequential embodiment of the expandable tissue stabilizer of a device assembly as disclosed herein wherein the tissue stabilizer housing catheter is pulled back to un-sheath half of the self-expanding oval shaped clips in the left atrium and the other half in the right atrium, thus sandwiching the interatrial septum.

Figure 73A:
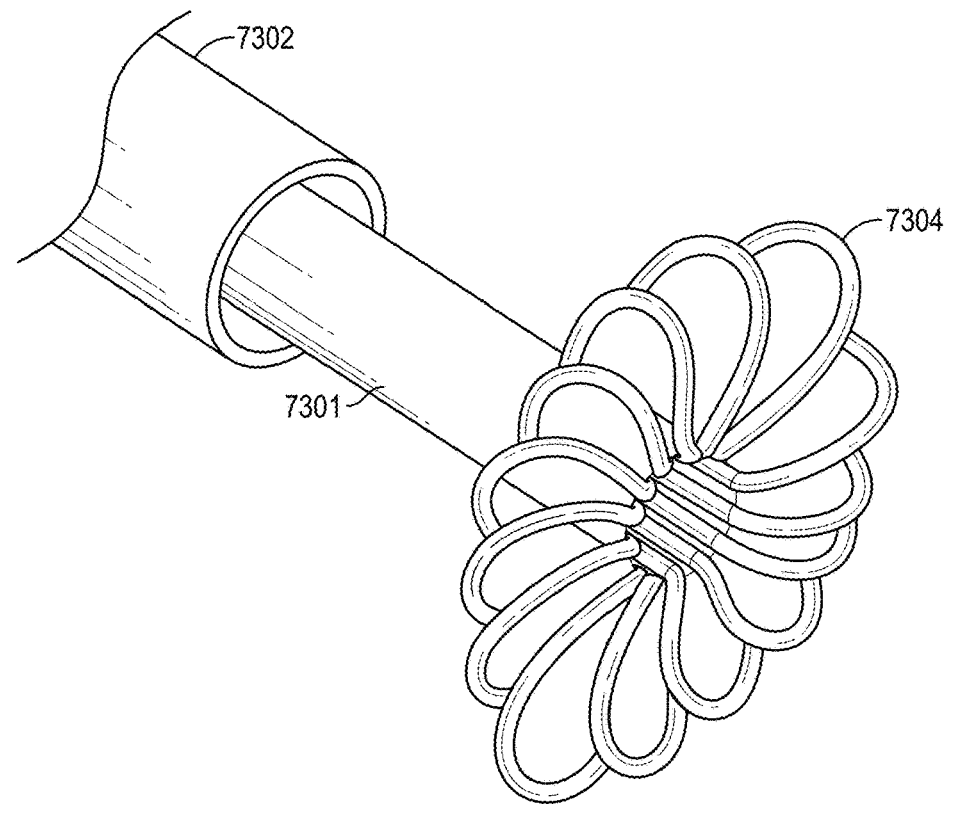
FIG. 73A shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat.
Figure 73B:
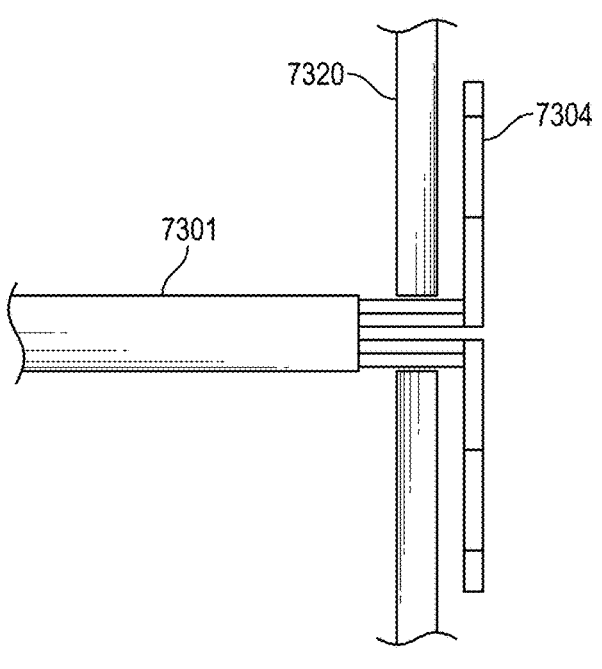
FIG. 73B shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat.
Figure 73C:
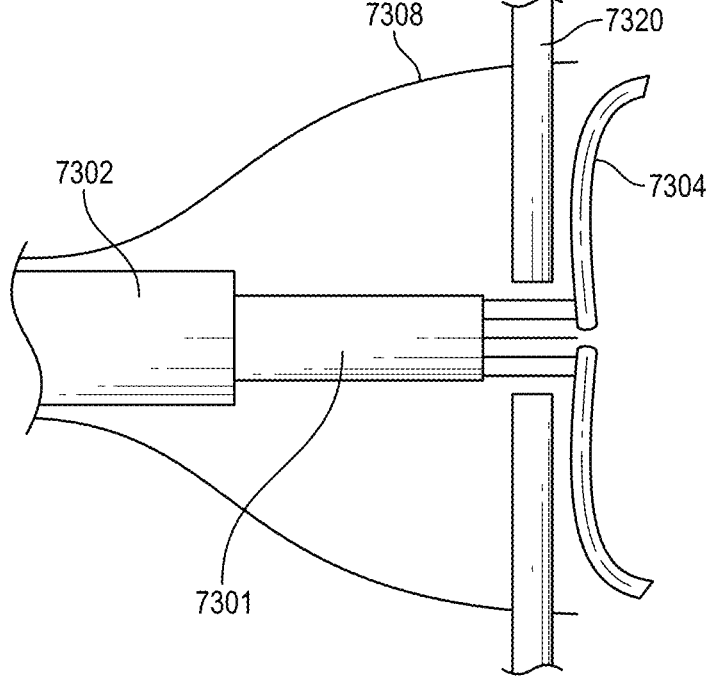
FIG. 73C shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat.

Further, in some embodiments, as shown in FIGS. 73A-73C, the tissue stabilizer 7304 would take the form of a rigid plate made out of shape memory alloy struts or a mesh made out of lassos or petals. In this embodiment, catheter 1, 7301, comprising the petals would be translated through catheter 2, 7302, until its distal tip was unsheathed in the left atrium. Upon unsheathing the distal tip of catheter 1, an array of shape memory struts would be allowed to expand to a flat 90 degree angle with the septum FIGS. 73A-73B, relative to the axis of the delivery catheter, which would ensure tissue capture and tissue stabilization during cutting motion. In some embodiments these shaped memory metal struts, optionally interlocking petals, would form an arc bending away from the septum 7320 upon unsheathing to prevent the struts from getting caught on the lips of the cutter 7308 while still allowing for tissue capture, as shown in FIG. 73C. FIG. 73A shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat. FIG. 73B shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat. FIG. 73C shows an exemplary sequential embodiment of the tissue stabilizer of a device assembly as disclosed herein wherein the tissue stabilizer takes the function of a rigid plate when deployed as it takes the form of a series interlocking petals when exposed distally out of a catheter in the left atrium such that in cross section would appear flat.

FIG. 74A shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74B shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74C shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

FIG. 74D shows an exemplary sequential embodiment of the tissue stabilizer of a device assembly as disclosed herein wherein the tissue stabilizer consists of a series of radially self-expanding struts connected circumferentially by a series of shape memory bridges. In addition, there exists an internal catheter 4 to the tissue stabilizer that allows for folding the struts and connected bridges proximally after the septum has been cut to fold the excised tissue inside of the folded struts and bridges.

In some embodiments, as shown in FIGS. 74A-74D, each of these struts could be bridged together by one or more shape memory metal bridges 7401 at any point along the length of the struts to create a more evenly supported cutting surface on the septum 7420 for the cutter to cut through. This would then be followed by the expanded cutter which would follow in the next coaxial catheter. After completing the tissue cutting, the expanded struts would be extended or collapsed, allowing for catheter 2, 7402, to be sheathed over the extended or collapsed struts and excised tissue, followed by removal of the assembly and the excised tissue from the body. In some embodiments, the shape memory struts are connected to catheter 1 and sheathed by a catheter 2 which travels over catheter 1. In some embodiments, the shape memory struts are connected to catheter 1 and sheathed by catheter 4 which travels within catheter 1, catheter 2 is housed in delivery catheter 3, 7403, which crosses the septum to deploy the struts. Catheter 2 is deployed in the left atrium by translating catheter 2 relatively distal to catheter 1 allowing the struts to be expanded in the left atrium. This would then be followed by the expanded cutter which would follow in the next coaxial catheter. Upon completion of the tissue excision, the struts are folded back up by translating catheter 2 relatively proximal to catheter 1, and in the process, collapsing the excised tissue 7420 into a folded state within the struts of catheter 1, as shown in FIG. 74D. After completion of the tissue and strut packing, the packaged struts and excised tissue would then allow for catheter 3 to be sheathed over catheter 2 and the struts and excised tissue followed by removal of the assembly and the excised tissue from the body.

Figures 75A, 75B, 75C, 75D, 75E:
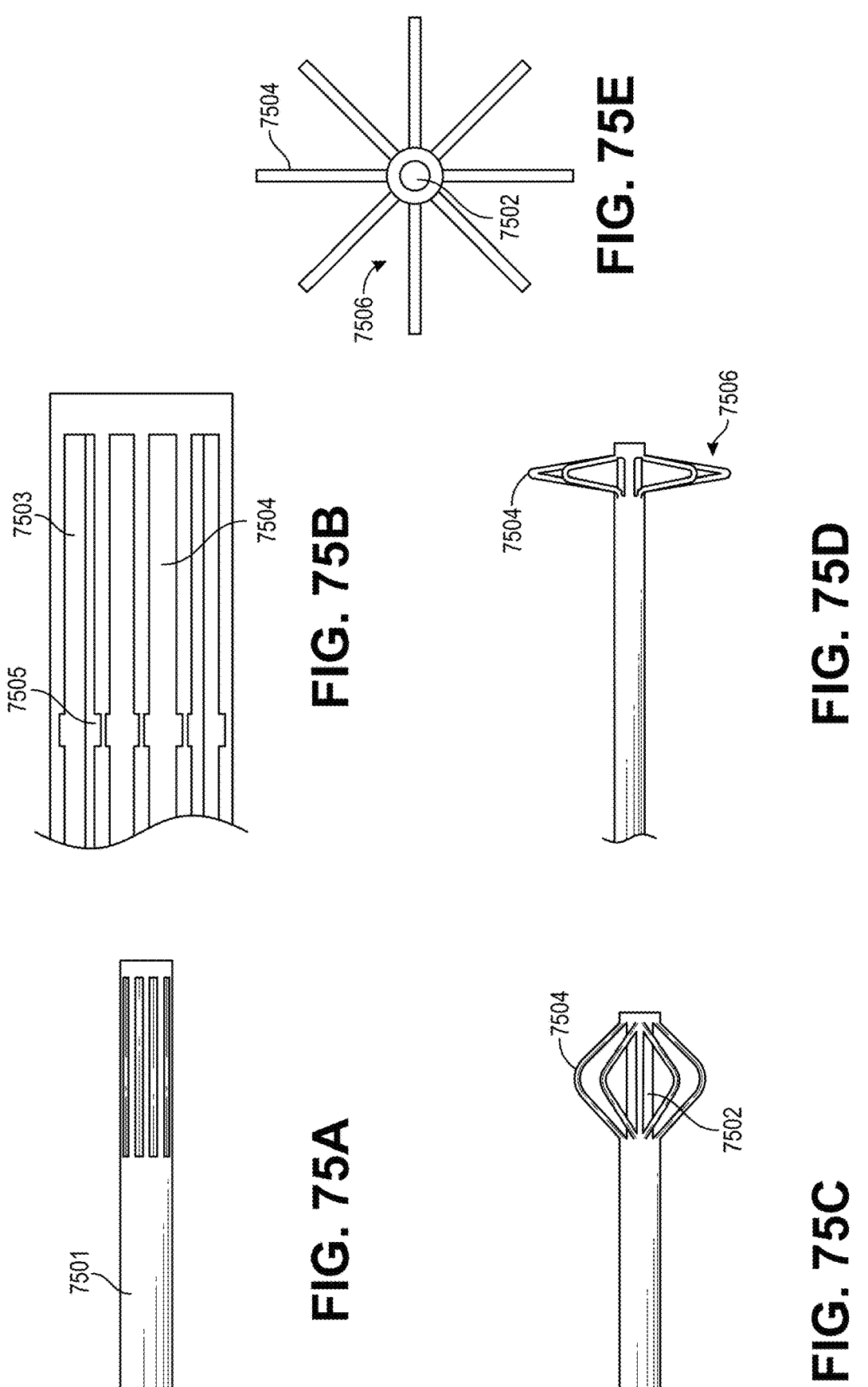
FIG. 75A shows an exemplary sequential embodiment of the tissue stabilizer of a device assembly as disclosed herein.
FIG. 75B shows an exemplary sequential embodiment of the tissue stabilizer of a device assembly as disclosed herein.

FIG. 75A-75E shows an exemplary sequential embodiment of the tissue stabilizer of a device assembly as disclosed herein. Referring to FIGS. 75A-75E, in a particular embodiment, the catheter comprising the tissue stabilizer is incorporated into the guide catheter 7501 that positions the tensioner, optionally perpendicularly, towards the septal wall, eliminating the need for a separate catheter that solely advances the tensioner. In some embodiments, the catheter comprising the tissue stabilizer is the guide catheter. The catheter, on which the tensioner is mounted, in some embodiments, resides in the blade catheter. In some embodiments, the OD of the catheter on which the tissue stabilizer is mounted is flush with the ID of the blade catheter. In this embodiment, the distal end of the catheter comprising the tensioner features slits 7503 numbering in the range from 2 to 20, each with a length of about 1 to 100 mm, about 1 to 50 mm, about 50 to 80 mm, about 1 to 30 mm, about 1 to 15 mm, about 15 to 40 mm, or about 25 to 55 mm, and a width of about 0.5 to 5.0 mm, about 0.5 to 1 mm, about 1 to 2 mm, about 2 to 3 mm, about 3-5 mm, about 1.5 to 3.5 mm, or about 2 to 4 mm. The tensioner, in some embodiments, consists of 2 to 20 struts 7504, each with a length of about 1 to 100 mm, about 1 to 50 mm, about 50 to 80 mm, about 1 to 30 mm, about 1 to 15 mm, about 15 to 40 mm, or about 25 to 55 mm, and a width of about 0.5 to 5.0 mm, about 0.5 to 1 mm, about 1 to 2 mm, about 2 to 3 mm, about 3-5 mm, about 1.5 to 3.5 mm, or about 2 to 4 mm. In some embodiments, the wall thickness of the struts is thicker or thinner than the wall thickness of the guide catheter or catheter comprising the tensioner. In some embodiments, the width of the struts narrows to a notch 7505 at the midpoint along the length of the struts, as shown in FIG. 75B. In some embodiments, the width of the notch 7505 at the midpoint of the length of the struts is about 1% to about 50%, about 1% to about 25%, about 25% to about 50%, about 1% to about 15%, about 15% to about 25%, about 25% to about 35%, or about 35% to about 50% smaller than the struts width beyond the notch. The notch has a length in the range of about 1 to 90 mm, about 1 to 50 mm, about 50 to 80 mm, about 1 to 30 mm, about 1 to 15 mm, about 15 to 40 mm, or about 25 to 55 mm. In some embodiments, the notches allow the struts to bend at their midpoint. In some embodiments, notches are also placed at the distal and proximal ends of the struts to reduce the amount of force required to radially deploy the struts.

Figure 71:
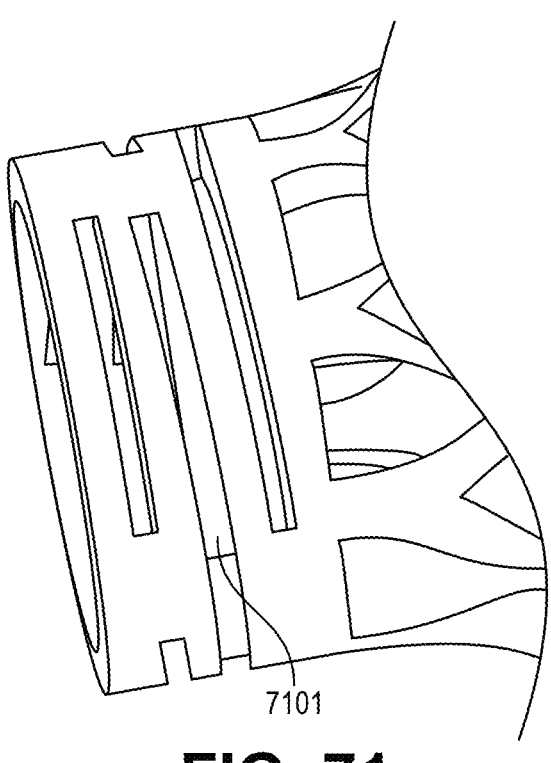
FIG. 71 shows an exemplary embodiment of the self-expanding blade of a device assembly as disclosed herein wherein the proximal edge of the self-expanding blade has a series of helical cut-out sections to facilitate robust attachment to a catheter.

In some embodiments, the catheter comprising the tensioner (catheter 1) 7501 is attached, at its distal end, to a second catheter 7502 that resides internal to the catheter comprising the tensioner. In some embodiments, catheter 1 comprises a series of helical cut-out sections, distal to the tensioner at the distal end of catheter 1, to facilitate secure attachment to a catheter 2. These helical cut-outs, similar to the cut-outs as shown in FIG. 71, facilitate the embedding of catheter 2 into catheter 1. Cut-out designs, in some embodiments, take an alternative geometry; non-limiting examples include: a circle; a square; a rectangle; a triangle; an oval; a polygon; or any other feasible geometrical shapes. FIG. 71 shows an exemplary embodiment of the self-expanding blade of a device assembly as disclosed herein wherein the proximal edge of the self-expanding blade has a series of helical cut-out sections to facilitate robust attachment to a catheter.

In its unexpanded state, as in FIG. 75A, the catheter comprising the tensioner crosses the septal wall from the right atrium to the left atrium. In some embodiments, the catheter(s) comprising the tensioner are translated over the guidewire left in place from a transseptal puncture procedure.

In some embodiments, the tensioner is deployed once the full length of the struts, (in their collapsed state), have crossed the septal wall into the left atrium. The tensioner, as in FIG. 75C, is deployed, in some embodiments, by pushing catheter 1, 7501, over catheter 2, 7502, to expand the struts outward into a flower-like shape 7506 as in FIGS. 75D-75E. The expanded struts, in some embodiments, is perpendicular in orientation to the septal wall and rigid enough resist bending in excess of 45° out of the radial plane. This, in some embodiments, helps prevent the struts from exhibiting significant risk of being pulled through the septal wall. In some embodiments, the tensioner is deployed by pulling catheter 2 towards catheter 1.

In some embodiments each strut is covered with a coating of silicone, latex, rubber, polymer, textile, polymeric or shape memory alloy mesh, or combination thereof at or around the notches that reside at the midpoint of the struts. In some embodiments, the length of the coating is in the range of about 1 to 100 mm, about 1 to 50 mm, about 50 to 80 mm, about 1 to 30 mm, about 1 to 15 mm, about 15 to 40 mm, or about 25 to 55 mm, and a width of about 0.5 to 5.0 mm, about 0.5 to 1 mm, about 1 to 2 mm, about 2 to 3 mm, about 3-5 mm, about 1.5 to 3.5 mm, or about 2 to 4 mm. The coating helps prevent the septal wall from being punctured by the tips of the expanded struts. In some embodiments, the coating is applied to the full length of the struts. In some embodiments, this coating is applied along the length of all struts as one layer; when the struts of the tensioner are expanded, the coating is expanded to impart an "umbrella" effect.

In some embodiments, the struts feature one or more radio-opaque markers. These markers will facilitate visualization of the tensioner throughout the procedure.

In some embodiments, the tissue stabilizer is made of stainless steel. In some embodiments, the tissue stabilizer or, equivalently, the tensioner comprises materials other than stainless steel. Non-limiting examples of such materials include, but are not limited to, one or more of the following: shape memory metal or alloy, shape memory polymer, aluminum, polymer, reinforced catheter, or a combination thereof.

In some embodiments, (not shown), the tissue stabilizer takes the form of a shape memory (e.g. shape memory alloy or metal) mesh that will have one of two configurations throughout the procedure: collapsed (within catheter 4 predeployment to the left atrium) and a bulbous structure (post-deployment in the left atrium). Once catheter 4 is placed within the left atrium, the tissue stabilizer is deployed through backward translation of catheter 4 over catheter 1 (the catheter that comprises the tissue stabilizer). The tissue stabilizer is resheathed through forward translation of catheter 4 (over catheter 1).

In some embodiments, (not shown) the tissue stabilization is actuated by sandwiching the septum between magnets on either side of the septum. In this embodiment, a catheter 4 which resides coaxially and translates in between catheter 1 (the catheter that houses the tissue stabilizer) and 2 (the catheter that comprises the expandable cutter), has a magnetic element around its distal tip. A catheter 5, which resides coaxially in catheter 1, has magnetic elements in its distal tip that expand radially upon translation out of the tip of catheter 1 to allow for tissue stabilization when the magnetic elements from catheter 5 and 4 are brought into close proximity.

In some embodiments, (not shown), the tissue stabilization is actuated by sandwiching the septum between a magnet on either side of the septum. In this embodiment, a catheter 4 which resides coaxially and translates in between catheter 1 and 2, has a magnetic element around its distal tip. Catheter 1 has a magnetic distal tip that has a gradual conical shape to allow for piercing through the septum and a flat proximal face to the conical shape to allow for tissue stabilization upon sandwiching the septum between the magnetic elements on catheter 1 and 4.

Figure 16A:
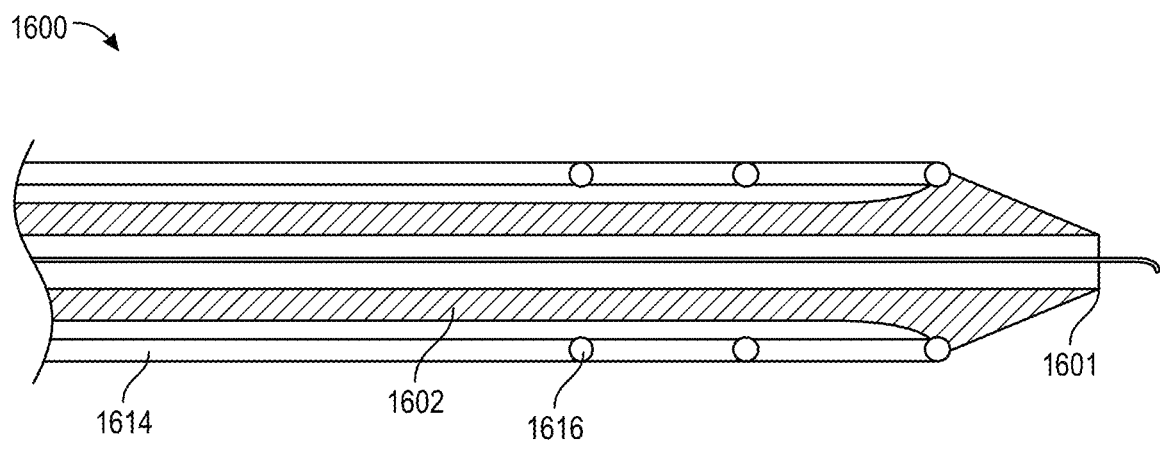
FIG. 16A is a representative illustration of an exemplary embodiment of a tissue stabilizer with an "umbrella-type" mechanism in an un-deployed state.
Figure 16B:
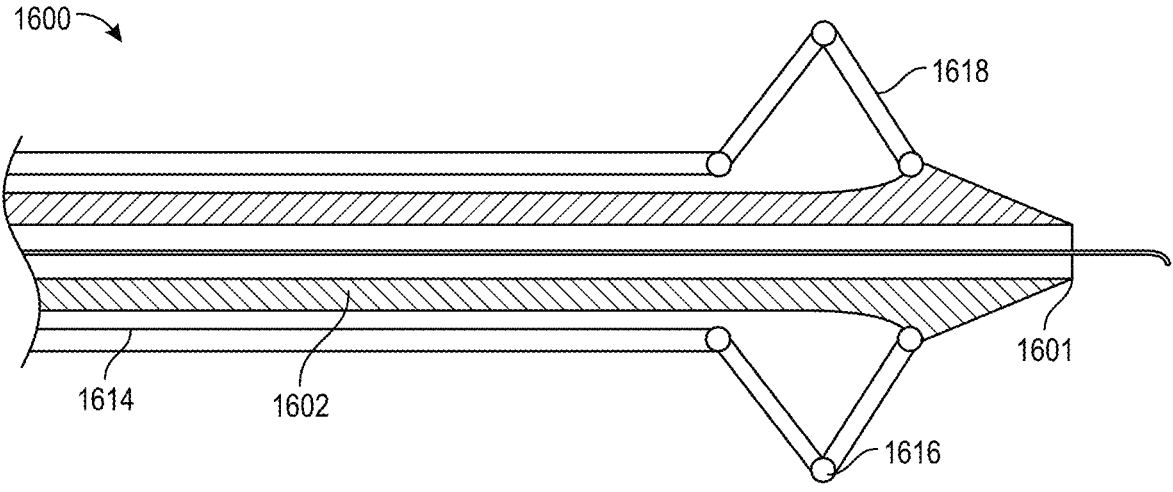
FIG. 16B is a representative illustration of FIG. 16A in a deployed state, wherein the tissue stabilizer is deployed via an "umbrella" mechanism whereas the stabilizing elements diameter increase is triggered by translating a catheter towards the tip of the catheter holding the tissue stabilizer, which in turn rotates two rigid struts up and together by flexing at hinge points where the two struts are connected to the deployment catheter, the holding catheter, and each other.

FIG. 16A is a representative illustration of an exemplary embodiment of a tissue stabilizer with an "umbrella-type" mechanism in an un-deployed state. FIG. 16B is a representative illustration of FIG. 16A in a deployed state, wherein the tissue stabilizer is deployed via an "umbrella" mechanism whereas the stabilizing elements diameter increase is triggered by translating a catheter towards the tip of the catheter holding the tissue stabilizer, which in turn rotates two rigid struts up and together by flexing at hinge points where the two struts are connected to the deployment catheter, the holding catheter, and each other.

In some embodiments, as shown in FIGS. 16A & 16B, the tissue stabilizer 1600 is deployed from catheter 1, 1602, tracking along a guidewire with a penetrating tip 1601 and is deployed via an "umbrella" mechanism 1618, whereas the stabilizing element's diameter increase is triggered by translating a catheter 4, 1614 towards the tip of catheter 1, 1602, which rotates two rigid struts 1618 up and together by flexing at live hinge points 1616 where the two struts are connected to catheter 4, 1616, catheter 1, 1602, and each other. The live hinges allow for flexure to the deployed state, but no further, preventing the struts from flexing beyond 90 degrees ensuring tissue retention. In some embodiments, the hinges and hinge points 1616 allow for flexure to the deployed state, but no further, to prevent the struts from flexing beyond 90 degrees and ensuring tissue retention.

In some embodiments, (not shown), the tissue stabilizer is formed by a rigid pigtail-shaped catheter or wire that, once deployed, is able to resist being pulled through the septum and allows for tissue stabilization. In some embodiments, the tissue stabilizer includes a balloon which has a diameter in the range of 2 mm to 12 mm in expanded state. In some embodiments, the balloon is armored to protect against inadvertent puncture by the cutter or other parts of the assembly.

In some embodiments, the tissue stabilizer is attached to a catheter (for example, catheter 1) or a wire (the guidewire or an additional wire). In some embodiments, a tissue stabilizer delivery catheter (for example, catheter 2) is used to deliver the tissue stabilizer to the left atrium in its compact state.

In some embodiments, a stent blade cutter is attached to a "blade catheter" (for example, catheter 3). A delivery catheter (for example, catheter 4) houses the stent blade cutter in its compact state. A guide catheter (for example, catheter 5), in some embodiments, defines the path that the cutter takes from the mouth of the delivery catheter up to the septum and ensures coaxial alignment during cutting of the septum.

In some embodiments, the device assembly disclosed herein includes a shape memory alloy or metal mesh catheter which offers tissue stabilization providing counter tension to the actuation of the cutter so as to minimize any unintended tissue deformation, rotation, or displacement due to unbalanced forces. The tissue stabilizer element also, in some embodiments, prevents the excised tissue from inadvertently coming free from the system and permits translation of the excised tissue into the delivery catheter prior to removal of the device assembly from the body.

In some embodiments, the shape memory alloy mesh housing catheter retains the tissue stabilizer in its compacted state before it is delivered to the left atrium and allows for its controlled deployment, because the tissue stabilizer is a self-expanding unit in this disclosure form.

Referring to FIG. 54, in some embodiments, the shape memory alloy mesh catheter features one or more shape memory alloy mesh discs 5404a distal to the one in contact with the septum 5404b to serve as a failsafe to 1) ensure that excised (or partially excised) tissue 5420 does not come free from the interatrial septum and device assembly, and 2) allow for the blade to continue translating through the septum in the event that one of the shape memory alloy mesh plugs is inadvertently pulled through the septum prior to completion of a full circumferential cut, as shown in FIG. 54. FIG. 54 shows an exemplary embodiment of the device assembly as disclosed herein in which the shape memory alloy mesh catheter features one or more shape memory alloy mesh discs distal to the one in contact with the septum to serve as a failsafe to 1) ensure that excised (or partially excised) tissue does not come free from the interatrial septum and device, and 2) allow for the blade to continue translating through the septum in the event that one of the shape memory alloy mesh plugs is inadvertently pulled through the septum prior to completion of a full circumferential cut.

FIGS. 55A-55B show exemplary embodiments of the one or more shape memory alloy discs and their sizes relative to the cutter of a device assembly as disclosed herein. Referring to FIGS. 55A and 55B, in some embodiments, the shape memory alloy mesh features one or more shape memory alloy discs distal to the tissue stabilizing disc 5504b that is sized to be larger than the diameter of the stent blade in both of their expanded states to act as a dock to prevent the stent blade from translating past the shape memory alloy mesh into the left atrial free wall (or any other heart anatomy features not desired to be cut), as shown in FIG. 55A. In this particular embodiment shown in FIG. 55A, the disc at the distal end 5504a is oversized to the expanded diameter of the blade or cutter 5508 to capture the penetrating tips of the blade after completion of the cut. FIG. 55B shows a third disc 5504c that remains in the right atrium and together with the distal disc 5504b in contact with the septum 5520, sandwiches the septum which ensures that the tissue does not come free from the assembly during or after the procedure to potentially cause an embolic event. This proximal disc is undersized to the diameter of the stent blade in its expanded state, similar to the distal disc that engages with the septum 5504b.

Optionally, the shape memory alloy mesh, in some embodiments, takes the form of several overlapping petals 5604 when exposed enough to self-expand as shown in FIGS. 56A-56E. FIGS. 56A-56E show an exemplary sequential embodiment of the deployment of a shape memory alloy mesh of a device assembly wherein the delivered shape memory alloy mesh tissue stabilizer takes the form of several overlapping petals. In some embodiments, the diameter of the shape memory alloy mesh increases in diameter along its length from the proximal edge in contact with the interatrial septum towards its distal end; the distal diameter of the mesh 5704 is oversized with respect to the expanded diameter of the cutter 5708 in order to capture the tips of the cutter, as shown in FIG. 57. Thus, FIG. 57 shows an exemplary embodiment of the expandable tissue stabilizer of a device assembly as disclosed herein wherein the distal end of the truncated cone (trapezoid shape) tissue stabilizer is oversized to the expanded diameter of the blade to capture the penetrating tips of the cutter after completion of the cut.

Figure 58A:
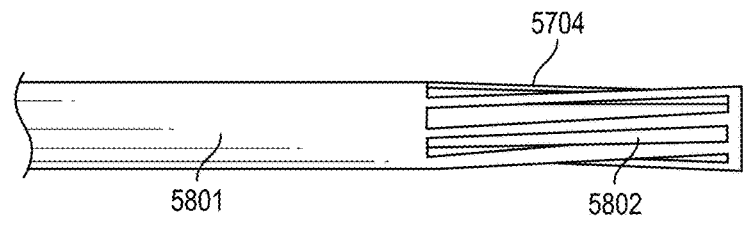
FIG. 58A shows another exemplary sequential embodiment of the expandable tissue stabilizer of a device assembly as disclosed herein, wherein the delivered shape memory alloy mesh tissue stabilizer folds into a flower-shaped pattern.
Figure 58B:
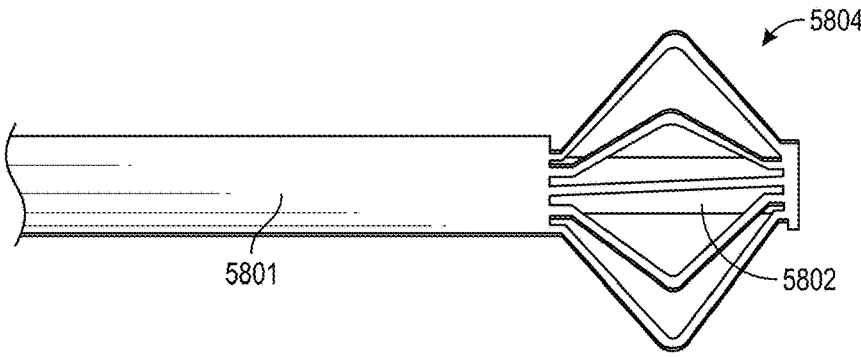
FIG. 58B shows another exemplary sequential embodiment of the expandable tissue stabilizer of a device assembly as disclosed herein, wherein the delivered shape memory alloy mesh tissue stabilizer folds into a flower-shaped pattern.
Figure 58C:
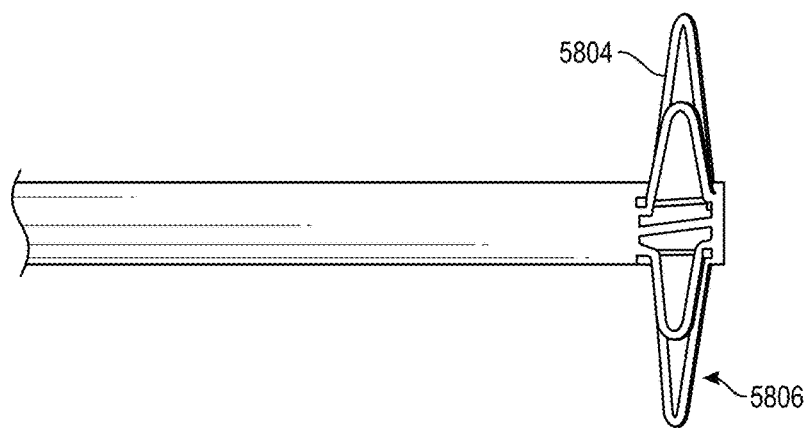
FIG. 58C shows another exemplary sequential embodiment of the expandable tissue stabilizer of a device assembly as disclosed herein, wherein the delivered shape memory alloy mesh tissue stabilizer folds into a flower-shaped pattern.
Figure 58D:
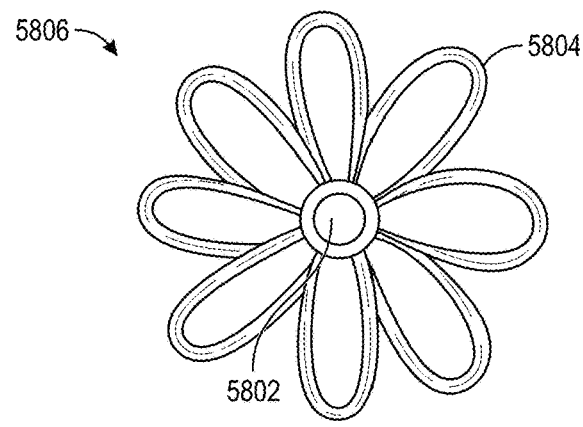
FIG. 58D shows another exemplary sequential embodiment of the expandable tissue stabilizer of a device assembly as disclosed herein, wherein the delivered shape memory alloy mesh tissue stabilizer folds into a flower-shaped pattern.

FIG. 58A shows another exemplary sequential embodiment of the expandable tissue stabilizer of a device assembly as disclosed herein, wherein the delivered shape memory alloy mesh tissue stabilizer folds into a flower-shaped pattern. FIG. 58B shows another exemplary sequential embodiment of the expandable tissue stabilizer of a device assembly as disclosed herein, wherein the delivered shape memory alloy mesh tissue stabilizer folds into a flower-shaped pattern. FIG. 58C shows another exemplary sequential embodiment of the expandable tissue stabilizer of a device assembly as disclosed herein, wherein the delivered shape memory alloy mesh tissue stabilizer folds into a flower-shaped pattern. FIG. 58D shows another exemplary sequential embodiment of the expandable tissue stabilizer of a device assembly as disclosed herein, wherein the delivered shape memory alloy mesh tissue stabilizer folds into a flower-shaped pattern. In some embodiments, therefore, the shape memory alloy mesh expands in diameter by translating the proximal end of the strings 5804 forward, as shown in FIG. 58A-58D. Unlike FIG. 75A-E in which longitudinal slits are cut out leaving several struts behind in one catheter, this embodiment comprises obliquely connected strings. In this particular embodiment as in FIGS. 58A-58D, the proximal end of the strings of the tissue stabilizer 5804 are connected to catheter 1, 5801 that slides over catheter 2, 5802 that holds the strings at its distal end, allowing the strings to fold into a flower-shaped pattern (FIG. 58D) when catheter 1, 5801 is moved toward the distal end of the catheter 2, 5802. Since the strings are obliquely connected they form the shape of petals. In some embodiments the proximal end of the strings are attached to the distal end of catheter 1 and the distal end of the strings are attached to catheter 2 that is moved proximally within the inner lumen of catheter 1, thus allowing the strings 5804 to fold into a flower or petals-shaped pattern 5806.

Figure 72A:
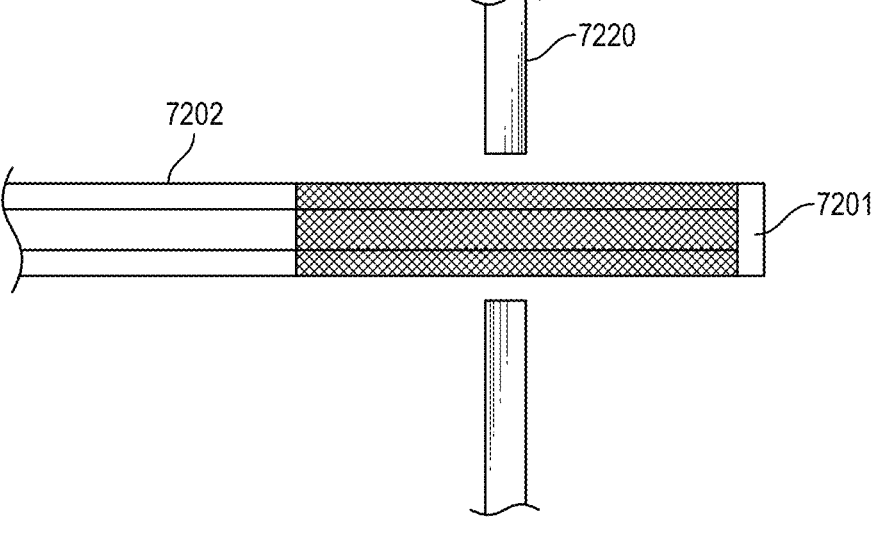
FIG. 72A shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation.
Figure 72B:
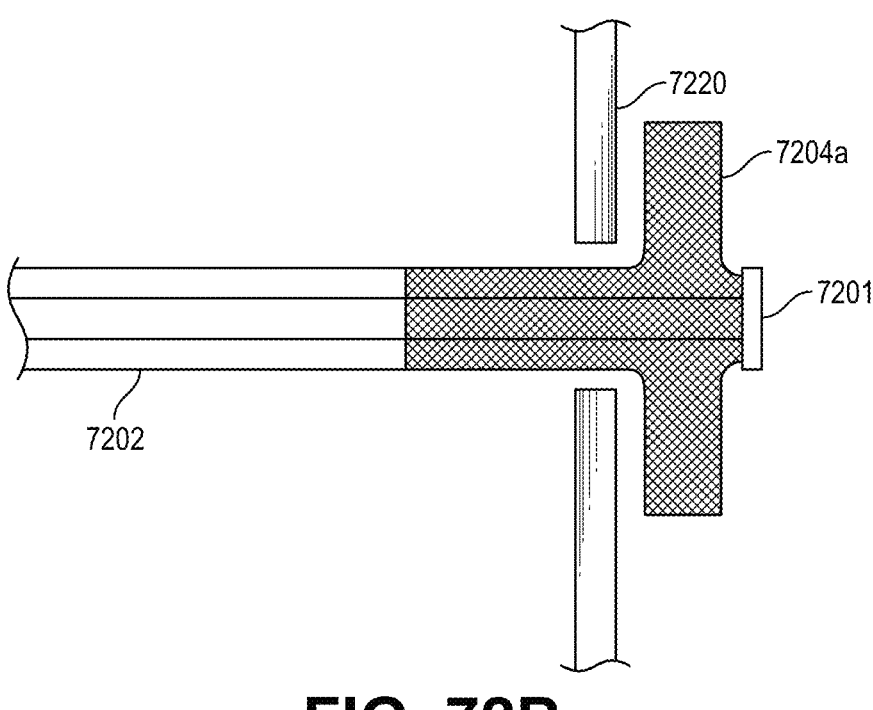
FIG. 72B shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation.
Figure 72C:
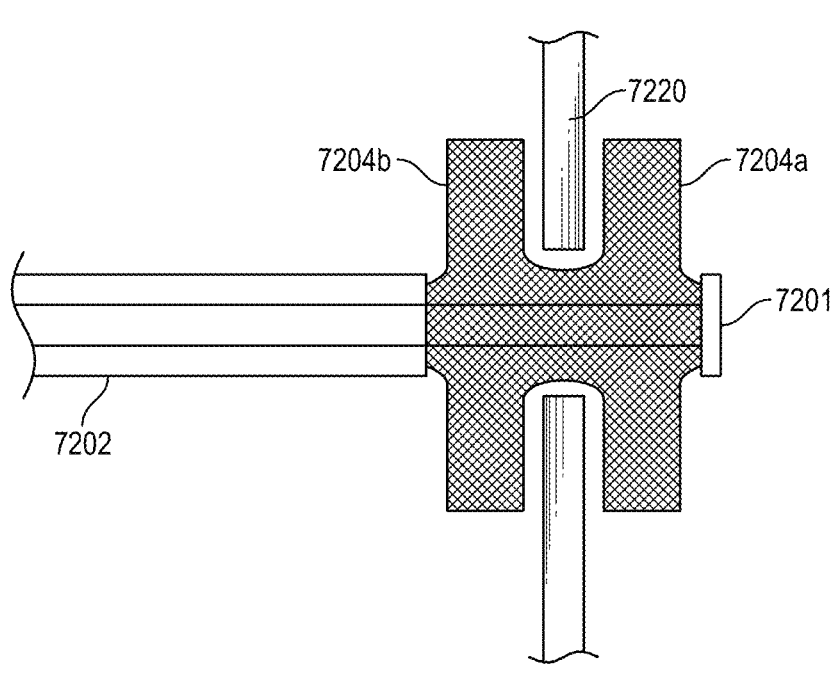
FIG. 72C shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation.

FIG. 72A shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation. FIG. 72B shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation. FIG. 72C shows an exemplary sequential embodiment of the tissue stabilizer of a device assembly as disclosed herein wherein the tissue stabilizer is a shape memory alloy mesh that is expanded by translating the proximal and distal edges towards one another, forming discs that sandwich the septum during that translation. In some embodiments, thus, the shape memory alloy mesh expands in diameter by translating the proximal and distal edges towards one another and sandwiches the septum with two shape memory alloy mesh discs during translation as shown in FIGS. 72A-72C. Referring to FIGS. 72A-72C in particular, the shape memory alloy mesh 7204, in this embodiment, advanced such that a distal portion of the mesh is in the left atrium connected to catheter 1, 7201 and the proximal portion of the mesh remains in the right atrium connected to catheter 2, 7202 before unsheathing the mesh. For unsheathing, the proximal portion of the mesh 7204b is pushed toward the septum 7220 by translating catheter 2 distally while the distal portion of the mesh 7204a stays relatively fixed with respect to the septum by moving catheter 1 proximally toward the septum. Such movement of the distal or the proximal portion of the mesh results in a reduction of the dimension along proximal-distal direction but expansion in the direction that is about perpendicular (with an angle in the range of 75 to 105 degrees) to the proximal-distal direction (or to the axis of a guide catheter, housing catheter, or delivery catheter at or in close vicinity) to the septum and forms two discs; 7204a, 7204b that sandwich the septum.

In some embodiments, the shape memory alloy tissue stabilizer is in its crimped form similar to a compressed stent in its crimped form; and in its deployed state sandwiches the interatrial septum between its mesh discs, bulbs, or plugs; and is deployed as described in FIGS. 42A-42F. FIGS.

42A-42F show an exemplary embodiment of sequential steps using the device assembly as disclosed herein resulting in the deployment of a dogbone shaped expandable tissue stabilizer, sandwiching the interatrial septum. Some embodiments do not have the need to introduce the tissue stabilizer housing catheter similar to FIGS. 38A-38D or do not have the need to introduce the tissue stabilizer housing catheter nor the tissue stabilizer catheter similar to FIGS. 60A-60D. FIGS. 38A-38D show an exemplary sequential embodiment of a device assembly herein eliminating the need for an additional mesh housing catheter to deploy the tissue stabilizing element as the guide catheter has a smaller OD at the distal end to ensure that it crosses the interatrial septum while running over the guidewire. Referring to FIGS. 60A-60D, in an exemplary embodiment, the guide catheter 1 6002 has a predetermined bend and comprises a self-expanding tissue stabilizer 6004a, 6004b that is deployed in both the left and right atrium by pulling proximally the catheter 6005 that houses the tissue stabilizer as well as the guide catheter. FIG. 60A shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back the catheter that houses the tissue stabilizer as well as the guide catheter. FIG. 60B shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back the catheter that houses the tissue stabilizer as well as the guide catheter. FIG. 60C shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back the catheter that houses the tissue stabilizer as well as the guide catheter. FIG. 60D shows an exemplary sequential embodiment of the tissue stabilizer of a device assembly as disclosed herein wherein the guide catheter has a predetermined bend and comprises a self-expanding tissue stabilizer that is deployed in both the left and right atrium by pulling back the catheter that houses the tissue stabilizer as well as the guide catheter.

Figure 61A:
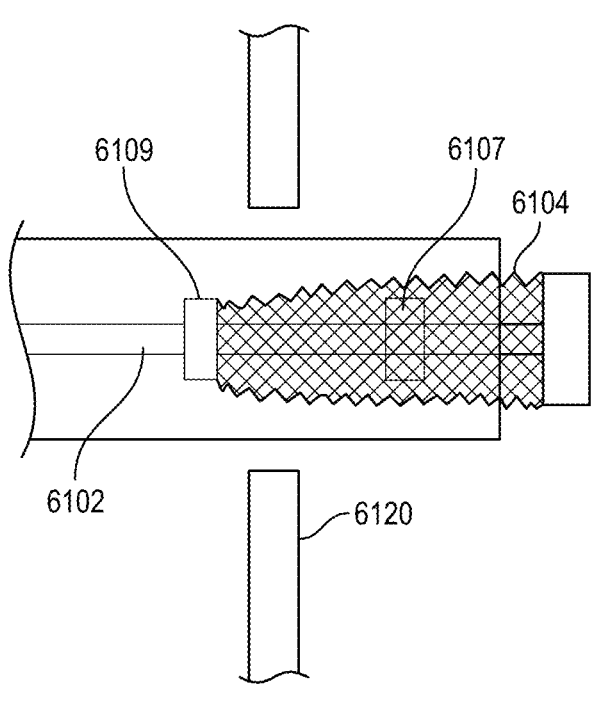
FIG. 61A shows an exemplary sequential embodiment of the tissue stabilizer of a device assembly as disclosed herein wherein the proximal portion of the self-expanding mesh is connected to a first ring that allows to translate towards the distal end of the catheter that comprises the tissue stabilizer, once the catheter that houses the tissue stabilizer is pulled back unsheathing the mesh.
Figure 61B:
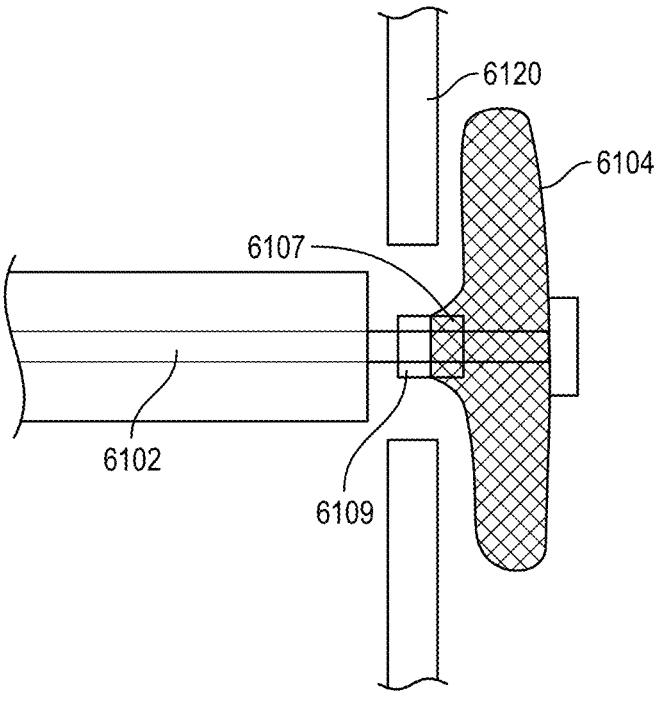
FIG. 61B shows an exemplary sequential embodiment of the tissue stabilizer of a device assembly as disclosed herein wherein the proximal portion of the self-expanding mesh is connected to a first ring that allows to translate towards the distal end of the catheter that comprises the tissue stabilizer, once the catheter that houses the tissue stabilizer is pulled back unsheathing the mesh.

FIG. 61A shows an exemplary sequential embodiment of the tissue stabilizer of a device assembly as disclosed herein wherein the proximal portion of the self-expanding mesh is connected to a first ring that allows to translate towards the distal end of the catheter that comprises the tissue stabilizer, once the catheter that houses the tissue stabilizer is pulled back unsheathing the mesh. A second ring that is mounted on the catheter that comprises the tissue stabilizer and is placed proximal to the tissue stabilizer will act as a stop to the first ring that is connected to the self-expanding mesh. The self-expanding mesh is able to translate over the second ring; however, the ID of the first ring is undersized with respect to the OD of the second ring. FIG. 61B shows an exemplary sequential embodiment of the tissue stabilizer of a device assembly as disclosed herein wherein the proximal portion of the self-expanding mesh is connected to a first ring that allows to translate towards the distal end of the catheter that comprises the tissue stabilizer, once the catheter that houses the tissue stabilizer is pulled back unsheathing the mesh. A second ring that is mounted on the catheter that comprises the tissue stabilizer and is placed proximal to the tissue stabilizer will act as a stop to the first ring that is connected to the self-expanding mesh. The self-expanding mesh is able to translate over the second ring; however, the ID of the first ring is undersized with respect to the OD of the second ring. Referring, therefore, to FIGS. 61A-61B, in particular, the self-expanding tissue stabilizer 6104 has a stiff internal element 6107 attached to catheter 1, 6102 that comprises the tissue stabilizer at its distal end. The proximal end of the nitinol mesh is connected to a ring that is slidably engaged with catheter 1, 6102, wherein the ring 6109 is able to translate distally as the nitinol mesh self-expands over the ring after being unsheathed. In this particular embodiment, optionally after the proximal end of the mesh is advanced to the left atrium, the proximal end is translated toward the stiff element 6107 while the distal end optionally stays fixed relative to the stiff internal element thus causing the mesh to self-expand to a disc, bulb, or plug-like shape. The stiff internal element is attached to catheter 6102 and has a larger OD than the ID of the ring 6109, preventing the ring to translate more distally after being unsheathed. The expanded stabilizer, in some embodiments, then is pulled backward to touch the septum 6120 for stabilization during tissue excision.

In some embodiments, the shape memory alloy mesh 6104 is advanced such that a distal portion of the mesh is in the left atrium and the proximal portion of the mesh remains in the right atrium before unsheathing the mesh. For unsheathing, as shown in FIGS. 72A-72C, the proximal portion of the mesh 7204b, in some embodiments, is pushed toward the septum 7220 while the distal portion of the mesh stays relatively fixed with respect to the septum or move proximally toward the septum. Such movement of the distal or the proximal portion of the mesh results in reduction in the dimension along a proximal-distal direction but expansion in the direction that is about perpendicular (having an angle in the range of 75 to 105 degrees or in the range of 80 to 100 degrees) to the proximal-distal direction (or to the axis of a guide catheter, housing catheter, or delivery catheter at or in close vicinity) and forms two discs 7204a, 7204b that sandwich the septum.

In some embodiments, the shape memory alloy tissue stabilizer is similar to a compressed stent in its crimped state; and in its deployed state sandwiches the interatrial septum between its struts; and is deployed as described in FIGS. 42A-42F and FIGS. 44A-44F; and whose proximal portion is connected to the distal portion of the guide catheter. FIG. 62 shows an exemplary embodiment of the tissue stabilizer of a device assembly as disclosed herein wherein the self-expanding mesh disc has a concave side only allowing the outer edges of the mesh to touch the interatrial septum, to help prevent the mesh disc from being pulled through the interatrial septum. Thus, in some embodiments, as shown in FIG. 62, the shape memory alloy tissue stabilizer 6204 has a concave side optionally at its proximal side, only allowing the outer edges of the mesh to touch the interatrial septum 6220. As the stabilizer is deformable, it, in some embodiments, further extends to a larger diameter as the concave surface flattens out to help prevent the mesh disc from being pulled through the interatrial septum. In this particular embodiment, the disc 6204 stays touching the septum 6220 while a pulling or other proximally orientated forces is applied up toward a threshold. After the force exceeds the threshold the concave surface flattens or even become a convex surface so that the disc 6204 is resheathed after the procedure with the device assembly herein finishes.

Figure 63C:
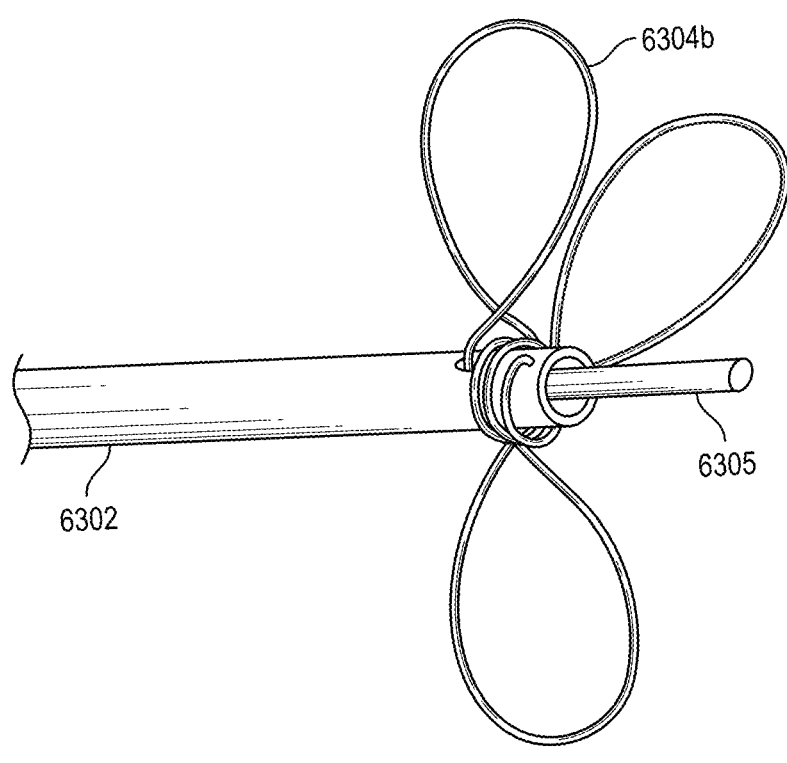
FIG. 63C shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire or expand the tissue stabilizer through a pothole at the distal end of catheter 1.
Figure 63D:
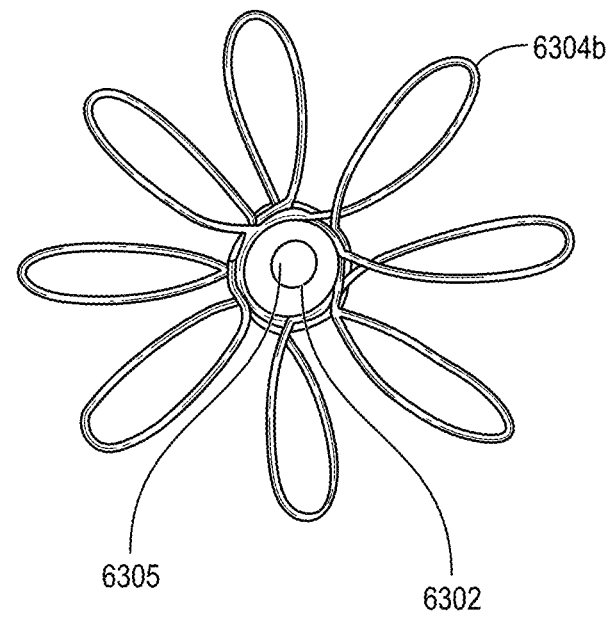
FIG. 63D shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire or expand the tissue stabilizer through a pothole at the distal end of catheter 1.

In some embodiments, a shape memory alloy self-coiling wire 6304a is wound and resides in catheter 1, 6302, when the device assembly is un-deployed, the proximal end of the wire is connected to a catheter 6305 that is rotated or moved distally from the septum 6320 in the left atrium, thereby causing the proximal end of the wire to rotate or move distally. As a result, such coiling, uncoiling, or distal movement causes unwinding of the wire or expansion of the tissue stabilizer through a porthole at the distal end of catheter 1. As a result, such coiling or uncoiling and distal movement causes unwinding of the wire or expansion of the tissue stabilizer through a porthole at the distal end of catheter 1. Catheter 1 comprises the distal end of the wire, optionally connected to the distal end of the wire, allowing the wire to take a shape of a mesh of flower or petals 6304b, as shown in FIG. 63A-63D. FIG. 63A shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire/expand the tissue stabilizer through a pothole at the distal end of catheter 1. FIG. 63B shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire/expand the tissue stabilizer through a pothole at the distal end of catheter 1. FIG. 63C shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire/expand the tissue stabilizer through a pothole at the distal end of catheter 1. FIG. 63D shows an exemplary sequential embodiment of the tissue stabilizer of a device assembly as disclosed herein wherein a self-coiling wire is wound and resides in catheter 1, its proximal end is connected to a catheter that is rotated and moved distally to unwind the wire/expand the tissue stabilizer through a pothole at the distal end of catheter 1.

In some embodiments, a balloon catheter 6404b, 6504b is housed coaxially inside the shape memory alloy mesh catheter 6404a 6504a and is undersized with respect to the diameter of the blade, optionally, the diameter of the cutter when expanded, such that when the internal balloon is inflated, the balloon prevents the shape memory alloy mesh from being inadvertently collapsed during the cutting motion, providing secondary stabilization support internal to the shape memory alloy mesh, as shown in FIGS. 64-65. FIG. 64 shows an exemplary side view embodiment of the tissue stabilizer of a device assembly as disclosed herein wherein the tissue stabilizer comprises a self-expanding mesh disc that is surrounding an undersized balloon that once inflated will prevent the tissue stabilizer from being pulled through the interatrial septum towards the right atrium. FIG. 65 shows an exemplary end view embodiment of the tissue stabilizer of a device assembly as shown in FIG. 64 and as disclosed herein wherein the tissue stabilizer comprises a self-expanding mesh disc that is surrounding an undersized balloon that once inflated will prevent the tissue stabilizer from being pulled through the interatrial septum towards the right atrium. The balloon 6404b, 6504b is, in some embodiments, inflated with gas, fluidic liquid, or any other possible form of fillings. In this particular embodiment, the balloon is of a diameter that is no greater than the cut diameter of the septum, the expanded diameter of the mesh, and the expanded diameter of the blade. In some embodiments, the balloon is of a diameter that is equal to or greater than the cut diameter of the septum, the expanded diameter of the mesh, and the expanded diameter of the blade. In some embodiments, such diameter is of the cross-section, or about perpendicular (having an angle in the range of 75 to 105 degrees or in the range of 80 to 100 degrees) to the proximal-distal direction (or to the axis) of a guide catheter, housing catheter, or delivery catheter at or in close vicinity.

Referring to FIGS. 64 and 65, in these embodiments, the self-expanding shape memory alloy element takes the form of a self-expanding mesh disc 6404a, 6504a, that is surrounding an undersized balloon 6404b, 6504b that once inflated will prevent the tissue stabilizer from being pulled through the interatrial septum towards the right atrium in its deployed state, such self-expanding mesh disc 6404a, 6504a spread out when the guide catheter or the housing catheter is moved into the right atrium and the balloon is expanded thereby expanding the mesh in the left atrium. In some embodiments, the outermost edges are of a diameter that is slightly undersized with respect to the expanded diameter of the cutter to provide proper stabilization during cutting.

In some embodiments, the self-expanding shape memory alloy element takes the form of one large coil when expanded, by advancing it beyond the housing catheter in the left atrium, as shown in FIG. 66. FIG. 66 shows an exemplary embodiment of the tissue stabilizer of a device assembly as disclosed herein wherein the tissue stabilizer is a self-expanding coil. Referring to FIG. 66, in a particular embodiment, such coil 6604 spreads out when the guide catheter or the housing catheter is moved proximally thereby unsheathing the coil. In some embodiments, the outer most edges are of a diameter that is slightly undersized with respect to the expanded diameter of the cutter to provide proper stabilization during cutting. In some embodiments, the expanded coil is collapsed back into catheter(s) after tissue excision by movement of the coil into the distal end of the catheters. In some embodiments, the coil is of the cross-section, or is about perpendicular (having an angle in the range of 75 to 105 degrees or in the range of 80 to 100 degrees) to the proximal-distal direction (or to the axis) of a guide catheter, housing catheter, or delivery catheter at or in close vicinity. In some embodiments, the center of the expanded coil will be on the same axis as the center of the distal cross-section of the guide catheter, housing catheter, or delivery catheter.

Figure 67:
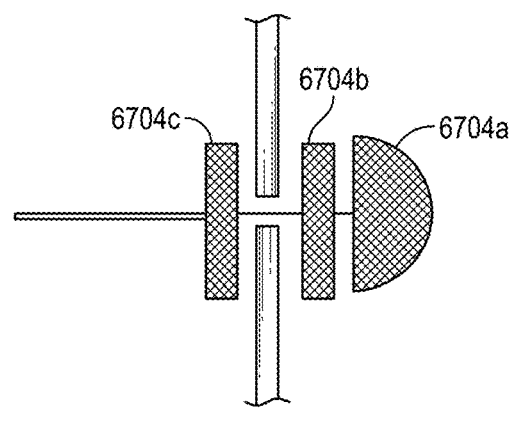
FIG. 67 shows an exemplary embodiment of the tissue stabilizer of a device assembly as disclosed herein wherein the tissue stabilizer comprises one or more self-expanding discs and one or more self-expanding hemisphere mesh plugs.
Figure 68:
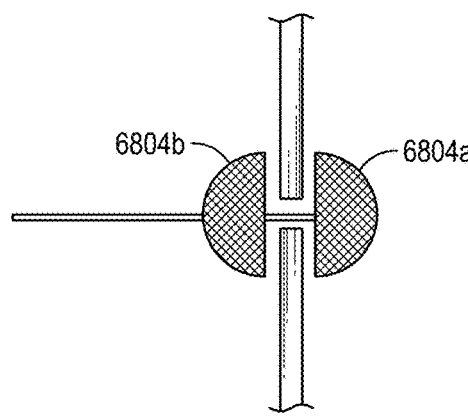
FIG. 68 shows an exemplary embodiment of the tissue stabilizer of a device assembly as disclosed herein wherein the tissue stabilizer comprises two self-expanding hemisphere plugs on each side of the interatrial septum that face the interatrial septum with the flat side of the hemisphere.

In some embodiments, one or more of the self-expanding shape memory alloy elements takes the form of a hemisphere 6704a when expanded by exposing it out of its housing catheter in the left atrium, FIG. 67. FIG. 67 shows an exemplary embodiment of the tissue stabilizer of a device assembly as disclosed herein wherein the tissue stabilizer comprises one or more self-expanding discs and one or more self-expanding hemisphere mesh plugs. In some embodiments, the element is distal to one or more shape memory alloy stabilizing elements 6704b, 6704c that are contacting the septum wall. In some embodiments, the shape memory alloy mesh when deployed across the septum takes the form of a shape memory alloy stabilizing dumbbell 6804a, 6804b that sandwiches the septum, stabilizing it during the cutting motion, FIG. 68. FIG. 68 shows an exemplary embodiment of the tissue stabilizer of a device assembly as disclosed herein wherein the tissue stabilizer comprises two self-expanding hemisphere plugs on each side of the interatrial septum that face the interatrial septum with the flat side of the hemisphere. In some embodiments, the shape memory alloy tissue stabilizer is similar to a compressed stent in its crimped state; and in its deployed state sandwiches the interatrial septum between its discs, bulbs, plugs, or hemispheres; and is deployed as described in FIG. 42A-42F; and whose proximal portion is connected to the distal portion of the guide catheter.

Figure 69A:
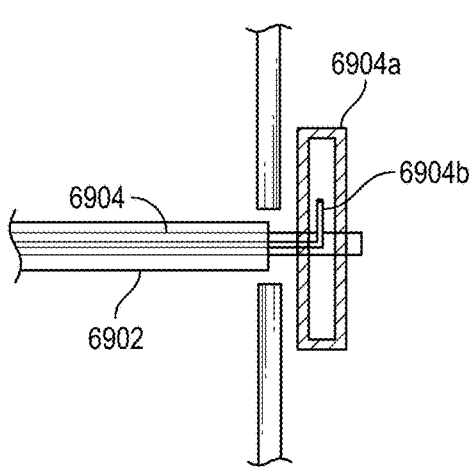
FIG. 69A shows an exemplary sequential embodiment of the tissue stabilizer of a device assembly as disclosed herein wherein the tissue stabilizer contains a self-expanding hollow mesh that is filled with self-coiling wire.
Figure 69B:
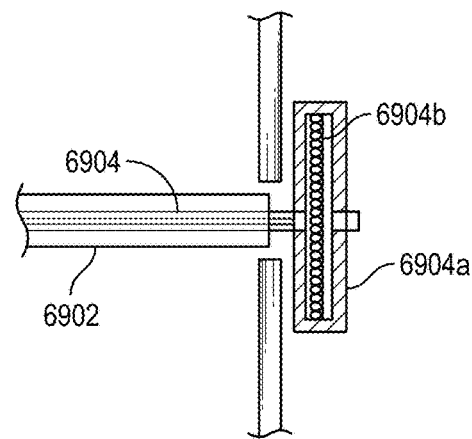
FIG. 69B shows an exemplary sequential embodiment of the tissue stabilizer of a device assembly as disclosed herein wherein the tissue stabilizer contains a self-expanding hollow mesh that is filled with self-coiling wire.
Figure 70A:
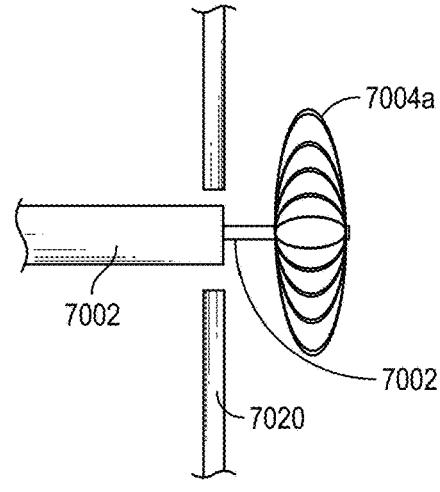
FIG. 70A shows an exemplary side view and front view embodiment of the tissue stabilizer of a device assembly as disclosed herein wherein the tissue stabilizer is a self-expanding oblate spheroid.
Figure 70B:
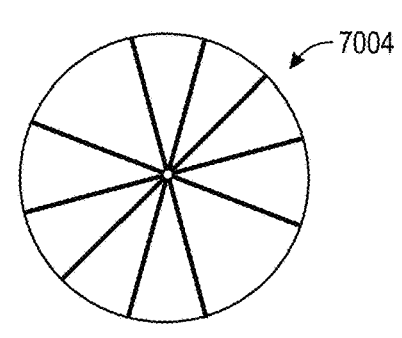
FIG. 70B shows an exemplary side view and front view embodiment of the tissue stabilizer of a device assembly as disclosed herein wherein the tissue stabilizer is a self-expanding oblate spheroid.

In some embodiments, the shape memory alloy mesh, when deployed additionally, has a self-coiling wire inside of it which provides additional radial rigidity preventing accidental collapse of the shape memory alloy mesh during the cutting motion and stabilizing it during the cutting motion, FIGS. 69A-69B. FIG. 69A shows an exemplary sequential embodiment of the tissue stabilizer of a device assembly as disclosed herein wherein the tissue stabilizer contains a self-expanding hollow mesh that is filled with self-coiling wire. FIG. 69B shows an exemplary sequential embodiment of the tissue stabilizer of a device assembly as disclosed herein wherein the tissue stabilizer contains a self-expanding hollow mesh that is filled with self-coiling wire. Referring, therefore, to FIGS. 69A-69B, when the mesh 6904a is being deployed by pulling catheter 1 6902 into the right atrium, the self-coiling wire 6904b is affected by a distal movement of the wire relative to the shape memory alloy mesh catheter 6904 comprising the mesh 6904a, thus causing the wire to un-sheath and coil correspondingly so that it reinforces the mesh and provides additional radial rigidity preventing accidental collapse of the shape memory alloy mesh during the cutting motion. In some embodiments, the self-expanding element includes a series of shape memory alloy wires connected at both ends such that when allowed to self-expand they take the shape of an oblate spheroid, as shown in FIGS. 70A-70B. FIG. 70A shows an exemplary side view and front view embodiment of the tissue stabilizer of a device assembly as disclosed herein wherein the tissue stabilizer is a self-expanding oblate spheroid. FIG. 70B shows an exemplary side view and front view embodiment of the tissue stabilizer of a device assembly as disclosed herein wherein the tissue stabilizer is a self-expanding oblate spheroid. Referring to FIGS. 70A-70B, when the mesh catheter 7004 is being deployed, the proximal end of shape memory alloy wires 7004a are also affected by a distal movement relative to catheter 1 7002 enclosing the wires, thus causing the wires to un-sheath and bend correspondingly so that they form oblate spheroids as shown in FIG. 70. FIG. 70A shows an exemplary side view and front view embodiment of the tissue stabilizer of a device assembly as disclosed herein wherein the tissue stabilizer is a self-expanding oblate spheroid. FIG. 70B shows an exemplary side view and front view embodiment of the tissue stabilizer of a device assembly as disclosed herein wherein the tissue stabilizer is a self-expanding oblate spheroid.

In some embodiments, the balloon aspect of the balloon catheter is armored to protect against inadvertent puncture by the cutter. In some embodiments, the balloon is a cryoballoon that uses cryoablation to freeze the targeted portion of the septum to the proximal edge of the balloon preventing it from moving out of control of the device assembly. In some embodiments, a tissue stabilizer material for anything other than the inflatable balloon comprises a shape memory alloy comprising: nickel-titanium, copper-aluminum-nickel, zinc-gold-copper; or a combination thereof. In some embodiments, the tissue stabilizer or, equivalently, the tensioning element comprises materials other than shape memory metal or alloy. Non-limiting examples of such materials include, but are not limited to, one or more of: stainless steel, reinforced catheter, polymer, or a combination thereof.

In some embodiments, the expanded dimension of the tissue stabilizer is significantly less than the expanded dimension of the cutter to permit tissue tenting of the interatrial septum such that the cutter creates an aperture larger than the expanded dimension of the cutter. In some embodiments, the expanded dimension of the tissue stabilizer is: about 1%, about 5%; about 10%; about 15%; about 20%; about 25%; about 30%; about 35%; about 40%; about 45%; about 50%; or as much as about 75%; less than the expanded dimension of the cutter. In some embodiments, the expanded dimension of the tissue stabilizer is measured at or near the distal end, or at or near the proximal end of the tissue stabilizer. In some embodiments, the expanded dimension of the cutter is measured at or near the distal end or at or near the proximal end of the cutter. In some embodiments, the expanded dimension of the tissue stabilizer is approximately equal to or slightly greater than the expanded dimension of the cutter in order to plug the distal end of the expanded cutter for retaining the excised tissue. In some embodiments, the expanded dimension of the tissue stabilizer is about 0.1% to about 15% greater that the expanded dimension of the cutter. In some embodiments, optionally, with more than one expanding mesh element positioned in a left atrium, the expanded dimension of the tissue stabilizer at its distal end is: about 5%; about 10%; about 15%; about 20%; about 25%; about 30% larger than the expanded dimension of the cutter to prevent the cutting teeth from inadvertently damaging structures other than the septum.

In some embodiments, when the delivery catheter is retracted proximally with the distal end of the second coaxial catheter, bringing with it, the tissue stabilizer, the cutter is configured to coaxially expand radially within the left atrium to an intended dimension, wherein the distal end of the delivery catheter is further retracted inside the right atrium to allow the tissue stabilizer to expand radially to a sufficiently large dimension, wherein the external expanded dimension (for example, expanded OD) of the cutter is less than the internal dimension (expanded ID) of the expanded tissue stabilizer, and the radially expanded dimension of the tissue stabilizer provides a supporting, tensioning effect on the right atrial side of the interatrial septum around the initial puncture site.

In some embodiments, a coaxial alignment mechanism provides centralization between the cutter, tissue stabilizer, and tissue retention elements. In some embodiments, a coaxial alignment mechanism provides centralization between the cutter, tissue stabilizer, or tissue retention elements. The coaxial aligner, in some embodiments, reduces the risk of incurring inadvertent interaction between the cutter and the tissue stabilizer (as catheter 1 is translated proximally into catheters 2 or 3 or 4). The coaxial aligner also serves as a means to ensure the cutter (connected to catheter 2) is advanced centrally over catheter 1 and through the septum. In some embodiments, the coaxial aligner also serves as a means to ensure that a pre-shaped element, such as a bent guidewire or shape memory alloy stabilizer that remains straight during the initial stage of deployment and further acts as a "straightener" or "collapsing feature" when the bent guidewire or shape memory alloy stabilizer element is retracted into the catheter.

Figure 17:
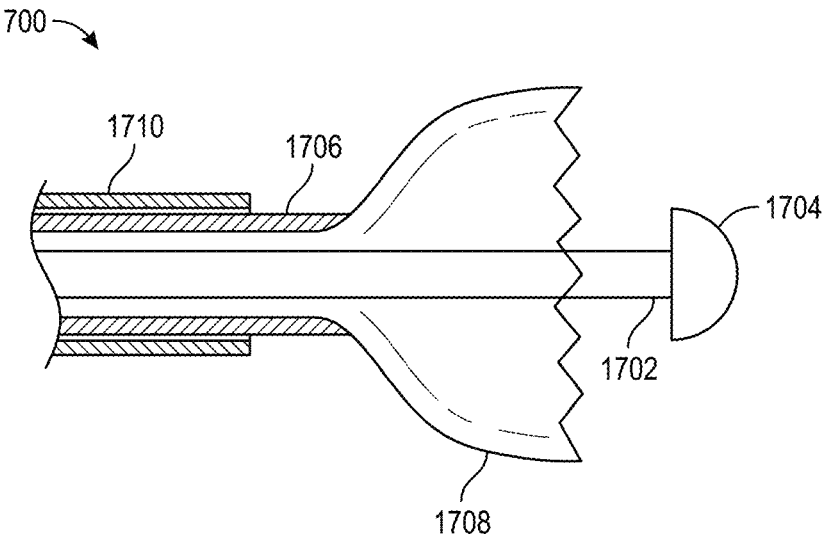
FIG. 17 is a representative illustration of an exemplary embodiment of a coaxial alignment mechanism achieved by the inner diameter (ID) of catheter 2 being flush with the outer diameter (OD) of catheter 1, and the OD of catheter 2 being flush with the ID of catheter 3.

FIG. 17 is a representative illustration of an exemplary embodiment of a coaxial alignment mechanism achieved by the inner diameter (ID) of catheter 2 being flush with the outer diameter (OD) of catheter 1, and the OD of catheter 2 being flush with the ID of catheter 3. In some embodiments, as illustrated in FIG. 17, the coaxial alignment mechanism 1700, is achieved by the inner diameter (ID) of catheter 2, 1706 being flush with the outer diameter (OD) of catheter 1, 1702, with a tissue stabilizer 1704 thereon, and the OD of catheter 2, 1706 being flush with the ID of catheter 3, 1710. In any of the embodiments described herein, the inner or outer diameters of catheter 1, catheter 2, catheter 3, catheter 4, or a combination thereof, have a hydrophilic or hydrophobic coating. In any of the embodiments described herein, the inner and outer diameters of catheter 1, catheter 2, catheter 3, catheter 4, or a combination thereof, have a hydrophilic or hydrophobic coating. FIG. 17 also shows the cutter, 1708.

Figure 18:
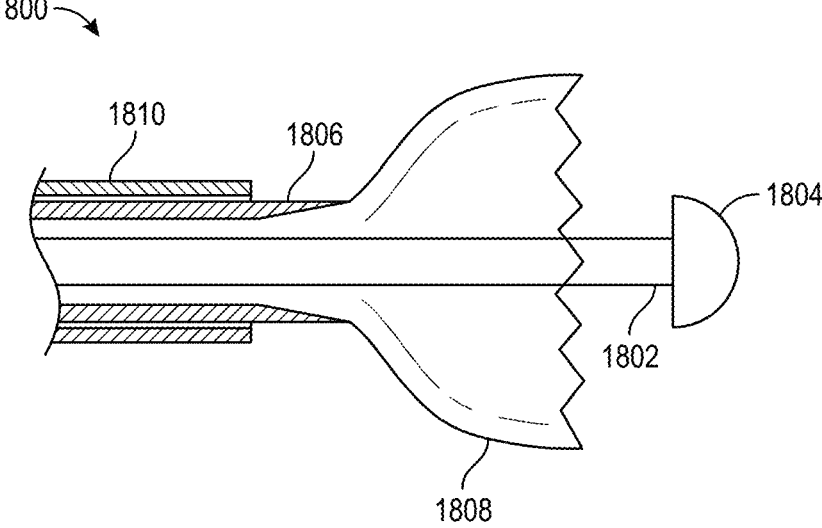
FIG. 18 is a representative illustration of an exemplary embodiment of the device assembly taking the form of the previous embodiment of FIG. 17 with the differentiation that the ID of catheter 2 is modified at its distal aspect to create a space between catheter 1 and catheter 2 that serves as a tissue retention pocket.

FIG. 18 is a representative illustration of an exemplary embodiment of the device assembly taking the form of the previous embodiment of FIG. 17 with the differentiation that the ID of catheter 2 is modified at its distal aspect to create a space between catheter 1 and catheter 2 that serves as a tissue retention pocket. In some embodiments, as illustrated in FIG. 18, the device assembly 1800 takes the form of the previous embodiment, comprising catheter 2, 1806 being flush with the outer diameter (OD) of catheter 1, 1802, with a tissue stabilizer 1804 thereon, and the OD of catheter 2, 1806 being flush with the ID of catheter 3, 1810; with the differentiation that the ID of catheter 2, 1806 is modified at its distal portion to create a space between catheter 1, 1802 and catheter 2, 1806 that serves at least as a tissue retention pocket. Excised tissue, in some embodiments, is then easily translated into catheter 2 prior to the system removal from the body. In some embodiments, the OD of catheter 2 in the previously-described embodiment of coaxial alignment, is not flush with the ID of catheter 3. In some embodiments, excised tissue is translated into catheter 2 prior to system removal. In some embodiments, the OD of catheter 2 in the previously-described embodiment of coaxial alignment is not flush with the ID of catheter 3. In some embodiments, an additional catheter 4 (coaxial to catheter 1) with an ID flush with the OD of catheter 1 and with an OD that is flush with the ID of catheter 2 is used to provide coaxial alignment along its length. FIG. 18 also shows the cutter, 1808.

In some embodiments, (not shown), a catheter 4 (coaxial to catheter 1) whose ID is flush with the OD of catheter 1 and whose OD is flush with the ID of catheter 2 provides coaxial alignment along its length.

Figure 19:
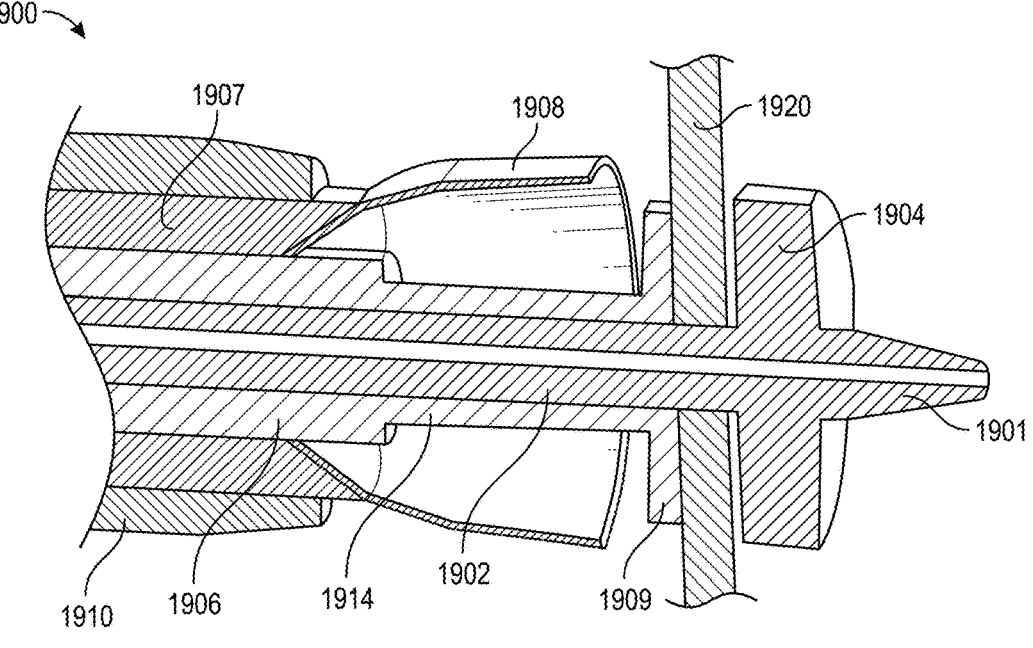
FIG. 19 is a representative illustration of an exemplary embodiment of a catheter 2, 1914 (coaxial to catheter 1, 1902), with an ID that is flush with the OD of catheter 1, 1902.

FIG. 19 is a representative illustration of an exemplary embodiment of a catheter 2, 1914 (coaxial to catheter 1, 1902), with an ID that is flush with the OD of catheter 1, 1902. Catheter 2 comprises an increased wall thickness proximal that allows for coaxial alignment along its length 1906, here the OD is flush with the ID of catheter 1907, and has an increased diameter at its distal edge 1908 to aid in tissue stabilization during the cutting process. In some embodiments 1900, as illustrated in FIG. 19, a catheter 2, 1914 comprising a second tissue stabilizing element 1909, to aid in tissue capture, stabilization during the cutting process, (coaxial to catheter 1, 1902), whose ID is flush with the OD of catheter 1, 1902 also comprising a penetrating tip 1901 and a first tissue stabilizing element 1904. Catheter 2 comprises an increased wall thickness proximally that allows for coaxial alignment along its length 1906, here the OD is flush with the ID of catheter, 1907 that comprises the cutter. Catheter 2, 1914, 1906, is translatable between catheter 1, 1902, and catheter 1907. Catheter 1907, which comprises the cutter 1908 also comprises an increased ID at its distal end to aid in tissue capture and removal during the device assembly extraction process. FIG. 19 also shows the delivery catheter 3 as 1910. The tissue stabilizing element 1904 will be stored, in its collapsed state, in the ID of catheter 2, 1914, before it gets expanded in the left atrium. The second tissue stabilizing element that will be placed on the proximal side of the septum 1920, in the right atrium, will be stored in its collapsed state, in catheter 1907. In some embodiments, an additional catheter will be used to store the second tissue stabilizing element 1909. This additional catheter will reside between the OD of catheter 2 and ID catheter 3.

In some embodiments, the device assemblies disclosed herein include a cutter, a cutter, a blade, a plurality of blades, or use of the same. A cutter (connected to catheter 2), in some embodiments, comprises a support or scaffold and features at least one bladed edge at its distal tip. In some embodiments, the cutter is delivered to the interatrial septum and, upon deployment and actuation, incises a portion of the interatrial septum, yielding an aperture (anastomosis shunt). The bladed edge assumes a form factor that reduces the amount of force required to drive the cutter through the septum.

Figure 20:
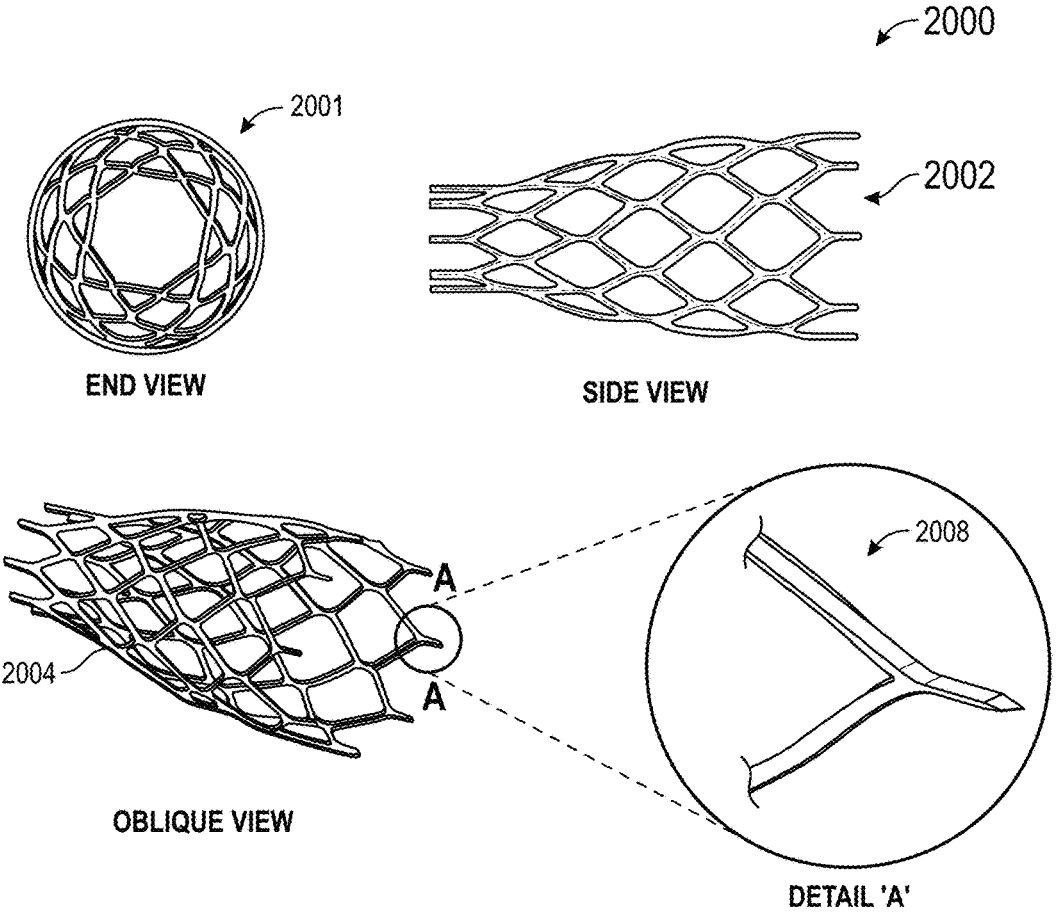
FIG. 20 shows representative illustrations and multiple views of one embodiment of the cutter, wherein the cutter takes the form of an expandable lattice, equivalently herein, an expandable stent, made of self-expanding material (i.e.: shape memory alloy; e.g. nitinol) with a proximal end that is mounted to the distal end of catheter 2 (catheter that comprises an expanding cutter), and with a distal portion that is sharpened to create one or more cutting blades.

FIG. 20 shows representative illustrations and multiple views of one embodiment of the cutter, wherein the cutter takes the form of an expandable lattice/stent made of self-expanding material (i.e.: shape memory alloy; e.g. nitinol) with a proximal end that is mounted to the distal end of catheter 2 (catheter that comprises an expanding cutter), and with a distal portion that is sharpened to create one or more cutting blades. In some embodiments, as illustrated in FIG. 20, the cutter 2000 described herein takes the form of an expandable lattice or equivalently, stent 2001, 2002, 2004 made of self-expanding material (e.g. shape memory alloy or metal) with a proximal end that is mounted to the distal end of catheter 2, and whose distal portion is sharpened to create one or more cutting blades 2008, as illustrated in Detail "A" of FIG. 20. The lattice or equivalently stent cell structure or geometry of the cutter allows the cutter to collapse down to a smaller diameter in a collapsed state so as to minimize the risk of diametral vascular complications during insertion, while resisting deformations in radius or length during the cutting actuation in an expanded state.

Upon delivery to the site of the interatrial septum where the treatment takes place, the cutter is deployed and simultaneously expanded so as to take on a diameter greater than the catheter through which it was inserted. The distal end of the cutter comprises a plurality of teeth distributed circumferentially or radially, with the tip of each blade having a sharp acute angle (e.g. between 0° and 90° in its fully expanded state), for example, as shown in Detail "A" of FIG. 20. This configuration allows tissue to be easily penetrated by the plurality of perforating blades that form a closed perimeter, figure, or shape. The bladed teeth allow for significantly less force to be required for tissue disruption than would be required by a plain or flat blade having one continuous sharp edge.

In some embodiments, the sharpened end resembles one or more of scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises a continuous blade comprising a shape memory alloy, and wherein the distal end of the continuous blade comprises: a single smooth sharpened knife edge; or a plurality of sharpened serrations along the continuous blade; configured to perform as a continuous tissue cutting blade. In some embodiments, the single smooth sharpened knife edge or the plurality of sharpened serrations along the continuous blade are configured to perform as fully-circumferential (continuous) tissue cutting blades. In some embodiments, the expandable cutter is configured to penetrate and cut through an interatrial septum. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Minimization of the force required to create the aperture is advantageous as the force required for penetrating tissue must be translated along the length of the entire catheter system without imparting excessive strain on the bladed cutter, the delivery catheter, or surrounding vasculature. In some embodiments, a serrated and scalloped blade is used, which cuts soft, flexible tissue without tearing or ripping, thus reducing load on the catheter system and potential damage to surrounding soft tissues of the heart. In some embodiments, a serrated or scalloped blade is used, which cuts soft, flexible tissue without tearing or ripping, thus reducing load on the catheter system and potential damage to surrounding soft tissues of the heart. This becomes critical, in some embodiments, if multiple cuts are required in a single use device assembly.

In some embodiments, the distal edge of cutter has a multitude of serrations or teeth and forms an aperture that is polygonal in cross-section. It is noted that the more teeth arranged radially, the closer the resulting orifice shape approximates the area of a circle. One of skill in the art would immediately recognize upon reading this disclosure that the distal shape of the cutter is configurable with a variable plurality of serrations or teeth ranging from 3 serrations or teeth, to as many as 20, or more serrations or teeth. As catheter 2 exits catheter 3 through proximal translation of catheter 3 or forward pushing of catheter 2, the cutter self-expands, in some embodiments, to take on its original expanded state (maximum diameter).

In some embodiments, the cutter includes one or more types of shape memory metal to facilitate its proper functionality. In some embodiments, a cutter material comprises a shape memory alloy or metal. Non-limiting examples of a shape memory alloy or metal includes: nickel-titanium; copper-aluminum-nickel; zinc-gold-copper; or a combination thereof. In some embodiments, the cutter comprises: a wire mesh; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, the cutter is configured such that a cutting tooth of the cutter comprises: a pointed single wire; a single-edge blade shape; a two-edged blade shape or a two-edged scissor blade; an inverted "v"-shape; or a "u"-shape (or scalloped shape); wherein a distal end of every tooth is a cutting point and cutting edges of the cutting teeth, when taken in combination, are configured to cut a complete aperture as the cutter fully crosses the interatrial septum.

Figure 36:
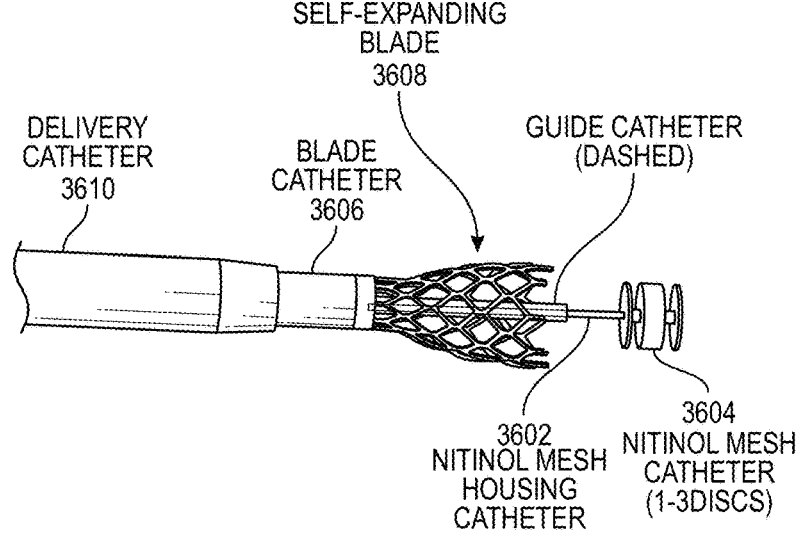
FIG. 36 is an exemplary embodiment of device assembly illustrating multiple shape memory alloy discs advanced over one or more catheters.

In some embodiments, the wall thickness of the cutter is about 0.1 mm to about 0.5 mm. In some embodiments, the wall thickness of the cutter is in the range of 0.005 to 0.6 mm. In some embodiments, the wall thickness of the cutter is about 0.01 mm to about 0.8 mm. In some embodiments, the cutter has a number of discrete points or equivalently, tips at its distal end. In some embodiments, the number of tips is between 3 to 12. In some embodiments, the distal end of the cutter is considered as a single blade with multiple pointed or sharp tips. In some embodiments, the distal end of the cutter also is considered as multiple blades connected together with or without sharp blades in between. In some embodiments, the OD at the distal end or distal tip of the cutter is less than about 8.0 mm in its collapsed state. In some embodiments, the OD at the distal end or distal tip of the cutter is about 5.0 mm to about 12.0 mm, about 3 mm to about 5 mm, about 6 mm to about 9 mm, about 7 mm to about 9 mm, about 8 mm to about 12 mm, about 9 mm to about 14 mm, or about 3 mm to about 14 mm, in its expanded state. In some embodiments, the expanded cutter with the OD disclosed herein includes an area of up to 200 mm$^2$, up to about 180 mm$^2$, up to about 160 mm$^2$, up to about 140 mm$^2$, up to about 120 mm$^2$, up to about 100 mm$^2$, up to about 80 mm$^2$, up to about 60 mm$^2$, up to about 40 mm$^2$, up to about 20 mm$^2$, up to about 10 mm$^2$, up to about 5 mm$^2$, from about 5 mm$^2$ to about 10 mm$^2$, from about 5 mm$^2$ to about 20 mm$^2$, from about 10 mm$^2$ to about 20 mm$^2$, from about 15 degree angle to about 30 mm$^2$, from about 20 mm$^2$ to about 40 mm$^2$, from about 30 mm$^2$ to about 45 mm$^2$, from about 35 mm$^2$ to about 50 mm$^2$, from about 40 mm$^2$ to about 60 mm$^2$, from about 50 mm$^2$ to about 70 mm$^2$, from about 60 mm$^2$ to about 80 mm$^2$, from about 70 mm$^2$ to about 90 mm$^2$, from about 80 mm$^2$ to about 110 mm$^2$, from about 90 mm$^2$ to about 130 mm$^2$, from about 100 mm$^2$ to about 150 mm$^2$, from 35 mm$^2$ to 65 mm$^2$, from 40 mm$^2$ to 75 mm$^2$, from 45 mm$^2$ to a 80 mm$^2$, from 50 mm$^2$ to 85 mm$^2$, from 20 mm$^2$ to 60 mm$^2$, from 30 mm$^2$ to 80 mm$^2$, or from 35 mm$^2$ to a 65 mm$^2$. In some embodiments, the cutter includes a stent lattice structure in its expanded state, transitioning sigmoidally from a smaller diameter (for example, less than about 4.0 mm) at its proximal end to a larger diameter (for example, about 5.0 to about 10.0 mm (having a range of 3 mm to 12 mm) at its distal tip. In some embodiments, the distal lattice cells distal tips, or both are parallel to the proximal end of the cutter that is mounted to catheter 2, straight in its expanded state as can be seen in FIG. 36. FIG. 36 is an exemplary embodiment of device assembly illustrating multiple shape memory alloy discs advanced over one or more catheters. Referring to FIG. 36, in a particular embodiment, the assembly wherein an additional internal guide catheter 3603 has a predetermined, but flexible bend and is outside of the internal catheter 1 3602 that comprises the expandable tissue stabilizer 3604, but still inside of the catheter 2 3606 that comprises the expandable cutter 3608 and the delivery catheter 3 3610; but the delivery catheter is strong enough to contain the bend without distortion of the entire delivery catheter. Upon distal deployment of the additional guide catheter, the device assembly bends generally in a direction to point orthogonally towards the fossa ovalis. In some embodiments, during deployment of the cutter, the fully expanded lattice is substantially sigmoidal or linear when viewed in side profile.

In some embodiments, the cutter includes various geometries of a stent pattern. In some embodiments, the lattice cells of the stent is comprised of a series of sinusoidal waves whose period gradually decreases as the stent expands along its length to form the sigmoidal or s-shape transition when viewed in cross section.

Figure 39:
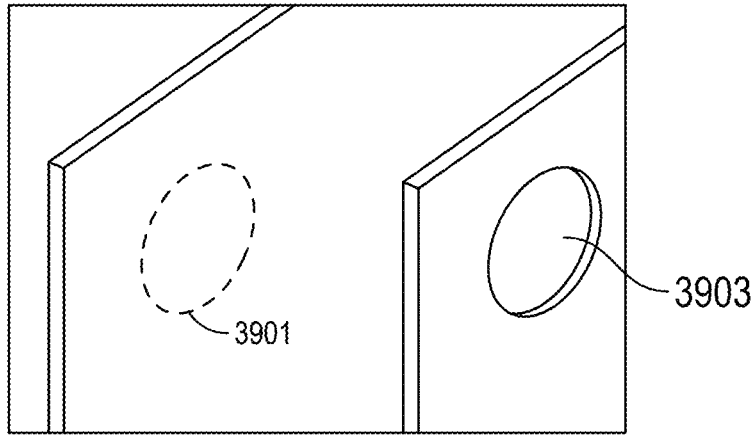
FIG. 39 shows an exemplary embodiment of cutter herein which initially creates a circumference of perforations, and then subsequently transitions to complete a full circumferential cut through forward translation through the septum.

FIG. 39 shows an exemplary embodiment of cutter herein which initially creates a circumference of perforations, and then subsequently transitions to complete a full circumferential cut through forward translation through the septum. Referring to FIG. 39, in some embodiments, the cutter initially creates a circumference of perforations 3901, and then subsequently transitions to complete a full circumferential cut 3903 through distal or proximal translation of the cutter or rotation of the cutter clockwise or counterclockwise or a combination of both translation and rotation. In some embodiments, the blade produces a full cut from initial contact. In some embodiments, post-cutting, the blade body or blade mouth serves as storage to retain excised tissue from the interatrial septum and ensure tissue retrieval (this is a safety measure to provide protection against embolic event due to circulation of excised tissue). In some embodiments, post-cutting, the blade collapses with the excised tissue within its body or mouth.

In some embodiments, post-cutting, the body or distal opening of the cutter serves as storage to retain excised septum and ensure tissue retrieval. Such tissue retention mechanism is a useful safety measure to provide protection against embolic event due to circulation of excised tissue. In some embodiments, post-cutting, the cutter collapses with the excised tissue within the body or distal opening of the blade. In some embodiments, proximal edge does not expand when stent is in its deployed stated and has 1 to 10 rectangular cut-outs arranged helically to facilitate embedding of the unexpanded proximal edge of the blade or cutter into the blade catheter.

In some embodiments, the cutter includes a stent with cells as shown in FIGS. 1 and 36. In some embodiments, the number of lattice cells distributed radially is between 3 to 30. In some embodiments, the number of lattice cells distributed radially is between 5 to 30, 8 to 30, 10 to 30, 12 to 30, 14 to 30, 18 to 30, 22 to 30, 25 to 30, 3 to 8, 3 to 10, 3 to 12, 3 to 14, 3 to 16, 3 to 18, 3 to 21, 3 to 24, or 3 to 27. In some embodiments, the number of lattice cells along its length or along the proximal-distal direction is about 2 to 30, 5 to 30, 8 to 30, 10 to 30, 12 to 30, 14 to 30, 18 to 30, 22 to 30, 25 to 30, 3 to 8, 3 to 10, 3 to 12, 3 to 14, 3 to 16, 3 to 18, 3 to 21, 3 to 24, or 3 to 27. In some embodiments, the length of each point or tip of the cutter along the proximal to distal direction is about 2 mm to about 3 cm, about 1.5 mm to about 2.5 mm, about 2.5 mm to about 3.5 mm, or about 2.2 mm to about 2.8 mm.

In some embodiments, the proximal edge of the cutter does not expand evenly, or in some cases, not at all, when exposed outside of its enclosing catheter. In some embodiments, the proximal edge or proximal portion, including the proximal edge of the cutter, includes a number of helical cut-outs. Such helical cut-outs 7101, as shown in FIG. 71, facilitate embedding of the unexpanded proximal edge of the stent blade into a catheter (for example, catheter 2) for housing the cutter. In some embodiments, (not shown), the cutter is designed to additionally permit partial unsheathing so as to enable the creation of an aperture having a diameter less than the possible maximum diameter of the cutter (when fully unsheathed).

In some embodiments, the cutter features radiopaque markers so as to orient its positioning in the body, its relation to other system components and its current state (expanded or collapsed); additional radiopaque markings is added to other elements to provide visualization of their relative positioning to each other under fluoroscopic guidance.

In some embodiments, (not shown), the distal portion of the cutter is one continuous blade, optionally serrated (as opposed to multiple blades).

In some embodiments, the cutter is constructed from a balloon expandable non-memory metal, (e.g.: stainless steel, as opposed to self-expanding shape memory alloy, which is described elsewhere herein). This embodiment permits gradual and controlled expansion and collapse of the cutter. In some embodiments, the cutter comprises an expandable balloon element within the proximal inner diameter of the cutter that is controllably expanded and monitored radiographically, to a controlled diameter, while still providing enough exposure of the cutting teeth to penetrate the interatrial septum and capture the excised tissue. In this configuration, the proximal portion of the cutter is rarely fully unsheathed so as to permit easier resheathing of the cutter through either proximal translation of catheter 2 into catheter 3, or distal translation of catheter 3, over catheter 2.

Figure 21:
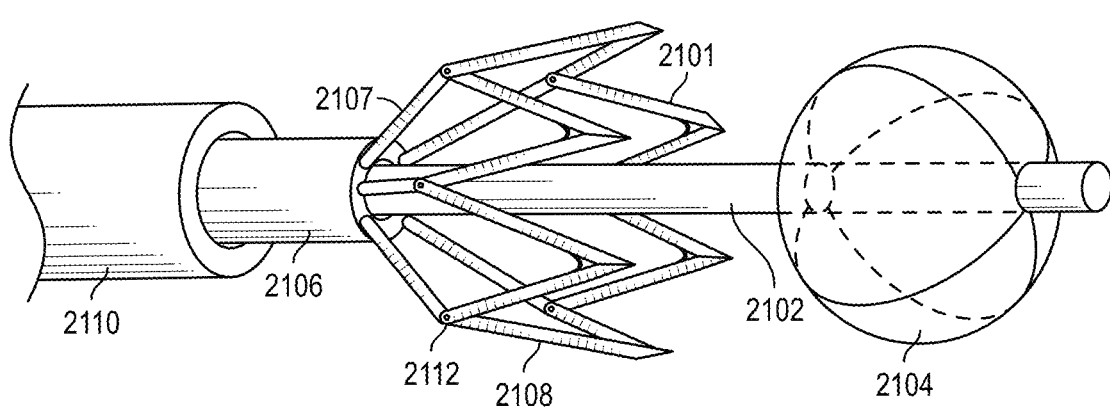
FIG. 21 is a representative illustration of an exemplary embodiment of the cutter in an expanded form, wherein the distal edge of cutter has a multitude of (e.g. eight) serrations or equivalently, teeth and forms an aperture that is polygonal (e.g. octagonal) in cross-section.

FIG. 21 is a representative illustration of an exemplary embodiment of the cutter in an expanded form, wherein the distal edge of cutter has a multitude of (e.g. eight) serrations/teeth and forms an aperture that is polygonal (e.g. octagonal) in cross-section. The blade(s) of the cutter is/are deployed through the expansion of radially-distributed struts, where the accordion spring shaped blades act as scissors with one edge sharpened. The blades are connected through hinges at the proximal end of the blades. The struts are connected to the proximal hinges that allow the blades to be folded and expanded. The distal ends of the blades are connected through a spring that ensures that they remain under tension and that the tips meet when the blades are expanded by the struts.

Figure 22:
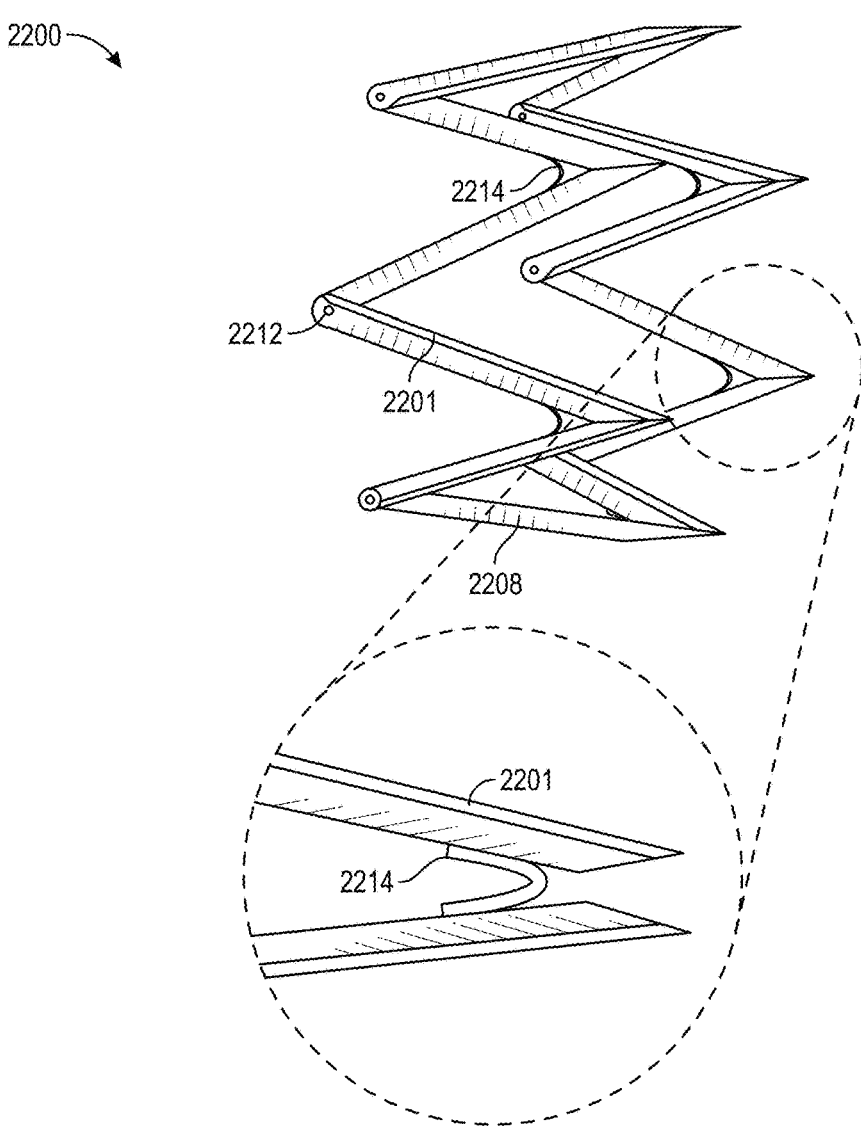
FIG. 22 is a detail representative illustration of the blades shown in FIG. 21 with a closer view (circled) showing two cutting edges on each tooth of the cutter in an expanded form and a detail of the tips at the distal end of the blades connected by a spring.

FIG. 22 is a detail representative illustration of the blades shown in FIG. 21 with a closer view (circled) showing two cutting edges on each tooth/serration of the cutter in an expanded form and a detail of the tips at the distal end of the blades connected by a spring. The distal tips of blades rotate in the same plane and allow the blades to meet in a penetrating sharpened tip.

In some embodiments, as illustrated in FIGS. 21 & 22, the blades 2101, 2201 or cutting edges of the cutter 2100, 2200 are deployed from delivery catheter 3, 2110, through the expansion of radially-distributed struts 2107 that are mounted to catheter 2, 2106. In this configuration, the proximal portion of the cutter is usually fully unsheathed so as to permit clearance of the cutters 2108, 2208 to fully clear the diameter of the tissue stabilizer 2104, deployed from catheter 1, 2102, as they pass through the septum, and then are retracted into catheter 2 and catheter 3, 2106, 2110. The struts in some embodiments preferably comprise a shape memory material; however, the blades are fabricated from either a shape memory alloy or non-shape-memory alloy. Hinges 2112, 2212 connect the proximal ends of the blades, allowing for the accordion spring to open up when the struts 2107 are unsheathed. A spring 2214 connecting the distal end of the blades 2101, 2201 allow the tips of the blades to touch when fully expanded.

Figure 23:
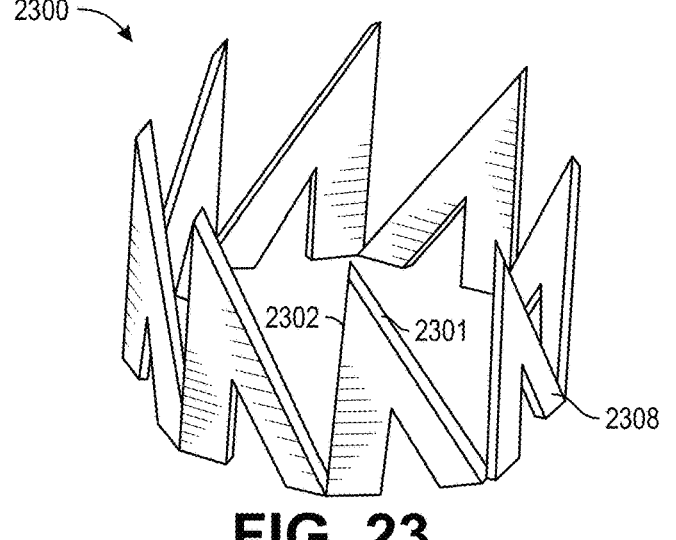
FIG. 23 is a representative illustration of an exemplary embodiment of the cutter in an expanded form, wherein the blade(s) of the cutter is deployed showing a modified cutting pattern requiring only one cutting edge on each tooth or serration of the cutter.

FIG. 23 is a representative illustration of an exemplary embodiment of the cutter in an expanded form, wherein the blade(s) of the cutter is/are deployed showing a modified cutting pattern requiring only one cutting edge on each tooth/serration of the cutter. In this embodiment, as illustrated in FIGS. 21 & 22, at least one edge of each blade 2101, 2201 of each tooth features a sharpened surface or a blade surface, creating a scissor effect as the blades are alternately sharpened on the inside and outside of the blades. Each hinge connects a blade that is sharpened on the inside and outside. This configuration lends itself to both plunge-cutting and rotational cutting in either direction.

FIG. 24A is a representative illustration of an embodiment, illustrating the cutter's teeth shaped in a series of scallops that come to a narrow point. FIG. 24B is a representative illustration of an embodiment, illustrating the cutter's teeth shaped in a series of "U"'s to create a crown like appearance with pointed edges. In some embodiments of the cutter 2300, as illustrated in FIG. 23, only one edge 2301 of each tooth 2308 is sharpened. In the aforementioned embodiment, the non-sharpened edge 2302 of each tooth is approximately perpendicular to tissue during penetration. In some embodiments, alternative cutters have a single continuous cutting blade with one cutting edge.

In some embodiments, as illustrated in FIGS. 24A & 24B, the cutter's teeth are shaped in a series of "U"'s, 2402 to create a crown-like appearance with pointed edges. In some embodiments, the cutter's teeth are shaped in a series of scallops, 2401 that come to a narrow point.

In some embodiments, the cutter takes the form of one or more blades that penetrate the septum and are either rotated or plunged before, during or after penetration, to form a complete circumferential or O-shaped cut.

In some embodiments, the cutter takes the form of one or more blades that penetrate the septum with reciprocating, rotated cuts, or plunged motions. In some embodiments, the cutter takes the form of two or more blades that penetrate the septum with reciprocating, rotated cuts or plunged motions.

In some embodiments, the cutter takes the form of one or more blades that penetrate the septum with vibratory motions. In some embodiments, the cutter takes the form of two or more blades that penetrate the septum with vibratory motions. In some embodiments, the vibration is mechanically, electrically, hydraulically, pneumatically, magnetically, or sonically generated.

In some embodiments, the device assemblies disclosed herein includes an optional mechanism at or about the proximal end of the device assembly configured to provide a user with alternative actuation and movement of the cutter. In some embodiments, such alternative actuation mechanism includes a handle; a knob; a hydraulic connection; a pneumatic connection; an electrical motor connection; or a sonic, ultrasonic, or otherwise vibratory connection. In some embodiments, the alternative actuation and movement includes rotary and reciprocating movement.

In any of these auxiliary motion methods, one of skill in the art would recognize that plunged, oscillatory, rotational, and vibrational motions incorporated into deployment or actuation of the cutter, in some embodiments, reduces the force required to translate the cutting blade(s) through tissue. In any of these auxiliary motion methods, one of skill in the art would recognize that plunged, oscillatory, rotational, or vibrational motions incorporated into deployment or actuation of the cutter.

In any of the preceding embodiments and examples, the shape of the anastomosis generated by the cutting blade is optionally different from round. Rather, in order to produce a shunt configuration with improved patency, the shape of the anastomosis is configurable to have a shape generally comprising: a circle; a square; a rectangle; a triangle; an oval; a polygon; or any other feasible geometrical shapes.

In some embodiments, the expanded dimension of the tissue stabilizer is less than the expanded dimension of the cutter. In some embodiments, the expanded dimension of the cutter is between about 1% and about 50% (in the range of 0.1% to 65%) larger than the expanded dimension of the tissue stabilizer. In some embodiments, the expanded dimension of the cutter is between about 0.1% and about 10% larger than the expanded dimension of the tissue stabilizer. In some embodiments, the expanded dimension of the cutter is between about 0.1% and about 20% larger than the expanded dimension of the tissue stabilizer. In some embodiments, the expanded dimension of the cutter is between about 0.1% and about 25% larger than the expanded dimension of the tissue stabilizer. In some embodiments, the expanded dimension of the cutter is between about 1% and about 15% larger than the expanded dimension of the tissue stabilizer. In some embodiments, the expanded dimension of the cutter is between about 1% and about 20% larger than the expanded dimension of the tissue stabilizer. In some embodiments, the expanded dimension of the cutter is between about 1% and about 35% larger than the expanded dimension of the tissue stabilizer.

In some embodiments, one of skill in the art would recognize that the direction of the cut could be reversed from the left atrium to the right atrium with proper engineering of the device assembly.

Figure 25D:
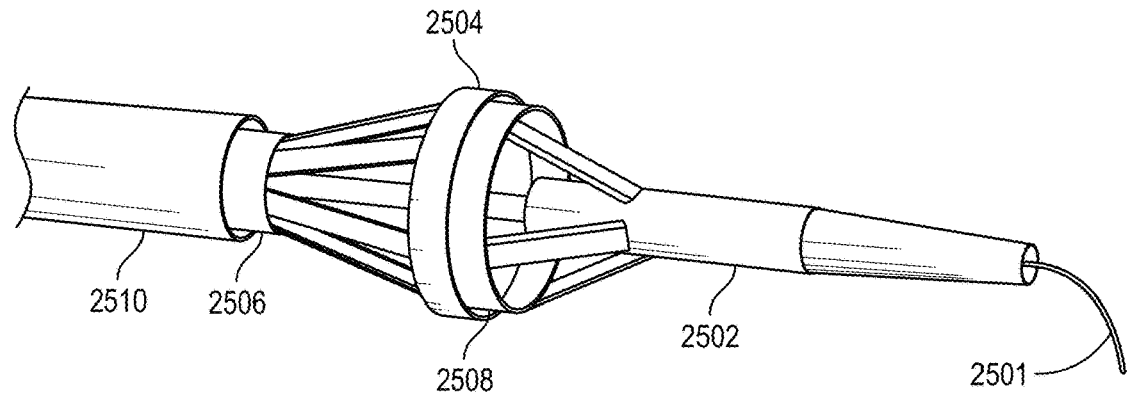
FIG. 25D is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3.

For example, FIG. 25A is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3. Catheter 3 is then advanced through the septum, until the cutter is positioned on the distal side of the septum and tensioning element positioned on proximal side of septum. FIG. 25B is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3. Catheter 3 is then advanced through the septum, until the cutter is positioned on the distal side of the septum and tensioning element positioned on proximal side of septum. FIG. 25C is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3. Catheter 3 is then advanced through the septum, until the cutter is positioned on the distal side of the septum and tensioning element positioned on proximal side of septum. FIG. 25D is a sequential representative illustration of an exemplary embodiment of a reversed cutting action, wherein the cutter is mounted to catheter 1 (which remains in the right atrium) and tissue stabilizing element is mounted to catheter 2 and is slidably engaged in the lumen of catheter 3. Catheter 3 is then advanced through the septum, until the cutter is positioned on the distal side of the septum and tensioning element positioned on proximal side of septum.

As illustrated in FIGS. 25A-25D, in some embodiments, the device assembly 2500 includes a guidewire 2501 which is used to penetrate the interatrial septum and provide a guided pathway for the device assembly. However, the cutter 2508 is mounted to catheter 1, 2502 which comprises a larger diameter at its distal end and a smaller diameter at its proximal side where it is slidably engaged with catheter 2, and the tissue stabilizing element, or equivalent, the tissue tensioning element 2504 is mounted to catheter 2, 2506. In this configuration, both the cutter and the tissue stabilizing element are made from shape memory material and are housed within delivery catheter 3, 2510 in their collapsed state. Catheter 3 is then advanced through the septum, until the cutter, 2508 is positioned on the distal side of the septum and tissue stabilizing element, or equivalently, tissue tensioning element, 2504 is positioned on the proximal side of septum. Once the cutter and tissue stabilizing element are in proper position with respect to the septum, catheter 3 is retracted proximally, exposing catheter 1, 2502, thereby permitting expansion of the cutter on the distal side of the septum, exposing catheter 2, 2506, thereby permitting expansion of the tissue stabilizing element or equivalently, tissue tensioning element on the proximal side of the septum. Catheters 1 and 2, in some embodiments, are then translated with respect to one another to penetrate and cut the interatrial septum. In this embodiment, the cutter is undersized with respect to the tensioning element such that the cutter lies housed within the tissue stabilizing element after cutting. Catheter 3, 2510 in some embodiments, is then advanced distally with respect to catheters 2, 2506 and 1,

2502 thereby collapsing both the tensioning element 2504 and the cutter 2508 simultaneously. In some embodiments, the expanded circumference or the area enclosed cross-sectionally by the cutter 2508 is smaller than the expanded circumference or the area enclosed cross-sectionally by the stabilizing element 2504.

Figure 26A:
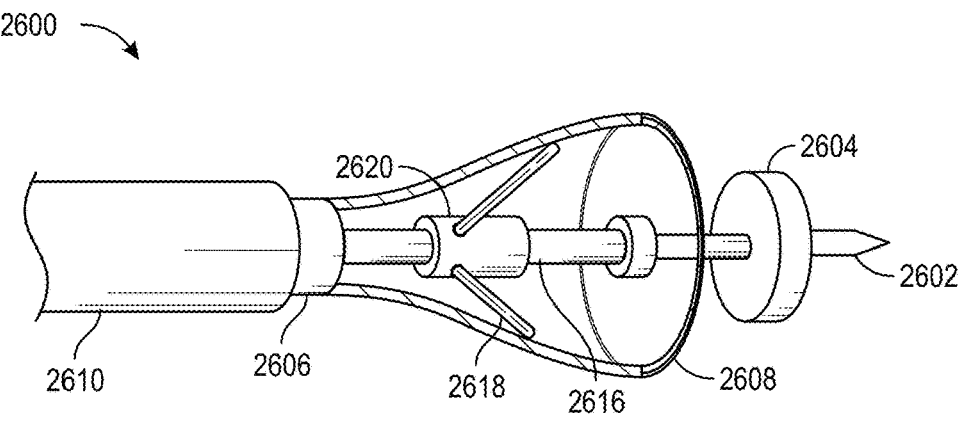
FIG. 26A is a representative illustration of an embodiment of the cutter in a partially-expanded or partially-deployed state using an "umbrella" mechanism.
Figure 26B:
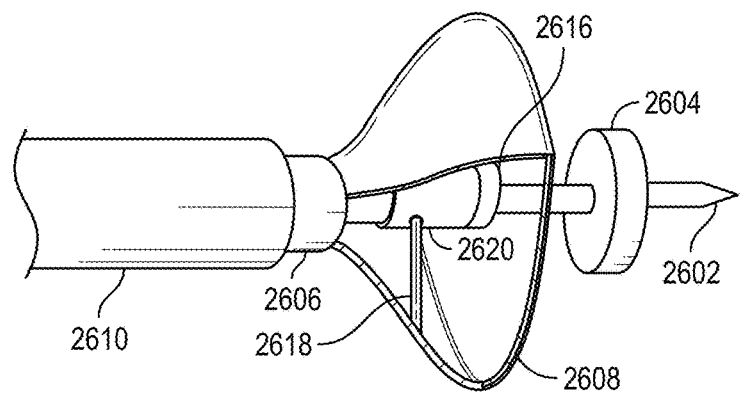
FIG. 26B is a representative illustration of FIG. 26A in a fully deployed, or equivalently, expanded state.

FIG. 26A is a representative illustration of an embodiment of the cutter in a partially-expanded/partially-deployed state using an "umbrella" mechanism. FIG. 26B is a representative illustration of FIG. 26A in a fully deployed/expanded state. Thus, in some embodiments, such as 2600, illustrated in FIGS. 26A & 26B, the cutter 2608 is expanded outside of delivery catheter 3, 2610 using an "umbrella" strut mechanism 2618. A rigid strut 2618 connects a translatable slider 2620 and the cutter, 2608 such that the translation of the slider over catheter 4, 2616 in relation to the cutter causes the strut to rotate outwardly, but no farther than 90 degrees, causing the cutter 2608 to expand in diameter. An internal catheter 4, 2616, also housing catheter 1, 2602 and comprising a tissue stabilizer 2604, is deployable from within catheter 3, whereas catheter 1 is slidably engaged within catheter 4. Catheter 2 allows the slider to move distally towards the tip of catheter 4 that will prohibit the struts connected to the slider from rotating outwardly farther than 90 degrees. In a similar embodiment, the translation of the slider 2620 and the expansion of the cutter are triggered by a spring and un-deployed by the proximal translation of the cutter. In some embodiments, a rigid strut connects a translatable catheter 4, 2616, and the cutter 2608 such that the translation of catheter 4 in relation to the cutter causes the strut to rotate upwards but no farther than 90 degrees causing the cutter to expand in diameter. FIGS. 26A & 26B also show catheter 2, 2606 and the umbrella stem or slider, 2620 supporting the struts.

Figure 27A:
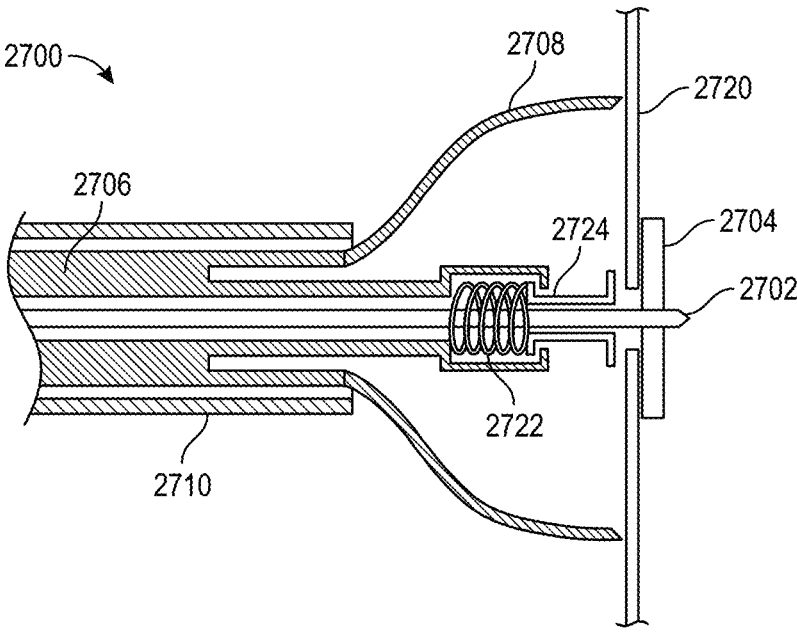
FIG. 27A is a representative illustration of an embodiment of the cutter in a partially-expanded or partially-deployed state wherein catheter 2 is connected to a coaxial alignment mechanism with a spring mechanism housed in its distal tip.
Figure 27B:
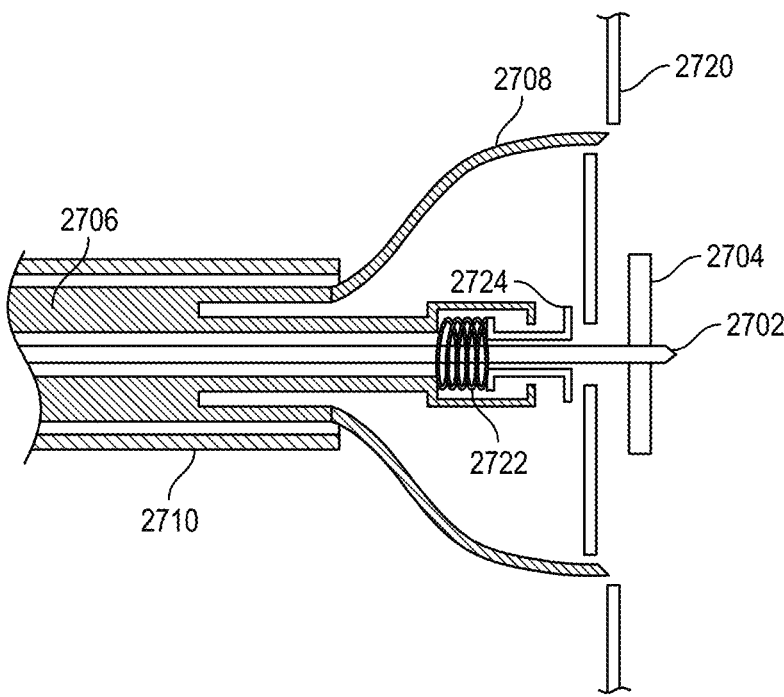
FIG. 27B is a representative illustration of the deployed spring-plunger mechanism of FIG. 27A wherein the spring pushes the excised tissue distal to the cutter.

In some embodiments such as 2700, as illustrated in FIGS. 27A & 27B, catheter 2, 2706 is connected to a coaxial alignment mechanism with a spring mechanism 2722 housed in its distal tip. On the other side of the spring, is a coaxial alignment plunger 2724 which extends out farther than the plane in which the deployed cutter rests in. Catheter 1, 2702 runs through the spring mechanism and its tissue stabilizing mechanism 2704 is deployed on the left atrial side of the septum. Upon actuating the cutter 2708 towards the septum, the plunger is forced to compress the spring first such that when the cut is completed the spring pushes the excised tissue distal to the cutter. FIGS. 27A & 27B also show delivery catheter 3, 2710, the tissue stabilizer, 2704, and the septum, 2720. FIG. 27A is a representative illustration of an embodiment of the cutter in a partially-expanded/partially-deployed state wherein catheter 2 is connected to a coaxial alignment mechanism with a spring mechanism housed in its distal tip. FIG. 27B is a representative illustration of the deployed spring-plunger mechanism of FIG. 27A wherein the spring pushes the excised tissue distal to the cutter.

In some embodiments, a therapy is applied to the cut edge of tissue during or after tissue disruption for the purpose of promoting scar formation or fibrosis and maintenance of aperture patency. This therapy in some embodiments, takes the form of electrocautery, radiofrequency ablation, cryoablation, pharmacologic infusion, dilation of a pharmacologic-coated balloon, or placement of radial sutures to create tissue imbrication. Patency, in some embodiments, also is achieved by an implanted device assembly made of bioresorbable material which stents open the aperture for a defined period of time prior to its resorption.

In some embodiments, in any one of the cutter embodiments described, the cutter is configurable with a thermocouple wire near the tip of the cutter to aid in tissue cutting by cauterizing the tissue as it is cut. The thermocouple wire is heated by running an electric current through the metal thermocouple wire. In addition, this would aid in maintaining long term shunt patency.

In some embodiments, a cutter includes a support or scaffold and feature at least one bladed edge at its distal tip. In some embodiments, the cutter is delivered to the interatrial septum and, upon deployment and actuation, incises a portion of the interatrial septum that yields an aperture. The bladed edge, in some embodiments, assumes a form factor that reduces the amount of force required to drive the cutter through the septum. In some embodiments, the cutting dimension of a cutting element or a cutter is the dimension of the cutter in the expanded state. In some embodiments, the cutting dimension of a cutter is the dimension of the cutter expanded and at its distal end where it touches and cuts the tissue. In some embodiments, the cutting dimension is the dimension of the tissue cut by the cutter.

In some embodiments, the expandable cutter is expanded via relative movement between the delivery catheter of the device assembly and cutter. In some embodiments, the cutter is expanded by moving the cutter out of the delivery catheter, optionally toward the septum, while the delivery catheter remains still relative to the septum. In some embodiments, the cutter is expanded by moving the delivery catheter away from the septum while the cutter remains relatively still to the septum during expansion. In some embodiments, the cutter is moved toward the septum after expansion. In some embodiments, the cutter and the delivery catheters is moved in combination so none of them remain still relative to the septum, while the net movement of the two is that the cutter moves out of the distal end of the delivery catheter and being expanded.

In some embodiments, the fully expanded cutter engages or traverses the left atrial side of the interatrial septum such that the cutter pierces and cuts completely through the interatrial septum, optionally removing the cut tissue, thereby creating an interatrial pressure relief opening in the interatrial septum. In some embodiments, the tissue excised by the cutter is at least a portion of the interatrial septum. In some embodiments, the tissue excised by the cutter is only a portion of the septum. In some embodiments, the interatrial pressure relief opening is sufficiently sized to allow blood flow through the interatrial pressure relief opening from the left atrium to the right atrium such that no more than 50% of left atrial blood is shunted to the right atrium. In some embodiments, the interatrial pressure relief opening is sufficiently sized, and or of such shape, in order to slow a natural healing process of the tissue to maintain patency of the interatrial pressure relief opening in the interatrial septum without implanting a stent, a valve, or any other mechanical implant therein.

In some embodiments, the expandable cutter is exposed and expands from a collapsed dimension to an expanded shape coaxial with an adjustable dimension to the first internal coaxial catheter when the distal end of the delivery catheter is pulled back proximally. In some embodiments, the adjustable dimension of the expandable cutter is controllable by the amount of proximal pull-back of the delivery catheter. In some embodiments, the expandable cutter comprises an expandable lattice and wherein the distal end of the expandable cutter lattice comprises sharpened ends configured to perform as tissue cutting blades. In some embodiments, the plurality of sharpened ends configured to perform as tissue cutting blades comprise a tissue penetrating end and one or more lateral edges having a sharpened knife-like edge.

The tissue retention mechanism is defined herein as any component or combination of components of the device assembly that is configurable for capturing the excised tissue from the interatrial septum.

In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises a continuous blade comprising a shape memory alloy, and wherein the distal end of the continuous blade comprises: a single smooth sharpened knife edge; or plurality of sharpened serrations or teeth along the continuous blade; configured to perform as a fully-circumferential (continuous) tissue cutting blade. In some embodiments, the single smooth sharpened knife edge or the plurality of sharpened serrations along the continuous blade are configured to perform as tissue cutting blades. In some embodiments, the delivery catheter is at least partially retracted distally to expose the cutter such that it is expanded, and wherein the third catheter is translated distally such that the slider element is slidably engaged within the cutter causing the two or more struts to engage and radially increase the size of the cutter such that it is greater than the size of the stabilizing element.

In some embodiments, the excised portion of tissue (speared by catheter 1) is secured and removed from the body. In some embodiments, the tissue retention element prevents the excised tissue from inadvertently separating from catheter 1 and permits translation of the excised tissue into delivery catheter 3 prior to removal of the device assembly from the body.

In some embodiments, the tissue retention mechanism comprises the tissue stabilizer, the tensioning element, or the like. In some embodiments, the tissue retention mechanism comprises a hooked end of the guidewire. In some embodiments, the tissue retention mechanism comprises the space along the length of the first catheter between the cutter and the tissue stabilizer. In some embodiments, the tissue retention mechanism comprises the cutting mechanism in combination with the first catheter. In some embodiments, the tissue retention mechanism comprises the cutting mechanism in combination with the first catheter and the tissue stabilizer. In some embodiments, the tissue retention mechanism comprises the cutting mechanism alone, wherein the cutting mechanism collapses over the excised tissue, capturing it internally within the cutting mechanism as it is retracted into the delivery catheter.

In some embodiments, the first internal coaxial catheter further comprises an expandable balloon to controllably inflate the expandable cutter, wherein the dimension of the cutter is controlled by the inflation of the expandable balloon, the balloon optionally positioned within a central portion of the cutter. In some embodiments, first internal coaxial catheter further comprises expandable struts configured to controllably engage the internal dimension of the expandable cutter, wherein the dimension of the cutter is controlled by the expansion of the expandable struts, optionally positioned within a central portion of the cutter.

In some embodiments, the delivery catheter as disclosed herein includes a unidirectional or bidirectional steerable sheath. In some embodiments, the delivery catheter is a deflectable catheter. In some embodiments, the delivery catheter is a wire-reinforced or braided catheter. In some embodiments, the delivery catheter is a standard catheter. In some embodiments, the delivery catheter includes metal, alloy, polymer, plastic, biomaterials, or their combinations. In some embodiments, the delivery catheter includes a reinforced distal tip. Such reinforced distal tip, in some embodiments, provides radial rigidity and permit unsheathing and sheathing of the cutter. In some embodiments, the delivery catheter includes one or more metal, alloy, or mesh for reinforcement. In some embodiments, the delivery catheter has a bend radius of about 0.5 to about 4 inches, about 0.4 inches to 4.5 inches, about 0.5 to about 1.5 inches, about 0.5 to about 2 inches, about 1 inch to about 2 inches, about 1 inch to about 3 inches, about 1.5 inches to about 3.5 inches, about 2 inches to about 3 inches, about 2.5 inches to about 4 inches, about 3 inches to about 4 inches, or about 3 inches to about 4.5 inches. In some embodiments, the delivery catheter is the main housing catheter for the rest of the device assembly. The blade or cutter catheter is housed in the distal portion of the delivery catheter that keeps the blade compacted until it is ready to be deployed. It also allows for packing of the excised tissue inside of it.

In some embodiments, the delivery catheter could be composed of a combination of polymer, metal, or braided or coiled reinforcement using metal, polymer, or their combination to allow for sufficient pushability during the introduction of the whole device assembly. The delivery catheter could have a porthole to allow for rapid wire exchange during its introduction into the body. The delivery catheter could contain 1 or more radiopaque markers to aid in its proper delivery to the interatrial septum. In some embodiments, the delivery catheter is a unidirectional or bidirectional steerable or deflectable sheath capable of supporting and maintaining its degree of deflection during the cutting motion. In some embodiments, the delivery catheter has a preformed bend oriented towards the interatrial septum upon having a rod sufficiently rigid enough to straighten removed from its internal lumen. In some embodiments, the distal edge of the delivery catheter is reinforced with a rigid metal, polymer, or their combinations, or shape memory metal, polymer, or their combination to permit easier unsheathing, sheathing, or both unsheathing and sheathing of the stent blade. In some embodiments, the distal edge of the delivery catheter is reinforced with additional radial rigidity to permit easier unsheathing, sheathing, or both unsheathing and sheathing of the stent blade.

The delivery catheter ranges, in some embodiments, in sizes from 8 to 18 Fr in size. In some embodiments, the delivery catheter comprises a material sufficiently rigid enough to straighten the shaft of the second catheter while it is within the delivery catheter and wherein other catheters are freely translatable therein. In some embodiments, the delivery catheter is rigid enough to straighten out the components housed therewithin while they are inside of the delivery catheter but also allows free sliding or translation therewithin.

In some embodiments, the guide catheter which defines the path that the cutter takes from the mouth of the delivery catheter up to the septum and ensures coaxial alignment during cutting of the septum and also aids in coaxial alignment. In some embodiments, a coaxial alignment mechanism provides centralization between the cutter, tissue stabilizer, and tissue retention elements. The coaxial aligner, in some embodiments, reduces the risk of incurring inadvertent interaction between the cutter and the tissue stabilizer. The coaxial aligner also serves as a means to ensure the cutter (connected to catheter 2) is advanced centrally over the tissue stabilizer and through the septum.

In some embodiments, the guide catheter 3803 houses the guidewire 3801 therein as shown in FIGS. 38A-38D. In some embodiments, the guide catheter as disclosed herein, in some embodiments, includes a unidirectional or bidirectional steerable sheath. In some embodiments, the guide catheter is a deflectable catheter. In some embodiments, the guide catheter is a wire-reinforced or braided catheter. FIGS. 38A-38D also show the shape memory alloy mesh catheter 3804. FIGS. 38A-38D show an exemplary sequential embodiment of a device assembly herein eliminating the need for an additional mesh housing catheter to deploy the tissue stabilizing element as the guide catheter has a smaller OD at the distal end to ensure that it crosses the interatrial septum while running over the guidewire.

Figure 37:
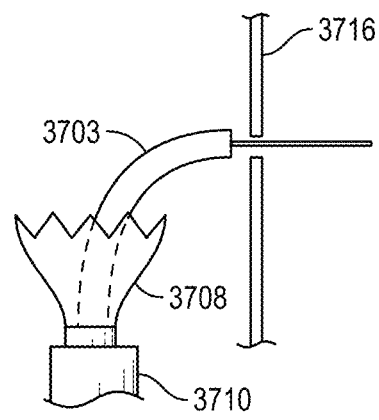
FIG. 37 is an exemplary embodiment of device assembly as disclosed herein with a guide catheter that has a predetermined bend.
Figure 38A:
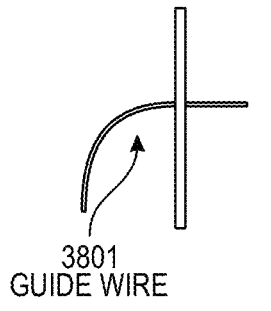
FIGS. 38A-38D show an exemplary sequential embodiment of device assembly herein eliminating the need for an additional mesh housing catheter to deploy the tissue stabilizing element as the guide catheter has a smaller OD at the distal end to ensure that it crosses the interatrial septum while running over the guidewire.
Figure 38B:
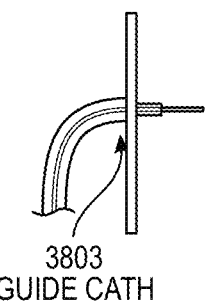
Figure 38C:
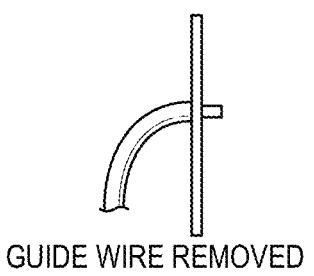
Figure 38D:
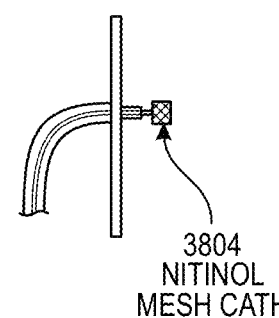

In some embodiments, the guide catheter 3703 has a preformed bend oriented towards the interatrial septum 3716 upon being advanced beyond the tip of the delivery catheter 3 3710 or cutter 3708, for example, as shown in FIG. 37. In some embodiments, the guide catheter translates over the shape memory alloy mesh housing catheter once the balloon or shape memory alloy mesh plug(s) is expanded to anchor the system to the septum. In addition, the guide catheter is rigid enough to withstand deflection when the blade catheter is translated over it or during cutting of the septum. FIG. 37 is an exemplary embodiment of device assembly as disclosed herein with a guide catheter that has a predetermined bend.

In some embodiments, the guide catheter is built up of any combination of polymer, metal, metal or polymer based braided or coiled reinforcement. In some embodiments, the guide catheter could have a porthole to allow for rapid wire exchange during its introduction into the body. In some embodiments, the guide catheter could contain 1 or more radiopaque markers to aid in its proper delivery to the interatrial septum. In some embodiments, the guide catheter is a unidirectional or bidirectional steerable or deflectable sheath capable of supporting and maintaining its degree of deflection during the cutting motion. In some embodiments, the metallic catheter has a softer tip with smaller diameter eliminating the need for an additional shape memory alloy mesh housing catheter to deploy the tissue stabilizing element 3804 (as in FIGS. 38A-38D). In some embodiments, the guide catheter has a narrow tip at its distal edge to ensure coaxial alignment with the shape memory alloy mesh catheter. In some embodiments, the guide catheter has the tissue stabilizer connected to and built into its distal tip; such that once the distal tip of the guide catheter is inserted into the left atrium and the tissue stabilizer is actuated past the tip of the guide catheter, the tissue stabilizer is deployed and anchors the system to the atrium providing tissue stabilization during tissue cutting.

In some embodiments, the guide catheter has a proper stiffness that permits adjustment of its orientation towards the septum in order to guide other parts of the device assembly, such as the cutter and tissue stabilizer. In some embodiments, the guide catheter is a standard catheter. In some embodiments, the guide catheter includes metal, alloy, polymer, or their combinations.

In some embodiments, a guide catheter 4103, 4203, 4303, 4403 takes a preformed bend upon leaving the delivery catheter. In some embodiments, the preformed bend is formed in the guide catheter automatically upon leaving the delivery catheter, at least partly. In some embodiments, the preformed bend is formed by additional triggers upon leaving the delivery catheter. In some embodiments, the preformed bend is towards and up to the interatrial septum. In some embodiments, the preformed bend is towards or up to the interatrial septum. In some embodiments, the bend is not pre-formed but formed by additional maneuver or actuation. In some embodiments, while being advanced, optionally beyond the tip of the delivery catheter or other housing part enclosing the guide catheter, the guide catheter translates over the guidewire 4101, 4201, 4301, 4401 the tissue stabilizer delivery catheter, or the proximal portion of the tissue stabilizer while the tissue stabilizer is deployed to anchor the rest of the device assembly to the septum as shown in FIGS. 38, 41A-E, 42A-E, 43A-E, and 44A-E. In some embodiments, the guide catheter is withdrawn after it has been successfully advanced to deliver one or more parts to the desired location in heart. In some embodiments, the guidewire is pulled out before or after cutting of the interatrial septum. In some embodiments, the guide catheter is stiff enough to not deflect when catheter 2 or catheter enclosing the cutter is translated over it or during the cutting of the interatrial septum. FIGS. 41A-E, 42A-E, 43A-E, and 44A-E also show the shape memory alloy mesh housing catheter 4102, 4202, 4302, 4402, and the shape memory alloy mesh catheter 4104, 4204, 4304 and 4404.

Referring to FIGS. 38A-38D, in some embodiments, the guide catheter disclosed herein is a metallic catheter with a softer tip of smaller diameter (for example, polymeric tip). In some embodiments, such guide catheter eliminates the need for an additional shape memory alloy mesh housing catheter, and the shape memory alloy mesh plugs or tissue stabilizer is directly housed within the guide catheter.

In some embodiments, the shape memory alloy mesh catheter or catheter housing the tissue stabilizer is delivered over the guidewire. In some embodiments, the shape memory alloy mesh catheter features an inner lumen that allows the guidewire to properly fit therethrough.

Figure 40:
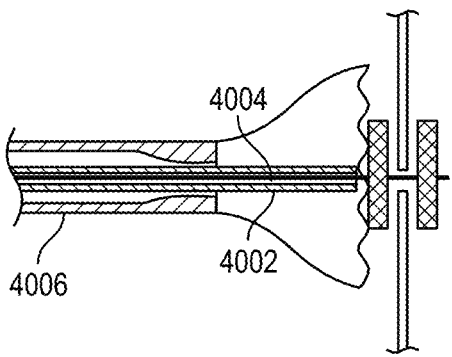
FIG. 40 shows an exemplary embodiment of the cutter catheter disclosed herein, which optionally has a smaller inner lumen at its distal end to ensure coaxial alignment with the balloon catheter or shape memory alloy mesh housing catheter.
Figures 41A, 41B, 41C, 41D, 41E:
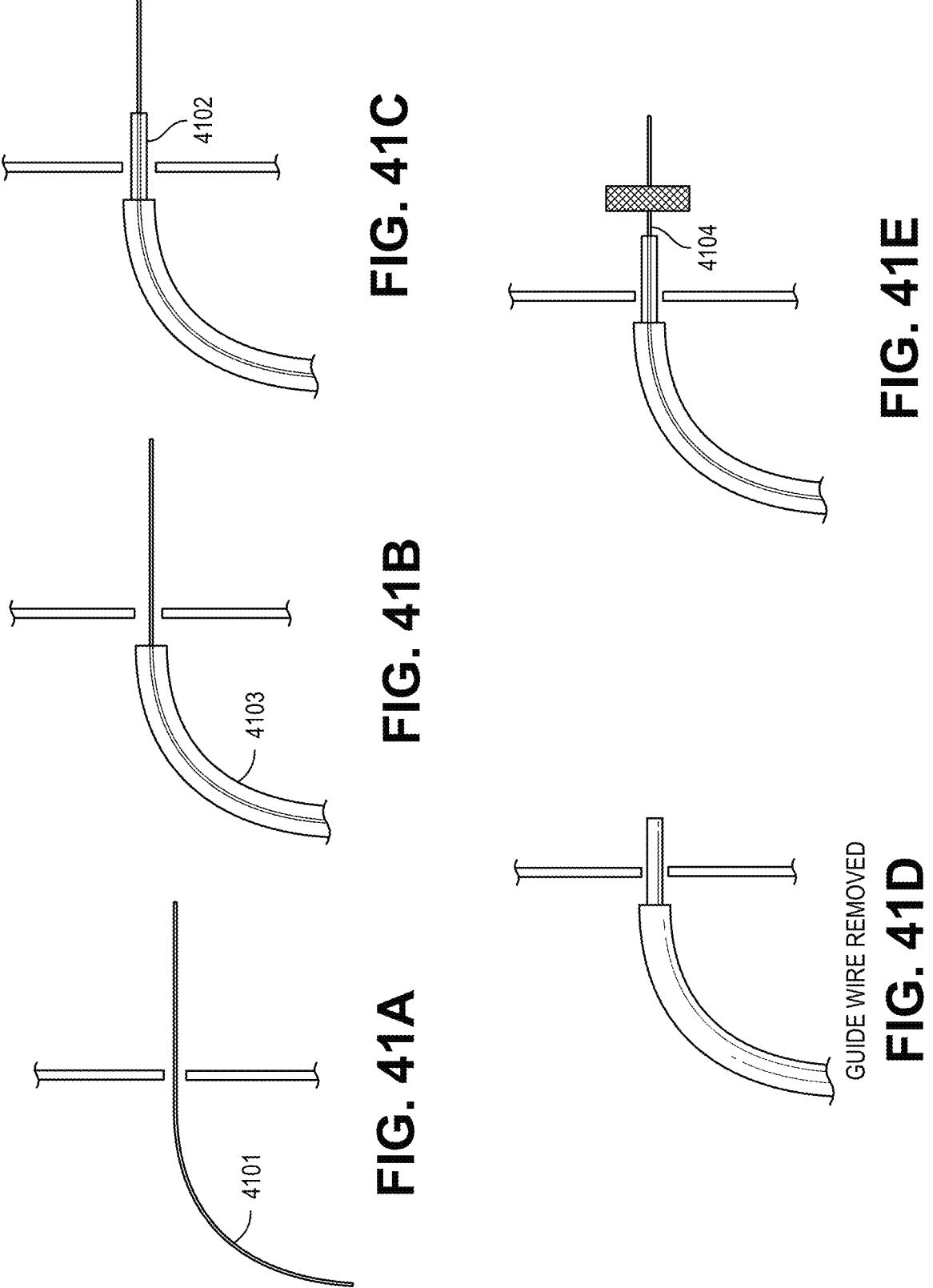
FIGS. 41A-41E show an exemplary embodiment of sequential procedural steps of applying the device assembly as disclosed herein.
Figures 42A, 42B, 42C, 42D, 42E, 42F:
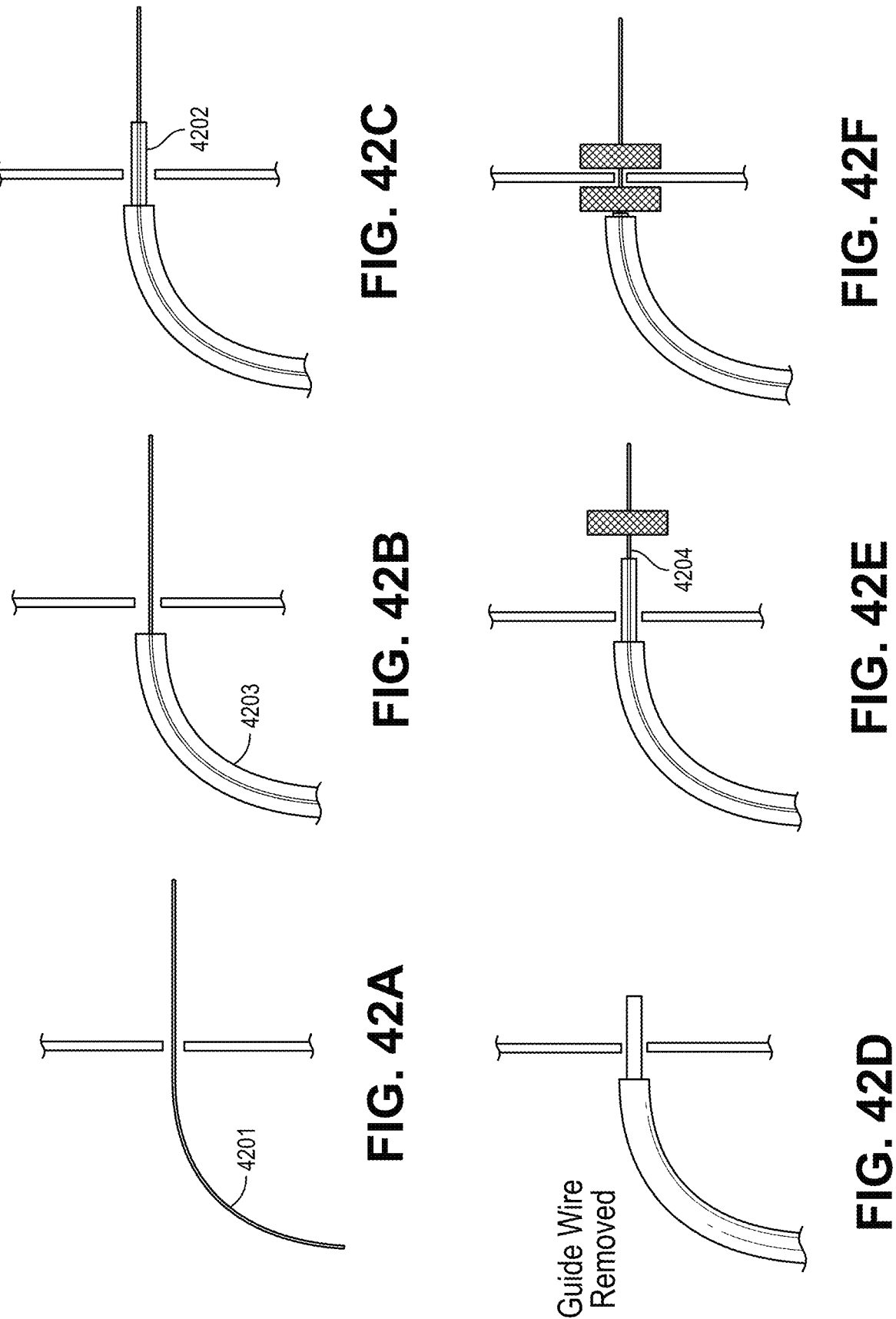
FIGS. 42A-42F show an exemplary embodiment of sequential steps using the device assembly as disclosed herein resulting in the deployment of a dogbone shaped expandable tissue stabilizer, sandwiching the interatrial septum.
Figures 44A, 44B, 44C, 44D, 44E:
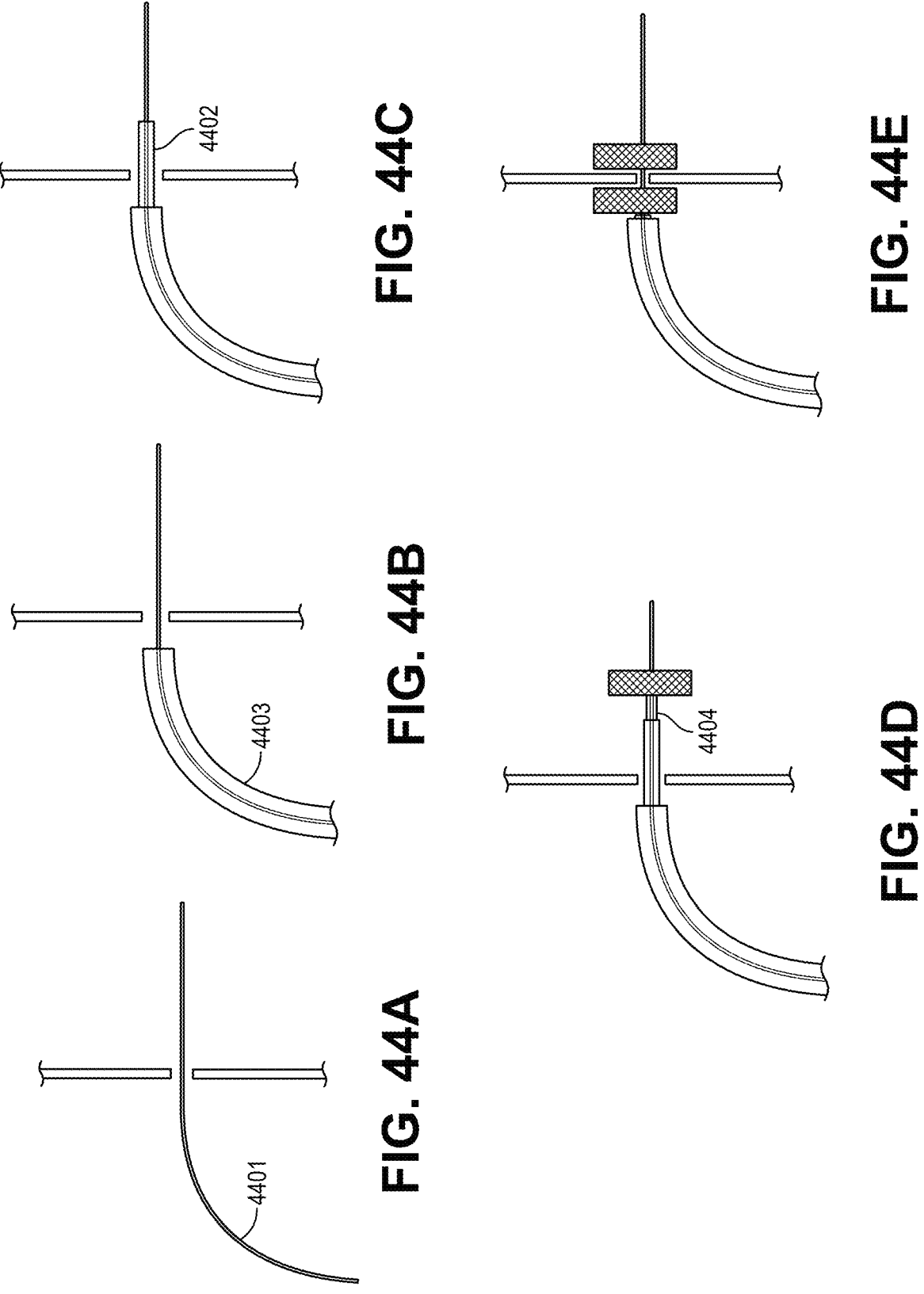
FIGS. 44A-44E show an exemplary embodiment of sequential steps using the device assembly as disclosed herein eliminating the need to remove the guidewire as the catheter comprising the expandable tissue stabilizer is able to run over the guidewire and is deployed in the left atrium followed by the right atrium sandwiching the interatrial septum.

In some embodiments, catheter 2 or the catheter for enclosing the cutter is wire-reinforced or a braided catheter. In some embodiments, catheter 2 or the catheter for enclosing (delivery catheter) the cutter includes one or more shape memory materials, such as shape memory metal. Referring to FIG. 40, in some embodiments, catheter 2, 4006, features a smaller inner lumen at its distal end to ensure coaxial alignment with catheter(s) housed within it (guide catheter shape memory alloy mesh housing catheter 4002, or both). In some embodiments, the distal tip of the guide catheter is of a smaller diameter and includes a flexible portion 4004 that is used to cross the septum and introduce the shape memory alloy mesh tissue stabilizer into the left atrium removing the need for an additional shape memory alloy mesh housing catheter. FIG. 40 shows an exemplary embodiment of the blade/cutter catheter disclosed herein, which optionally has a smaller inner lumen at its distal end to ensure coaxial alignment with the balloon catheter or shape memory alloy mesh housing catheter.

Figure 53A:
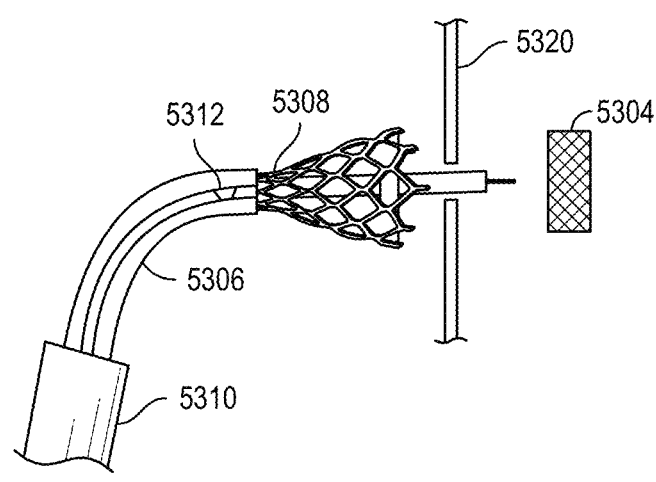
FIGS. 53A-53B show exemplary embodiments of the device assembly as disclosed herein, in which the distal tip of the guide catheter includes a smaller diameter and more flexible portion than that is used to cross the septum and introduce the shape memory alloy mesh tissue stabilizer into the left atrium.
Figure 53B:
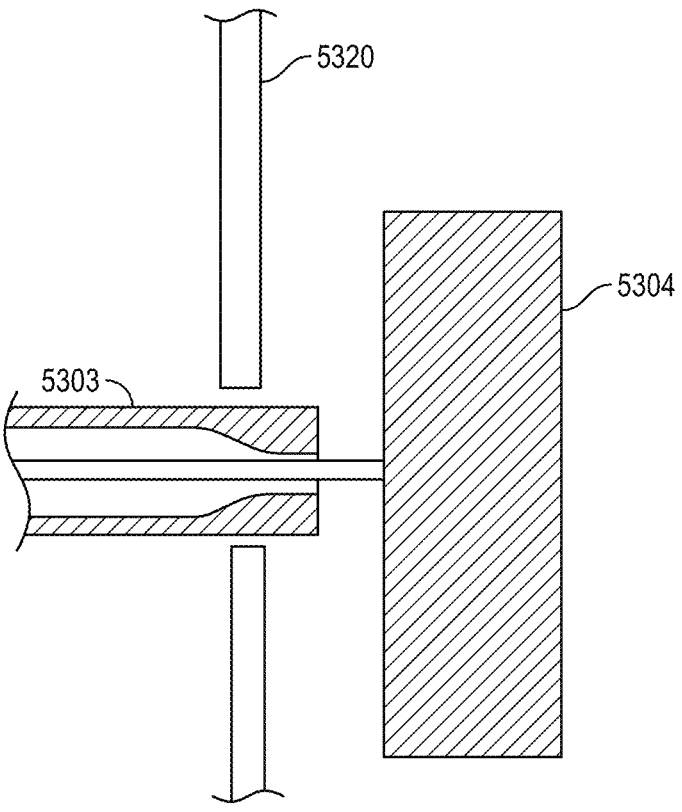

Referring to FIGS. 53A-53B, in some embodiments, the distal tip of the guide catheter 5303 has a smaller diameter to ensure coaxial alignment (FIG. 53B) and a more flexible portion 5312 that is used to cross the septum 5320 and introduce the shape memory alloy mesh tissue stabilizer 5304 into the left atrium removing the need for an additional shape memory alloy mesh housing catheter to deploy the shape memory alloy mesh; and the guide catheter 5303 has a flexible portion before or after the bend to help secure stability of the system during cutting, as shown in FIG. 53A. FIGS. 53A-53B show exemplary embodiments of the device assembly as disclosed herein, in which the distal tip of the guide catheter includes a smaller diameter and more flexible portion than that used to cross the septum and introduce the shape memory alloy mesh tissue stabilizer into the left atrium. The other elements of the device assembly, the cutter 5308, the cutter catheter 2 5306, the delivery catheter 3 5310 is advanced to the right atrium before the distal tip of the guide catheter crosses the septum. In some embodiments, the balloon catheter or catheter 1 include a shape memory alloy mesh. In some embodiments, the shape memory alloy mesh is expandable and includes a collapsed state and an expanded state. In some embodiments, the shape memory alloy mesh has one or more radiopaque markers thereon for imaging the tissue stabilizer or guiding the procedure using these markers. In some embodiments, the shape memory alloy mesh has one or more radiopaque markers thereon for imaging the tissue stabilizer and guiding the procedure using these markers.

In some embodiments, the assemblies disclosed herein include a shape memory alloy mesh catheter, a shape memory alloy mesh housing catheter, or both. In some embodiments, the shape memory alloy mesh catheter includes one or more structures that are similar to a disc, plug, bulb, or the like. In some embodiments, one or more discs of the shape memory alloy mesh catheter are sized with respect to the blade size to pack tissue and plug distal end of delivery catheter. In some embodiments, the guide catheter or guidewire includes a steerable metal, alloy, or polymer. Such steerable guidewire, in some embodiments, permits slight adjustments in orientation towards interatrial septum. In some embodiments, the device assembly herein includes a transseptal needle. In some embodiments, the distal end of the needle includes a plastic or polymer material.

In some embodiments, the shape memory alloy mesh catheter features a dog-bone mesh. In some embodiments, the shape memory alloy mesh catheter features one or more discs, bulbs, or plugs that have a dog-bone shape, either alone or in combination with other discs, bulbs, plugs, or their combinations. In some embodiments, the shape memory alloy mesh catheter is kept perpendicular to at least a part of the septum during at least part of the procedure. In some embodiments, one or more discs, bulbs, or plugs of the shape memory alloy mesh catheter are kept perpendicular to at least a part of the septum before, during, or after the septum is sandwiched therewithin. In some embodiments, the guidewire or its distal tip is kept perpendicular to at least a part of the septum during or after its penetration to the left atrium. In some embodiments, the shape memory alloy mesh catheter or one or more of the discs, bulbs, plugs, or their combinations includes an armor to protect it against inadvertent puncture or other damage by other parts of the assembly. In some embodiments, the shape memory alloy mesh catheter or one or more of the discs, bulbs, plugs, or their combinations has a stiffness that ensures its protection from inadvertent puncture or inadvertent pull back of the discs, bulbs, plugs, or their combinations through the initial puncture site in the interatrial septum or other damage by other parts of the assembly.

In some embodiments, the cutter catheter could be built up of any combination of polymer, metal, braided or coiled reinforcement of metal, polymer, or both to allow for sufficient pushability during the cutting of the tissue and collapsing or deployment of the blade when unsheathing the blade. In some embodiments, the blade catheter could have a porthole to allow for rapid wire exchange during its introduction into the body. In some embodiments, the blade catheter could contain 1 or more radiopaque markers to aid in its proper delivery to the interatrial septum. In some embodiments, the blade catheter is a unidirectional or bidirectional steerable or deflectable sheath capable of supporting and maintaining its degree of deflection during the cutting motion. In some embodiment, the blade catheter has a preformed bend oriented towards the interatrial septum upon being advanced beyond the tip of the delivery catheter. In some embodiments, the blade catheter translates over the shape memory alloy mesh housing catheter once the tissue stabilizing element is deployed to anchor the system to the septum. In addition, the blade catheter is rigid enough to prevent deflection when the blade catheter is being translated through the septum. In some embodiments, the blade catheter has a smaller inner lumen such that its ID is flush with the OD of the catheter(s) within it (which serve as a guide or a means of tissue tensioning and stabilization at its distal end to ensure coaxial alignment with catheter(s) within.

In some embodiments, the outer diameter of the distal portion of catheter 1 shall dictate, govern, or limit the inner diameter and the distal portion of catheter 2 such that catheter 1 fully occupies the inner lumen of catheter 2 (distal portion). This ensures coaxial alignment between the tissue stabilizer and the cutter (and respective catheters 1 and 2). In some embodiments, coaxial alignment is also achieved through a separate centralizer component that occupies space between catheter 1 and catheter 2 (distal portion). Coaxial alignment also is, in some embodiments, achieved by dimensioning the distal portion of catheter 1 to occupy the full lumen of catheter 2. In some embodiments, the delivery catheter includes a central lumen that houses all other components of the assembly therewithin when the assembly is sheathed or undeployed before usage.

In some embodiments, the delivery catheter (catheter 3) features radiopaque markers to aid in orientation and positioning within the right atrium and to permit visualization of its relationship to other system components (e.g. confirmation of sheathed or unsheathed state of the cutting blade).

Additionally, any of the embodiments described herein are adaptable to accommodate and incorporate steerability, using mechanical means or a robotic catheter system. In some embodiments, an off-the-shelf steerable catheter is employed, over the delivery catheter of the device assembly.

Further, any of the embodiments described herein are adaptable to permit reversed cutting and excision of the septum from the left atrium to the right atrium, such that the tissue stabilizing element is deployed within the right atrium and the cutter is delivered to and deployed within the left atrium.

In some embodiments, as illustrated in FIG. 28A, a catheter 2, 2806, internal to the steerable delivery catheter 3, 2810, has a predetermined bend, such that upon exiting the steerable delivery catheter 3, the internal catheter 2 is configured to aim the whole device assembly to be orthogonal to the fossa ovalis of the interatrial septum 2820. In some embodiments, the steerable delivery catheter 3 is rigid enough to straighten out catheters 1 and 2, while still inside of the steerable delivery catheter; and catheters 1 and 2 still translate freely through catheter 3. In some embodiments, the bend on catheter 2 is steerable through a series of cables. In some embodiments, an off-the-shelf, or integral steerable catheter provides limited directional orientation of the Transcatheter Device into the interatrial septum, whereas the internal catheter is configurable to then perform fine aiming adjustment of the cutter to be orthogonal to the fossa ovalis of the interatrial septum. In some embodiments, as illustrated in FIG. 28B, an additional catheter 4 has been introduced and resides within the delivery catheter and is slidably engaged with the outside diameter of catheter 2 and is steerable eliminating the need for delivery catheter 3 to be steerable. FIG. 28A is a representative illustration of an embodiment of the assembly wherein the internal catheter 2 (catheter that comprises an expanding cutter) has a predetermined, but flexible bend in one of the internal catheters inside of the delivery catheter; but the delivery catheter is strong enough to contain the bend without distortion of the entire delivery catheter. FIG. 28B is an representative illustration of an embodiment of the assembly of FIG. 28A wherein an additional internal catheter has a predetermined, but flexible bend and is outside of the internal catheters, but still inside of the delivery catheter; but the delivery catheter is strong enough to contain the bend without distortion of the entire delivery catheter. Upon distal deployment of the additional internal catheter, the device bends generally in an orthogonal direction to point towards the fossa ovalis.

Additionally, the inventors have recognized the ability to combine one or more embodiment of the device assemblies described herein and the Atrial Shunting Device (ASD) 2900 as a system with an automated auscultation device for long term non-invasive monitoring of the flow or pressures through or across the created shunt.

Creating the ASD adds a third heart sound that is, in some embodiments, monitored non-invasively with auscultation through a digital microphone on a device intended to go home with the patient after the creation of the ASD. A change in the third heart sound previously calibrated to the patient would signal a change in the shunting dynamics. Creation of the shunt combined with auscultation monitoring, allows for monitoring of the flow through that shunt in order to monitor for early signs of excess flow which could cause right sided heart failure or the lack of flow which could be a sign of inadequate shunting, and the combination would allow for early changes in patient management.

In some embodiments, using the device assembly disclosed herein includes one or more of the following steps. While some of these steps must be performed in a particular order, some is performed out of order, as an alternative process arrangement. One embodiment of order of steps is provided below, however, the steps may be rearranged.

Process Step 1: Vascular access is achieved through the femoral vein using standard techniques (Seldinger method).

Process Step 2: Transseptal puncture through the fossa ovalis 200 of the interatrial septum is performed using standard techniques), leaving a guidewire 201 in place (as illustrated in FIG. 2). FIG. 2 is an illustration of an exemplary embodiment of a transseptal puncture through the fossa ovalis. FIG. 2 also shows the tissue stabilizer 204.

Process Step 3: A tissue stabilizer (e.g.: balloon catheter) is advanced over the transseptal guidewire and across the septum.

Process Step 4: The tissue stabilizing element 304 is deployed to provide tensioning to the septum when either pulled proximally or held stationary with respect to advancement of the cutter (as illustrated in FIG. 3). FIG. 3 is an illustration of an exemplary embodiment of a balloon catheter with balloon inflated in left atrium. FIG. 3 also shows the guidewire 301, fossa ovalis 300, and catheter 1, 302.

Process Step 5: A cutter (self-expanding shape memory stent with sharpened blades on the distal end) is delivered (sheathed) to the right atrium.

Figure 4B:
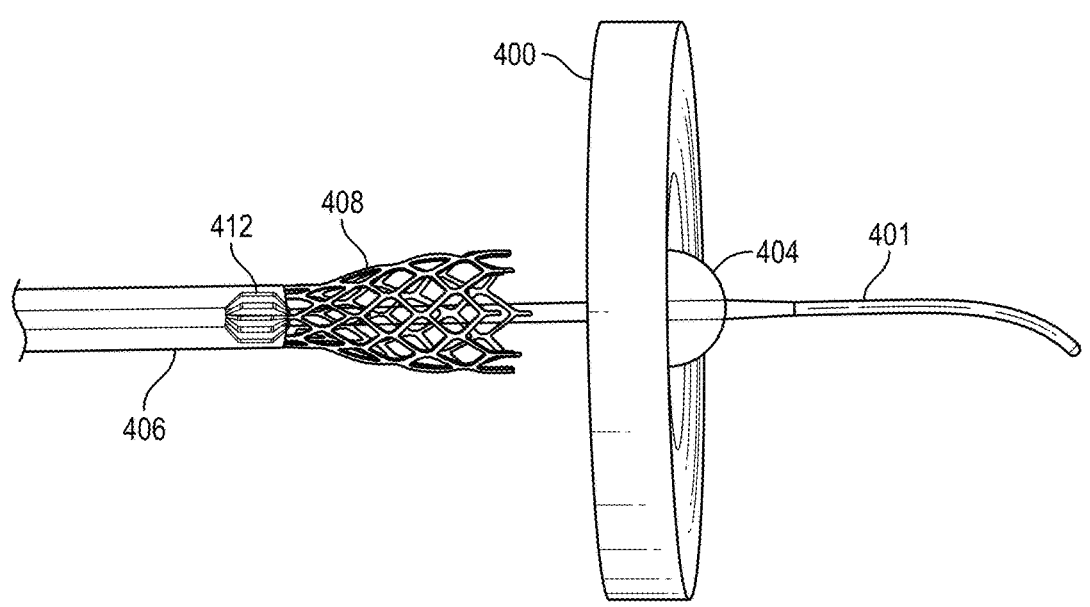
FIG. 4B is an illustration of an exemplary embodiment of the cutter, a self-expanding shape memory stent with sharpened blades on the distal end, delivered (and either partially or wholly un-sheathed) to the right atrium, with a coaxial aligner.

Process Step 6: The cutter 408 is unsheathed (either partially or wholly) in the right atrium via pullback on the delivery catheter or by pushing the catheter to which the cutter is mounted on forward (FIGS. 4A & 4B). FIG. 4A is an illustration of an exemplary embodiment of the cutter, a self-expanding shape memory stent with sharpened blades on the distal end, delivered (and either partially or wholly un-sheathed) to the right atrium. FIG. 4B is an illustration of an exemplary embodiment of the cutter, a self-expanding shape memory stent with sharpened blades on the distal end, delivered (and either partially or wholly un-sheathed) to the right atrium, with a coaxial aligner. FIGS. 4A & 4B also show the guidewire 401, fossa ovalis 400, and catheter 1, 402, tissue stabilizer 404, catheter 2, 406, and coaxial aligner 412.

Figure 5A:
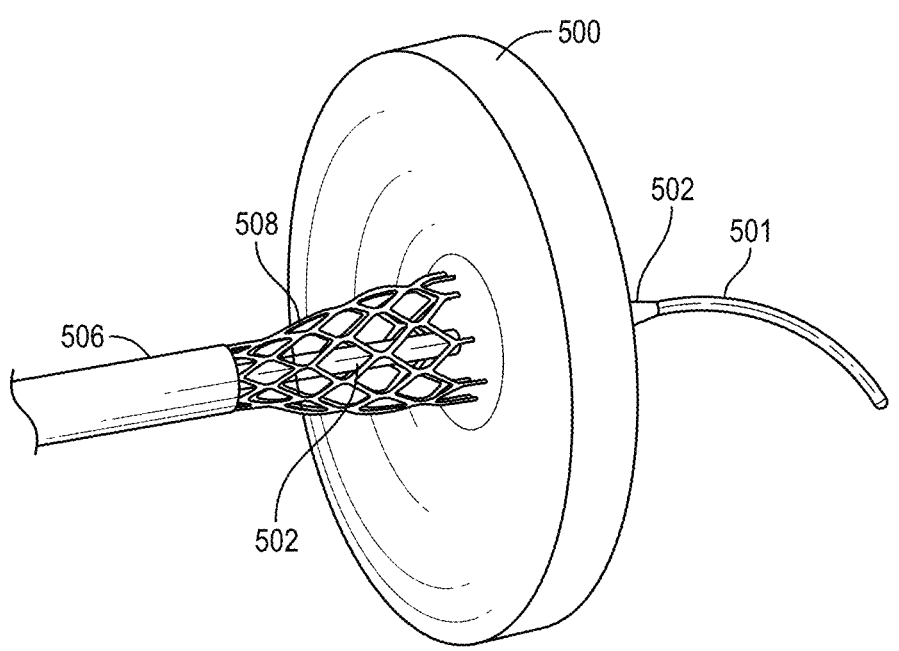
FIG. 5A is an illustration of an exemplary embodiment of the cutter translated forward to pierce and cut the interatrial septum while the tissue stabilizer (balloon) applies counter tension on the opposite side.
Figure 5B:
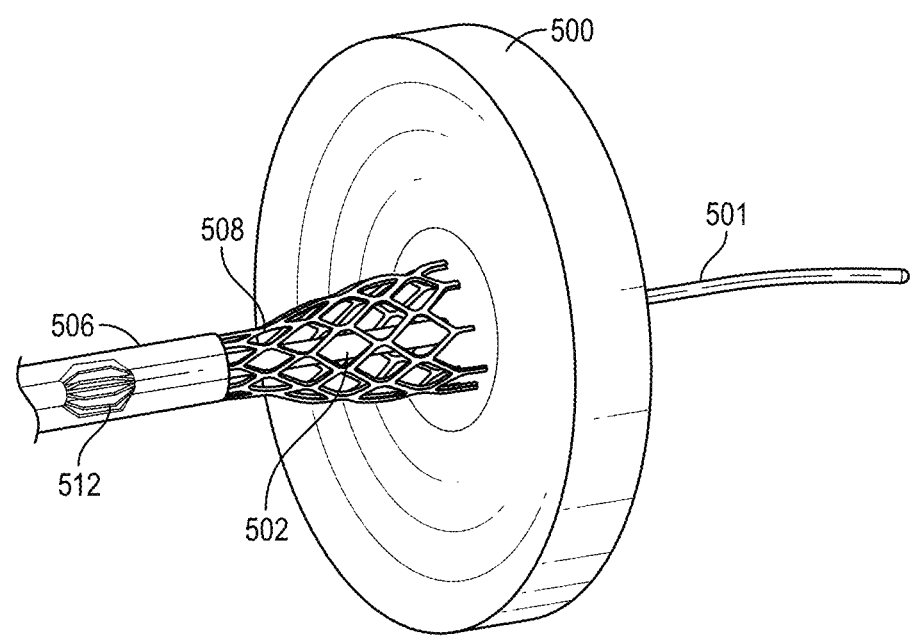
FIG. 5B is an illustration of an exemplary embodiment of the cutter, with a coaxial aligner, translated forward distally to pierce and cut the interatrial septum while the tissue stabilizer (balloon) applies counter tension on the opposite side.
Figure 6A:
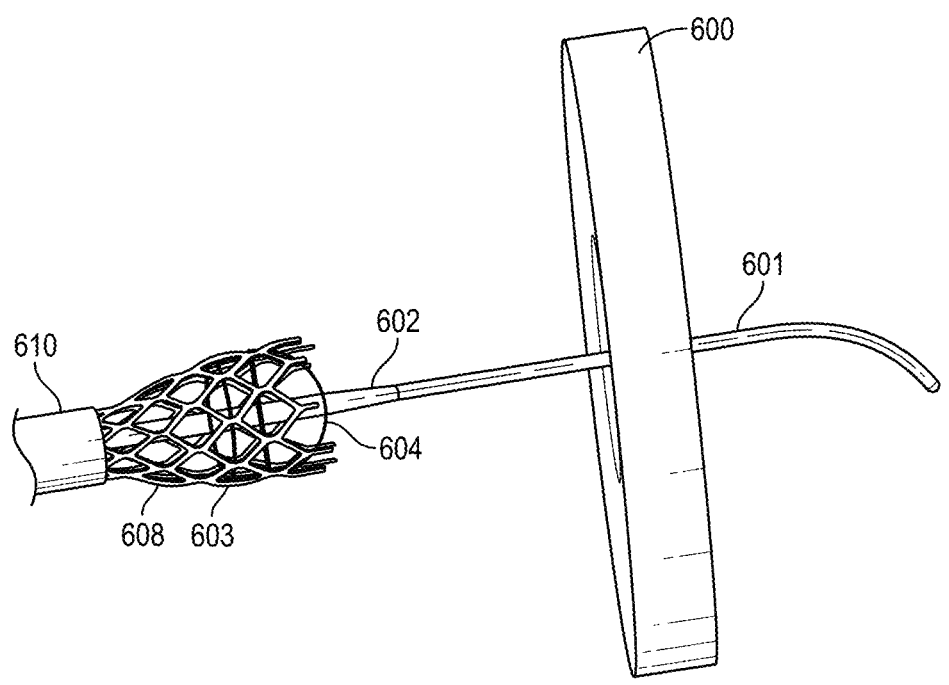
FIG. 6A is an illustration of an exemplary embodiment of the tissue stabilizer (balloon catheter)—with the excised tissue speared onto its respective catheter, being pulled proximally into the inner lumen and mouth of the cutter, prior to resheathing the cutter.
Figure 6B:
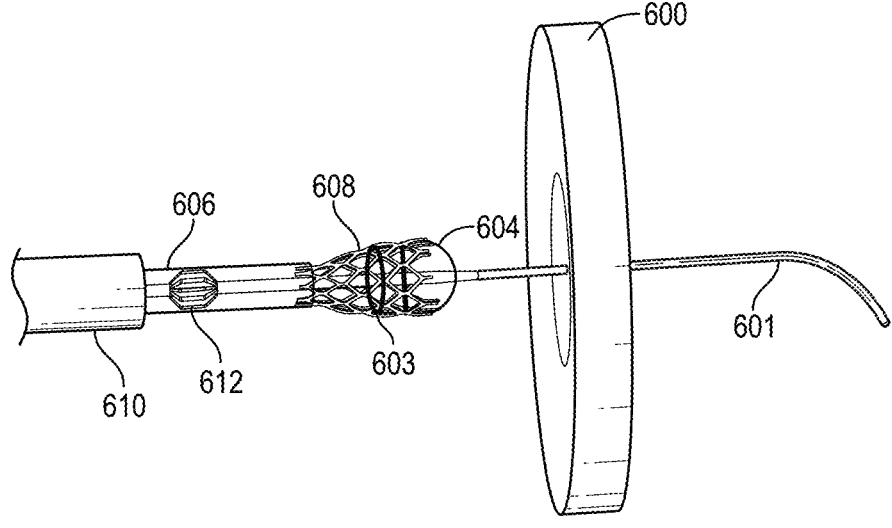
FIG. 6B is an illustration of an exemplary embodiment of the tissue stabilizer (balloon catheter) of FIG. 6A—with the excised tissue speared onto its respective catheter, being pulled backwards into the inner lumen and mouth of the cutter, with a coaxial aligner, prior to resheathing the cutter.

Process Step 7: The cutter 508 is translated forward to pierce and cut the septum while the tissue stabilizer (balloon) applies counter tension (FIGS. 5A & 5B). FIG. 5A is an illustration of an exemplary embodiment of the cutter translated forward to pierce and cut the interatrial septum while the tissue stabilizer (balloon) applies counter tension on the opposite side. FIG. 5B is an illustration of an exemplary embodiment of the cutter, with a coaxial aligner, translated forward to pierce and cut the interatrial septum while the tissue stabilizer (balloon) applies counter tension on the opposite side. FIGS. 5A & 5B also show the guidewire 501, fossa ovalis 500, and catheter 1, 502, catheter 2, 506, and coaxial aligner 512. Process Step 8A: FIG. 6A is an illustration of an exemplary embodiment of the tissue stabilizer (balloon catheter)—with the excised tissue speared onto its respective catheter, being pulled proximally into the inner lumen/mouth of the cutter, prior to resheathing the cutter. FIG. 6B is an illustration of an exemplary embodiment of the tissue stabilizer (balloon catheter) of FIG. 6A with the excised tissue speared onto its respective catheter, being pulled proximally into the inner lumen/mouth of the cutter, with a coaxial aligner, prior to resheathing the cutter. FIGS. 6A & 6B also show the guidewire 601, fossa ovalis 600, and catheter 1, 602. Process Step 8A is represented, as an exemplary embodiment of steps, in FIGS. 6A & 6B as follows:

A. The tissue stabilizing element 604 is at least partially deployed, as in FIG. 6A

B. The tissue stabilizing element (e.g.: balloon catheter)—with the excised tissue 603 speared onto its respective catheter, catheter 2, 606, is pulled proximally, and optionally into the inner lumen/mouth of the cutter 608, as in FIG. 6B.

C. The cutter is resheathed via:
   i. Pullback (proximal movement) of the cutter into the delivery catheter 3, 610, with alignment being maintained by coaxial aligner 612, or
   ii. Advancing the delivery catheter over the cutter.

Alternative Process—Step 8B:

A. The cutter is resheathed via:
   i. Pullback (proximal movement) of the cutter into the delivery catheter, or
   ii. Advancing the delivery catheter over the cutter.

B. The tissue stabilizing element is at least partially deflated to the diameter of the delivery catheter.

C. The tissue stabilizer is pulled back proximally (with the excised tissue) into the mouth of the delivery catheter, together with the excised tissue.

Process Step 9: The device assembly (catheter assembly) is removed from the body. In some embodiments, the steps of using the device assembly disclosed herein include one or more of the following steps. While some of these steps must be performed in a particular order, some may be performed out of order, as an alternative process arrangement. One embodiment of order of steps is provided below, however, the steps may be rearranged.

Process Step 1: Vascular access is achieved through the femoral vein using standard techniques (Seldinger method).

Process Step 2: Transseptal puncture through the fossa ovalis of the interatrial septum is performed using standard techniques), leaving a guidewire 4601 in place (as illustrated in FIG. 46). FIG. 46 shows an exemplary embodiment of a procedural step using the device assembly as disclosed herein, which is a transseptal puncture through the fossa ovalis of the interatrial septum, leaving a guidewire in place.

Process Step 3: The device assembly is introduced over the guidewire into the right atrium.

Process Step 4: The guide catheter 4703 is introduced out of the delivery catheter 4710 over the guidewire 4701 and brought into contact with the septum 4720. (FIG. 47) FIG. 47 shows an exemplary embodiment of a procedural step using the device assembly as disclosed herein, wherein the guide catheter is introduced out of the delivery catheter over the guidewire and brought into contact with the septum.

Process Step 5: A shape memory alloy mesh delivery catheter 1, 4802 is introduced over the guidewire into the left atrium and the guidewire is removed. (FIG. 48) FIG. 48 shows an exemplary embodiment of a procedural step using the device assembly as disclosed herein, wherein the shape memory alloy mesh delivery catheter is introduced from the guide catheter over the guidewire through the atrial septum at approximately 90 degrees.

Step 6: Through the shape memory alloy mesh delivery catheter 1, 4902 the shape memory alloy mesh tissue stabilizing element 4904 is introduced into the left atrium where it is deployed through self-expansion (FIG. 49), optionally via a guide catheter 4903. FIG. 49 shows an exemplary embodiment of a procedural step using the device assembly as disclosed herein, wherein through the shape memory alloy mesh delivery catheter the shape memory alloy mesh tissue stabilizing element is introduced into the right atrium where it is deployed through self-expansion. In some embodiments, the tissue stabilizer expands in an outward direction to approximately a 90° angle after passing through the septum, the angle is shown in FIG. 48.

Figure 50A:
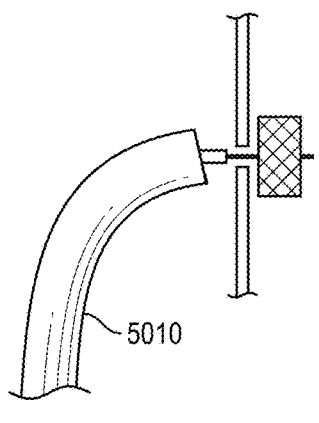
FIGS. 50A-50C show an exemplary embodiment of a procedural step using the device assembly as disclosed herein, wherein a cutter (self-expanding shape memory alloy stent or lattice with sharpened blades at the distal end) is delivered (sheathed) to the right atrium, and the cutter is unsheathed in the right atrium via pullback on the delivery catheter.
Figure 50B:
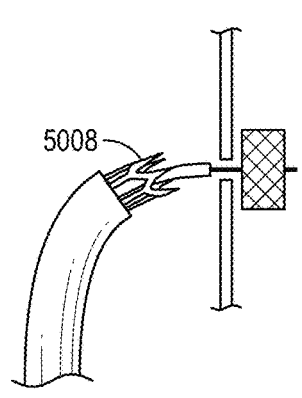
Figure 50C:
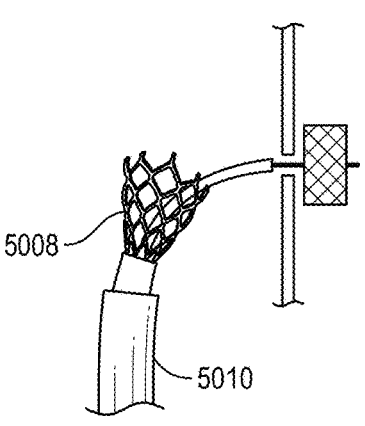

Process Step 7: A cutter 5008 (self-expanding shape memory stent with sharpened blades on the distal end) is delivered (sheathed) to the right atrium, and the cutter is unsheathed in the right atrium via pullback proximally on the delivery catheter 3 5010 or by pushing the catheter that comprises the cutter forward (FIGS. 50A-50C). FIGS. 50A-50C show an exemplary embodiment of a procedural step using the device assembly as disclosed herein, wherein a cutter (self-expanding shape memory alloy stent or lattice with sharpened blades at the distal end) is delivered (sheathed) to the right atrium, and the cutter is unsheathed in the right atrium via pullback on the delivery catheter.

Figure 51:
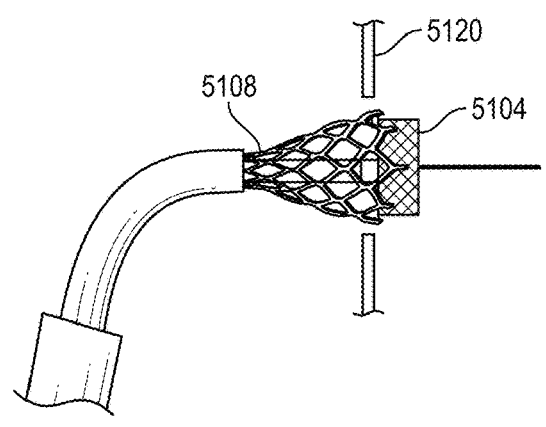
FIG. 51 shows an exemplary embodiment of a procedural step using the device assembly as disclosed herein, wherein the cutter is translated forward to pierce and cut the interatrial septum while the tissue stabilizer applies counter tension.

Process Step 8: The cutter 5108 is translated forward to pierce and cut the septum 5120 while the tissue stabilizer 5104 applies counter tension. (FIG. 51). FIG. 51 shows an exemplary embodiment of a procedural step using the device assembly as disclosed herein, wherein the cutter is translated forward to pierce and cut the interatrial septum while the tissue stabilizer applies counter tension.

Figure 52A:
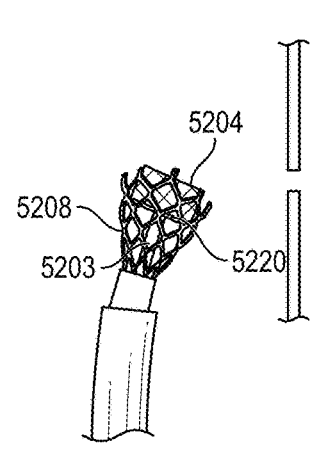
FIG. 52A shows an exemplary embodiment of a procedural step using the device assembly as disclosed herein, wherein the blade catheter, guide catheter, shape memory alloy mesh delivery catheter, tissue cut-out, and shape memory alloy mesh tissue stabilizer are all withdrawn from the atrial septum.
Figure 52B:
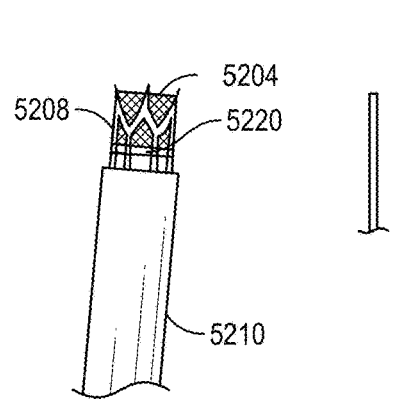
FIG. 52B shows an exemplary embodiment of a procedural step using the device assembly as disclosed herein, wherein the blade catheter, guide catheter, shape memory alloy mesh delivery catheter, tissue cut-out, and shape memory alloy mesh tissue stabilizer are all packaged into the delivery catheter, just prior to the whole system being removed from the body.

Process Step 9: The blade catheter, guide catheter 5203, shape memory alloy mesh delivery catheter, cutter 5208, excised tissue 5220, and shape memory alloy mesh tissue stabilizer 5204 are all packaged into the delivery catheter 3 5210, keeping the tissue trapped in between the mouth of the cutter 5208 and the mesh tissue stabilizer 5204, or trapped within the mouth of the cutter 5208 with the mesh tissue stabilizer enclosing the opening of the blade, and the whole system is removed from the body. (FIGS. 52A-52B). FIG. 52A shows an exemplary embodiment of a procedural step using the device assembly as disclosed herein, wherein the blade catheter, guide catheter, shape memory alloy mesh delivery catheter, tissue cut-out, and shape memory alloy mesh tissue stabilizer are all withdrawn from the atrial septum. FIG. 52B shows an exemplary embodiment of a procedural step using the device assembly as disclosed herein, wherein the blade catheter, guide catheter, shape memory alloy mesh delivery catheter, tissue cut-out, and shape memory alloy mesh tissue stabilizer are all packaged into the delivery catheter, just prior to the whole system being removed from the body.

In some embodiments, the approximately 90 degree angle is in the range of 80 to 100 degrees, 85 to 95 degrees, or 75 to 105 degrees. In some embodiments, the angle is with respect to the septum or a portion of the septum that is being cut or penetrated. In some embodiments, the angle is between an axis of the mesh delivery catheter (axis 1 in FIG. 49) and the septum. In some cases, the axis of the mesh delivery catheter is within a portion of the mesh delivery catheter in close vicinity to the septum. In some embodiments, the axis is approximately straight. In some embodiments, the axis connects a center point of the mesh delivery catheter at it distal tip or face to another center point that is proximal to its distal tip. In some cases, the axis is approximately perpendicular to the septum. In some embodiments, the axis is approximately perpendicular to a portion of the septum that is being cut or penetrated.

In some embodiments, the device assemblies disclosed herein include a shape memory alloy mesh over one or more catheters. In some embodiments, the device assemblies disclosed herein include a shape memory alloy mesh catheter 3604, a shape memory alloy mesh housing catheter 1 3602, or both as shown in FIG. 36. FIG. 36 also show guide catheter 3603, cutter 3608, and delivery catheter 3 3610. In some embodiments, the shape memory alloy mesh has one or more imaging markers. In some embodiments, the shape memory alloy mesh is not as rigid as the guidewire. In some embodiments, the shape memory alloy mesh is reinforced. In some embodiments, one or more catheters of the assembly do not advance over the guidewire. In some embodiments all internal catheters of the assembly are advanced over the guidewire. In some embodiments the guidewire needs to be removed from the body after the initial puncture in the interatrial septum has been crossed with an internal catheter (e.g. the guide catheter or the catheter that houses the shape memory alloy mesh). In some embodiments, the shape memory alloy mesh catheter cannot advance over the guidewire. In some embodiments, the blade catheter 2 3606 or the housing catheter 1 3602 cannot advance over the guidewire.

FIGS. 41A-41E show an exemplary embodiment of sequential procedural steps of applying the device assembly as disclosed herein. Referring to FIGS. 41A-41E, in some embodiments, a guidewire 4101 is previously placed optionally via transseptal puncture. In some embodiments, the guidewire has a rigid material so that its stiffness is larger than that of any other part of the assembly. In some embodiments, the guidewire is stiffer than the catheters of the assembly. In some embodiments, the guide catheter 4103 is delivered over the guidewire into the right atrium, optionally up to the septum and optionally not including a shape memory alloy mesh catheter 4104. The shape memory alloy mesh housing catheter 4102 is advanced across interatrial septum to left atrium afterwards. The guidewire is then optionally removed from the body. Optionally, the guidewire stays within the body until removal of the device assembly after the procedure. In some embodiments, the guidewire extends to the left atrium. The shape memory alloy mesh catheter, in some embodiments, is inserted through its housing catheter and the distal edge is delivered to the left atrium; shape memory alloy mesh discs, bulbs, plugs, or a combination thereof are then unsheathed or expanded optionally by pushing the self-expanding part past its housing catheter in the left atrium. In some embodiments, discs sandwich the septum or all discs are left in the left atrium. Optionally, the proximal edge of the expanded shape memory alloy mesh is then pulled against the septum, thus sandwiching the septum between the distal edge of the guide catheter and the proximal edge of the expanded shape memory alloy mesh. Following this step, the cutter is unsheathed or expanded by advancing the blade catheter past the tip of the delivery catheter and or by pulling the delivery catheter behind the self-expanding portion of the blade. The blade catheter is translated forward through the interatrial septum to create a full circumferential cut following the guide catheter while the shape memory alloy mesh disc, bulb, plug, or a combination thereof is pulled proximally towards the septum. The shape memory alloy mesh plug(s) then is pulled proximally into the mouth or opening of the expandable blade with the excised tissue sandwiched in-between two adjacent discs, bulbs, plugs, or a combination thereof or in-between a discs, bulb, plug, or a combination thereof and the cutter to ensure tissue capture and retrieval. In some embodiments, the blade catheter, guide catheter, shape memory alloy mesh housing catheter are pulled into the delivery catheter followed by the shape memory alloy mesh catheter packaging the tissue away inside of the delivery catheter. In some embodiments, the shape memory alloy mesh disc is left at the distal edge of the delivery catheter, plugging its mouth during removal to ensure safe tissue capture during device assembly removal.

FIGS. 42A-42F show an exemplary embodiment of sequential steps using the device assembly as disclosed herein resulting in the deployment of a dogbone shaped expandable tissue stabilizer, sandwiching the interatrial septum. Referring to FIG. 42A-42F, in some embodiments, the device assembly is delivered over the guidewire 4201 to the right atrium. In some embodiments, the shape memory alloy mesh housing catheter 4202, is advanced across the interatrial septum to left atrium through the guide catheter 4203. The guidewire is then removed from the body. The shape memory alloy mesh catheter 4204 is inserted through its housing catheter and delivered to the left atrium; one shape memory alloy mesh disc, bulb, or plug is unsheathed by pushing the first self-expanding proximal edge of the shape memory alloy mesh catheter past the mouth of the shape memory alloy mesh housing catheter in the left atrium or by deploying one shape memory alloy mesh disc, bulb, or plug by unsheathing the shape memory alloy mesh housing catheter in the left atrium. The proximal edge of the expanded shape memory alloy mesh disc is then pulled flush with the septum by pulling the shape memory alloy mesh catheter proximally. The shape memory alloy mesh housing catheter is pulled proximally into the right atrium to unsheath a second disc, bulb, or plug, thus sandwiching the septum between the two discs, bulbs, or plugs. The distal portion of the guide catheter 4203 is then to be brought up in contact with the proximal edge of the shape memory alloy mesh disc that was unsheathed in the right atrium. The cutter is unsheathed by advancing the blade past the delivery catheter or by pulling the delivery catheter behind the self-expanding portion of the blade. The blade is then optionally translated through the interatrial septum to create a full circumferential cut. The shape memory alloy mesh discs, bulbs, or plugs then is pulled into the mouth of the expandable blade with the excised tissue sandwiched in-between two adjacent discs, bulbs, or plugs or in-between one disc, bulb, or plug and the cutter to ensure tissue capture and retrieval. In some embodiments, the blade catheter, guide catheter, shape memory alloy mesh housing catheter are pulled into the delivery catheter followed by the shape memory alloy mesh catheter packaging the tissue away inside of the delivery catheter. The distal shape memory alloy mesh disc is left at the distal edge of the delivery catheter plugging its mouth during removal to ensure safe tissue capture during device assembly removal.

After tissue capture, in some embodiments, the cutter is resheathed (with tissue captured within) by advancing the delivery catheter forward (over the blade). In some embodiments, the blade is resheathed by pulling the blade into the delivery catheter. In some embodiments, the shape memory alloy mesh includes a diameter of about 4 mm to about 10 mm (in the range of 3 mm to 12 mm) in its expanded state. In some embodiments, the diameter is about 3 mm to about 5 mm, about 4 mm to about 6 mm, about 5 mm to about 7 mm, about 6 mm to about 8 mm, about 7 mm to about 9 mm, about 8 mm to about 10 mm, or about 9 mm to about 12 mm, up to about 12 mm, up to about 11 mm, up to about 10 mm, up to about 9 mm, up to about 8 mm, up to about 8 mm, up to about 7 mm, up to about 6 mm, or up to about 5 mm. In some embodiments, the shape memory alloy mesh catheter features one or multiple discs, bulbs, or plugs to serve as a failsafe to ensure that excised (or partially excised) tissue does not come free from the interatrial and device assembly, and 2) allow for the blade to continue translating through the septum—in the event that one of the mesh discs, bulbs, or plugs is inadvertently pulled through the septum prior to completion of a full circumferential cut. In some embodiments, the shape memory alloy mesh housing catheter is used to sheath and unsheath the shape memory alloy mesh catheter. In some embodiments, the shape memory alloy mesh catheter includes 1-3 discs, bulbs, or plugs. In some embodiments, there are distances in between adjacent discs, bulbs, or plugs in the expanded state. In some embodiments, the diameter of all the discs, bulbs, or plugs is smaller than the diameter of the distal opening or mouth of the cutter. In some embodiments, the diameter of one or all the discs, bulbs, or plugs is larger than the diameter of the distal opening or mouth of the cutter. In some embodiments, all the discs, bulbs, or plugs enter the left atrium. In some embodiments, two adjacent discs, bulbs, or plugs of the shape memory alloy mesh catheter sandwiches the septum therebetween. In some embodiments, it requires 0.1 to 1000 MPa of pressure to collapse the shape memory alloy mesh discs, bulbs, or plugs. In some embodiments, the shape memory alloy mesh discs, bulbs, or plugs each is about 1 to about 8 mm in diameter, and about 0.5 to 6.0 mm (in the range of 0.3 to 6.5 mm) in width. In some embodiments, each mesh disc, blub, or plug is about 2 to about 4 mm, about 3 to about 5 mm, about 4 to about 6 mm, about 5 to 7 mm, about 6 to about 8 mm in diameter. In some embodiments, each mesh disc, blub, or plug is about 0.2 to about 1 mm, about 0.3 to about 1.3 mm, about 1 to about 2 mm, about 1.5 to 3 mm, about 2 to about 3 mm, about 3 to about 4 mm, about 4 to about 5 mm, about 5 to about 7 mm in width. In some embodiments, the inherent stiffness in the wire that the disc, bulb, or plug is woven from prevents the structure from collapsing when pulled in tension during cutting of the septum; at the same time, the structure maintains sufficient flexibility to be collapsible and sheathed when pulled into the delivery catheter.

In some embodiments, the shape memory alloy mesh catheter features a central lumen to permit translation over a guidewire. FIGS. 43A-43D show an exemplary embodiment of sequential steps using the device assembly as disclosed herein eliminating the need to remove the guidewire as the catheter comprising the expandable tissue stabilizer is able to run over the guidewire and is deployed in the left atrium. Referring to FIGS. 43A-43D, after guidewire 4301 is previously placed via transseptal puncture, a guide catheter 4303 is optionally inserted and delivered to the right atrium, sometimes up to the septum, following a guidewire insertion. The shape memory alloy mesh housing catheter 4302 is delivered across interatrial septum to left atrium over the guidewire through the guide catheter. The guidewire optionally stays. The shape memory alloy mesh catheter is inserted and delivered through the housing catheter to the left atrium over the guidewire. The shape memory alloy mesh disc, bulb, or plug 4304 is unsheathed by pushing the self-expanding part past its housing catheter in the left atrium or by deploying the self-expanding part by unsheathing its housing catheter. The expanded proximal edge of the shape memory alloy mesh catheter is then pulled to the septum. The cutter or equivalent, blade is unsheathed by advancing the blade beyond the tip of the delivery catheter or by pulling the delivery catheter behind the self-expanding portion of the blade. The blade catheter is translated forward through the interatrial septum to create a full circumferential cut following the guide catheter while the shape memory alloy mesh disc, bulb, or plug is pulled against the septum. Then, the shape memory alloy mesh disc, bulb, or plug is, in some embodiments, pulled backwards proximally into the mouth of the expandable blade, with the excised tissue sandwiched between one blade and the disc, bulb, or plug to ensure tissue capture and retrieval or the excised tissue is sandwiched in-between two adjacent discs, bulbs, or plugs if the catheter comprises out of more than one disc, bulb, or plug similar to FIG. 44A-44E. In some embodiments, the blade catheter, guide catheter, shape memory alloy mesh housing catheter are pulled into the delivery catheter followed by the shape memory alloy mesh catheter packaging the tissue away inside of the delivery catheter. The shape memory alloy mesh disc, bulb, or plug(s) is, in some embodiments, left at the distal edge of the delivery catheter plugging its mouth during removal to ensure safe tissue capture during device assembly removal.

In some embodiments, the shape memory alloy mesh catheter features a central lumen to permit translation over a guidewire. FIGS. 44A-44E show an exemplary embodiment of sequential steps using the device assembly as disclosed herein eliminating the need to remove the guidewire as the catheter comprising the expandable tissue stabilizer is able to run over the guidewire and is deployed in the left atrium followed by the right atrium sandwiching the interatrial septum. Referring, therefore, to FIGS. 44A-44E, in some embodiments, after the guidewire 4401 is previously placed via a transseptal puncture, the shape memory alloy mesh housing catheter 4402 is delivered across interatrial septum to left atrium over the guidewire. FIGS. 44B-44E also show the guide catheter 4403. Subsequently, the shape memory alloy mesh catheter 4404 is, in some embodiments, inserted and delivered to the left atrium over the guidewire; a first shape memory alloy mesh disc, bulb, or plug is unsheathed by pushing the first self-expanding proximal edge of the shape memory alloy mesh catheter past the mouth of the shape memory alloy mesh housing catheter in the left atrium or by deploying the self-expanding part by unsheathing its housing catheter. The proximal edge of the self-expanded shape memory alloy mesh disc is then pulled flush with the septum by pulling the shape memory alloy mesh catheter backwards or proximally. The shape memory alloy mesh housing catheter is, in some embodiments, pulled back proximally into the right atrium to unsheath additional discs, bulbs, or plugs in the right atrium. The process of self-expanding the proximal and distal discs (first disc and other discs) thus sandwiches the septum between the two discs, bulbs, or plugs securing it in place during and post-tissue cutting. Afterwards, the blade is, in some embodiments, unsheathed by advancing the blade past the delivery catheter or by pulling the delivery catheter behind the self-expanding portion of the blade. The blade is, in some embodiments, translated through the interatrial septum to create a full circumferential cut optionally by translating the blade catheter forward over the guide catheter. The shape memory alloy mesh discs, bulbs, or plugs are, in some embodiments, pulled backward proximally into the mouth of the expandable blade with the excised tissue sandwiched in-between to ensure tissue capture and retrieval. In some embodiments, the blade catheter, guide catheter and shape memory alloy mesh housing catheter are pulled into the delivery catheter followed by the shape memory alloy mesh catheter packaging the tissue away inside of the delivery catheter. The shape memory alloy mesh disc, bulb, or plug(s) is, in some embodiments, left at the distal edge of the delivery catheter plugging its mouth during removal to ensure safe tissue capture during device assembly removal.

In some embodiments, after guidewire is previously placed via transseptal puncture, the shape memory alloy mesh housing catheter is delivered across the interatrial septum to the left atrium. The guidewire is, in some embodiments, removed from the body. Subsequently, the shape memory alloy mesh catheter is, in some embodiments, inserted through its housing catheter and its distal edge is, in some embodiments, delivered to the left atrium; the shape memory alloy mesh disc, bulb, or plug is, in some embodiments, expanded by pushing self-expanding part past its housing catheter in the left atrium or by deploying the self-expanding part by unsheathing its housing catheter. The expanded proximal edge of the expanded shape memory alloy mesh disc is then pulled to the septum optionally by pulling the shape memory alloy mesh catheter proximally. The remainder of device assembly is, in some embodiments, advanced up into the right atrium following the shape memory alloy mesh catheter (whose body takes the place of the guidewire. Afterwards, the guide catheter is, in some embodiments, delivered to the right atrium optionally up to the septum. Afterwards, the blade is, in some embodiments, unsheathed by advancing the blade past the delivery catheter or by pulling the delivery catheter behind the self-expanding portion of the blade. The blade is, in some embodiments, translated forward through the interatrial septum to create a full circumferential cut optionally by translating the blade catheter forward over the guide catheter. The shape memory alloy mesh discs, bulbs, or plugs is, in some embodiments, pulled proximally into the mouth of the expandable blade with the excised tissue sandwiched in-between to ensure tissue capture and retrieval. In some embodiments, the blade catheter, guide catheter, shape memory alloy mesh housing catheter are pulled into the delivery catheter followed by the shape memory alloy mesh catheter packaging the tissue away inside of the delivery catheter. The shape memory alloy mesh disc is, in some embodiments, left at the distal edge of the delivery catheter plugging its mouth during removal to ensure safe tissue capture during device assembly removal.

In some embodiments, the blade is resheathed (with tissue captured within) by advancing the delivery catheter forward (over the blade). In some embodiments, the blade is, in some embodiments, resheathed by pulling the blade in the delivery catheter. In some embodiments, the shape memory alloy mesh includes a diameter of about 4 mm to about 10 mm (in the range of 3 mm to 12 mm) in its expanded state. In some embodiments, the shape memory alloy mesh includes a diameter of about 4 mm to about 10 mm (in the range of 3 mm to 12 mm) in its expanded state. In some embodiments, the shape memory alloy mesh catheter is translated over a guidewire. In some embodiments, the shape memory alloy mesh features multiple discs, bulbs, plugs, or their combinations to serve as a failsafe to 1) ensure that excised (or partially excised) tissue does not come free from the interatrial septum and device assembly, and 2) allow for the blade to continue translating through the septum—in the event that one of the mesh discs, bulbs, or plugs is inadvertently pulled through the septum prior to completion of a full circumferential cut. In some embodiments, the shape memory alloy mesh housing catheter is used to sheath and unsheath the shape memory alloy mesh.

In some embodiments, the shape memory alloy mesh plug(s) or the balloon is used to plug the delivery catheter (optionally as opposed to the mouth of the blade).

In some embodiments, the diameter of the shape memory alloy mesh plug(s), in their expanded state(s), is sized with respect to the diameter of the cutter at its distal end, in its expanded state, to facilitate packing of the excised tissue within the body of the cutter itself.

In some embodiments, the tissue stabilizer, for example, a balloon, or one or more discs, bulbs, or plugs of the shape memory alloy mesh catheter plugs the mouth (distal opening) of the blade to entrap excised the tissue and ensure the tissue does not come free from the assembly during or after the procedure to potentially cause an embolic event. In some embodiments, one of the discs, blubs, or plugs is oversized so that it captures the mouth of the cutter completely therewithin. In some embodiments, the oversized disc, 4504a, has a larger diameter, width, length, circumference, radius, area, or a combination thereof than that of the cutter 4508 at its distal edge or distal end. In some embodiments, the balloon catheter or the shape memory alloy mesh housing catheter 4505 features a larger outer diameter, for example, about 0.5 to 5 mm (in the range of 0.3 mm to 6 mm), close to or at its distal end, for example, about 0 to 10 cm (in the range of 0 to 11 cm) to its distal length to ensure coaxial alignment with the expandable cutter 4508, as shown in FIG. 45. FIG. 45 shows an exemplary embodiment of the balloon catheter or nitinol mesh housing catheter disclosed herein, which features a larger outer diameter at its distal end to ensure coaxial alignment with the guide catheter or blade catheter. FIG. 45 shows the expanded shape memory alloy discs 4504*a* and 4504*b* sandwiching the septum 4520. In some embodiments, the tissue stabilizer comprises: an inflatable balloon; expanding tines; an expanding mesh; at least one curved wire; an expanding plate; an expanding disc; an expanding fan; a spring coil; at least one strut; at least one hinged arm; an umbrella stretcher; or a combination thereof. In some embodiments, a tissue stabilizer material for anything other than an inflatable balloon comprises a shape memory alloy comprising: nickel-titanium, copper-aluminum-nickel, zinc-gold-copper; or a combination thereof. In some embodiments, a cutter material comprises a shape memory alloy comprising: nickel-titanium; copper-aluminum-nickel; zinc-gold-copper; or a combination thereof. In some embodiments, the cutter comprises: a wire mesh; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, the cutter is configured such that a cutting tooth of the of the cutter comprises: a pointed single wire; a single-edge blade shape; a two-edged blade shape or a two-edged scissor blade; an inverted "v"-shape; or a "u"-shape (or scalloped shape); wherein a distal end of every tooth is a cutting point and cutting edges of the cutting teeth when taken in combination are configured to cut a discrete aperture or hole when the cutter pierces the interatrial septum. In some embodiments, the cutter is configured to cut an aperture or hole that is: circular in shape; oval in shape; triangular in shape; squared shaped; rectangular in shape; or polygon in shape; or a combination thereof. In some embodiments, the expanded dimension of the tissue stabilizer is less than the expanded dimension of the cutter. In some embodiments, the expanded dimension of the cutter is between about 1% and about 50% (in the range of 0% to 65%) larger than the expanded dimension of the tissue stabilizer. In some embodiments, the device assembly further comprises a hydrophilic coating on the guidewire. In some embodiments, the device assembly further comprises a hydrophilic coating on the internal, external, or both internal and external surfaces of the catheters. In some embodiments, the device assembly further comprises a hydrophobic coating on the guidewire. In some embodiments, the device assembly further comprises a hydrophobic coating on the internal surface, external surface, or internal and external surfaces of the catheters. In some embodiments, the device assembly further comprises a force sensor or pressure sensor incorporated into the distal tip of the guidewire. In some embodiments the device assembly, further comprises an oxygen saturation sensor incorporated into the guidewire. In some embodiments, the device assembly further comprises a cutting point or edge incorporated into the distal tip of the guidewire. In some embodiments, the device assembly further comprises a curved or shaped end incorporated into the distal tip of the guidewire. In some embodiments, the tissue stabilizer comprising the inflatable balloon further comprises a flat face that assumes a flush configuration with respect to the tissue plane when pulled against the left atrial side of the interatrial septum. In some embodiments, the distal end of the balloon tissue stabilizer comprises a shape that is: rounded; squared; rectangular; tapered; oval shaped; triangular shaped; polygonal shaped; parallel to an interatrial septum; or atraumatic on the portion facing the left atrial free wall. In some embodiments, the tissue stabilizer comprising the inflatable balloon is axially configured to assume a "dogbone" or "dumbbell" shape wherein a portion of the inflated balloon resides on each side of the septum, thereby 'sandwiching' the septum. In some embodiments, the axially shaped inflated balloon comprises two balloons which are filled separately and or simultaneously. In some embodiments, the axially configured inflatable balloon is one continuous balloon comprising: the same dimension for each portion of the "dogbone" or "dumbbell", differing dimensions for each portion of the "dogbone" or "dumbbell", or individually translatable portions of the "dogbone" or "dumbbell" (with respect to one another). In some embodiments, the more proximal balloon of the "dogbone" or "dumbbell" shaped balloon allows for an early warning if the most distal and tissue retaining balloon is at risk of being damaged by the cutter. In some embodiments, the expanded dimension of the tissue stabilizer is significantly less than the expanded dimension of the cutter to permit tissue tenting of the interatrial septum such that the cutter creates an aperture larger than the dimension of the expanded cutter. In some embodiments, the expanded dimension of the tissue stabilizer is: about 5%; about 10%; about 15%; about 20%; about 25%; about 30%; about 35%; about 40%; about 45%; about 50%; or as much as about 75%; less than the expanded dimension of the cutter. In some embodiments, the tissue stabilizer further comprises radiopaque markers or bands at strategic locations to: guide or orient device positioning within the body, orient positioning of the tissue stabilizers with respect to other system components, and to permit visualization and confirmation of its deployed state, (i.e.: expanded or collapsed). In some embodiments, the tissue stabilizer further provides embolic protection by ensuring that any excised tissue speared by the first catheter is captured and retained within the device assembly. In some embodiments, the tissue stabilizer comprising the balloon features a protective skirt to protect the proximal edges of the inflated balloon. In some embodiments, the protective skirt comprises: a single tine element; multiple tine elements; an expanding mesh; at least one curved wire; an expanding disc; an expanding fan; a spring coil; or at least one hinged arm. In some embodiments, the protective skirt expands and collapses relative to the state of the balloon. In some embodiments, the tissue stabilizer comprises: tines that extend and expand in an outward direction after completely passing through the septum having a dimension that is less than the cutter dimension and are configured to be pulled to engage the septum; the tines further comprise barbs to engage the septum tissue and stabilize it prior to and after engagement with the cutter; and wherein, following engagement of the cutter, the tines are collapsed in the same direction from which they opened, capturing an excised tissue cut from the septum during a resheathing step such that the cutter, the excised tissue and tines collapse into the delivery catheter. In some embodiments, a tissue stabilizer comprises: tines that extend and expand in an outward direction after completely passing through the septum having a dimension that is less than the cutter dimension, and are configured to be pulled to engage the septum; the tines further comprise barbs to engage the septum tissue and stabilize it prior to and after engagement with the cutter; and wherein, following engagement of the cutter, the tines bend backward from the original deployment state, capturing an excised tissue cut from the septum during a resheathing step such that the cutter, the excised tissue and tines collapse into the delivery catheter. In some embodiments, the tissue stabilizer comprises: an expanding mesh; an expanding plate; an expanding disc; or an expanding fan; wherein the tissue stabilizer is fabricated from a shape memory alloy that expands in an outward direction to approximately a 90° angle after completely passing through the septum having a dimension that is less than the cutter dimension, and is configured to be pulled to engage the septum, to stabilize it prior to and after engagement with the cutter, and wherein, following engagement of the cutter, the tissue stabilizer is collapsed in the same direction from which it opened, capturing an excised tissue cut from the septum during a resheathing step such that the cutter, the excised tissue and tissue stabilizer collapse into the delivery catheter. In some embodiments, the tissue stabilizer comprises: at least one strut; at least one hinged arm; or an umbrella stretcher; wherein the tissue stabilizer expands in an outward direction to approximately a 90° angle after completely passing through the septum, having a dimension that is less than the cutter dimension, and is configured to be pulled to engage the septum, to stabilize it prior to and after engagement with the cutter; and wherein following engagement of the cutter, the tissue stabilizer is collapsed in the same direction from which it opened, capturing an excised tissue cut from the septum during a resheathing step such that the cutter, the excised tissue and tissue stabilizer collapse into the delivery catheter. In some embodiments, a tissue stabilizer comprises: at least one curved wire; or a spring coil; wherein the tissue stabilizer is fabricated from a shape memory alloy that is configured to expand after completely passing through the septum, in an outward direction approximately orthogonal to the longitudinal centerline of the catheter and having a radial dimension that is less than the cutter dimension and is configured to be pulled to engage the septum, to stabilize it prior to and after engagement with the cutter; and wherein following engagement of the cutter, the tissue stabilizer is collapsed in the same direction from which it opened, capturing an excised tissue cut from the septum during a resheathing step such that the cutter, the excised tissue and tissue stabilizer fit into the delivery catheter.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter; and a coaxial alignment mechanism having a third lumen slidably engaged with the outside diameter of the first internal coaxial catheter, slidably engaged with the inside diameter of the second internal coaxial catheter and within the central delivery lumen of the delivery catheter.

In some embodiments, the first internal coaxial catheter having a first lumen, further comprises a needle-like puncture tip configured to penetrate the interatrial septum. In some embodiments, the device assembly further comprising a coaxial guidewire slidably engaged within the first lumen of the first internal coaxial catheter, configured to provide a working track for the device assembly. In some embodiments, a cutting dimension of the expandable cutter is adjustable and wherein a dimension of the expandable tissue stabilizer is adjustable. In some embodiments, the coaxial alignment mechanism is a third internal coaxial catheter positioned along the entire length of the first and second internal catheters. In some embodiments, a distal end of the coaxial alignment mechanism has a larger dimension to aid in tissue stabilization during a cutting process of an interatrial septum.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; an expandable cutter having a proximal end and a distal end, the proximal end attached to the distal end of a first internal coaxial catheter, coaxial to the central delivery lumen of the delivery catheter and configured to collapse such that it resides and slidably traverse or engage within the delivery catheter. In some embodiments, the device assembly further comprises a second internal coaxial catheter having a second lumen slidably engaged within the first lumen of the first internal coaxial catheter. In some embodiments, the second internal coaxial catheter further comprises a needle-like puncture tip configured to penetrate the interatrial septum. In some embodiments, the device assembly further comprising a coaxial guidewire slidably engaged within the second lumen of the second internal coaxial catheter, configured to provide a working track for the device assembly. In some embodiments, a cutting dimension of the expandable cutter is adjustable. In some embodiments, a cutter material comprises a shape memory alloy comprising: nickel-titanium; copper-aluminum-nickel; zinc-gold-copper; or a combination thereof. In some embodiments, the cutter comprises: a wire mesh configuration; a wire that connects sharpened teeth; a collapsible hole saw configuration; a collapsible, open-end cylinder-shape configuration; a collapsible, open-end barrel-shape configuration; a collapsible, open-end cone-shaped configuration; or a combination thereof. In some embodiments, the expandable cutter is configured to have an expanded cross-sectional shape generally comprising: a circle; a square; a rectangle; a triangle; an oval; or a polygon. In some embodiments, the expandable cutter is exposed and expands from a collapsed dimension to an expanded shape coaxial with an adjustable dimension to the first internal coaxial catheter when the distal end of the delivery catheter is pulled back proximally. In some embodiments, the adjustable dimension of the expandable cutter is controllable by the amount of proximal pull-back of the delivery catheter. In some embodiments, the expandable cutter comprises an expandable lattice and wherein the distal end of the expandable cutter lattice comprises a plurality of sharpened ends configured to perform as tissue cutting blades. In some embodiments, the expandable cutter comprises an expandable lattice comprising a shape memory alloy, and wherein the distal end of the expandable cutter lattice comprises a plurality of sharpened ends configured to perform as tissue cutting blades. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises an expandable continuous blade comprising a shape memory alloy, and wherein the distal end of the expandable continuous blade comprises: a single smooth sharpened knife edge; a plurality of sharpened serrations along the continuous blade; a single bevel knife edge; a double bevel knife edge; or a combination thereof; configured to perform as a continuous tissue cutting blade. In some embodiments, the single smooth sharpened knife edge or the plurality of sharpened serrations along the continuous blade are configured to perform as tissue cutting blades. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof. In some embodiments, the first internal coaxial catheter further comprises an expandable balloon configured to controllably inflate the expandable cutter, wherein the dimension of the cutter is controlled by the inflation of the expandable balloon positioned within a central portion of the cutter. In some embodiments, the first internal coaxial catheter further comprises expandable struts configured to controllably engage the internal dimension of the expandable cutter, wherein the dimension of the cutter is controlled by the expansion of the expandable struts positioned within a central portion of the cutter.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; an expandable cutter attached to, and positioned along the outer length of, the first internal coaxial catheter near a distal end thereof; a second internal coaxial catheter having a second lumen slidably engaged over the first internal coaxial catheter and within the central delivery lumen of the delivery catheter; and an expandable tissue stabilizer attached to, and positioned along the outer length of, the second internal coaxial catheter and over the cutter on the first internal coaxial catheter and configured to slidably traverse or engage within the central delivery lumen of the delivery catheter. In some embodiments, the first internal coaxial catheter having the first lumen, further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter, is configured to provide a working track for the device assembly. In some embodiments, a coaxial guidewire is configured to extend from a distal end of the first lumen of the first internal coaxial catheter and pass through an initial puncture site in an interatrial septum between a right atrium and a left atrium of a heart of a mammal at approximately a fossa ovalis to provide a working track for the device assembly into the left atrium. In some embodiments, the delivery catheter is extended distally such that the distal end of the first internal coaxial catheter and the distal end of the second coaxial catheter are configured to traverse along the track of the guidewire and pass through the initial puncture site in an atrial septum such that the cutter also extends past the interatrial septum into the left atrium. In some embodiments, the delivery device is configured such that when the delivery catheter is retracted proximally with the distal end of the second coaxial catheter back into the right atrium, bringing with it, the tissue stabilizer, the cutter is configured to coaxially expand radially within the left atrium to an intended dimension, wherein the distal end of the delivery catheter is further retracted back inside the right atrium to allow the tissue stabilizer to expand radially to a sufficiently large dimension, wherein the external expanded dimension of the cutter is less than the internal dimension of the expanded tissue stabilizer, and the radially expanded dimension of the tissue stabilizer provides a supporting, tensioning effect on the right atrial side of the interatrial septum around the initial puncture site. In some embodiments, the internal dimension of the tissue stabilizer is larger than the external dimension of the cutter. In some embodiments, the first internal coaxial catheter is then retracted distally such that the expandable cutter is slidably retracted back to the left atrial side of the interatrial septum and coaxially to the tissue stabilizer. In some embodiments, the first internal coaxial catheter is further retracted until the fully expanded cutter engages or traverses the left atrial side of the interatrial septum such that the cutter pierces and cuts completely through the interatrial septum, thereby creating an interatrial pressure relief opening in the interatrial septum. In some embodiments, the interatrial pressure relief opening is sufficiently sized to allow blood flow through the interatrial pressure relief opening from the left atrium to the right atrium such that no more than 50% of left atrial blood is shunted to the right atrium. In some embodiments, the interatrial pressure relief opening is sufficiently sized and or of such shape in order to slow a natural healing process of the tissue to maintain patency of the interatrial pressure relief opening in the interatrial septum without implanting a stent or valve therein. In some embodiments, an excised tissue cut from the interatrial septum is captured and maintained between the cutter and the tissue stabilizer. In some embodiments, the stabilizing element is partially collapsed over the cutter by partially retracting said stabilizing element into the delivery catheter and approximately at the same time, the first internal coaxial catheter is retracted and the cutter is pulled into an opening of the partially collapsed tissue stabilizer positioned on the second internal coaxial catheter, wherein the cutter with the captured tissue stabilizer is fully collapsed and retracted completely into the delivery catheter with the captured excised tissue. In some embodiments, the device assembly further comprises a coaxial alignment component. In some embodiments, said coaxial alignment component is configured to provide centralization between the cutter and the tissue stabilizer. In some embodiments, the tissue stabilizer comprises: expanding tines; an expanding mesh; at least one curved wire; an expanding cup; an expanding cone; an expanding cylinder; a spring coil; at least two or more struts; at least two or more hinged arms; or a combination thereof. In some embodiments, a tissue stabilizer material comprises a shape memory alloy comprising: nickel-titanium; copper-aluminum-nickel; zinc-gold-copper; or a combination thereof. In some embodiments, a cutter material comprises a shape memory alloy comprising: nickel-titanium; copper-aluminum-nickel; zinc-gold-copper; or a combination thereof. In some embodiments, the cutter shape comprises: a collapsible hole saw configuration; a collapsible, open-end cylinder-shape configuration; a collapsible, open-end barrel-shape configuration; a collapsible, open-end box-shape configuration; a collapsible, open-end cone-shaped configuration; or a combination thereof. In some embodiments, the tissue stabilizer shape comprises: a collapsible hole saw configuration; a collapsible, open-end cylinder-shape configuration; a collapsible, open-end barrel-shape configuration; —a collapsible, open-end box-shape configuration; a collapsible, open-end cone-shaped configuration; or a combination thereof. In some embodiments, the expandable cutter is configured to have an expanded cross-sectional shape generally comprising: a circle; a square; a rectangle; a triangle; an oval; or a polygon. In some embodiments, the expandable cutter comprises an expandable lattice comprising a shape memory alloy, and wherein the distal end of the expandable cutter lattice comprises a plurality of sharpened ends configured to perform as tissue cutting blades. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises an expandable continuous blade comprising a shape memory alloy, and wherein the distal end of the expandable continuous blade comprises: a single smooth sharpened knife edge; a plurality of sharpened serrations along the continuous blade; a single bevel knife edge; a double bevel knife edge; or a combination thereof; configured to perform as a continuous tissue cutting blade. In some embodiments, the single smooth sharpened knife edge or the plurality of sharpened serrations along the continuous blade are configured to perform as tissue cutting blades. In some embodiments, the expandable cutter is configured to penetrate and cut through an interatrial septum. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; an expandable tissue stabilizer attached to, and positioned along the outer length of, the first internal coaxial catheter, at or about the distal end; a third internal coaxial catheter having a third lumen slidably engaged over the outside diameter of the first internal coaxial catheter; a slider element, slidably engaged along the outside diameter of the third catheter and further comprising two or more struts; a second internal coaxial catheter having a second lumen slidably engaged over the third internal coaxial catheter and within the central delivery lumen of the delivery catheter; and an expandable cutter attached to and at a distal end of the second internal coaxial catheter and configured to slidably traverse or engage within the central delivery lumen of the delivery catheter, over the third coaxial catheter, the umbrella sliding element and the two or more struts. In some embodiments, the first internal coaxial catheter having a first lumen further comprises a penetrating tip configured to penetrate the interatrial septum. In some embodiments, the device assembly further comprises a coaxial guidewire slidably engaged within the first lumen of the first internal coaxial catheter. In some embodiments, a cutting dimension of the expandable cutter is adjustable and wherein a dimension of the expandable tissue stabilizer is adjustable. In some embodiments, the coaxial guidewire is configured to provide a working track for the device assembly. In some embodiments, an extended portion of the guidewire is pushed through an initial puncture site in an atrial septum into a left atrium, followed by the penetrating tip of the first internal coaxial catheter to an interatrial septum from a right atrium into a left atrium of a heart of a mammal at approximately the fossa ovalis. In some embodiments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the expanded size thereof is sufficiently large enough to prevent the tissue stabilizer from inadvertently pulling back through the initial puncture site and such that the tissue stabilizer provides a supporting, tensioning effect on the wall of the atrial septum surrounding the initial puncture site. In some embodiments, the delivery catheter is at least partially retracted distally to expose the cutter such that it is expanded, and wherein the delivery catheter is translated distally such that the slider element is slidably engaged within the cutter causing the two or more struts to engage and radially increase the size of the cutter such that it is greater than the size of the stabilizing element. In some embodiments, the coaxially expandable tissue stabilizer is configured to have an expanded cross-sectional shape generally comprising: a circle; a square; a rectangle; a triangle; an oval; or a polygon. In some embodiments, the expandable cutter comprises an expandable lattice and wherein the distal end of the expandable cutter lattice comprises a plurality of sharpened ends configured to perform as tissue cutting blades. In some embodiments, the expandable cutter comprises a shape memory alloy. In some embodiments, the plurality of sharpened ends configured to perform as tissue cutting blades comprise a tissue penetrating end and one or more lateral edges having a sharpened knife-like edge. In some embodiments, the expandable cutter is configured to penetrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened ends resemble: scalloped teeth; or straight teeth; and wherein the crest of the teeth are either pointed or rounded, or a combination thereof and wherein the roots of the teeth are either pointed or rounded, or a combination thereof. In some embodiments, the expandable cutter comprises an expandable continuous blade, and wherein the distal end of the expandable continuous blade comprises: a single smooth sharpened knife edge; a plurality of sharpened serrations along the continuous blade; a single bevel knife edge; a double bevel knife edge; or a combination thereof; configured to perform as a continuous tissue cutting blade. In some embodiments, the expandable cutter comprises a shape memory alloy. In some embodiments, the single smooth sharpened knife edge or the plurality of sharpened serrations along the continuous blade are configured to perform as tissue cutting blades. In some embodiments, the expandable cutter is configured to penetrate and cut through an intera- trial septum. In some embodiments, the expandable cutter is configured to have an expanded cross-sectional shape gen- erally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Disclosed herein, in some embodiments, are device assemblies for treating heart failure, the device assembly comprising: a delivery catheter having a central delivery lumen; a first internal coaxial catheter having a first lumen slidably engaged within the central delivery lumen of the delivery catheter; an expandable tissue stabilizer attached to, and positioned along the outer length of, the first internal coaxial catheter, at or about the distal end; a second internal coaxial catheter having a second lumen slidably engaged over the outside diameter of the first internal coaxial catheter and within the central delivery lumen of the delivery cath- eter; comprising a compression surface for engaging and supporting the septum against the tissue stabilizer; using a coaxial, spring loaded plunger element, slidably engaged along the outside diameter of the first catheter; and an expandable cutter attached to and at a distal end of the second internal coaxial catheter and configured to slidably traverse or engage within the central delivery lumen of the delivery catheter, over the first coaxial catheter and the spring loaded plunger. In some embodiments, the first inter- nal coaxial catheter having a first lumen further comprises a penetrating tip configured to penetrate interatrial septum. In some embodiments, the device assembly further comprises a coaxial guidewire slidably engaged within the first lumen of the first internal coaxial catheter. In some embodiments, a cutting dimension of the expandable cutter is adjustable and wherein a dimension of the expandable tissue stabilizer is adjustable. In some embodiments, the coaxial guidewire is configured to provide a working track for the device assem- bly. In some embodiments, an extended portion of the guidewire is pushed through an initial puncture site into the left atrium, followed by the penetrating tip of the first internal coaxial catheter to penetrate an interatrial septum from a right atrium into the left atrium of a heart of a mammal at approximately the fossa ovalis. In some embodi- ments, the distal end of the first internal coaxial catheter is configured to traverse along the track of the guidewire and pass through the initial puncture site in an atrial septum such that the tissue stabilizer also extends past the interatrial septum into the left atrium. In some embodiments, the tissue stabilizer is coaxially expanded within the left atrium such that the expanded size thereof is sufficiently large enough to prevent the tissue stabilizer from inadvertently pulling back through the initial puncture site and such that the tissue stabilizer provides a supporting, tensioning effect on the wall of the atrial septum surrounding the initial puncture site. In some embodiments, the delivery catheter is at least partially retracted distally to expose the cutter such that it is expanded, and wherein another catheter is translated distally such that the slider element is slidably engaged within the cutter causing the two or more struts to engage and radially increase the size of the cutter such that it is greater than the size of the stabilizing element. In some embodiments, the expandable tissue stabilizer is configured to have an expanded cross-sectional shape generally comprising: a circle; a square; a rectangle; a triangle; an oval; or a polygon. In some embodiments, the expandable cutter comprises an expandable lattice and wherein the distal end of the expand- able cutter lattice comprises a plurality of sharpened ends configured to perform as tissue cutting blades. In some embodiments, the expandable cutter comprises a shape memory alloy. In some embodiments, the plurality of sharp- ened ends configured to perform as tissue cutting blades comprise a tissue penetrating end and one or more lateral edges having a sharpened knife-like edge. In some embodi- ments, the expandable cutter is configured to penetrate and cut through an interatrial septum. In some embodiments, the expandable cutter is configured to have an expanded cross- sectional shape generally comprising: a circle; a square; a rectangle; a triangle; an oval; or a polygon. In some embodi- ments, the plurality of sharpened ends resemble: scalloped teeth; or straight teeth; and wherein the crest of the teeth are either pointed or rounded, or a combination thereof, and wherein the roots of the teeth are either pointed or rounded, or a combination thereof. In some embodiments, the expand- able cutter comprises an expandable continuous blade com- prising a shape memory alloy, and wherein the distal end of the expandable continuous blade comprises: a single smooth sharpened knife edge; a plurality of sharpened serrations along the continuous blade; a single bevel knife edge; a double bevel knife edge; or a combination thereof; config- ured to perform as a continuous tissue cutting blade. In some embodiments, the single smooth sharpened knife edge or the plurality of sharpened serrations along the continuous blade are configured to perform as tissue cutting blades. In some embodiments, the expandable cutter is configured to pen- etrate and cut through an interatrial septum. In some embodiments, the expandable cutter is configured to have an expanded cross-sectional shape generally comprising: a circle; a square; a rectangle; a triangle; an oval; or a polygon. In some embodiments, the plurality of sharpened serrations along the continuous blade resemble: scalloped teeth; or straight teeth; and wherein the crest of the serrations are either pointed or rounded, or a combination thereof and wherein the roots of the serrations are either pointed or rounded, or a combination thereof.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; a tissue stabilizer attached to, and posi- tioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter. In some embodiments, the first internal coaxial catheter having the first lumen, further comprises a needle- like puncture tip configured to penetrate interatrial septum. In some embodiments, the device assembly further com- prises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter, is configured to provide a working track for the device assembly. In some embodiments, the second internal coaxial catheter comprises a predetermined bend, such that upon exiting the central delivery lumen of the delivery catheter, aims the catheters and components therein in a direction orthogonal to an interatrial septum between a right atrium and a left atrium of a heart of a mammal. In some embodiments, the delivery catheter comprises a material sufficiently rigid enough to straighten the shaft of the second catheter while it is within the delivery catheter and wherein other catheters are freely translatable therein.

Disclosed herein, in some embodiments, are device assemblies for treating heart failure, the device assembly comprising: a delivery catheter having a central delivery lumen; a first internal coaxial catheter having a first lumen, slidably engaged within the central delivery lumen of the delivery catheter; a tissue stabilizer attached to, and positioned along the outer length of, the first internal coaxial catheter, at or near a distal end; a second internal coaxial catheter having a second lumen slidably engaged over the first internal coaxial catheter and within the central delivery lumen of the delivery catheter; an expandable cutter attached to, and positioned along the outer length of, the second internal coaxial catheter and configured to slidably traverse or engage within the central delivery lumen of the delivery catheter; and a third internal coaxial catheter having a third lumen slidably engaged with the outside diameter of the second internal coaxial catheter, slidably engaged within the central delivery lumen of the delivery catheter. In some embodiments, the first internal coaxial catheter having the first lumen, further comprises a needle-like puncture tip configured to penetrate the interatrial septum. In some embodiments, the device assembly further comprises a coaxial guidewire slidably engageable within the first lumen of the first internal coaxial catheter. In some embodiments, a cutting dimension of the expandable cutter is adjustable and wherein a dimension of the expandable tissue stabilizer is adjustable. In some embodiments, the coaxial guidewire slidably engaged within the first lumen of the first internal coaxial catheter, is configured to provide a working track for the device assembly. In some embodiments, the third internal coaxial catheter comprises a predetermined bend, such that upon exiting the central delivery lumen of the delivery catheter, aims the catheters and components therein in a direction orthogonal to an interatrial septum between a right atrium and a left atrium of a heart of a mammal. In some embodiments, the delivery catheter is rigid enough to straighten out the third catheter while it is inside of the delivery catheter and wherein the other catheters are still freely translatable therein. In some embodiments, the cutter further comprises: an electrocautery element; a cryoablation element; an RF (radio-frequency) element; a thermal ablation element; or a chemical or pharmacologic delivery element; configured to retard tissue regrowth. In some embodiments, the electrocautery element comprises: a monopolar element; or a bipolar element. In some embodiments, the device assembly further comprises radiopaque markers on the delivery catheter to aid in orientation and positioning within the right atrium and to permit visualization in relationship to other assembly components. In some embodiments, the device assembly further comprising a mechanism at or about the proximal end of the device assembly configured to provide a user with alternative actuation and movement of the cutter comprising: a handle; a knob; a hydraulic connection; a pneumatic connection; an electrical motor connection; or a sonic or vibratory connection, wherein the alternative actuation and movement includes rotary and reciprocating movement. In some embodiments, the device assembly further comprises an automated auscultation device for long term non-invasive monitoring of the flow or pressures through or across the created shunt.

In some embodiments, the delivery catheter, or the first or the second or the third internal coaxial catheter comprises a predetermined bend, such that upon exiting the central delivery lumen of the delivery catheter, aims the catheters and components therein in a direction orthogonal to an interatrial septum between a right atrium and a left atrium of a heart of a mammal. In some embodiments, the delivery catheter is rigid enough to straighten out the third catheter while it is inside of the delivery catheter and wherein the other catheters are still freely translatable therein. In some embodiments, the cutter further comprises: an electrocautery element; a cryoablation element; an RF (radio-frequency) element; a thermal ablation element; or a chemical or pharmacologic delivery element; configured to retard tissue regrowth. In some embodiments, the electrocautery element comprises: a monopolar element; or a bipolar element. In some embodiments, the device assembly further comprises radiopaque markers on the delivery catheter to aid in orientation and positioning within the right atrium and to permit visualization in relationship to other assembly components. In some embodiments, the device assembly further comprising a mechanism at or about the proximal end of the device assembly configured to provide a user with alternative actuation and movement of the cutter comprising: a handle; a knob; a hydraulic connection; a pneumatic connection; an electrical motor connection; or a sonic or vibratory connection, wherein the alternative actuation and movement includes rotary and reciprocating movement. In some embodiments, the device assembly further comprises an automated auscultation device for long term non-invasive monitoring of the flow or pressures through or across the created shunt.

In some embodiments, the first internal coaxial catheter is a balloon catheter, a shape memory alloy mesh housing catheter, a shape memory alloy mesh catheter, or a guide catheter. In some embodiments, the second internal coaxial catheter is a blade catheter. In some embodiments, the tissue stabilizer is armed or protected against the expandable cutter in its compressed or expanded state. In some embodiments, the cutter comprises one or more collapsible wave forms. In some embodiments, the cutter comprises one or more collapsible sinusoidal wave forms. In some embodiments, the tissue stabilizer comprises more than one expandable mesh discs. In some embodiments, the tissue stabilizer comprises more than one expandable mesh discs, at least one of the more than one expandable mesh discs expands when distal to interatrial septum and in the left atrium. In some embodiments, the tissue stabilizer comprises more than one expandable mesh discs, at least two of the more than one expandable mesh discs are of different thickness. In some embodiments, the guide catheter is configured to be inserted to a right atrium over a coaxial guide wire there within, the coaxial guide wire being previously inserted into the right atrium. In some embodiments, the shape memory alloy mesh housing catheter is configured to be advanced across an interatrial septum to a left atrium. In some embodiments, the coaxial guide wire is configured to be removed after insertion of the shape memory alloy mesh housing catheter to the left atrium. In some embodiments, a shape memory alloy mesh catheter is configured to be inserted through the shape memory alloy housing catheter to the left atrium. In some embodiments, the shape memory alloy mesh housing catheter is configured to enclose a shape memory alloy mesh catheter there within. In some embodiments, the shape memory alloy mesh catheter comprises one or more expandable shape memory alloy meshes configured to be expanded when outside of the shape memory alloy mesh housing catheter. In some embodiments, the one or more expandable shape memory alloy meshes includes at least two expandable shape memory alloy meshes that expands with an interatrial septum therebetween. In some embodiments, the expandable tissue stabilizer is self-expandable when unsheathed. In some embodiments, the expandable cutter is self-expandable when unsheathed. In some embodiments, the delivery catheter is wire-reinforced or braided. In some embodiments, the delivery catheter comprises a reinforced distal tip. In some embodiments, the delivery catheter includes a bend radius of about 0.5 inch to about 4 inches (in the range of 0.3 inches to 4.5 inches). In some embodiments, the guide catheter is configured to bend in a predetermined manner towards interatrial septum. In some embodiments, the expandable cutter, after expansion, is configured to create a plurality of perforations at an interatrial septum. In some embodiments, the expandable cutter is configured to translate through the interatrial septum thereby creating a complete cut at the interatrial septum after expansion. In some embodiments, the cutter comprises a proximal edge and a distal edge. In some embodiments, the proximal edge does not expand when the cutter is expanded. In some embodiments, the tissue stabilizer comprises more than one expandable mesh discs, at least one of the more than one expandable mesh discs expands when proximal to interatrial septum and in the right atrium. In some embodiments, two of the more than one expandable mesh discs sandwiches the interatrial septum in between when expanded. In some embodiments, two of the more than one expandable mesh discs contacts and sandwiches the interatrial septum in between when expanded. In some embodiments, the tissue stabilizer comprises more than one expandable mesh discs, one of the more than one expandable mesh discs is configured to plug a distal opening of the cutter or a distal opening of the delivery catheter when the tissue stabilizer is resheathed.

In some embodiments, disclosed herein are methods for transcatheter interatrial septum excision of a subject using a device assembly, the method comprising: allowing vascular access of the device assembly, the device assembly in a sheathed state; puncturing through a fossa ovalis of an interatrial septum of the subject and advancing a guidewire therethrough to a left atrium; advancing the device assembly over the guidewire into a right atrium in the sheathed state; advancing a guide catheter over the guidewire to be in contact with the interatrial septum; advancing a housing catheter over the guidewire into the left atrium; removing the guidewire from the subject; introducing the tissue stabilizer in a compressed state in a proximal edge of the housing catheter and advancing it towards a distal edge of the housing catheter; expanding the tissue stabilizer in the left atrium; delivering a cutter to the right atrium, wherein the cutter is enclosed in a delivery catheter in a second compressed state; expanding the cutter in the right atrium; translating the cutter forward to cut the interatrial septum while the tissue stabilizer applies counter tension; and resheathing the cutter into the delivery catheter with the cut interatrial septum. In some embodiments, the cut interatrial septum comprises at least a portion of the interatrial septum. In some embodiments, the device assembly comprises a delivery catheter, a guide catheter, a guidewire, a housing catheter of a tissue stabilizer, the tissue stabilizer, and a cutter. In some embodiments, the tissue stabilizer or the cutter is self-expandable. In some embodiments, expanding the tissue stabilizer is via self-expansion. In some embodiments, expanding the tissue stabilizer includes unsheathing one or more discs in the left atrium. In some embodiments, expanding the cutter in the right atrium is via movement of the delivery catheter relative to cutter. In some embodiments, the methods disclosed herein comprise resheathing the cutter, the guiding catheter, the housing catheter, and the tissue stabilizer into the delivery catheter. In some embodiments, the methods disclosed herein comprise removing the resheathed device assembly from the subject. In some embodiments, advancing the guide catheter over the guidewire to the interatrial septum comprises advancing the guide catheter out of the delivery catheter. In some embodiments, the methods disclosed herein comprise puncturing through a fossa ovalis of an interatrial septum of the subject using an off the shelf transseptal puncture kit in order to be able to leave a guidewire behind.

In some embodiments, disclosed herein are methods for transcatheter interatrial septum excision of a subject using a device assembly, the method comprising: advancing a guide catheter out of a delivery catheter to a right atrium over a guidewire; advancing a housing catheter of a tissue stabilizer out of the guide catheter across an interatrial septum into a left atrium over the guidewire, the tissue stabilizer enclosed in the housing catheter in a compressed state; expanding the tissue stabilizer in the left atrium by moving the tissue stabilizer out of the housing catheter over the guidewire and allowing the tissue-stabilizer to self-expand; expanding the cutter in the right atrium; translating the cutter forward to cut the interatrial septum while the tissue stabilizer applies counter tension to the interatrial septum; and resheathing the tissue stabilizer with the cut interatrial septum into the cutter. In some embodiments, the cut interatrial septum is at least a portion of the interatrial septum. In some embodiments, the methods disclosed herein comprise puncturing through a fossa ovalis of an interatrial septum of the subject and advancing a guidewire therethrough to a left atrium. In some embodiments, the methods disclosed herein comprise advancing the device assembly over a guidewire to a right atrium, the device assembly being sheathed. In some embodiments, the methods disclosed herein comprise moving the tissue stabilizer to be in contact with the interatrial septum at a proximal edge of the tissue stabilizer thereby sandwiching the interatrial septum between a distal edge of the guide catheter and the proximal edge of the tissue stabilizer. In some embodiments, expanding the cutter is via advancing the cutter relative to the right atrium or via pulling back of a delivery catheter relative to the right atrium behind a self-expanding portion of the cutter. In some embodiments, the tissue stabilizer plugs a distal opening of the delivery catheter during resheathing of the cutter and the tissue stabilizer. In some embodiments, the methods herein comprise resheathing the cutter into the delivery catheter, the cutter enclosing the tissue stabilizer and the cut interatrial septum there within. In some embodiments, the tissue stabilizer plugs a distal opening of the delivery catheter during resheathing. In some embodiments, the tissue stabilizer plugs a distal opening of the cutter during resheathing. In some embodiments, the methods herein comprise removing the resheathed device assembly from the subject. In some embodiments, the tissue stabilizer plugs a distal opening of the delivery catheter during removal of the resheathed device assembly. In some embodiments, the methods herein comprise expanding the tissue stabilizer comprises deploying more than one self-expanding discs simultaneously or at different time points. In some embodiments, one of said discs is deployed in the left atrium. In some embodiments, one of said discs is deployed in the right atrium. In some embodiments, expanding the tissue stabilizer in the left atrium by moving the tissue stabilizer out of the housing catheter and allowing the tissue-stabilizer to self-expand includes pushing at least a portion of a self-expanding part of the tissue stabilizer past the housing catheter in the left atrium. In some embodiments, the methods herein comprise removing the guidewire from the subject after advancing a housing catheter of a tissue stabilizer out of the guide catheter across an interatrial septum. In some embodiments, the methods herein comprise removing the guidewire from the subject before unsheathing the tissue stabilizer from the housing catheter and allowing the tissue-stabilizer to self-expand in the left atrium. In some embodiments, disclosed herein are methods for transcatheter interatrial septum excision of a subject using a device assembly, the method comprising: advancing a guide catheter out of a delivery catheter to a right atrium over a guidewire; advancing a housing catheter of a tissue stabilizer out of the guide catheter across an interatrial septum to a left atrium over the guidewire, the tissue stabilizer enclosed in the housing catheter in a compressed state; allowing a first self-expanding disc of the tissue stabilizer to expand in the left atrium; allowing a second self-expanding disc to expand in the right atrium thereby sandwiching the interatrial septum between the first and second self-expanding discs; expanding the cutter in the right atrium; translating the cutter forward to cut the interatrial septum while the tissue stabilizer applies counter tension; and resheathing the tissue stabilizer into the cutter with the cut interatrial septum. In some embodiments, the cut interatrial septum comprises at least a portion of the interatrial septum. In some embodiments, the methods herein comprise moving the housing catheter into the right atrium thereby allowing the first self-expanding disc to be in contact with the interatrial septum. In some embodiments, allowing the first self-expanding disc of the tissue stabilizer to expand is via movement of a self-expanding proximal edge of the cutter passing a distal edge of the housing catheter. In some embodiments, allowing a second self-expanding disc to expand in the right atrium is via movement of a distal edge of the housing catheter from the left atrium to the right atrium. In some embodiments, the methods disclosed herein comprise bringing a distal portion of the guide catheter to be in contact with a proximal edge of the second self-expanding disc after moving the housing catheter into the right atrium. In some embodiments, the cut interatrial septum is sandwiched in between the first and second self-expanding discs during resheathing. In some embodiments, the methods herein comprise removing the guidewire from the subject after advancing a housing catheter of a tissue stabilizer out of the guide catheter across an interatrial septum to a left atrium over the guidewire. In some embodiments, the methods herein comprise removing the guidewire from the subject before allowing a first self-expanding disc of the tissue stabilizer to expand in the left atrium. In some embodiments, the methods herein comprise puncturing through a fossa ovalis of an interatrial septum of the subject and advancing a guidewire therethrough to a left atrium. In some embodiments, the methods herein comprise advancing the device assembly over a guidewire to a right atrium, the device assembly being sheathed. In some embodiments, expanding the cutter is via advancing the cutter relative to the right atrium or via pulling back of a delivery catheter relative to the right atrium behind a self-expanding portion of the cutter. In some embodiments, the methods herein comprise resheathing the cutter into the delivery catheter, the cutter enclosing the tissue stabilizer and the cut interatrial septum therewithin. In some embodiments, the tissue stabilizer plugs a distal opening of the delivery catheter during resheathing. In some embodiments, the tissue stabilizer plugs a distal opening of the cutter during resheathing. In some embodiments, the cut interatrial septum is sandwiched in between the first and second self-expanding discs during resheathing. In some embodiments, the methods disclosed herein comprise removing the resheathed device assembly from the subject. In some embodiments, the cut interatrial septum is sandwiched in between the first and second self-expanding discs during removal of the resheathed device assembly from the subject. In some embodiments, deploying the tissue stabilizer comprises deploying more than one self-expanding discs simultaneously or at different time points. In some embodiments, at least one of said discs is deployed in the left atrium. In some embodiments, at least one of said discs is deployed in the right atrium. In some embodiments, wherein the more than one expandable mesh discs comprise shape memory alloy or metal.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

While preferred embodiments disclosed herein have been shown and described herein, it will be obvious to those skilled in the art that such embodiments are provided by way of example only. Numerous variations, changes, and substitutions will now occur to those skilled in the art without departing from the disclosure herein. It should be understood that various alternatives to the embodiments of the device assemblies described herein may be employed in practicing the device assemblies herein. It is intended that the following claims define the scope of the device assemblies herein and that methods and structures within the scope of these claims and their equivalents be covered thereby.

What is claimed is:

1. A device assembly for treating heart failure, the device assembly comprising:
   a first internal coaxial catheter having a first lumen;
   a tissue stabilizer attached to and positioned along a length of the first internal coaxial catheter;
   a second internal coaxial catheter having a second lumen slidably engaged over the first internal coaxial catheter;
   a cutter attached to and positioned along a length of the second internal coaxial catheter, wherein a diameter of the tissue stabilizer is less than a diameter of the cutter to permit tenting of an interatrial septum wall such that an aperture created by the cutter is larger than the diameter of the cutter; and a coaxial aligner slidably coupled to the first internal coaxial catheter proximal to the cutter, wherein an outer diameter of the coaxial aligner is flush with an inner diameter of the second lumen, the coaxial aligner configured to align the cutter and the tissue stabilizer.

2. The device assembly of claim 1, further comprising a coaxial guidewire slidably engageable within the first lumen of the first internal coaxial catheter.

3. The device assembly of claim 2, wherein the coaxial guidewire is configured to extend from a distal end of the first lumen of the first internal coaxial catheter and pass through an initial puncture site in an interatrial septum between a right atrium and a left atrium of a heart of a mammal at approximately a fossa ovalis to provide a working track for the device assembly into the left atrium.

4. The device assembly of claim 3, wherein the distal end of the first internal coaxial catheter is configured to traverse along the track of the guidewire and pass through the initial puncture site in an atrial septum such that the tissue stabilizer also extends past the interatrial septum into the left atrium.

5. The device assembly of claim 1, wherein the cutter comprises an open-end cylinder-shape configuration.

6. The device assembly of claim 1, wherein a distal end of the first lumen comprises a puncture tip configured to penetrate the interatrial septum.

7. The device assembly of claim 1, wherein the tissue stabilizer comprises:

tines;

at least one curved wire;

at least one strut; or a combination thereof.

8. The device assembly of claim 1, wherein a cutter material comprises a shape memory alloy comprising:

nitinol;

nickel-titanium;

stainless steel;

copper-aluminum-nickel;

zinc-gold-copper; or a combination thereof.

9. The device assembly of claim 1, wherein the cutter further comprises:

an electrocautery element;

an electrosurgery element;

an RF (radio-frequency) ablation element; or a thermal ablation element.

10. The device assembly of claim 1, wherein a tissue stabilizer material comprises a shape memory alloy comprising:

nitinol;

nickel-titanium;

copper-aluminum-nickel; or zinc-gold-copper.

11. The device assembly of claim 1, further comprising a delivery catheter having a central delivery lumen.

12. The device assembly of claim 11, wherein the delivery catheter is steerable or bendable.

13. The device assembly of claim 11, wherein the first lumen is slidably engaged within the central delivery lumen.

14. The device assembly of claim 11, wherein the second lumen is slidably engaged within the central delivery lumen.

15. The device assembly of claim 1, wherein the outer diameter of the coaxial aligner is greater than an outer diameter of the first internal coaxial catheter.

16. The device assembly of claim 1, wherein the coaxial aligner comprises a third lumen configured to slidably couple to an outer diameter of the first internal coaxial catheter.

17. The device assembly of claim 1, wherein the diameter of the tissue stabilizer is less than a diameter of the cutter to permit tenting of an interatrial septum wall proximal to a cutting face of the cutter.

* * * * *